US012537080B2

(12) United States Patent
Chang

(10) Patent No.: US 12,537,080 B2
(45) Date of Patent: Jan. 27, 2026

(54) EHR SYSTEM WITH ALERT FOOTER AND RELATED METHODS

(71) Applicant: Khai S. Chang, Mount Dora, FL (US)

(72) Inventor: Khai S. Chang, Mount Dora, FL (US)

( * ) Notice: Subject to any disclaimer, the term of this patent is extended or adjusted under 35 U.S.C. 154(b) by 95 days.

(21) Appl. No.: 18/510,904

(22) Filed: Nov. 16, 2023

(65) Prior Publication Data

US 2025/0166750 A1 May 22, 2025

(51) Int. Cl.

*G16H 10/60* (2018.01)
*G06F 3/0482* (2013.01)
*G06F 3/0483* (2013.01)
*G16H 50/30* (2018.01)

(52) U.S. Cl.

CPC ........... *G16H 10/60* (2018.01); *G06F 3/0482* (2013.01); *G06F 3/0483* (2013.01); *G16H 50/30* (2018.01)

(58) Field of Classification Search

None
See application file for complete search history.

(56) References Cited

U.S. PATENT DOCUMENTS

| | | | | |
|---|---|---|---|---|
| 8,090,742 | B2 | 1/2012 | Mok | |
| 8,249,895 | B2 | 8/2012 | Faulkner | |
| 8,326,651 | B2 | 12/2012 | McLaren | |
| 9,791,999 | B2 | 10/2017 | Flam | |
| 10,777,308 | B2 | 9/2020 | Kutty | |
| 2002/0042725 | A1 * | 4/2002 | Mayaud ................. | G16H 20/13 705/2 |
| 2009/0024411 | A1 | 1/2009 | Albro | |
| 2009/0192823 | A1 | 7/2009 | Hawkins et al. | |
| 2013/0044111 | A1 * | 2/2013 | VanGilder .............. | A61B 5/743 345/440 |
| 2013/0110548 | A1 | 5/2013 | Kutty | |
| 2014/0058750 | A1 | 2/2014 | Fotsch | |
| 2014/0067424 | A1 | 3/2014 | Ramakrishnan | |

(Continued)

OTHER PUBLICATIONS

Ahmed et al., "Novel Automated Fault Isolation System on Low Voltage Distribution Automation System", UKSim 15th International Conference on Computer Modelling and Simulation, IEEE Computer Society, Apr. 2013, pp. 593-599.

(Continued)

*Primary Examiner* — Peter H Choi
*Assistant Examiner* — John P Go
(74) *Attorney, Agent, or Firm* — ALLEN, DYER, DOPPELT, GILCHRIST, P.A.

(57) ABSTRACT

An EHR system is for providing an EHR GUI. The EHR GUI includes a switchable interface area configured to switch between EHR functions. The EHR GUI includes a navigation tab menu adjacent to a first side of the switchable interface area and having navigation tabs for accessing the EHR functions within the switchable interface area, and a patient history tab menu adjacent to a second side of the switchable interface area. The second side is opposite the first side. The patient history tab menu has patient history tabs for accessing different types of historical patient data from the given patient data in the EHR database. The EHR GUI also includes an alert footer menu below the switchable interface area, the alert footer menu having potential medical alerts for the given patient, and a specialist footer menu adjacent to the alert footer menu and having potential specialist notifications.

20 Claims, 135 Drawing Sheets

(56) References Cited

U.S. PATENT DOCUMENTS

| | | | | |
|---|---|---|---|---|
| 2014/0108048 | A1 | 4/2014 | Cohn | |
| 2014/0172458 | A1 | 6/2014 | Ueda | |
| 2014/0275819 | A1* | 9/2014 | Kassem | A61B 5/021 600/301 |
| 2014/0278584 | A1 | 9/2014 | Dart | |
| 2015/0269316 | A1* | 9/2015 | Hussam | G16H 10/60 705/3 |
| 2015/0317436 | A1 | 11/2015 | Kutty | |
| 2015/0347705 | A1 | 12/2015 | Simon | |
| 2015/0370968 | A1 | 12/2015 | Addis | |
| 2016/0217254 | A1 | 7/2016 | Douglass | |
| 2016/0217256 | A1 | 7/2016 | Kim | |
| 2017/0185739 | A1* | 6/2017 | Gomez | G01G 19/00 |
| 2018/0059895 | A1 | 3/2018 | McLaren | |
| 2019/0051420 | A1 | 2/2019 | Zhao et al. | |
| 2020/0167880 | A1* | 5/2020 | Jordan-Nowe | G16H 40/20 |
| 2020/0272379 | A1 | 8/2020 | Yada | |
| 2020/0296246 | A1 | 9/2020 | Nuggehalli | |

OTHER PUBLICATIONS

Wiklund et al., "Technical Basis for User Interface Design of Health IT", National Institute of Standards and Technology, GCR 15-996, U.S. Department of Commerce, Sep. 2015, pp. 1-192.

* cited by examiner

FROM FIG. 18Ba

EHR SYSTEM WITH ALERT FOOTER AND RELATED METHODS

TECHNICAL FIELD

The present disclosure relates to the field of an electronic health record system, and, more particularly, to a graphical user interface for an electronic health record and related methods.

BACKGROUND

Since the beginning of the modern medical era, the task of medical records has been an important core competency. For a given patient, the health record is an important history of past medical treatments and medical conditions. These are critical for medical professionals as they assist in diagnosing new ailments and in providing treatment. In the pre-computer age, the patient's health record was physical, typically contained in paper folders with handwritten notes. When the patient went from one doctor to another, the health record was regularly not transferred. Because of this, the new doctor had to replace the patient history manually based upon the memory of the patient.

One approach to this issue is the electronic health record (EHR). The EHR is a digital version of the traditional health record for the patient. Since the EHR is digital, transfer to the new doctor is theoretically easier. Nonetheless, there are some drawbacks to typical EHR approaches. For example, the EHR system is siloed for each medical professional. The EHR for each patient is not synchronized and updates from one medical professional are not viewable by others. Moreover, some typical EHR approaches have a poor user interface. In particular, these approaches have complicated menu structures with deep nested menus. Although these approaches have a great many functions, many users do not fully utilize the functions due to awkward and difficult to use user interfaces.

SUMMARY

Generally, an EHR system is for providing an EHR graphical user interface (EHR GUI). The EHR system includes a display, a memory, and a processor cooperating with the display and the memory. The processor is configured to store an EHR database for a plurality of patients, and render the EHR GUI on the display for accessing given patient data related to a given patient within the EHR database. The EHR GUI comprises a switchable interface area configured to switch between a plurality of EHR functions. Each EHR function is to provide access to a respective different type of information from the given patient data in the EHR database. The EHR GUI comprises a navigation tab menu adjacent to a first side of the switchable interface area and comprising a plurality of navigation tabs for accessing the plurality of EHR functions within the switchable interface area, and a patient history tab menu adjacent to a second side of the switchable interface area. The second side is opposite the first side. The patient history tab menu comprises a plurality of patient history tabs for accessing different types of historical patient data from the given patient data in the EHR database. The EHR GUI comprises an alert footer menu below the switchable interface area, the alert footer menu comprising a plurality of potential medical alerts for the given patient, and a specialist footer menu adjacent to the alert footer menu and comprising a plurality of potential specialist notifications.

More specifically, the alert footer menu may be persistently rendered for each of the plurality of EHR functions within the switchable interface area. The plurality of potential medical alerts for the given patient may comprise at least one of an allergy alert and a life threatening condition alert. The plurality of patient history tabs may comprise at least one of a patient prescription history tab, a patient surgical history tab, a patient medical history tab, and a patient problem list tab.

In some embodiments, the patient prescription history tab may comprise a medication name and an associated disease. The plurality of potential specialist notifications may comprise at least one of a practice specific specialty notification, and a doctor specific and location specific notification. Each potential specialist notification may comprise a visual indicator for a quantity of notifications. The switchable interface area may have a multi-page side-by-side format, and the alert footer menu may comprise a plurality of page navigation buttons.

For example, the plurality of navigation tabs may comprise at least one of a laboratory results tab, a radiology tab, a referral tab, and a prescription tab. Also, the plurality of EHR functions may comprise a consult function permitting selection of at least one of an assessment column, a specialty column, a referral doctor column, and a reason for consult column. Each of the assessment column, the specialty column, and the referral doctor column may comprise a respective search menu.

Another aspect is directed to a non-transitory computer-readable medium for an EHR system comprising a display. The EHR system provides an EHR GUI. The non-transitory computer-readable medium has computer-executable instructions for causing the EHR system to perform steps comprising storing an EHR database for a plurality of patients, and rendering the EHR GUI on the display for accessing given patient data related to a given patient within the EHR database. The EHR GUI comprises a switchable interface area configured to switch between a plurality of EHR functions. Each EHR function is to provide access to a respective different type of information from the given patient data in the EHR database. The EHR GUI comprises a navigation tab menu adjacent to the first side of the switchable interface area. The navigation tab menu comprises a plurality of navigation tabs for accessing the plurality of EHR functions within the switchable interface area. The EHR GUI also includes a patient history tab menu adjacent to a second side of the switchable interface area. The second side is opposite the first side. The patient history tab menu comprises a plurality of patient history tabs for accessing different types of historical patient data from the given patient data in the EHR database. The EHR GUI comprises an alert footer menu below the switchable interface area, the alert footer menu comprising a plurality of potential medical alerts for the given patient, and a specialist footer menu adjacent to the alert footer menu and comprising a plurality of potential specialist notifications.

Yet another aspect is directed to a method for operating an EHR system comprising a display, the EHR system providing an EHR GUI. The method comprises storing an EHR database for a plurality of patients, and rendering the EHR GUI on the display for accessing given patient data related to a given patient within the EHR database. The EHR GUI comprises a switchable interface area configured to switch between a plurality of EHR functions. Each EHR function is to provide access to a respective different type of information from the given patient data in the EHR database. The EHR GUI comprises a navigation tab menu adjacent to a first side of the switchable interface area. The navigation tab menu includes a plurality of navigation tabs for accessing the plurality of EHR functions within the switchable interface area. The EHR GUI also comprises a patient history tab menu adjacent to a second side of the switchable interface area. The second side is opposite the first side. The patient history tab menu comprises a plurality of patient history tabs for accessing different types of historical patient data from the given patient data in the EHR database. The EHR GUI comprises an alert footer menu below the switchable interface area, the alert footer menu comprising a plurality of potential medical alerts for the given patient, and a specialist footer menu adjacent to the alert footer menu and comprising a plurality of potential specialist notifications.

DETAILED DESCRIPTION

Figure 1:
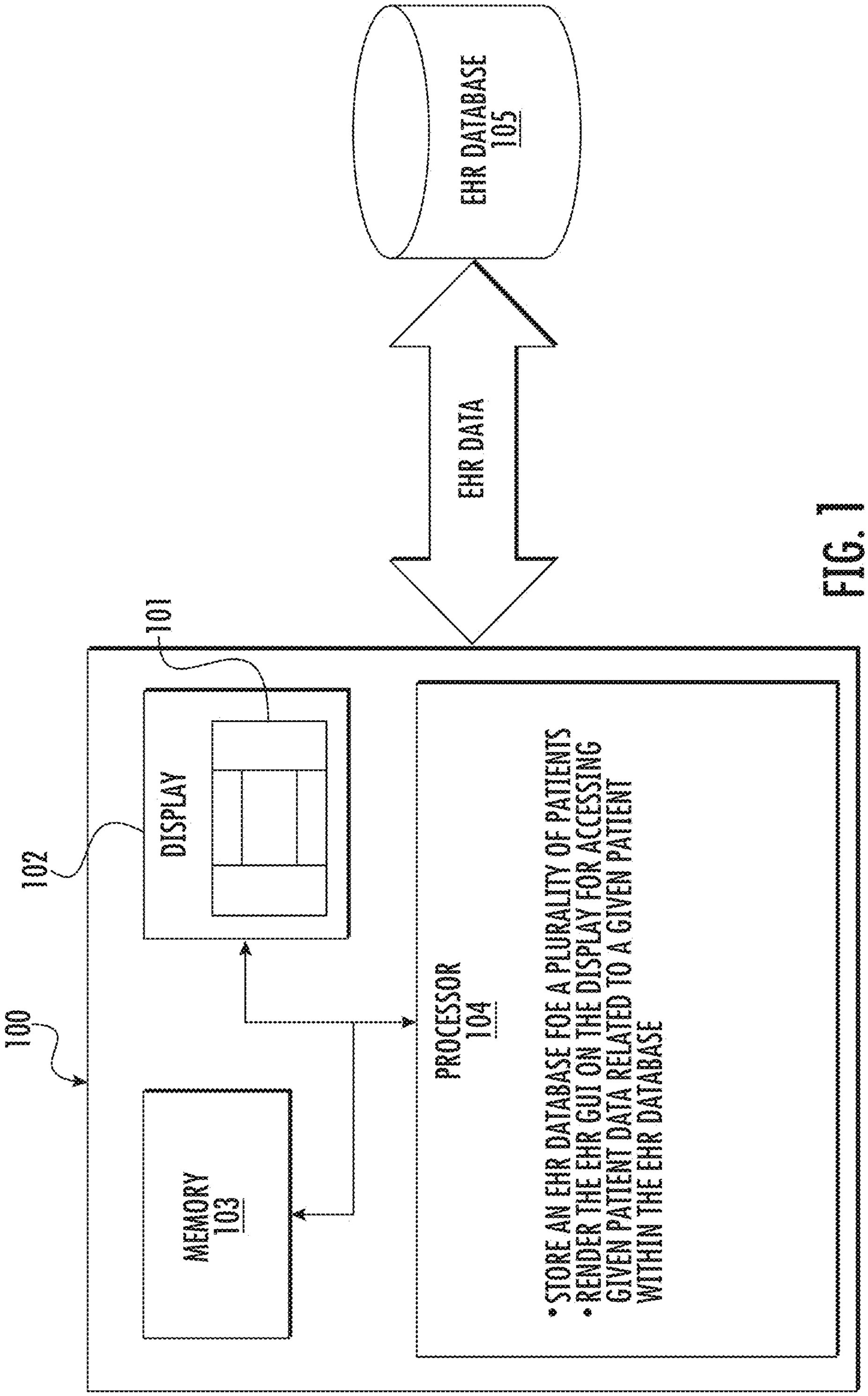
FIG. 1 is a schematic diagram of an EHR system, according to the present disclosure.

The present disclosure will now be described more fully hereinafter with reference to the accompanying drawings, in which several embodiments of the invention are shown. This present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art. Like numbers refer to like elements throughout, and base 100 reference numerals are used to indicate similar elements in alternative embodiments.

Referring initially to FIG. 1, an EHR system 100 according to the present disclosure is now described. The EHR system 100 is for providing an EHR GUI 101. The EHR system 100 includes a display 102, a memory 103, and a processor 104 cooperating with the display and the memory. The processor 104 is configured to store an EHR database 105 for a plurality of patients, and render the EHR GUI 101 on the display 102 for accessing given patient data related to a given patient within the EHR database.

Referring now additionally to FIGS. 2*a*-2*b*, 3A-3B, & 4Aa-5*b*, the EHR GUI 101 includes a switchable interface area 106 configured to switch between of a plurality of EHR functions. As will be appreciated, the switchable interface area 106 is configured to display contextual data from the given patient data associated with a selected EHR function selected from the plurality thereof. As perhaps best seen in FIGS. 5*a*-5*b*, the switchable interface area 106 is illustratively rectangle-shaped, and has opposing and first and second sides 107*a*-107*b* (i.e., second side is opposite the first side), and opposing first and second ends 110*a*-110*b* between the first and second sides (i.e., the ends on the top and bottom, and the sides on the left and right).

Each EHR function is to provide access to a respective different type of information from the given patient data in the EHR database 105. The EHR GUI 101 comprises a navigation tab menu 111 adjacent to the first side 107*a* of the switchable interface area 106 and comprising a plurality of navigation tabs 112*a*-112*n* for accessing the plurality of EHR functions within the switchable interface area 106. The plurality of navigation tabs 112*a*-112*n* illustratively comprises a back button and a forward button to allow for easier navigation from previously accessed EHR functions (See, e.g., FIGS. 2*a*-2*b*), a patient information tab, a history and physical tab, a progress note tab, an Annual Wellness Visit (AWV) tab, a chronic care management tab (CCMs), a fax tab, a growth chart tab, an immunization tab, a lab result tab, a medical test report tab, a medication trend tab, a messages tab, a pathology tab, a pre-op tab, a quality measures tab, a radiology report tab, a referral in tab, a referral out tab, a physical therapy (PT) tab, a new prescription tab (Rx New), a prescription refill tab, a prescription records tab, a screening tab, a surgical procedure tab, a Telemedicine tab, a PT tab, an occupational therapy (OT) tab, a speech therapy tab, an office records tab, a hospital records tab. There will be plurality of notifications on the tabs comprising a visual indicator for quantity of notifications. As will be appreciated, the illustrated plurality of navigation tabs 112*a*-112*n* is exemplary, and in some embodiments, new tabs may be added as the need arises due to changes in the healthcare industry and as medicine evolves in the future. Of course, in other embodiments, the tabs may also be deleted if they become redundant or unnecessary.

In some embodiments (See, e.g., FIGS. 7*a*-10*b*), the plurality of navigation tabs 112*a*-112*n* may comprise a visual indicator for a number of notifications within the plurality of EHR functions. In some embodiments, the plurality of navigation tabs 112*a*-112*n* may comprise a forward and back button to allow for easier navigation from previously accessed EHR functions. In some embodiments, the notifications may appear in other or all of the sub-menus and tabs of the EHR GUI 101 to indicate changes to the user.

The EHR GUI 101 illustratively comprises a patient history tab menu 113 adjacent to the second side 107*b* of the switchable interface area 106. The patient history tab menu 113 comprises a plurality of patient history tabs 114*a*-114*e* for accessing different types of historical patient data from the given patient data in the EHR database 105. The plurality of patient history tabs 114*a*-114*e* illustratively comprises a patient prescription history tab 114*a*, a patient medical history (PMH) tab 114*b*, a patient surgical history (PSH) tab 114*c*, a Hierarchical Condition Categories (HCC) tab 114*d*, and a patient problem list (PL) tab 114*e*.

Figure 2A:
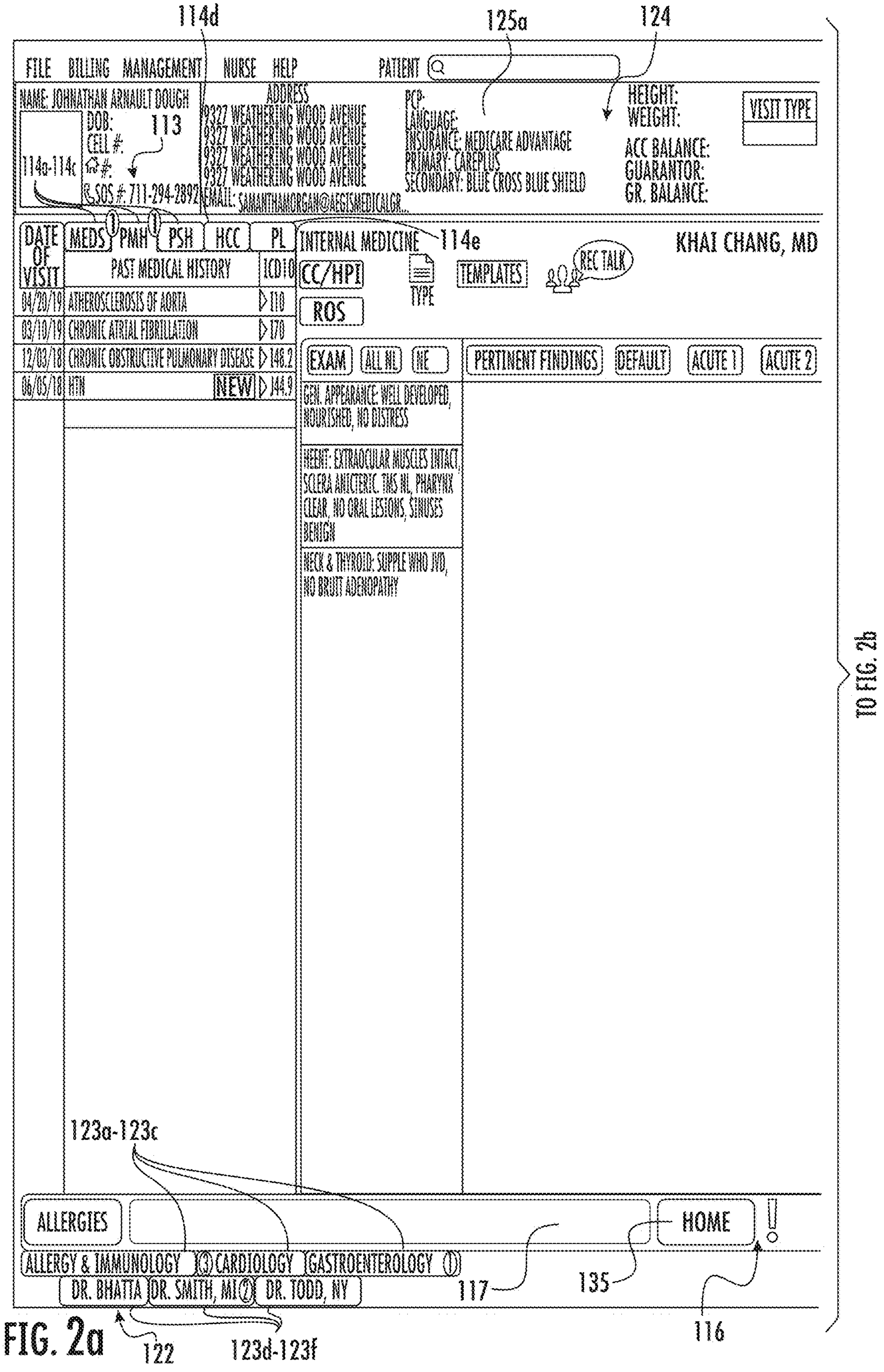
FIGS. 2*a*-2*b* is a screenshot of an example embodiment of a progress note function of the EHR GUI from the EHR system of FIG. 1.
Figure 2B:
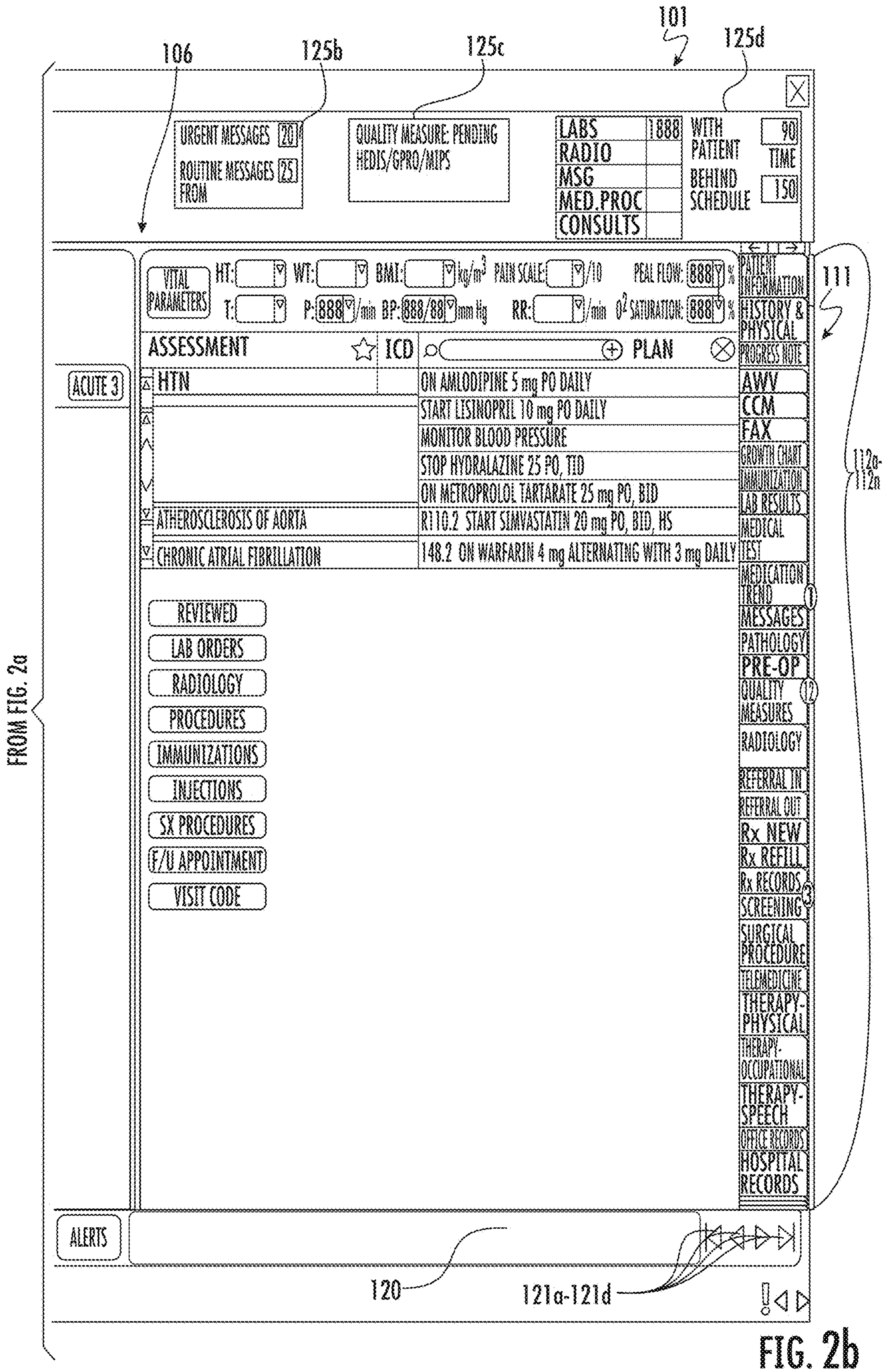
Figure 3A:
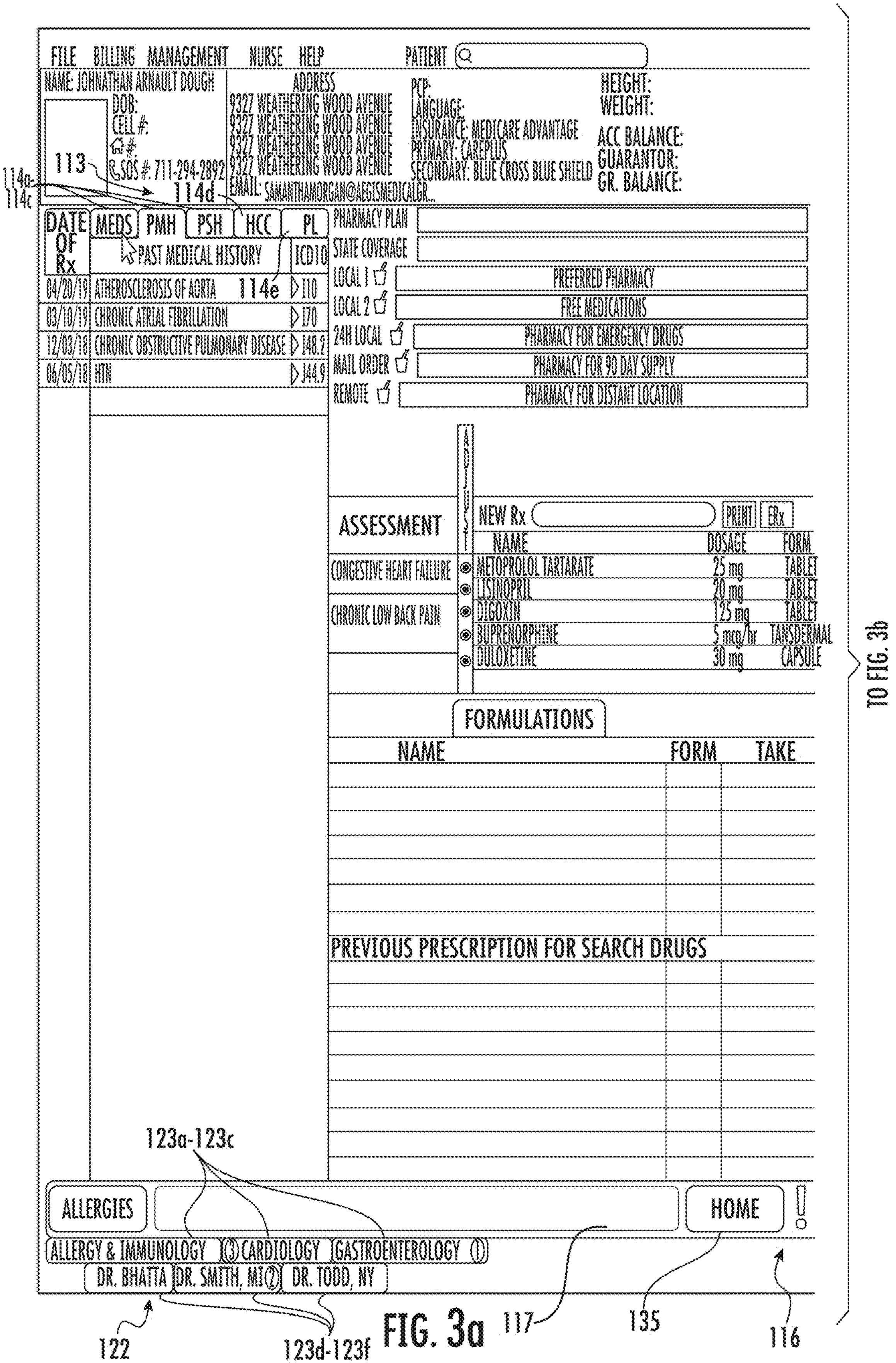
FIGS. 3A-3B is a screenshot of an example embodiment of a prescription refill function of the EHR GUI from the EHR system of FIG. 1.
Figure 3B:
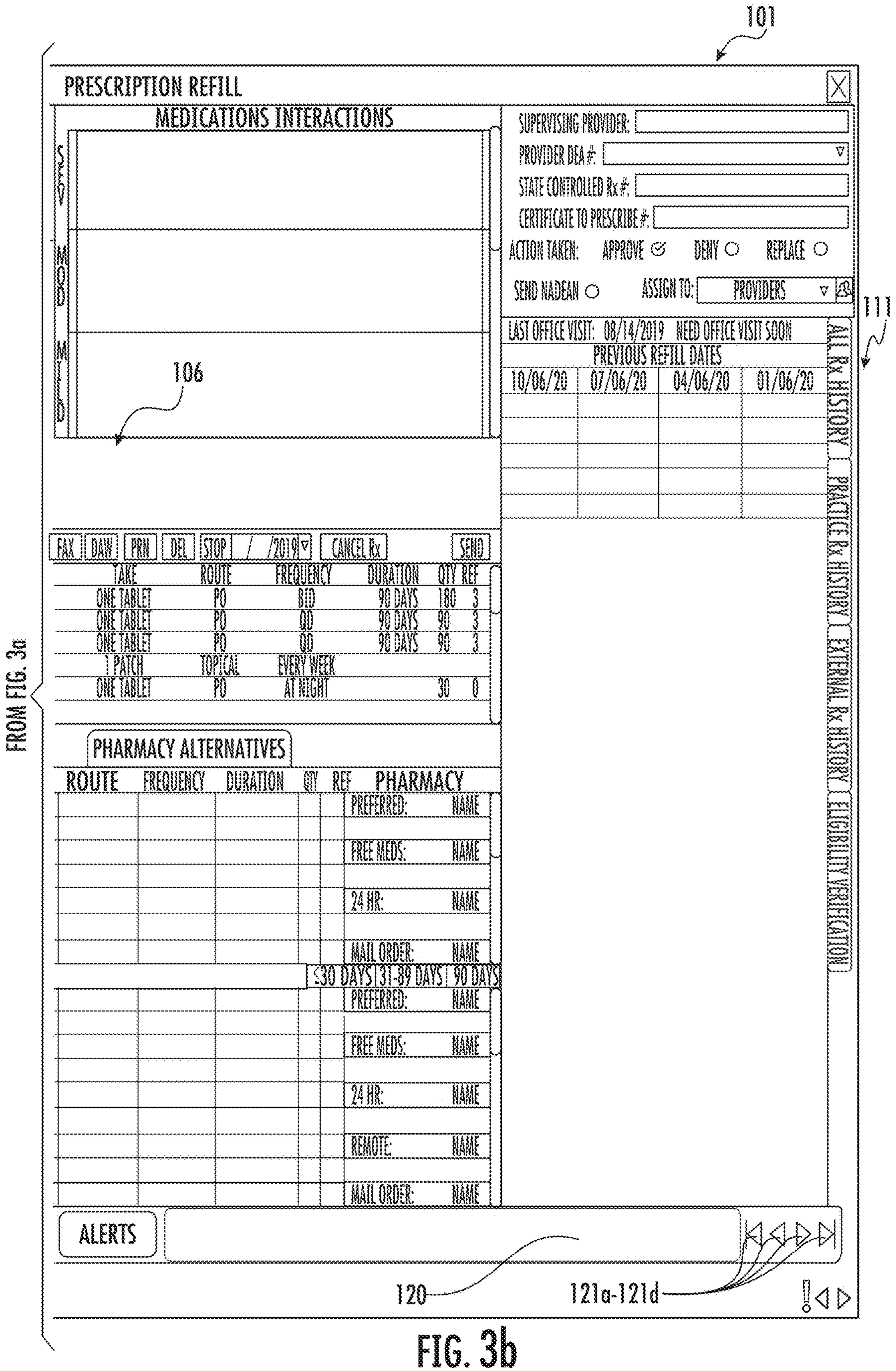

In FIGS. 2A-2B, each of the patient history tabs 114*a*-114*e* illustratively includes a visual indicator for a number of notifications therein. In some embodiments, the plurality of patient history tabs 114*a*-114*e* may also include a progress note tab where the respective visual indicator for a number of notifications may be helpful when another provider makes a change on the medication list of a patient even though they are on the same EHR but in a different practice. In this instance, the change in the medication list is not reflected when that provider makes a change to the medications from the last visit when a current medical professional saw the patient. The current medical professional does not know the change until and unless the patient himself tells the provider that. This feature will address the issue by bringing up recent medication changes from other specialties to the current medical professional.

Figure 4A:
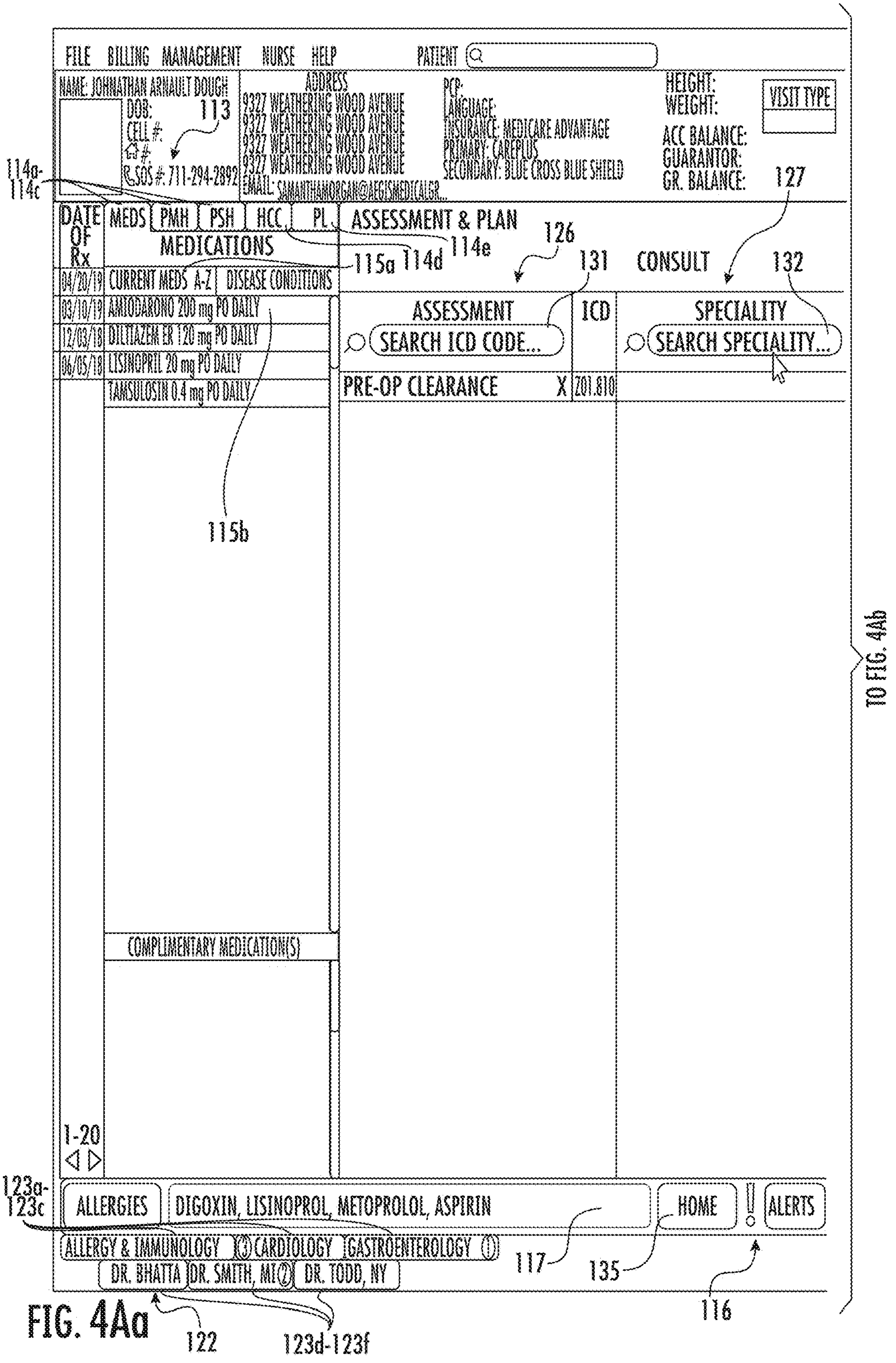
FIGS. 4Aa-4Bb are screenshots of an example embodiment of a progress note assessment and plan-consult function of the EHR GUI from the EHR system of FIG. 1.
Figure 4A:
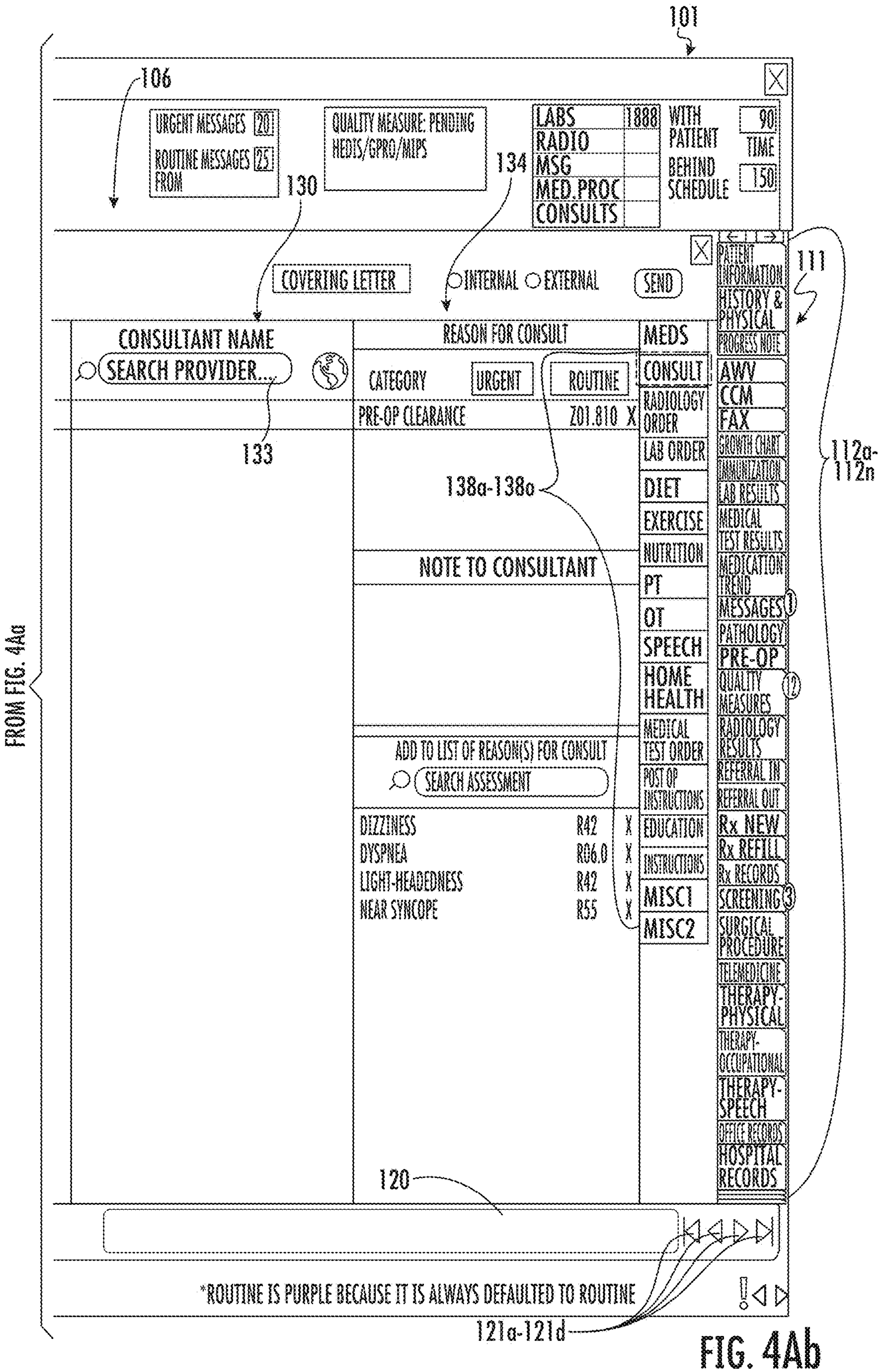
Figure 4B:
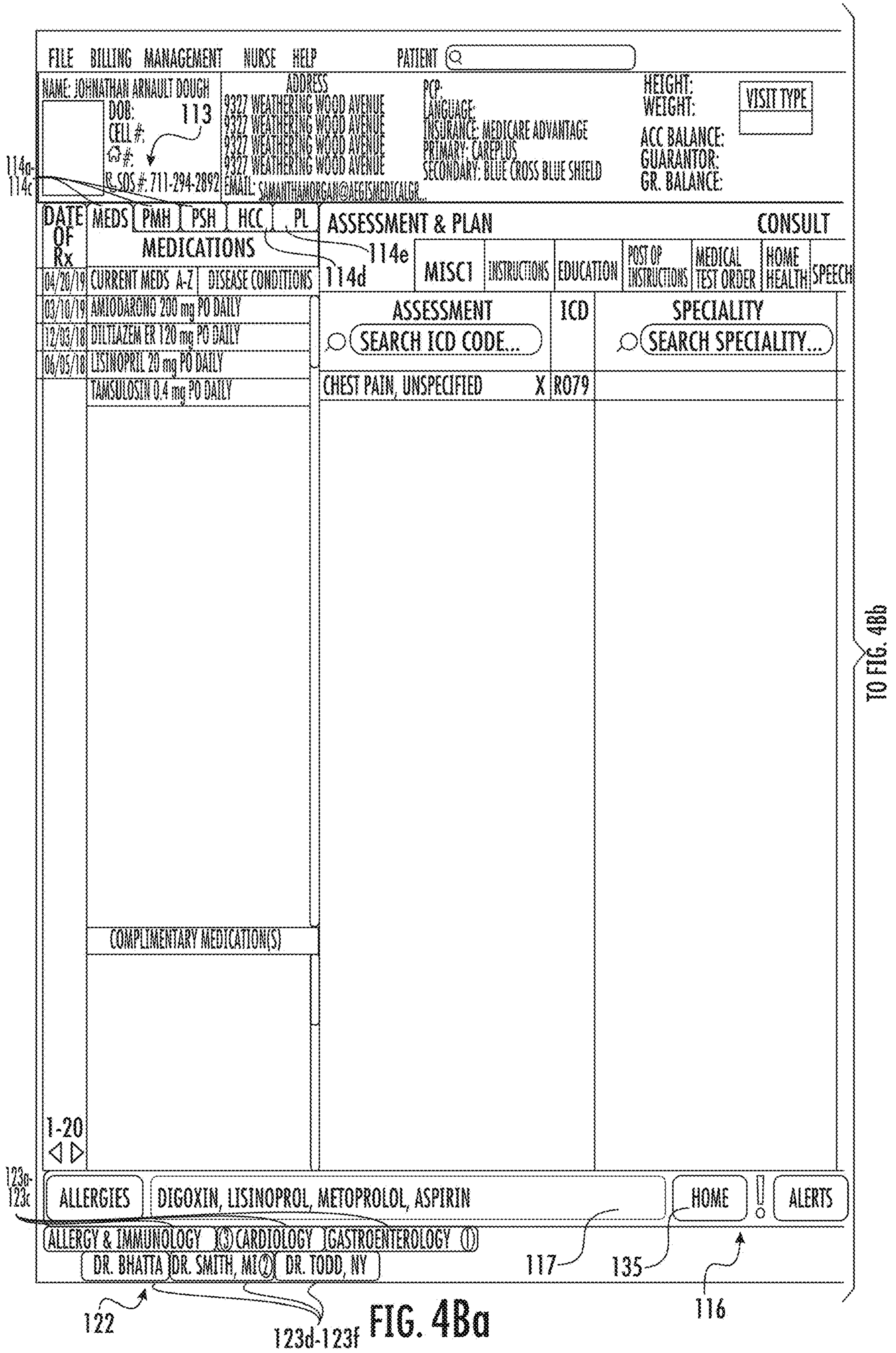
Figure 4B:
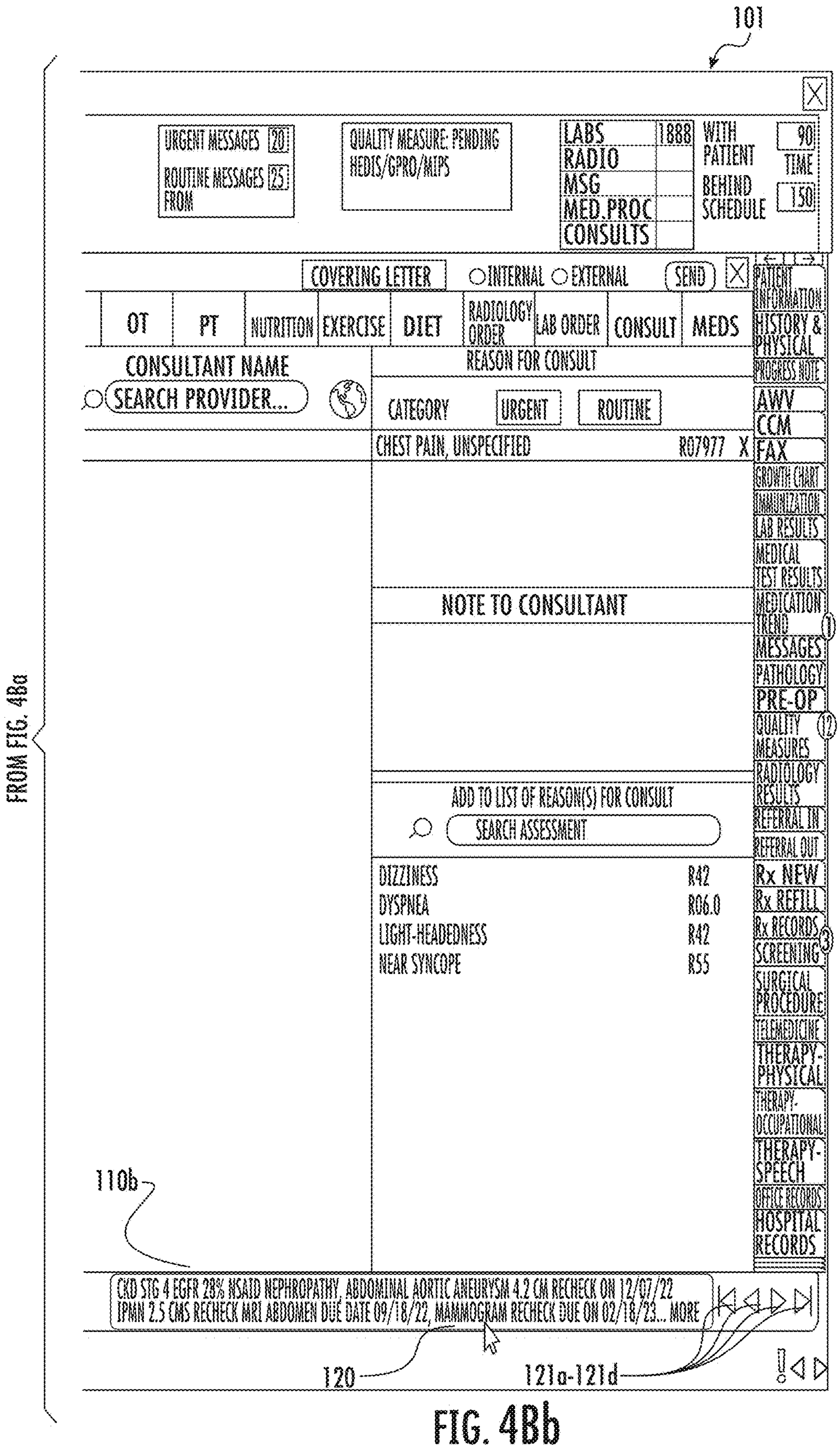
Figure 5A:
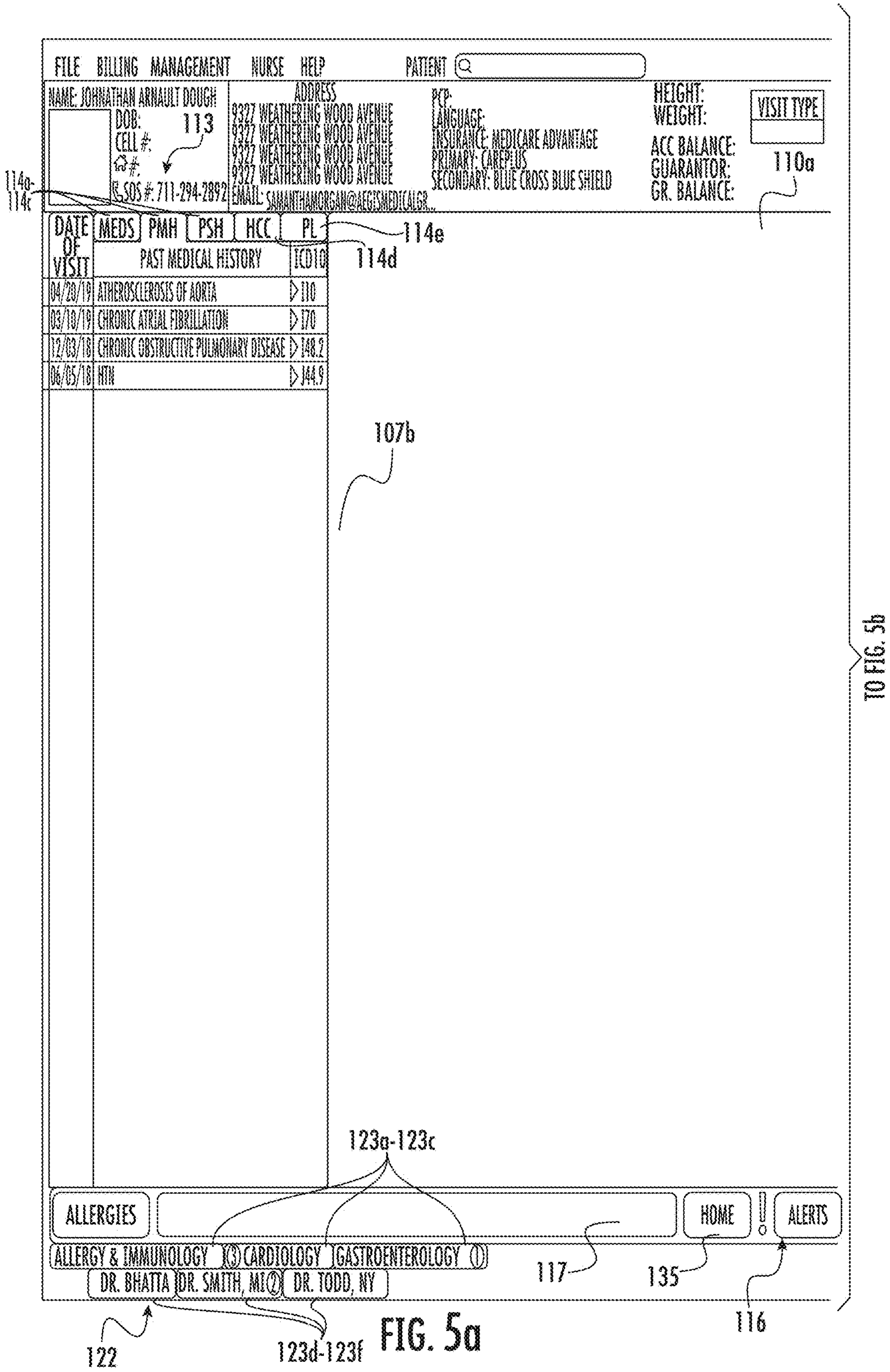
FIGS. 5*a*-5*b* is a screenshot of an example embodiment of an alert footer menu, an allergies menu, a specialist footer menu, a navigation tab menu, and a patient history tab menu of the EHR GUI from the EHR system of FIG. 1.
Figure 5B:
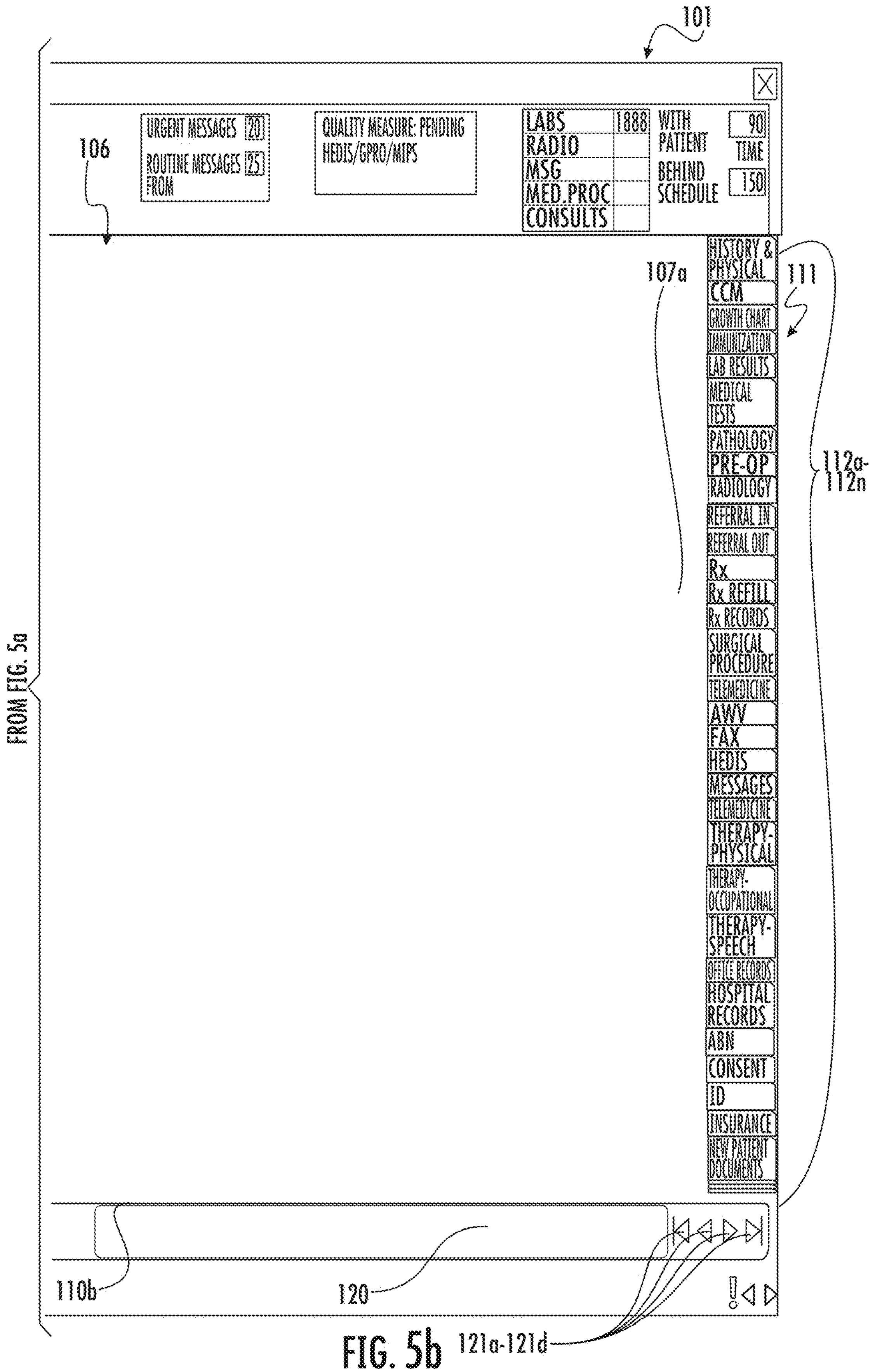
Figure 6A:
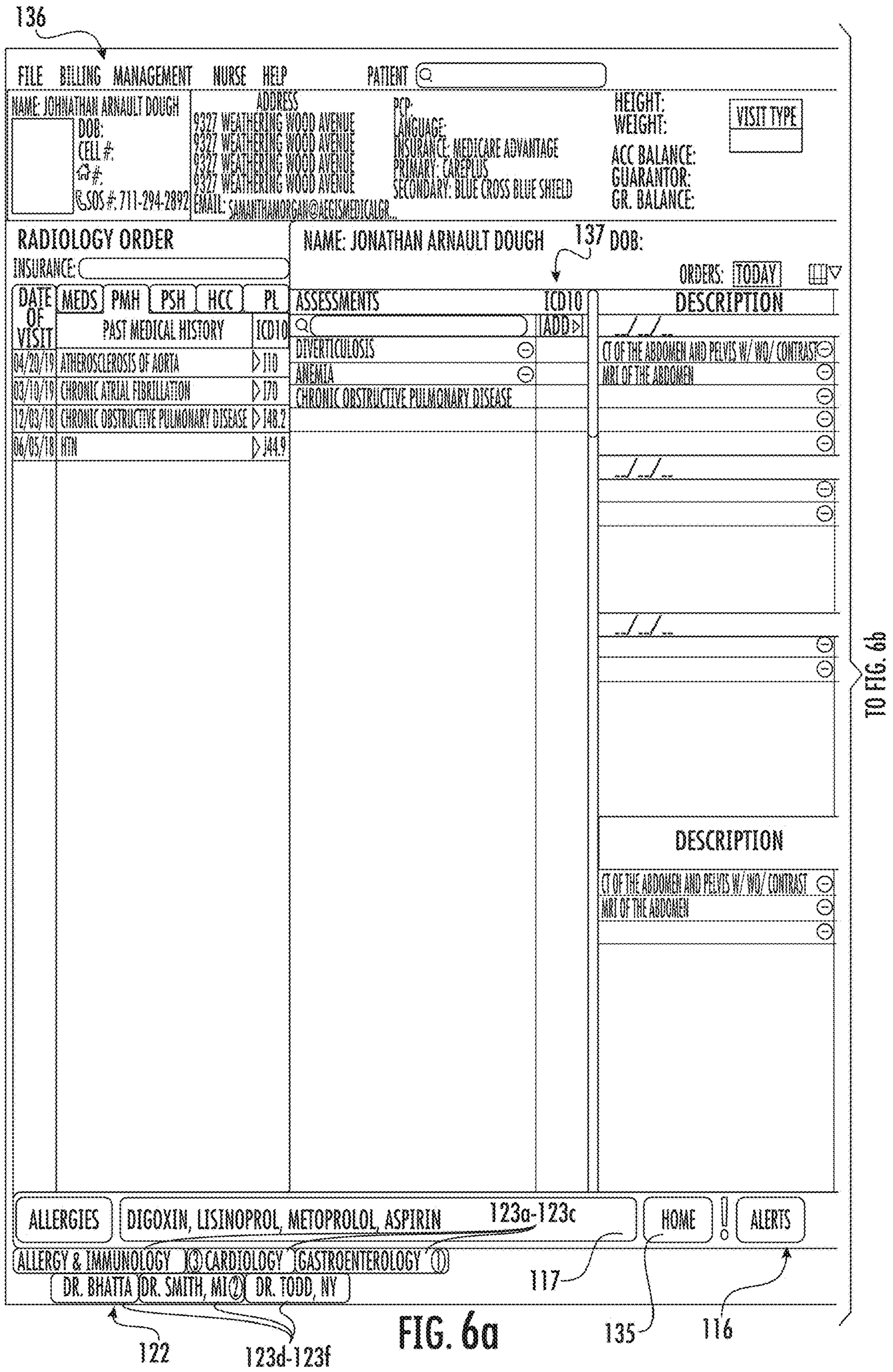
FIGS. 6*a*-6*b* is a screenshot of an example embodiment of a progress note assessment and plan-radiology order function of the EHR GUI from the EHR system of FIG. 1.
Figure 6B:
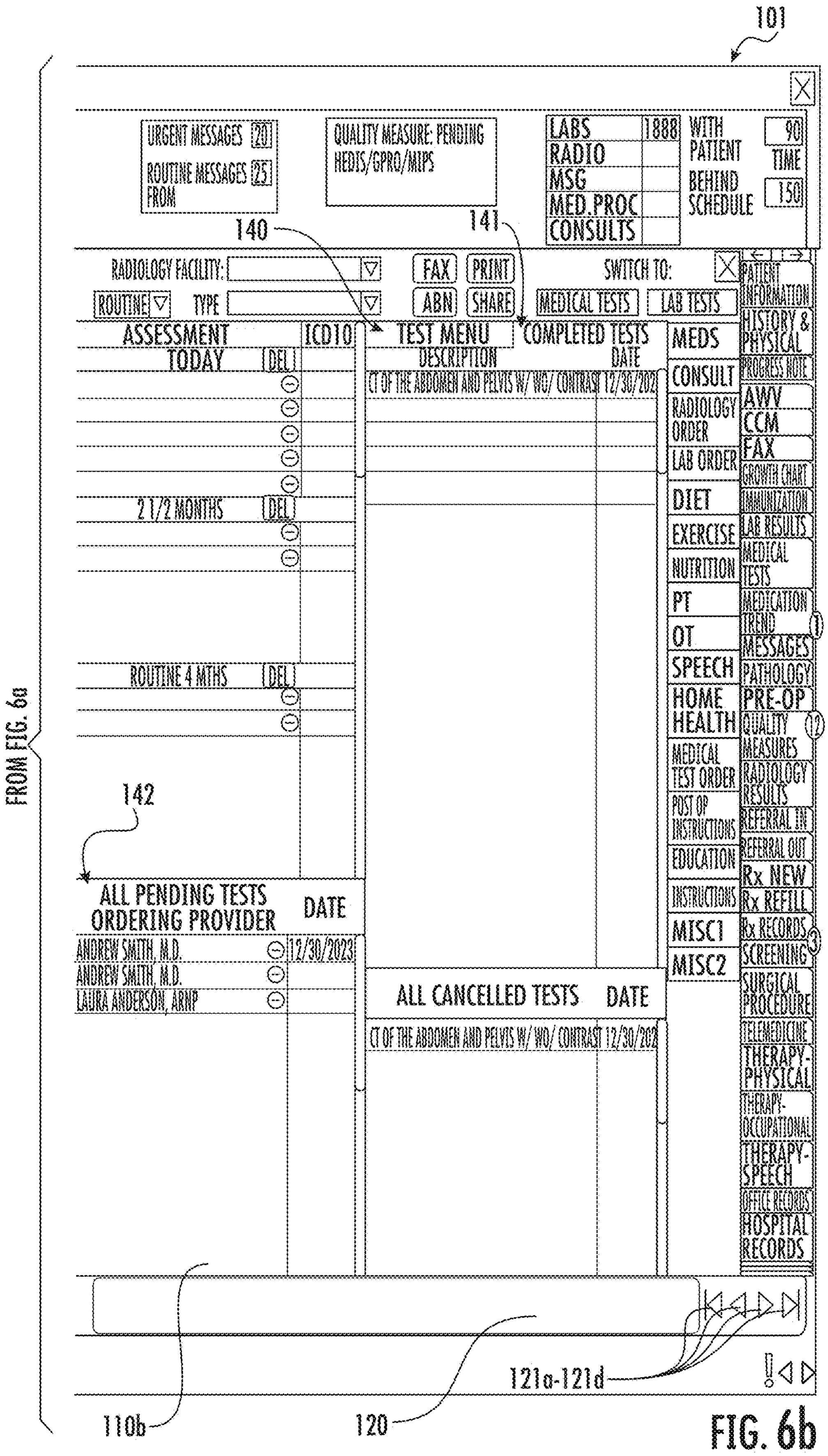

As shown in FIGS. 4Aa-4Bb, the patient prescription history tab 114*a* illustratively comprises a medication name button 115*a* and an associated disease button 115*b*. In particular, the patient prescription history tab 114*a* may provide a listing of medications in alphabetical order, and a listing of medications listed under disease conditions. Helpfully, the data presented in the patient prescription history tab 114*a* may be sorted either by the medication name or the disease.

The EHR GUI 101 comprises an alert footer menu 116 directly below the switchable interface area 106. The alert footer menu 116 illustratively extends substantially (i.e., 90% or more) horizontally across the entire display 102. The alert footer menu 116 comprises a plurality of potential medical alert display windows 117, 120 for the given patient. In particular, the first alert display window 117 comprises an allergy alert display window, and lists the allergies of the given patient. The second alert display window 120 comprises a patient medical condition alert display window and lists the serious medical conditions of the given patient (e.g., patient has diabetes). As perhaps best seen in FIGS. 2A-2B, the switchable interface area 106 is illustratively rendered with a multi-page side-by-side format. The alert footer menu 116 illustratively comprises a plurality of page navigation buttons 121*a*-121*d*. The plurality of page navigation buttons 121*a*-121*d* comprises a maximal rewind button 121*a* to bring the page to the current (latest) visit; a rewind button 121*b* to flip the progress note, one visit up at a time, toward the current visit if the progress note is in the past (e.g., if on page 10, then when this button is clicked, it will bring it to page 9, another click onto page 8); a forward button 121*c* to go into the past, one single progress note visit at a time (e.g., if on page 5, a click on this button will take it one further visit into the past to page 6, another click to page 7 and henceforth); and a maximal fast forward button 121*d* will take the visit to the first initial visit when the patient was seen in the office as a new patient.

The EHR GUI 101 comprises a specialist footer menu 122 adjacent to the alert footer menu 116 and comprising a plurality of potential specialist notifications 123*a*-123*f* (e.g., the illustrated notification pane with buttons). The plurality of potential specialist notifications 123*a*-123*f* may comprise a practice specific specialty notification 123*a*-123*c*, and a doctor specific and/or location specific notification 123*d*-123*f*. Each potential specialist notification 123*a*-123*f* illustratively comprises a visual indicator for a quantity of notifications. Helpfully, multiple medical professionals can access the given patient data in the EHR database 105. If the given patient has seen another medical professional since the last visit with the present medical professional, this will be noted within the plurality of potential specialist notifications 123*a*-123*f*.

The EHR GUI 101 illustratively comprises an information panel 124 above the and directly adjacent to the first end 110*a* of the switchable interface area 106. The information panel 124 may include a biographical data menu 125*a* for the given patient, a received message notification menu 125*b*, a quality measure menu 125*c*, and a patient schedule menu 125*d*.

Also, the alert footer menu 116 may be persistently rendered for each of the plurality of EHR functions within the switchable interface area 106. Given the critical nature of the information within the alert footer menu 116, this information is always or almost always presented to the medical professional regardless of the current EHR function. As perhaps best seen in FIGS. 5*a*-5*b*, the largely persistent elements of the EHR GUI 101 are shown and include the alert footer menu 116, the plurality of potential specialist notifications 123*a*-123*f*, the patient history tab menu 113, and the information panel 124. Indeed, in some screens where large format data is being displayed, one or more of the alert footer menu 116, the plurality of potential specialist notifications 123*a*-123*f*, the patient history tab menu 113, and the information panel 124 may be removed to allow for better display. This same concept will also apply to the other patient history tabs. This is to align the new findings which might have been disclosed to other providers, which the patient might have failed to disclose to the current provider.

As seen in FIGS. 4Aa-4Bb, the plurality of EHR functions illustratively comprises a consult function permitting selection of an assessment column 126, a specialty column 127, a referral doctor column 130, and a reason for consult column 134. The consult function is accessed via the "consult" tab noted with the dashed box. Each of the assessment column 126, the specialty column 127, the referral doctor column 130, and the reason for consult column 134 comprises a respective search menu 131-133.

The alert footer menu 116 illustratively includes a home button 135. When the home button 135 is activated, the EHR GUI 101 transitions out of any EHR function and returns to the current (latest) progress note function shown in FIGS. 2A-2B. Also, in the progress note, the assessment and plan function opens a second nested sets of navigation tabs, a plurality of sub-navigation tabs 138*a*-138*o*. In other embodiments, the plurality of sub-navigation tabs 138*a*-138*o* may be located in different parts of the EHR GUI 101. For example, the plurality of sub-navigation tabs 138*a*-138*o* may be located below the information panel 124. This is depicted in FIGS. 13Ba, 4Ba-4Bb, 16Ha-16Hb and 17Da-17Db, for example.

Figure 7A:
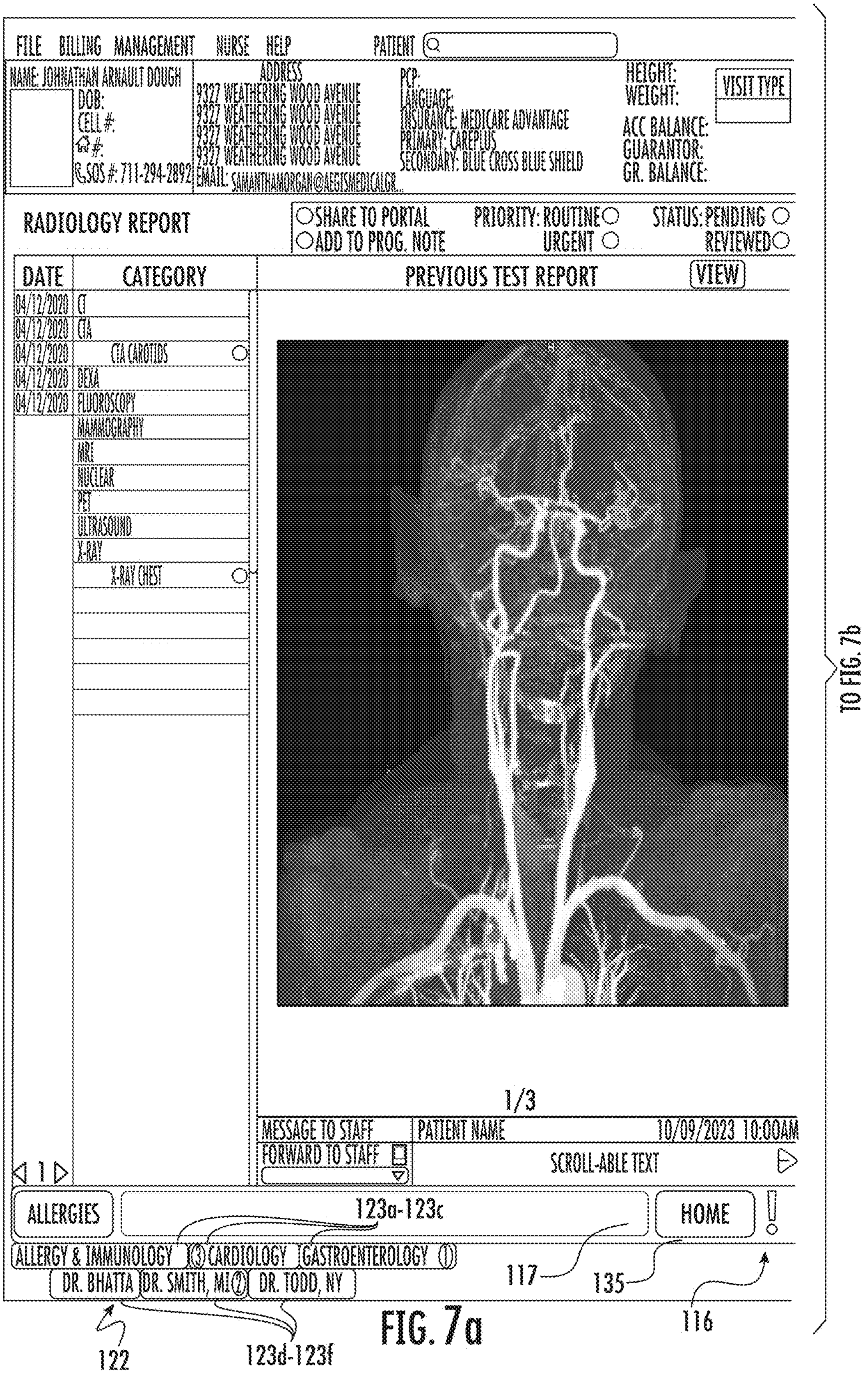
FIGS. 7*a*-7*b* is a screenshot of an example embodiment of the radiology report of the EHR GUI from the EHR system of FIG. 1.
Figure 7B:
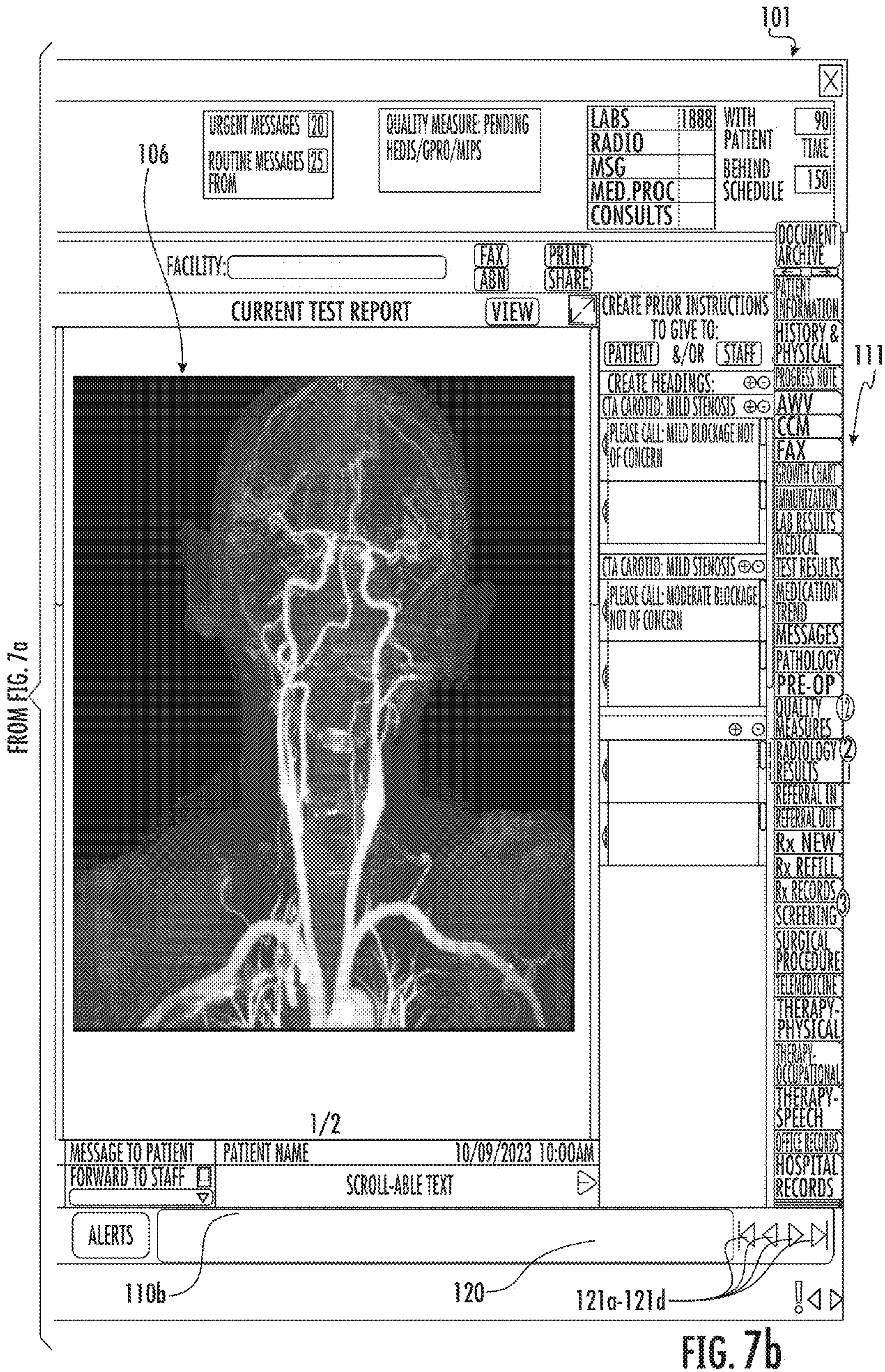
Figure 8A:
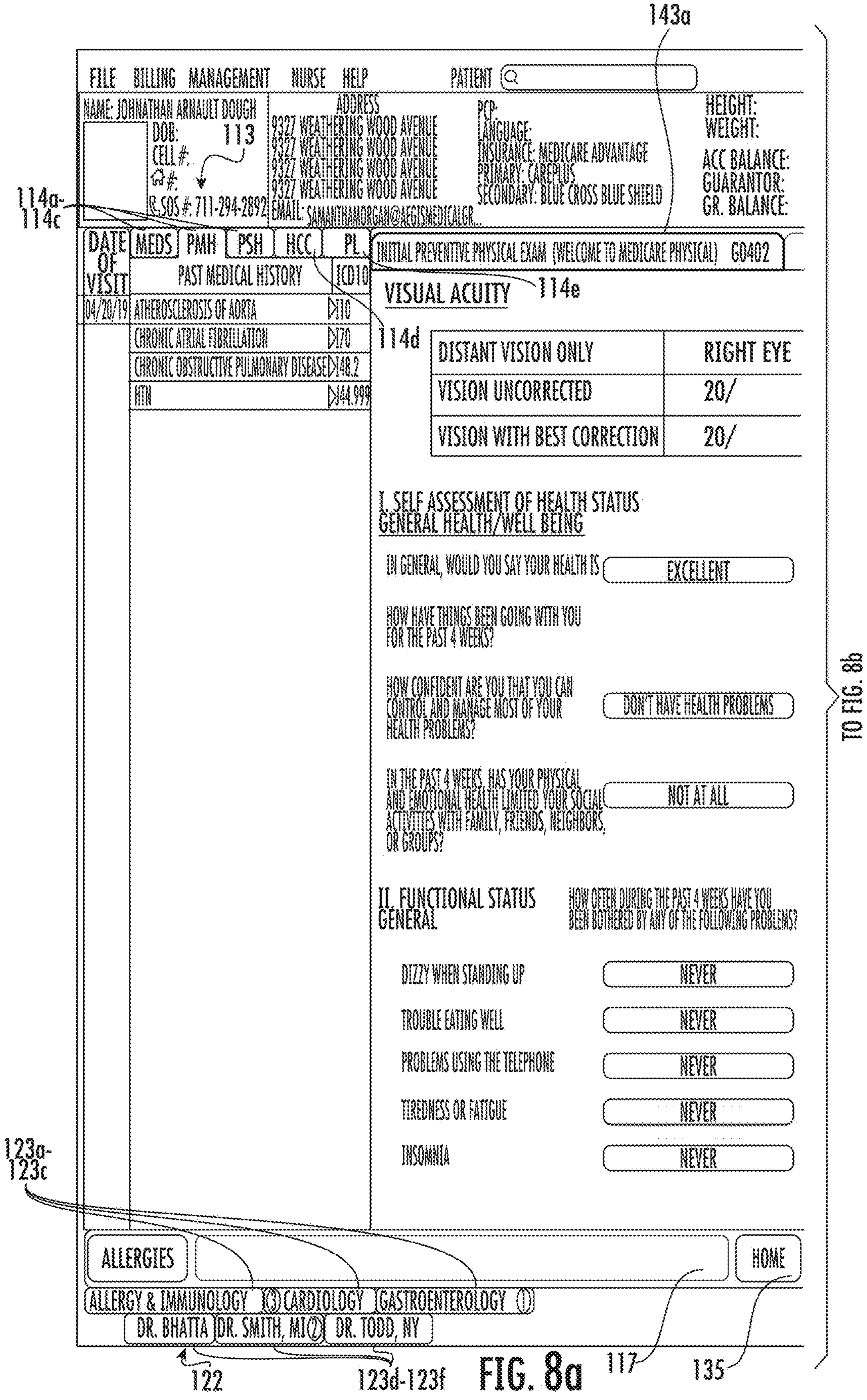
FIGS. 8*a*-8*b*, 9*a*-9*b*, & 10*a*-10*b* are screenshots of an example embodiment of an annual wellness visit function of the EHR GUI from the EHR system of FIG. 1.
Figure 8B:
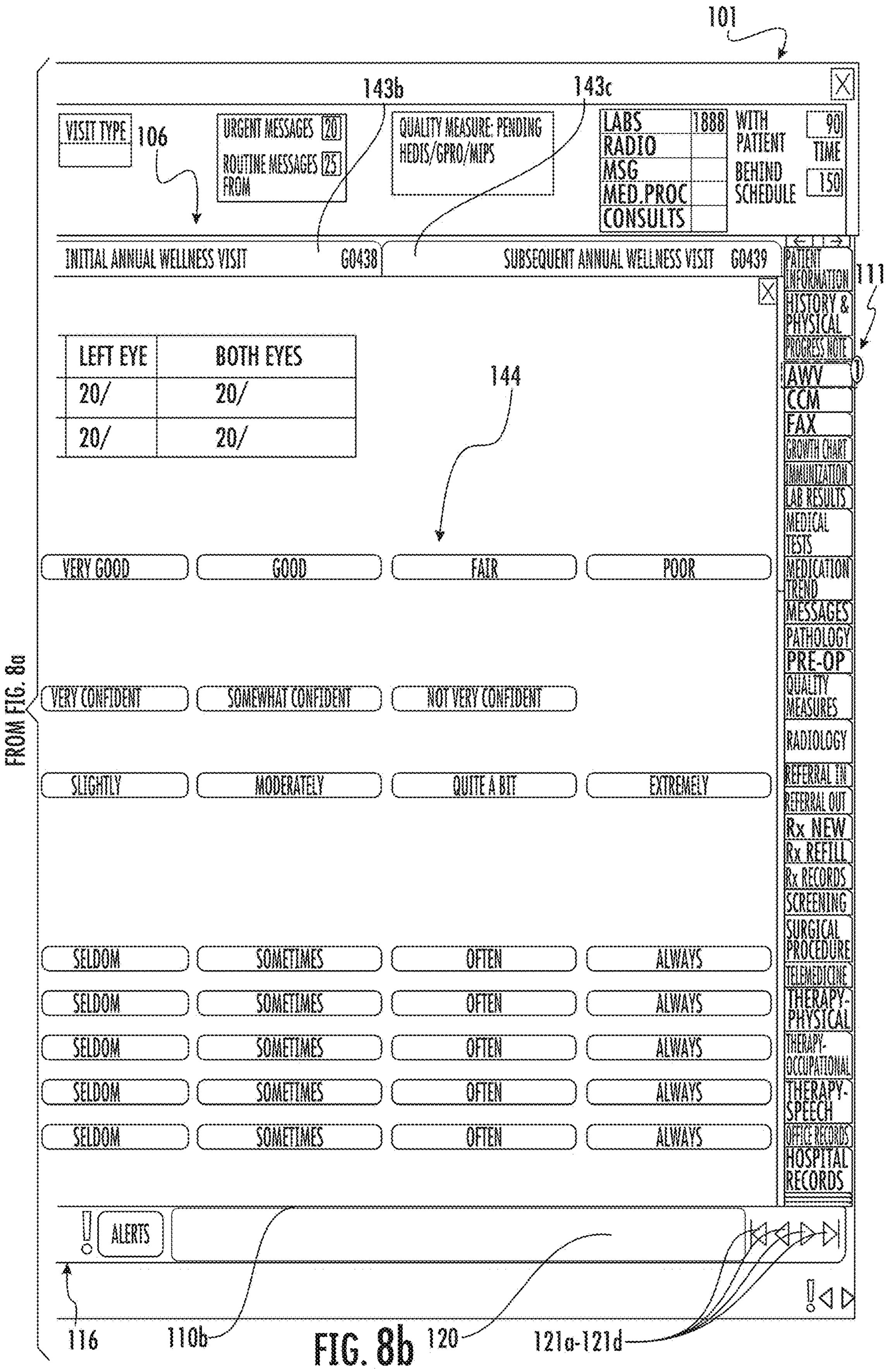
Figure 9A:
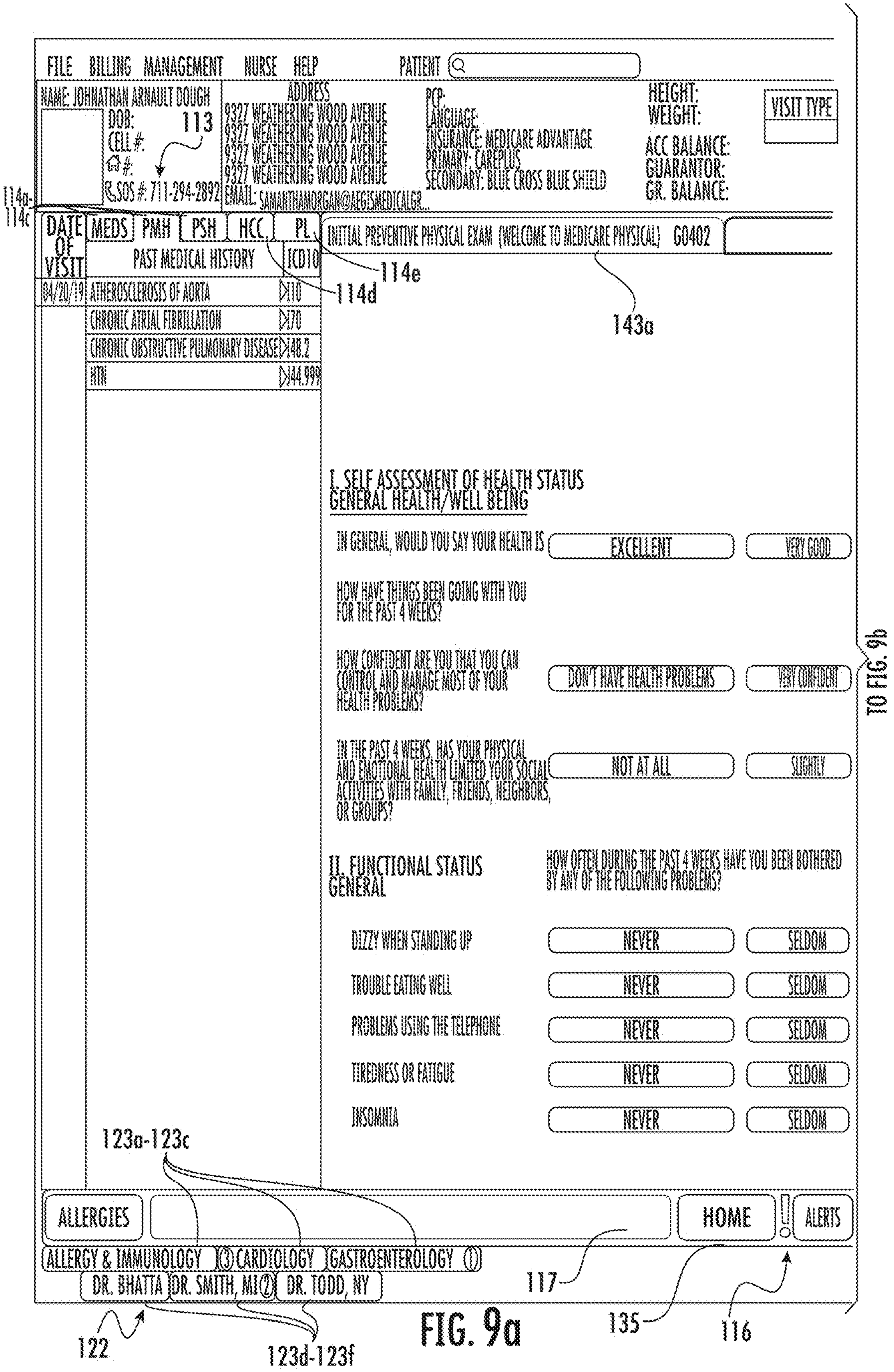
Figure 9B:
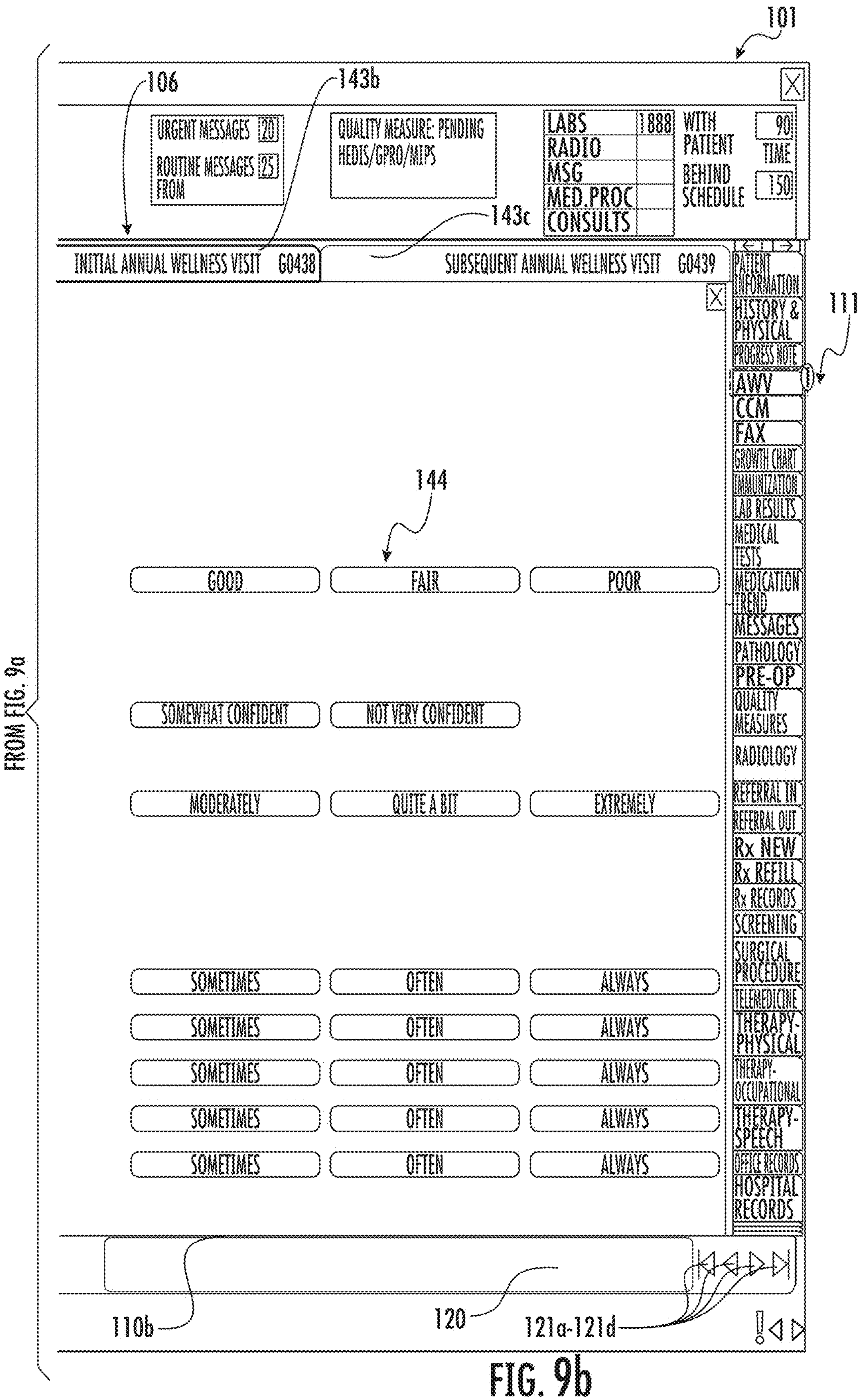
Figure 10A:
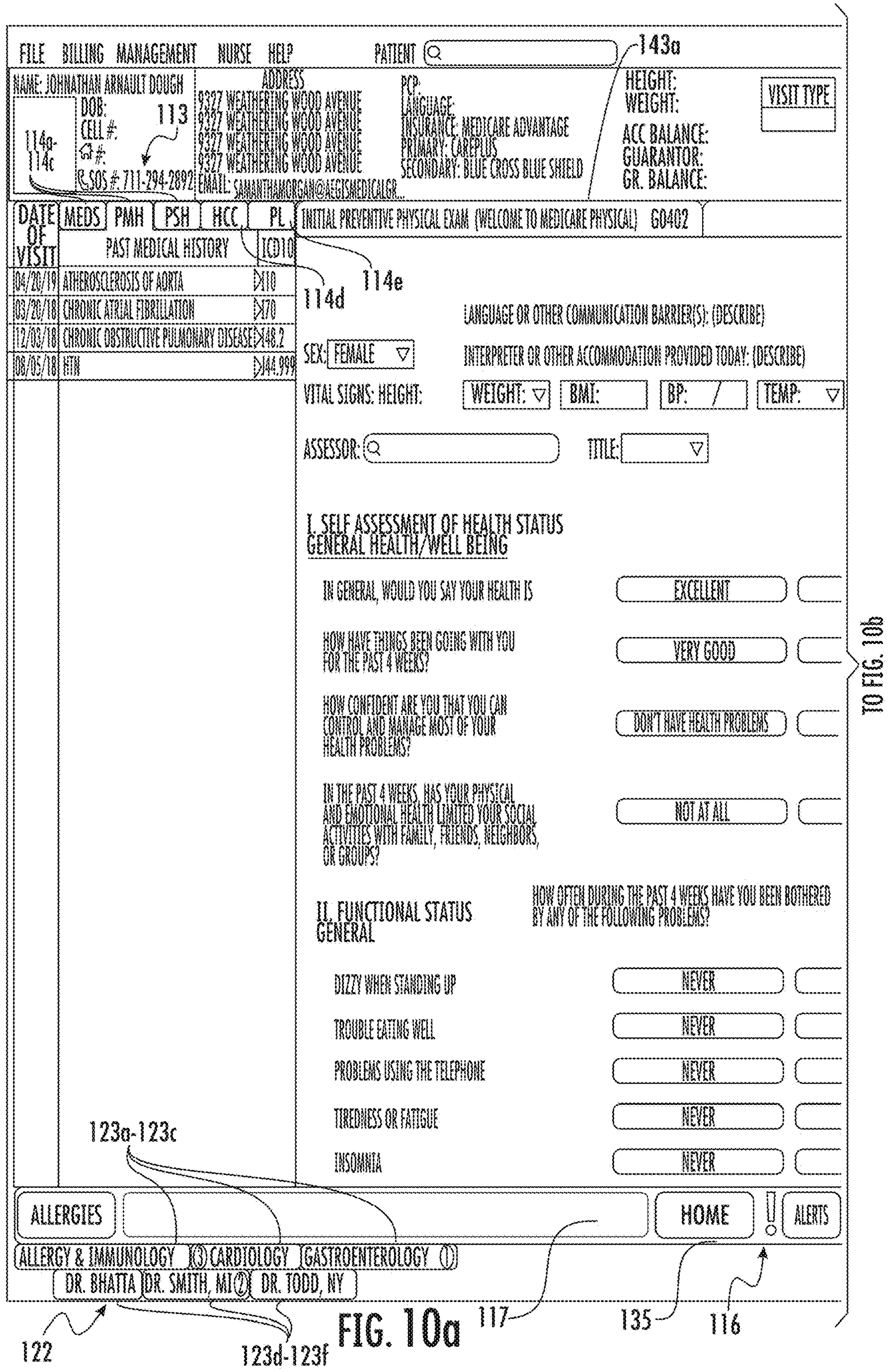
Figure 10B:
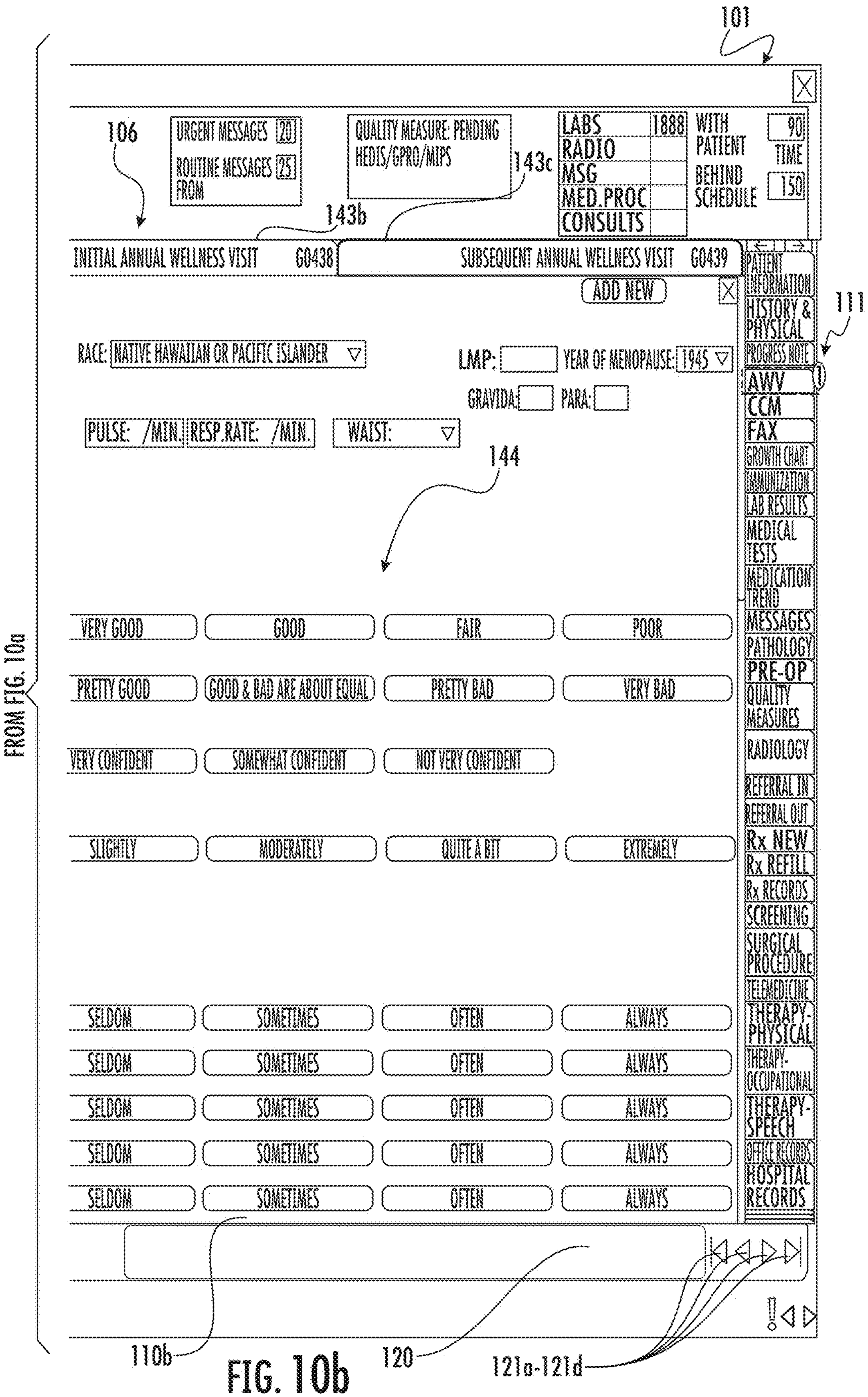

As seen in FIGS. 6*a*-6*b*-7*a*-7*b*, the plurality of EHR functions illustratively comprises a radiology function permitting review of prior radiology results for the given patient. The radiology function is accessed via the "radiology" tab noted with a dashed box. Within the radiology function, the EHR GUI 101 illustratively includes a radiology test order menu 136 comprising a plurality of radiology tabs. The plurality of radiology tabs comprises a date tab, a PMH tab, an assessment tab, and a code tab. The EHR GUI 101 illustratively includes an assessment menu 137 including a description column, and an assessment column, and a pending test menu 142 listing all pending radiology orders and respective dates. The EHR GUI 101 illustratively includes a test menu 140 for listing radiology orders to be placed, and a completed test menu 141 for listing prior completed radiology tests. In FIGS. 7*a*-7*b*, the EHR GUI 101 transitions to a mode for reviewing a radiology report. Here, the switchable interface area 106 takes on a side-by-side format (i.e., multi-page) for reviewing past and present radiology reports for the current patient. Helpfully, the switchable interface area 106 affords the medical professional with a large landscape shaped area for reviewing multiple time lapsed radiology reports, allowing for more efficient medical care.

Figure 12A:
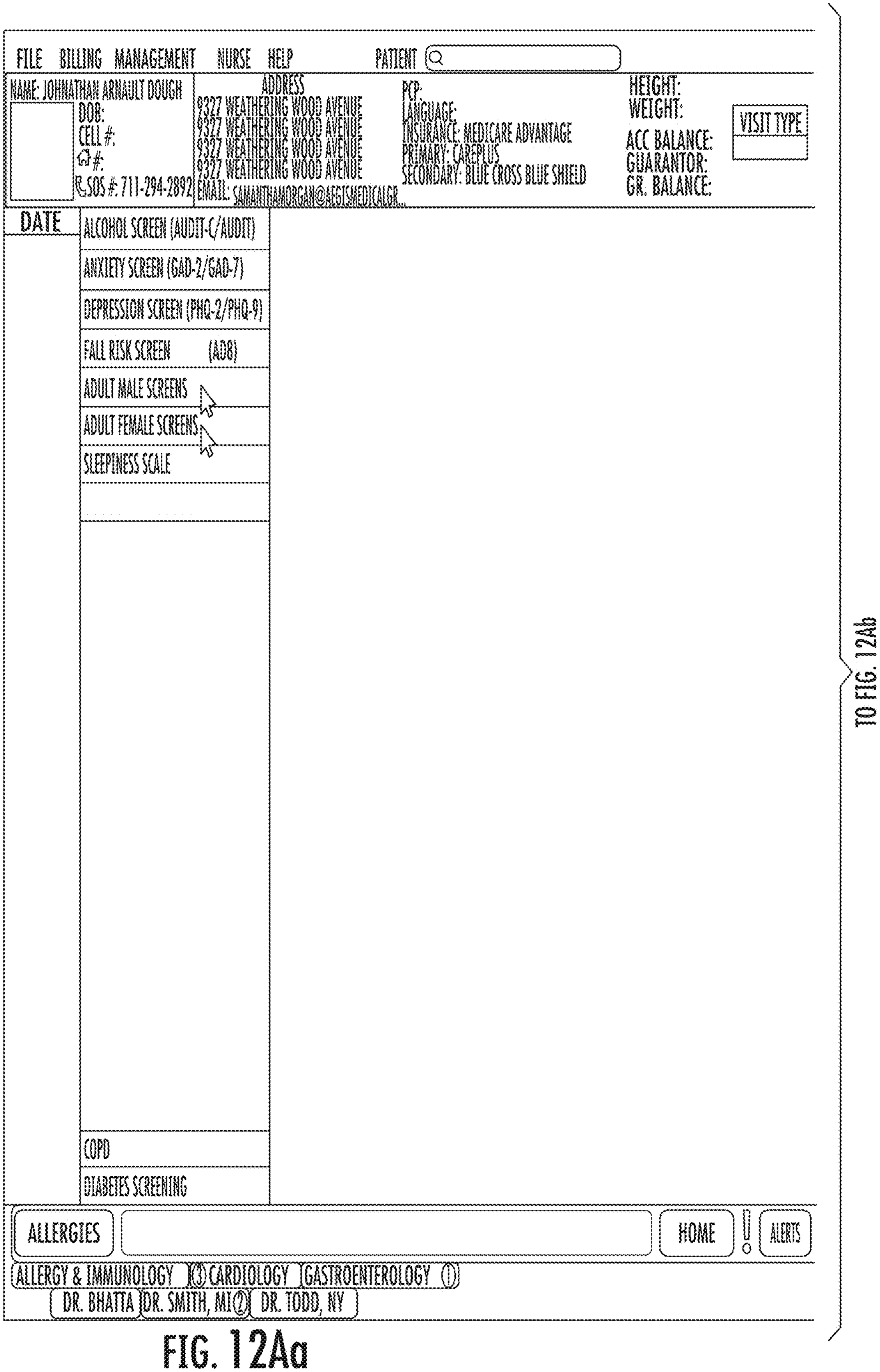
FIGS. 12Aa-12Cb are screenshots of an example embodiment of an adult female screening function of the EHR GUI from the EHR system of FIG. 1.
Figure 12A:
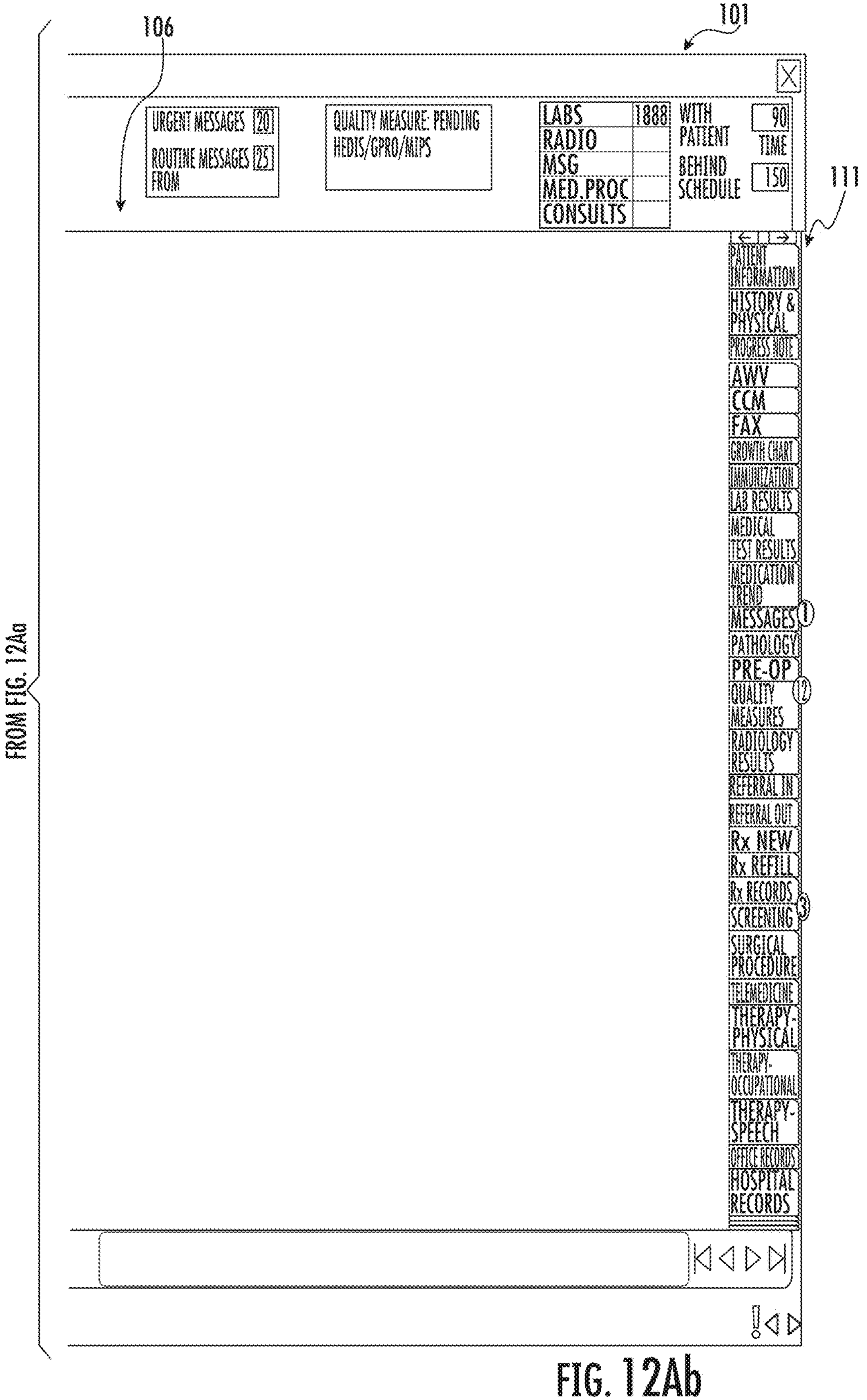
Figure 12B:
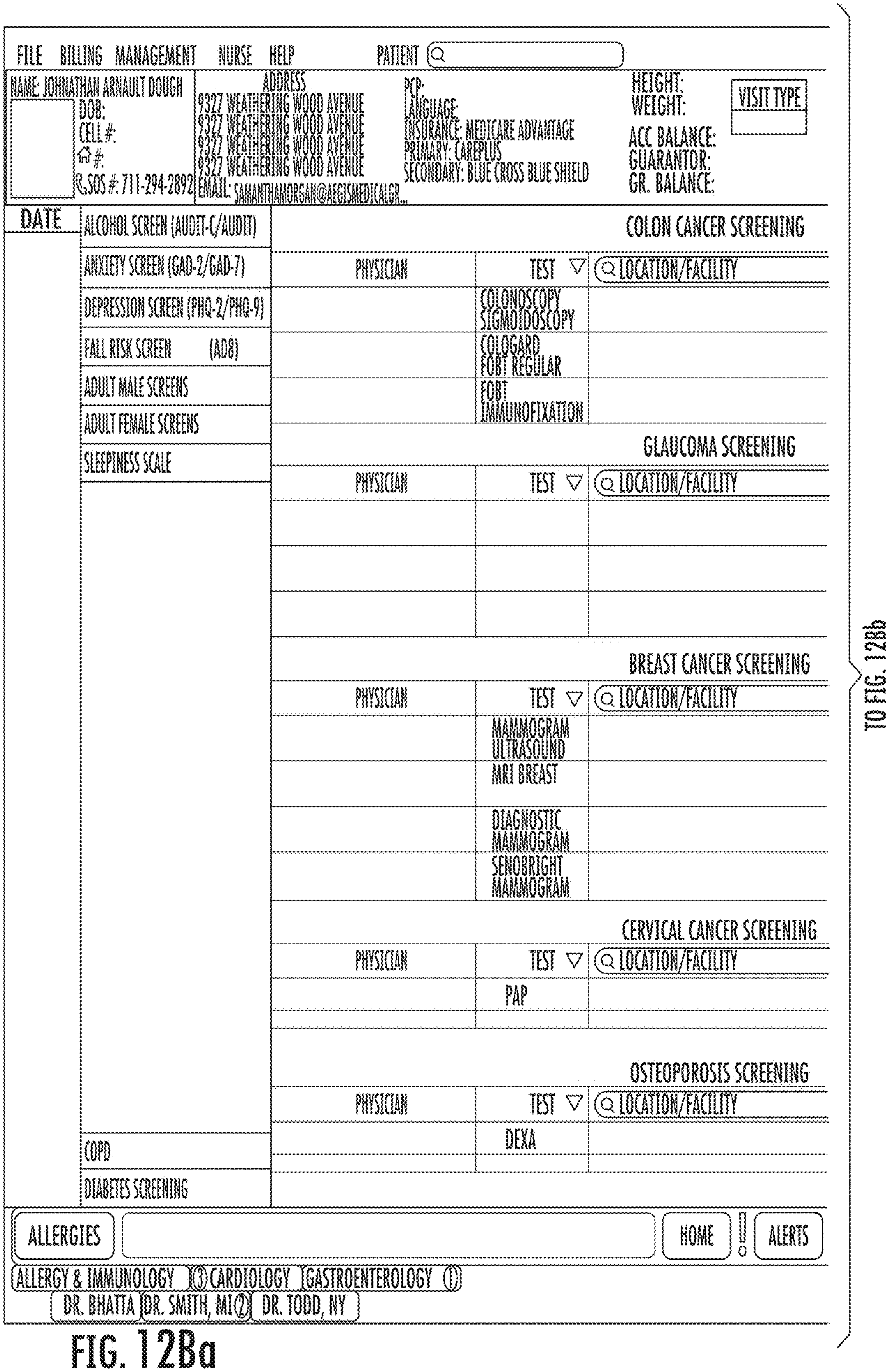
Figure 12B:
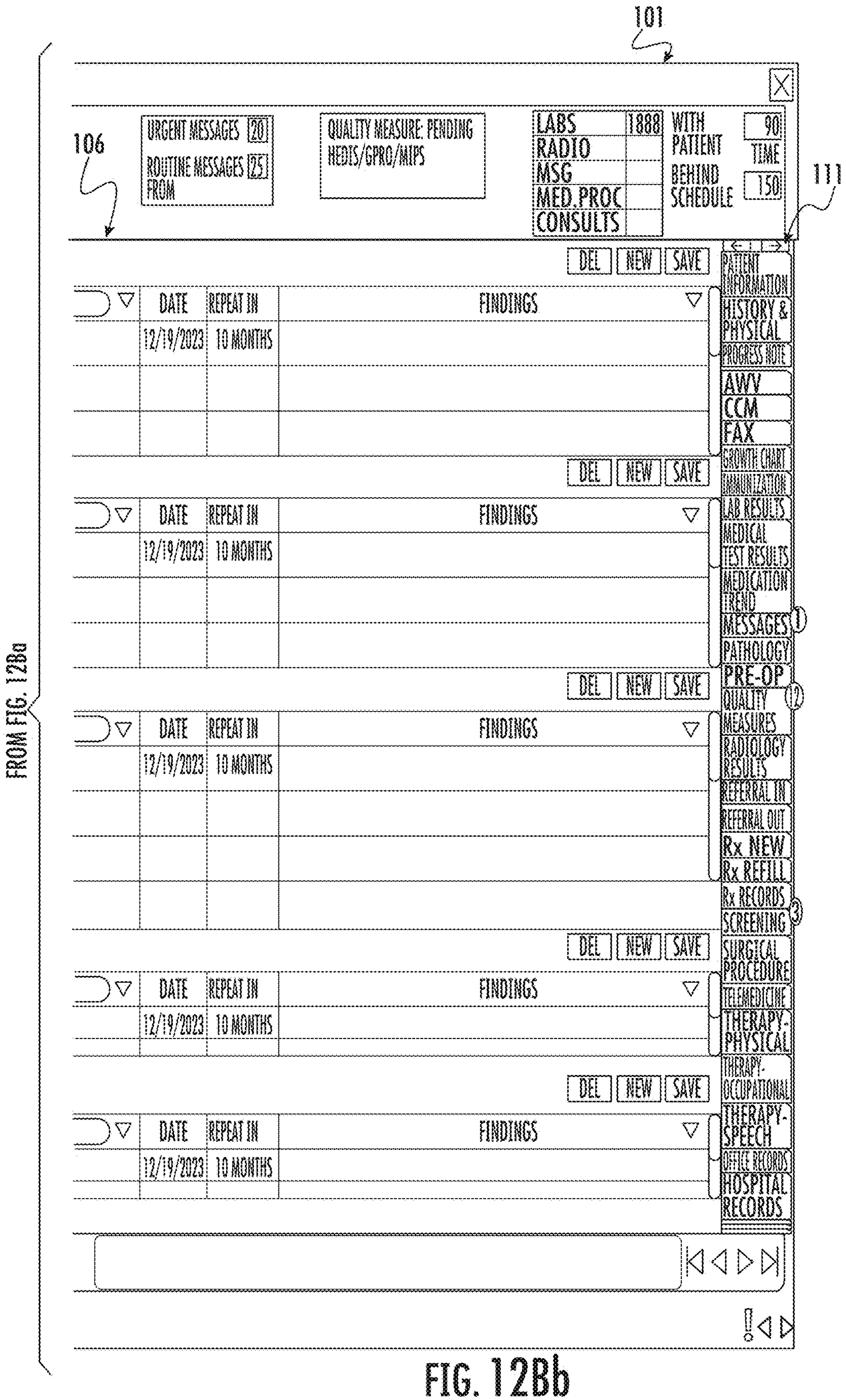
Figure 12C:
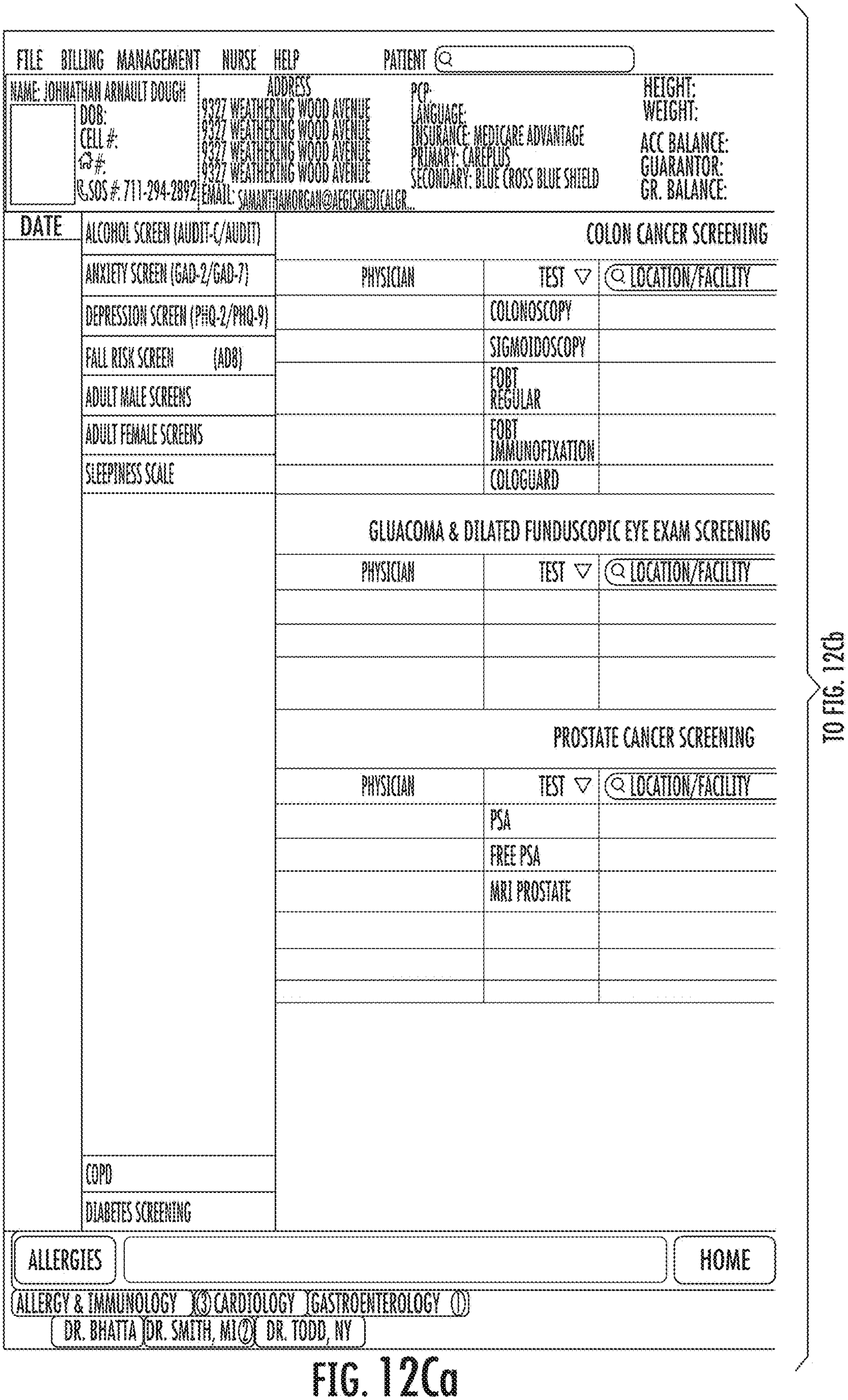
Figure 12C:
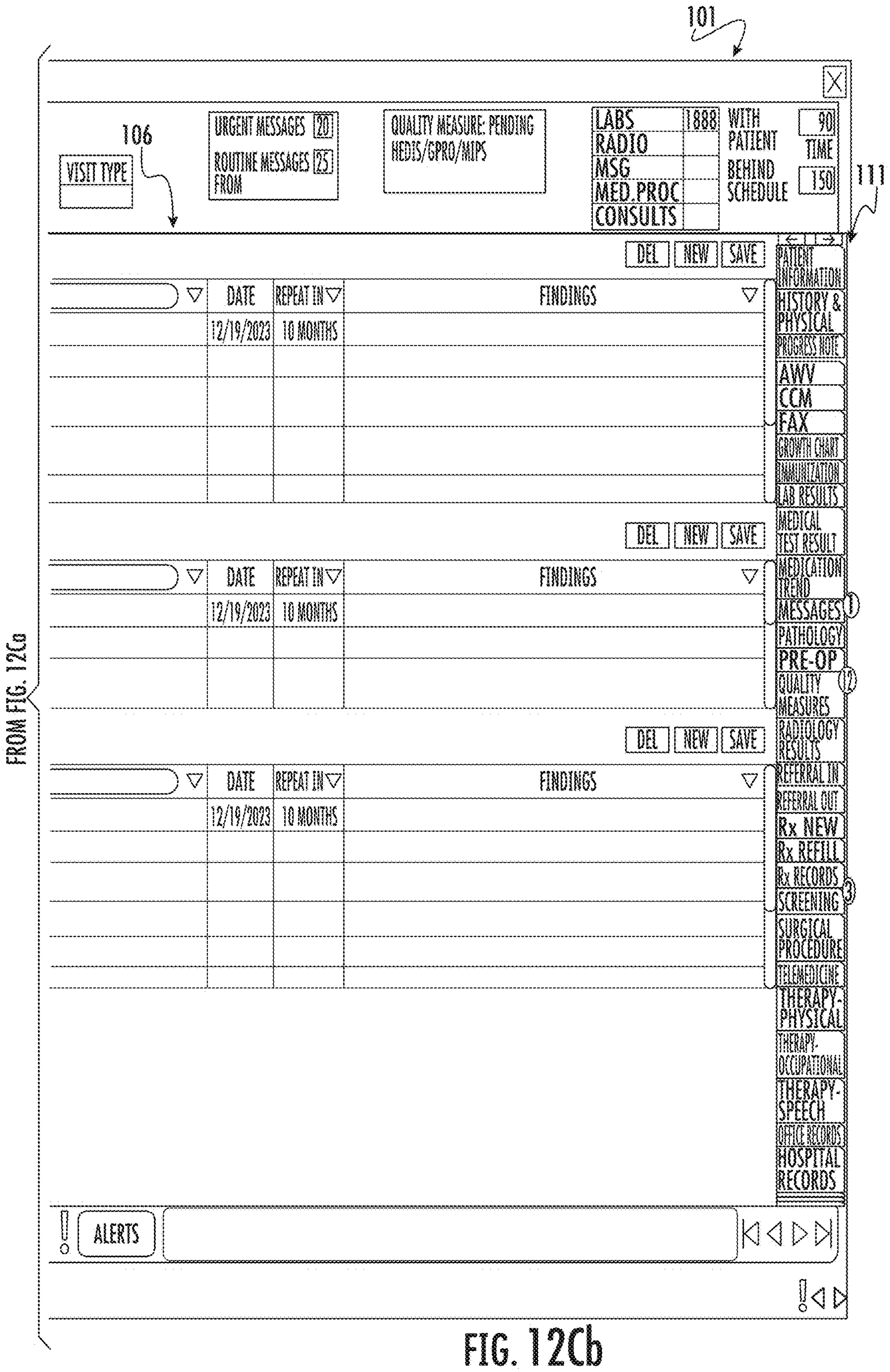

As seen in FIGS. 8*a*-8*b*, 9*a*-9*b*, & 10*a*-10*b*, the plurality of EHR functions illustratively comprises an annual wellness visit function permitting the medical professional to assess the given patient. The annual wellness visit function is accessed via the AWV tab noted with a dashed box. Here, the switchable interface area 106 comprises an initial preventative physical examination menu in FIGS. 8*a*-8*b*, an initial annual wellness check menu in FIGS. 9*a*-9*b*, and a subsequent annual wellness check menu in FIGS. 10*a*-10*b*. Each of these menus is accessible via a plurality of tabs 143*a*-143*c* at the top of the switchable interface area 106. Helpfully, each of these menus has an easy-to-use multi-button interface 144 of the medical professional to quickly assess the different aspects of patient health. FIGS. 12Aa-12Bb allow the medical professional to follow and order the next screening test when it is due.

Figure 11A:
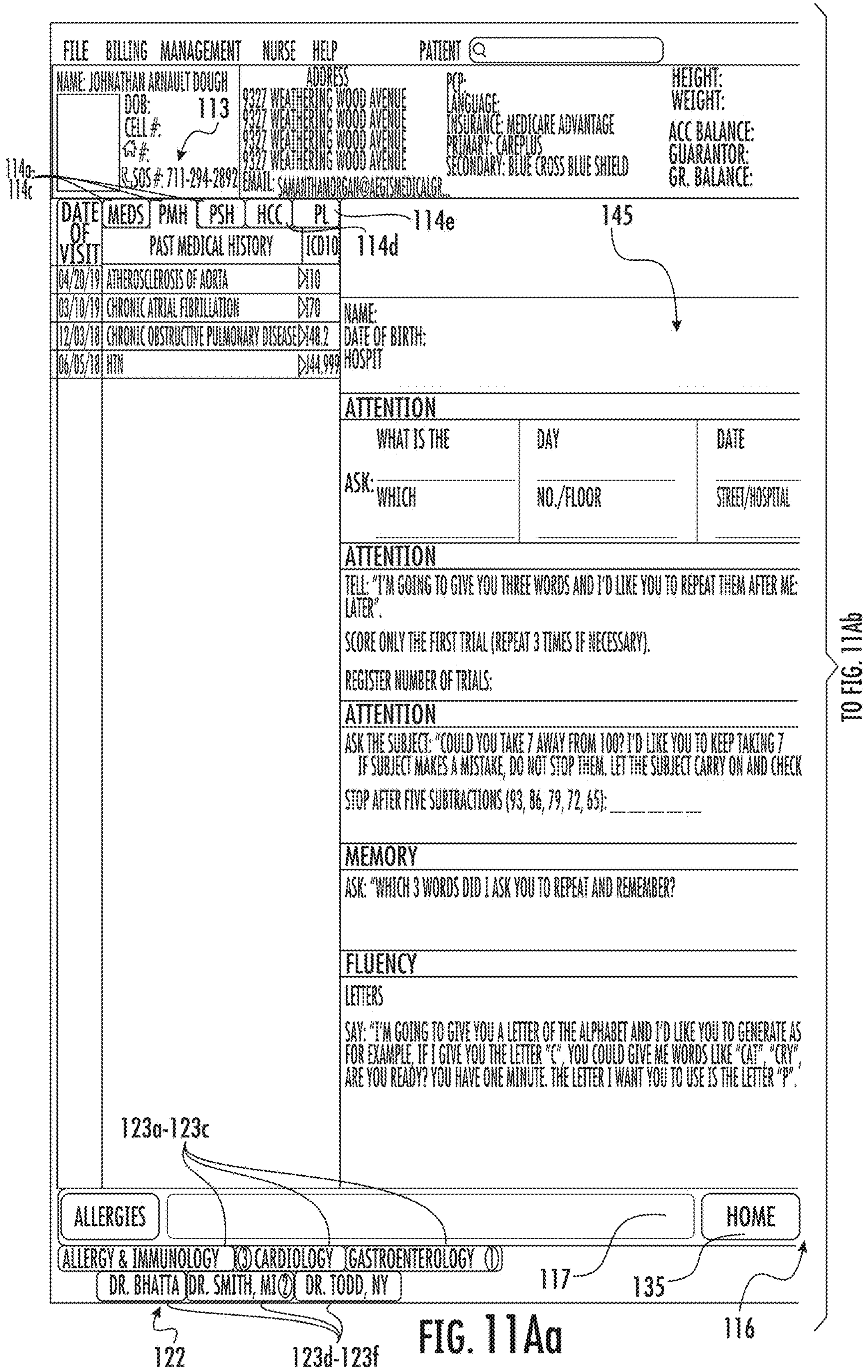
FIGS. 11Aa-11Bb are screenshots of an example embodiment of an adult male screening function of the EHR GUI from the EHR system of FIG. 1.
Figure 11A:
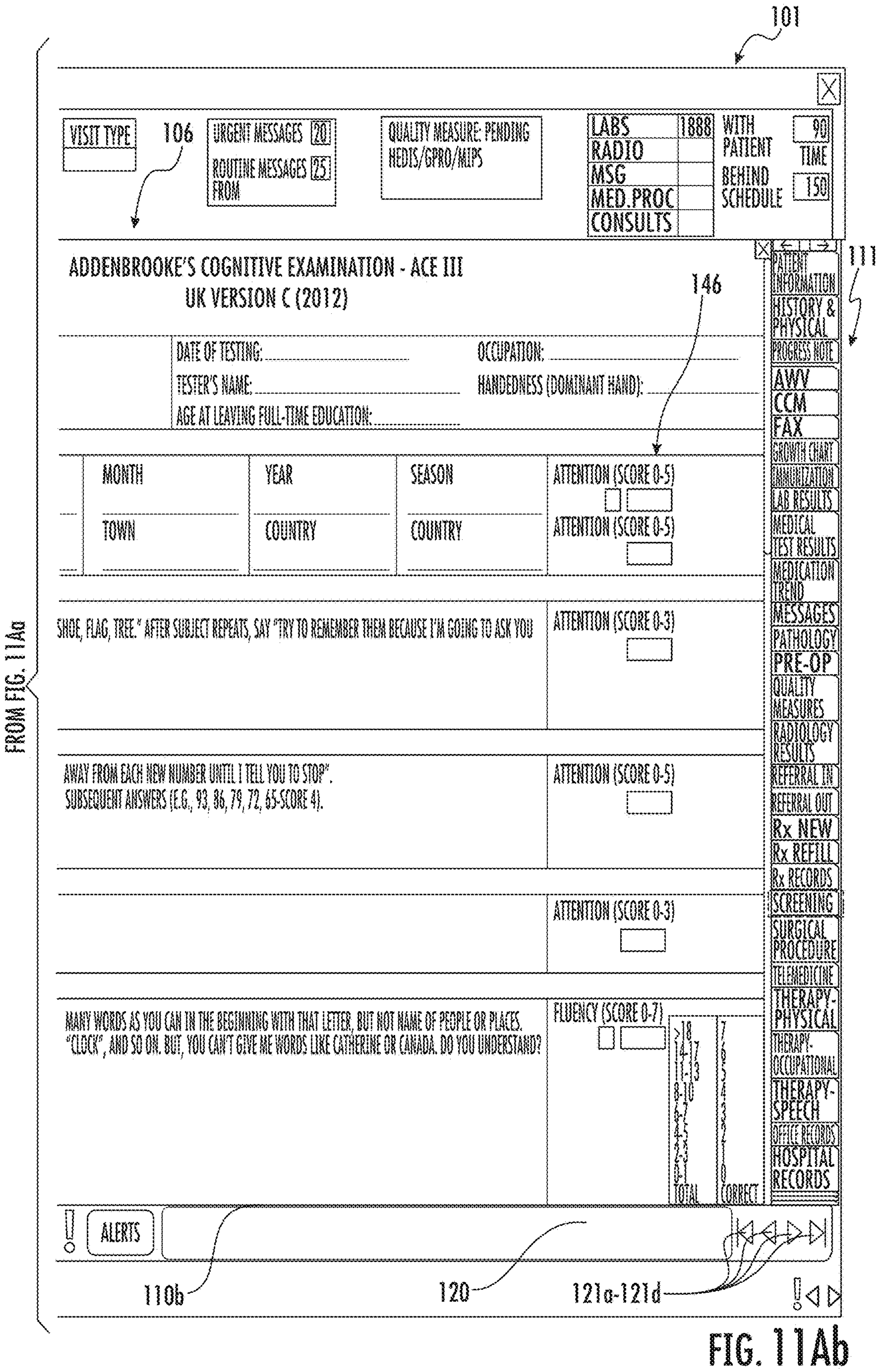
Figure 11B:
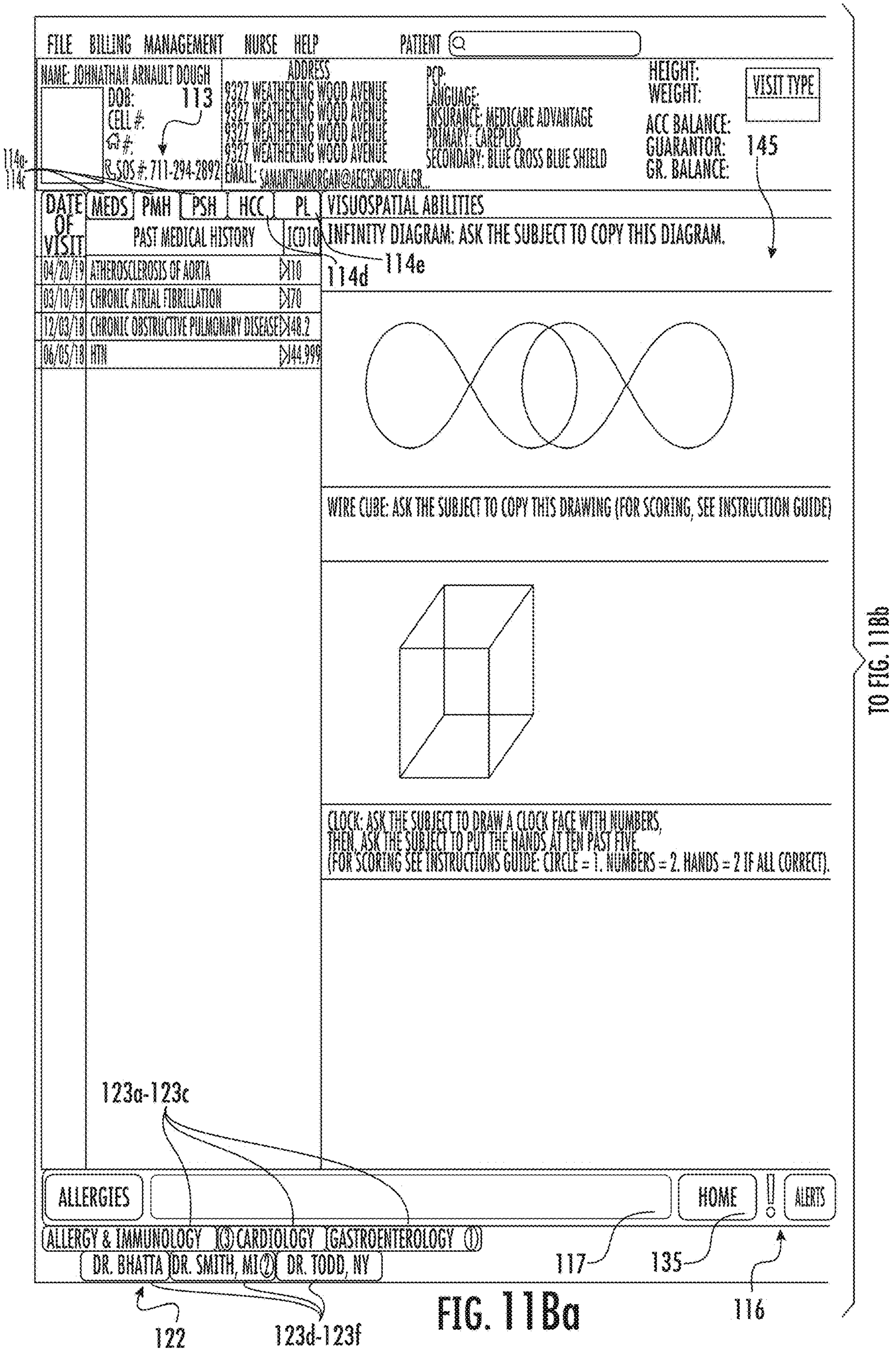
Figure 11B:
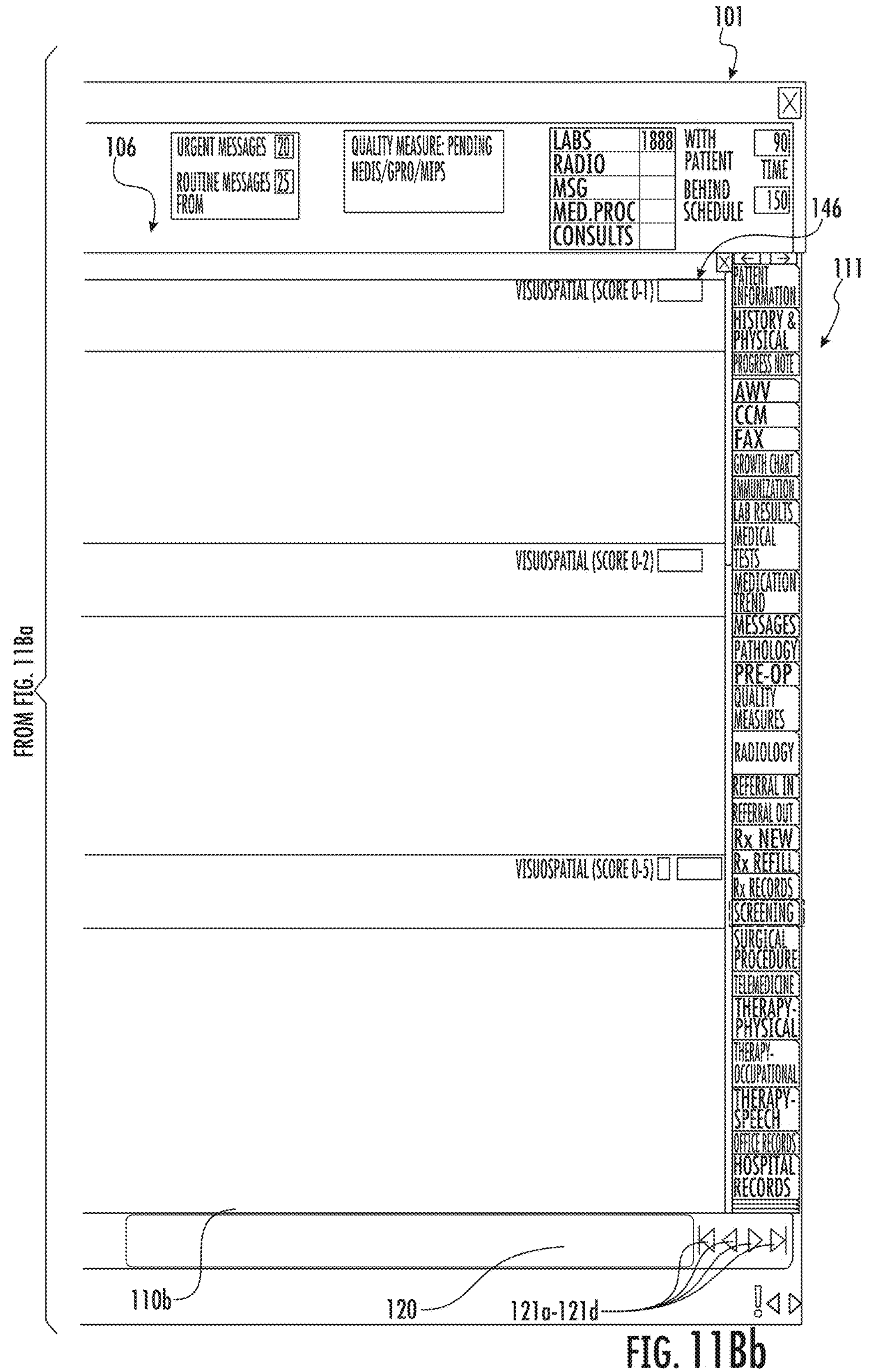

As seen in FIGS. 11Aa-11Bb & 12Aa-12Cb, the plurality of EHR functions illustratively comprises a screening function permitting the medical professional to screen the given patient for cognitive issues, as in the illustrated example (i.e., the Addenbroke's Cognitive Examination). The screening function is accessed via the "screening" tab noted with a dashed box. Here, the switchable interface area 106 comprises a screener test question 145 for the medical professional to offer to the given patient. Also, the switchable interface area 106 comprises data entry fields 146 for the medical professional to record the answers of the given patient.

Figure 13A:
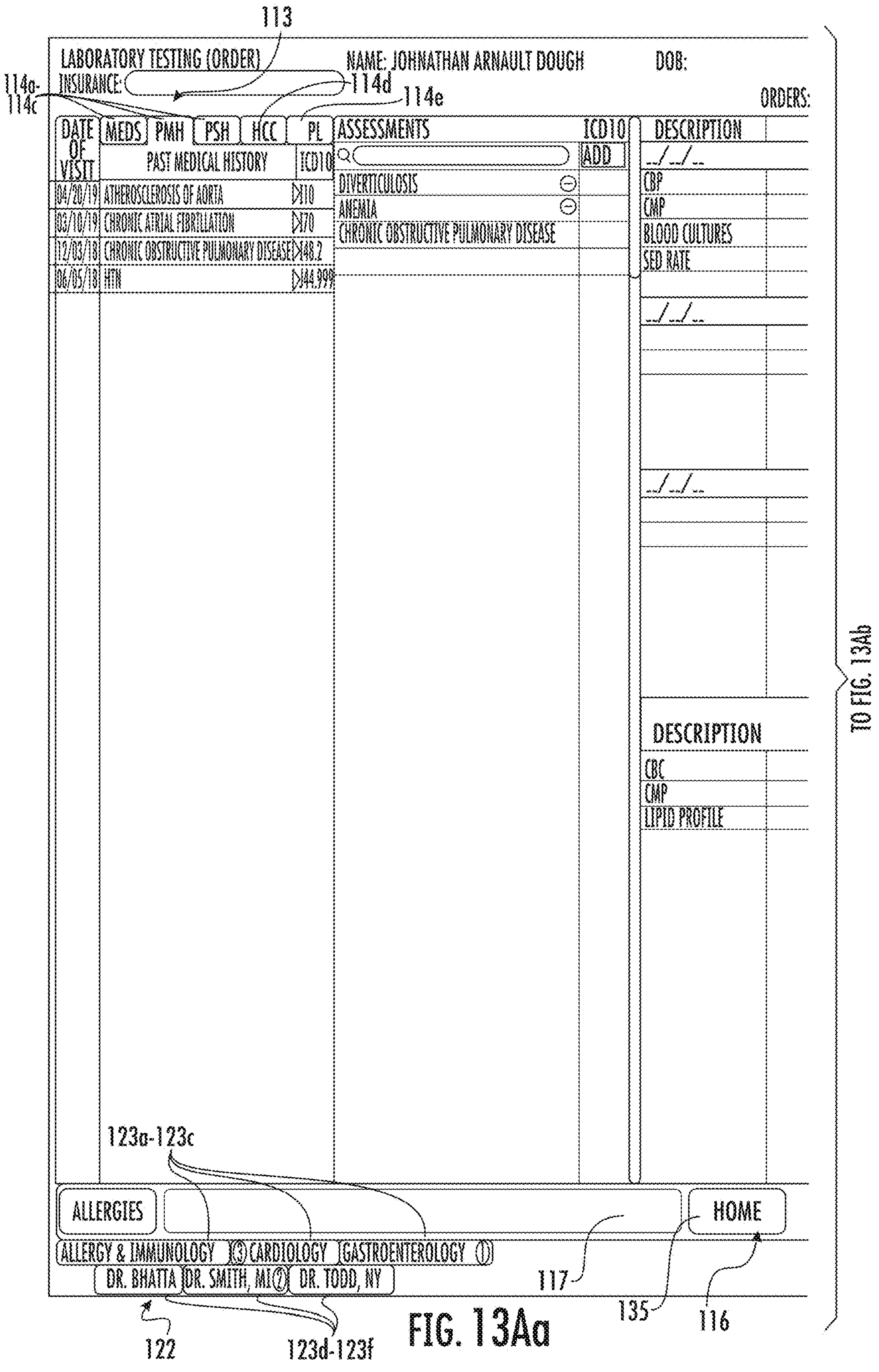
FIGS. 13Aa-13Bb are screenshots of an example embodiment of a laboratory order function of the EHR GUI from the EHR system of FIG. 1.
Figure 13A:
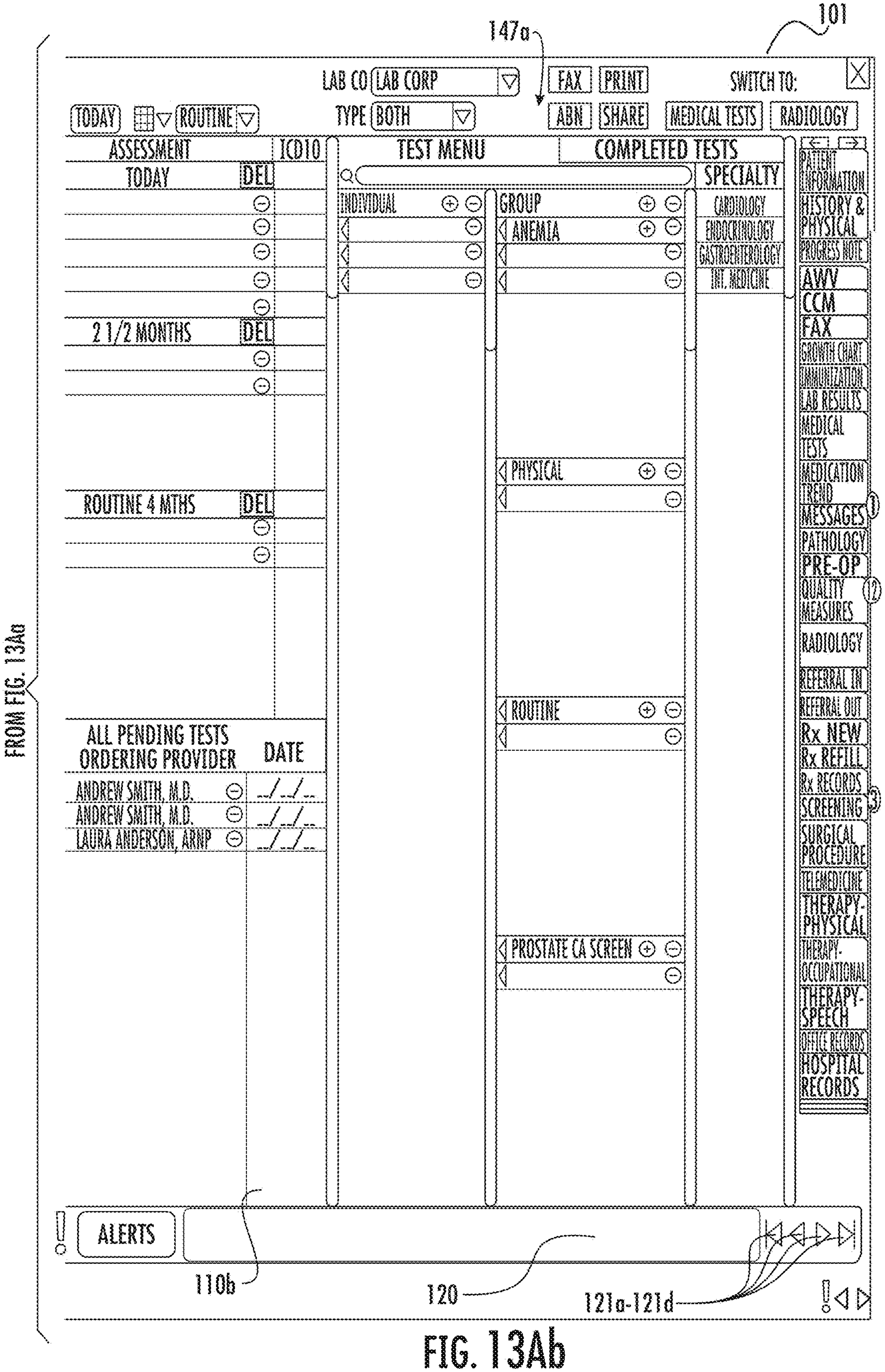
Figure 13B:
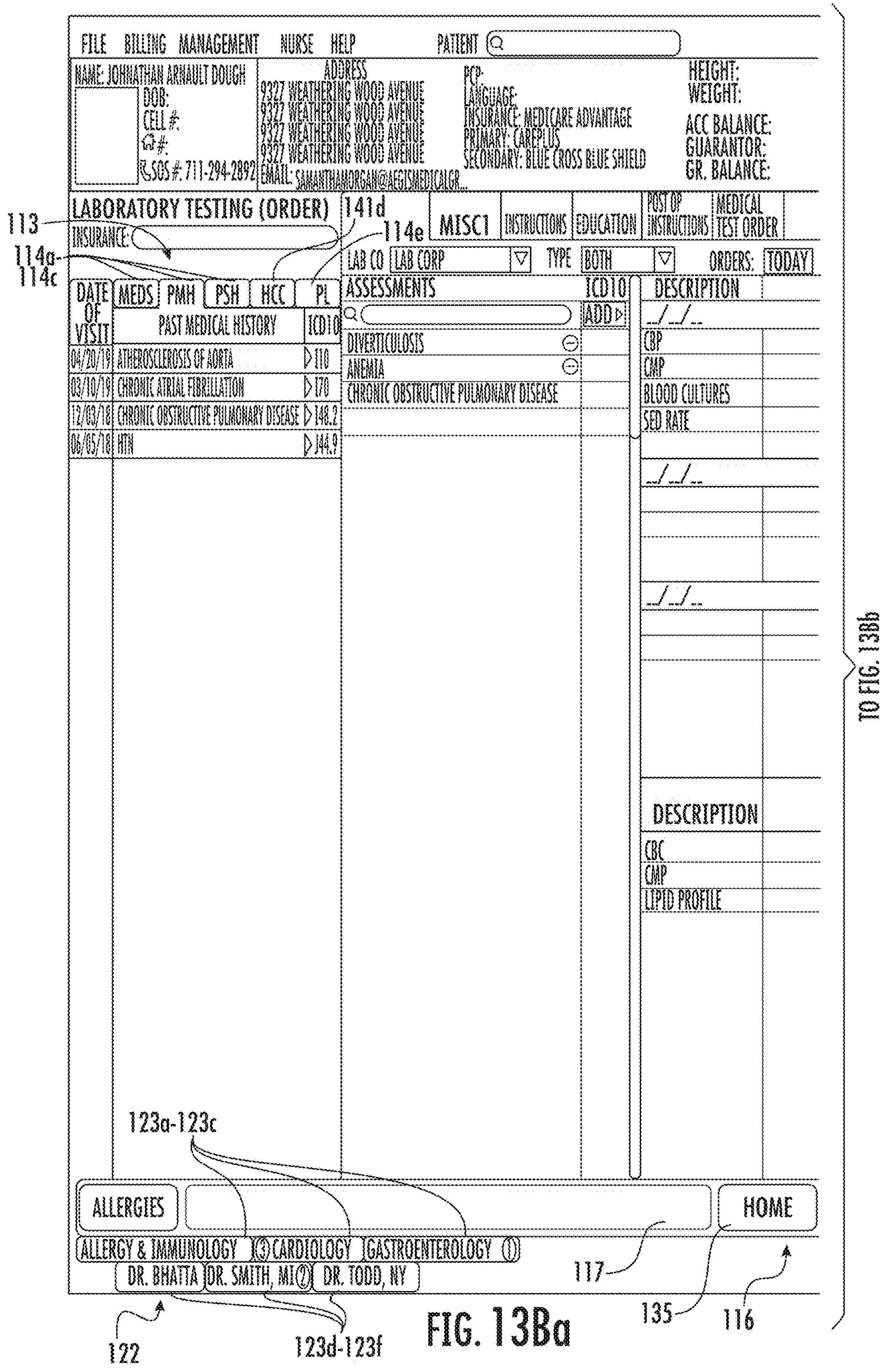
Figure 13B:
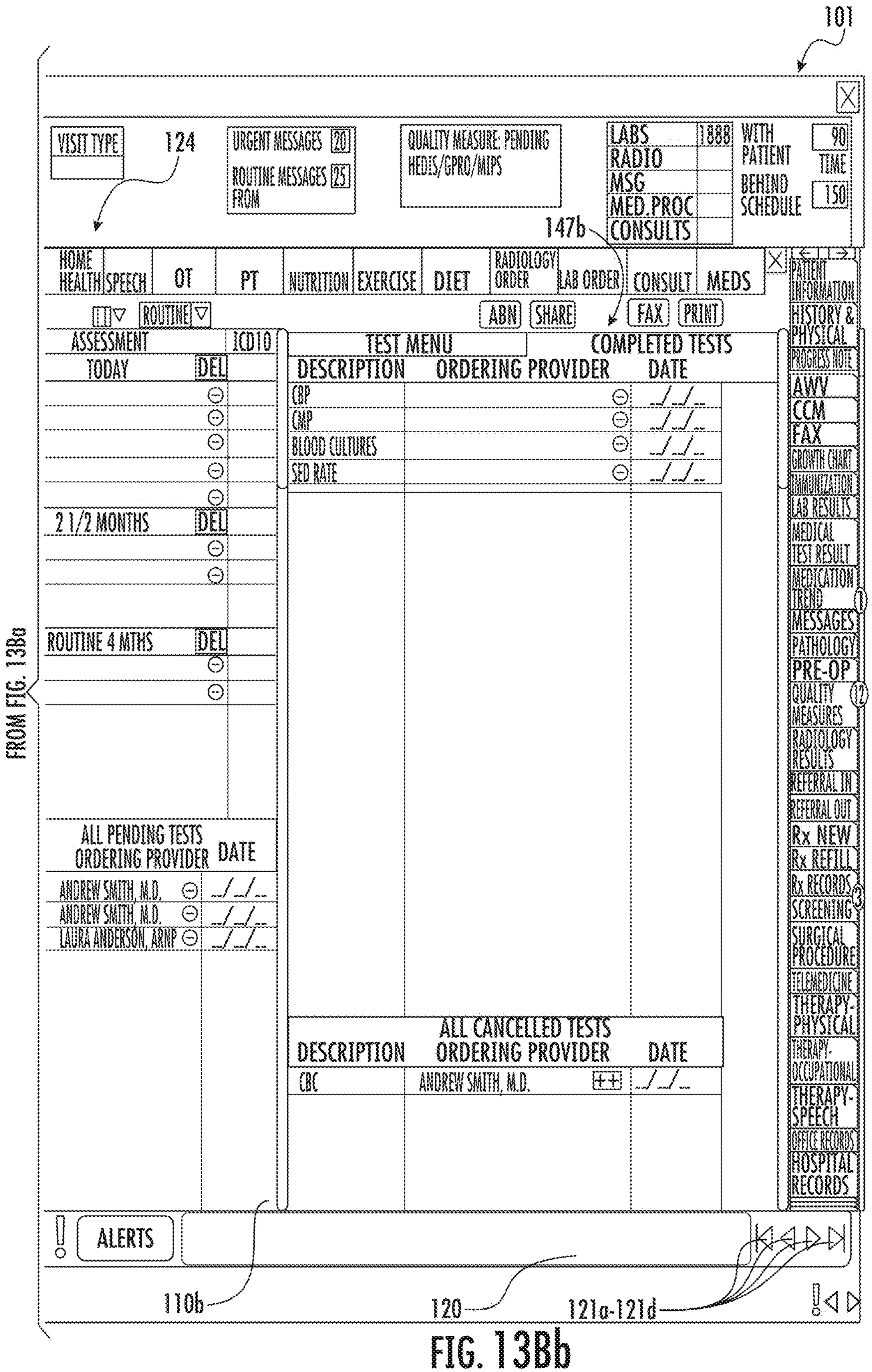

As seen in FIGS. 13Aa-13Bb, the plurality of EHR functions illustratively comprises a laboratory order function permitting the medical professional to order a laboratory test. Helpfully, the laboratory results function includes a test menu 147*a* configured to permit the medical profession to order new tests, and a completed test menu 147*b* for reviewing prior completed test results. Helpfully, this prevents the medical profession from ordering duplicates tests for the patient.

Figure 14A:
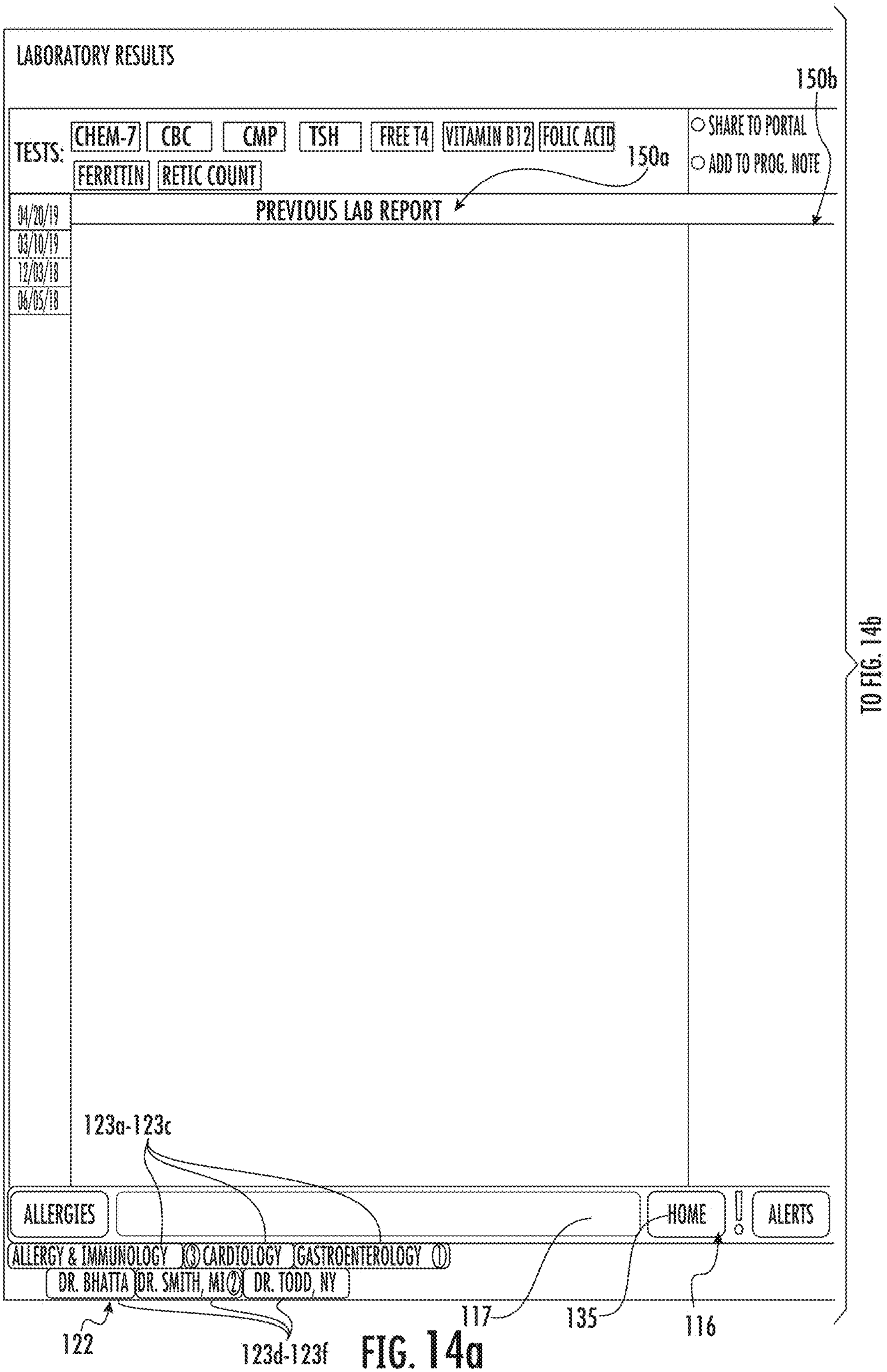
FIGS. 14*a*-14*b* is a screenshot of an example embodiment of a laboratory results function of the EHR GUI from the EHR system of FIG. 1.
Figure 14B:
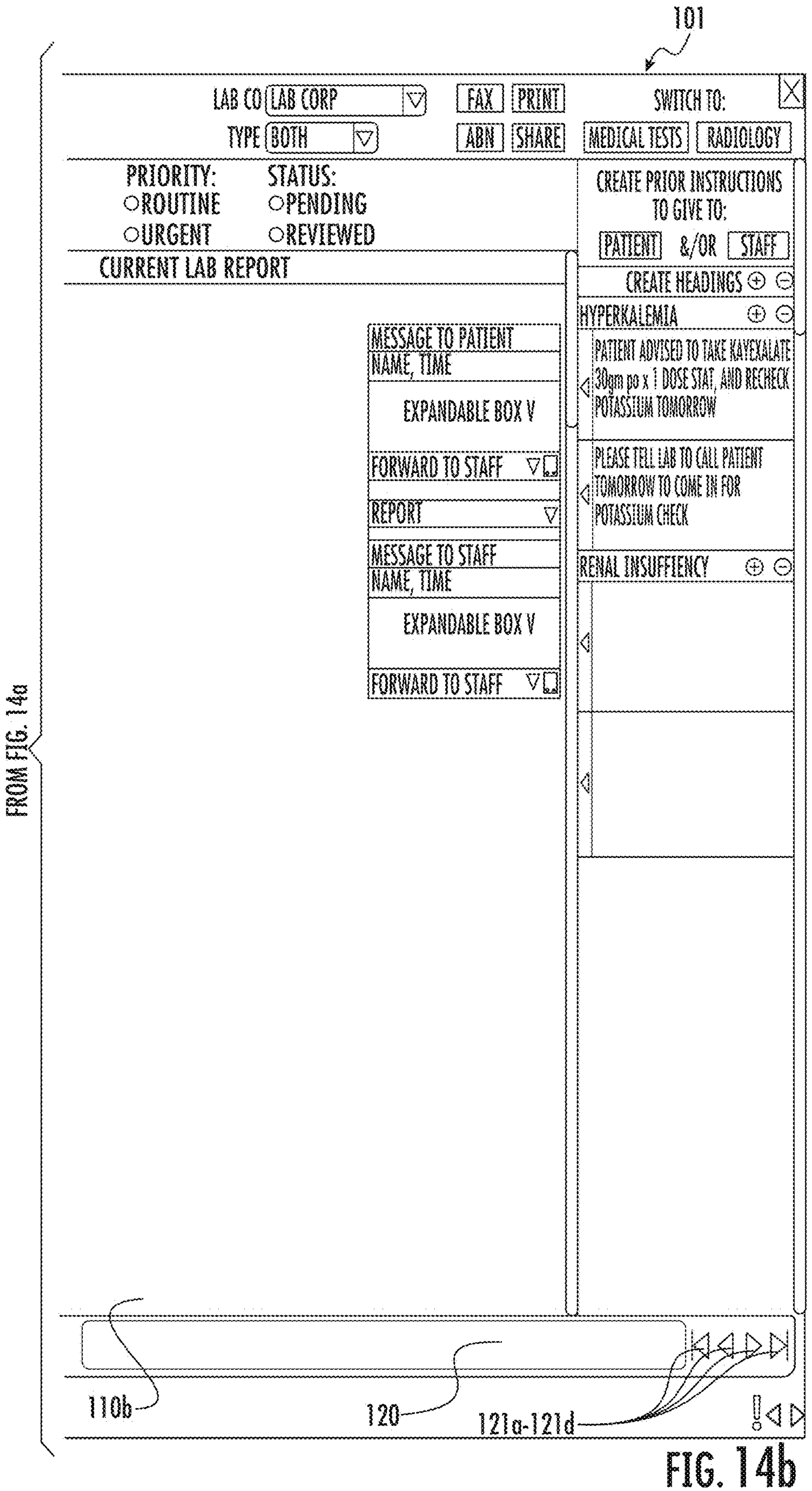

As seen in FIGS. 14*a*-14*b*, the plurality of EHR functions illustratively comprises a laboratory results function permitting the medical professional to review previously ordered laboratory test results. The laboratory results function uses a multi-page menu comprising a previous lab report panel 150*a*, and a current lab report panel 150*b*. Helpfully, this may allow the medical profession to review changes in the patient's lab results.

Figure 15A:
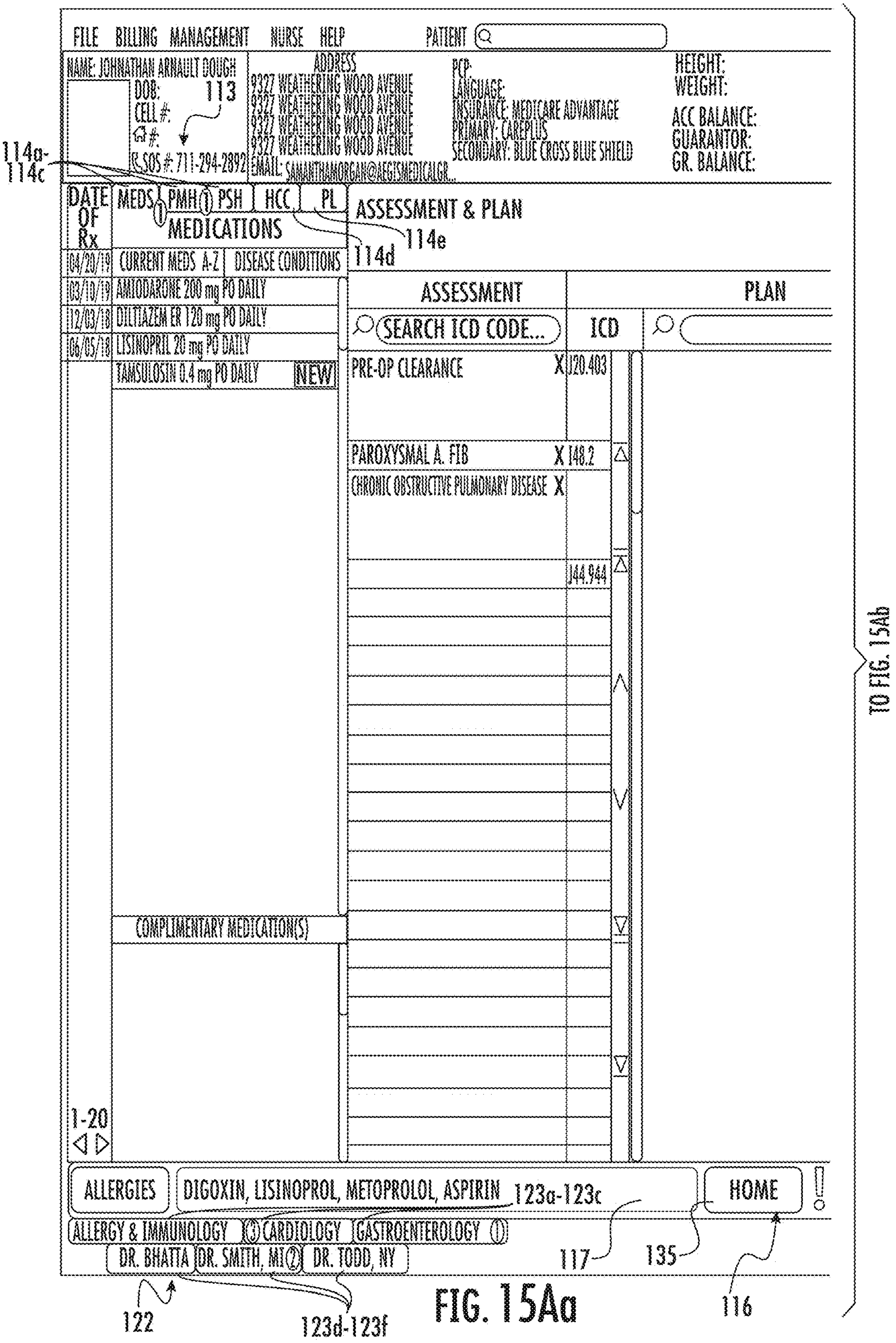
FIGS. 15Aa-15Bb are screenshots of an example embodiment of a progress note assessment and plan-instructions and exercise function of the EHR GUI from the EHR system of FIG. 1.
Figure 15A:
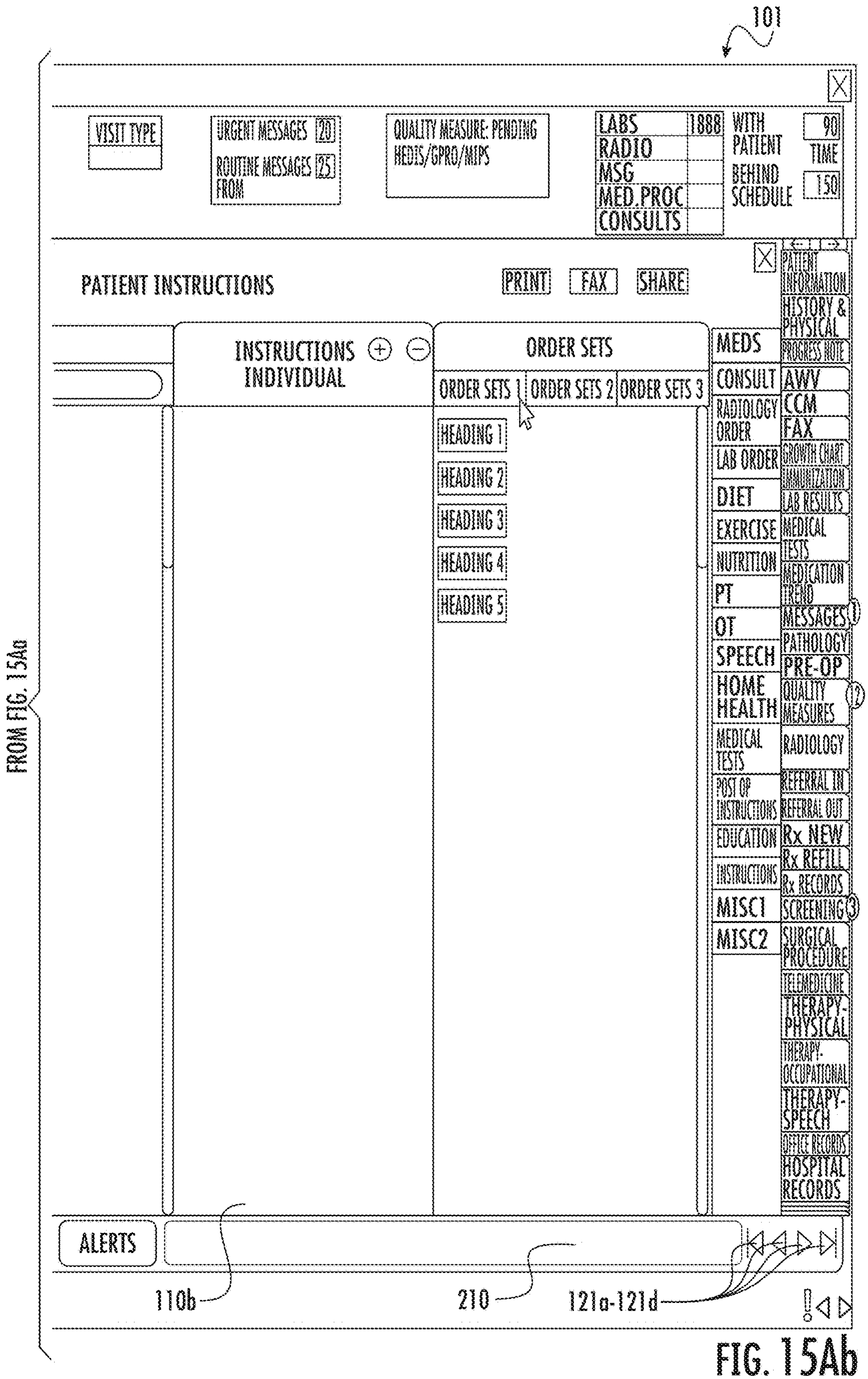
Figure 15B:
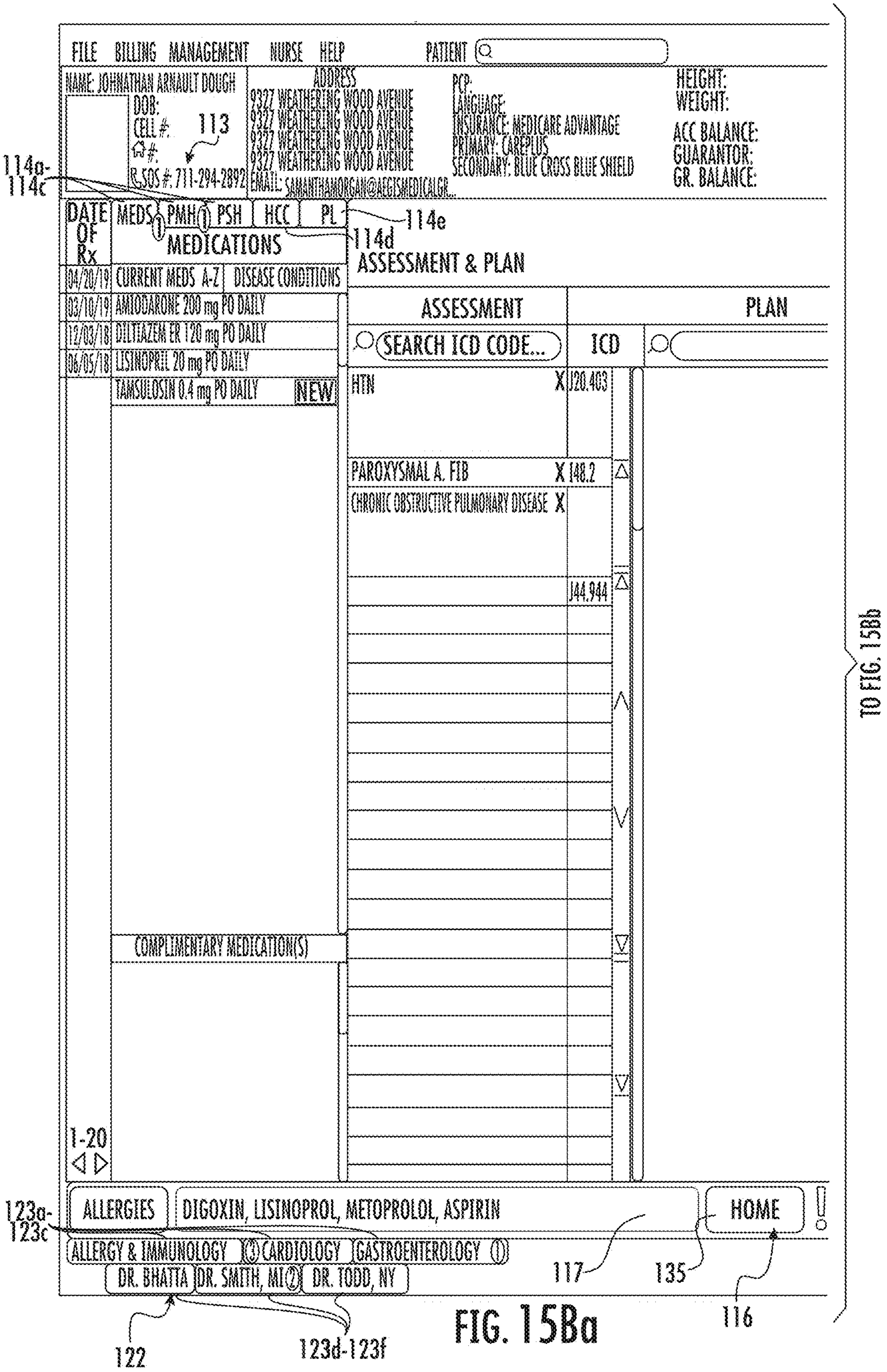
Figure 15B:
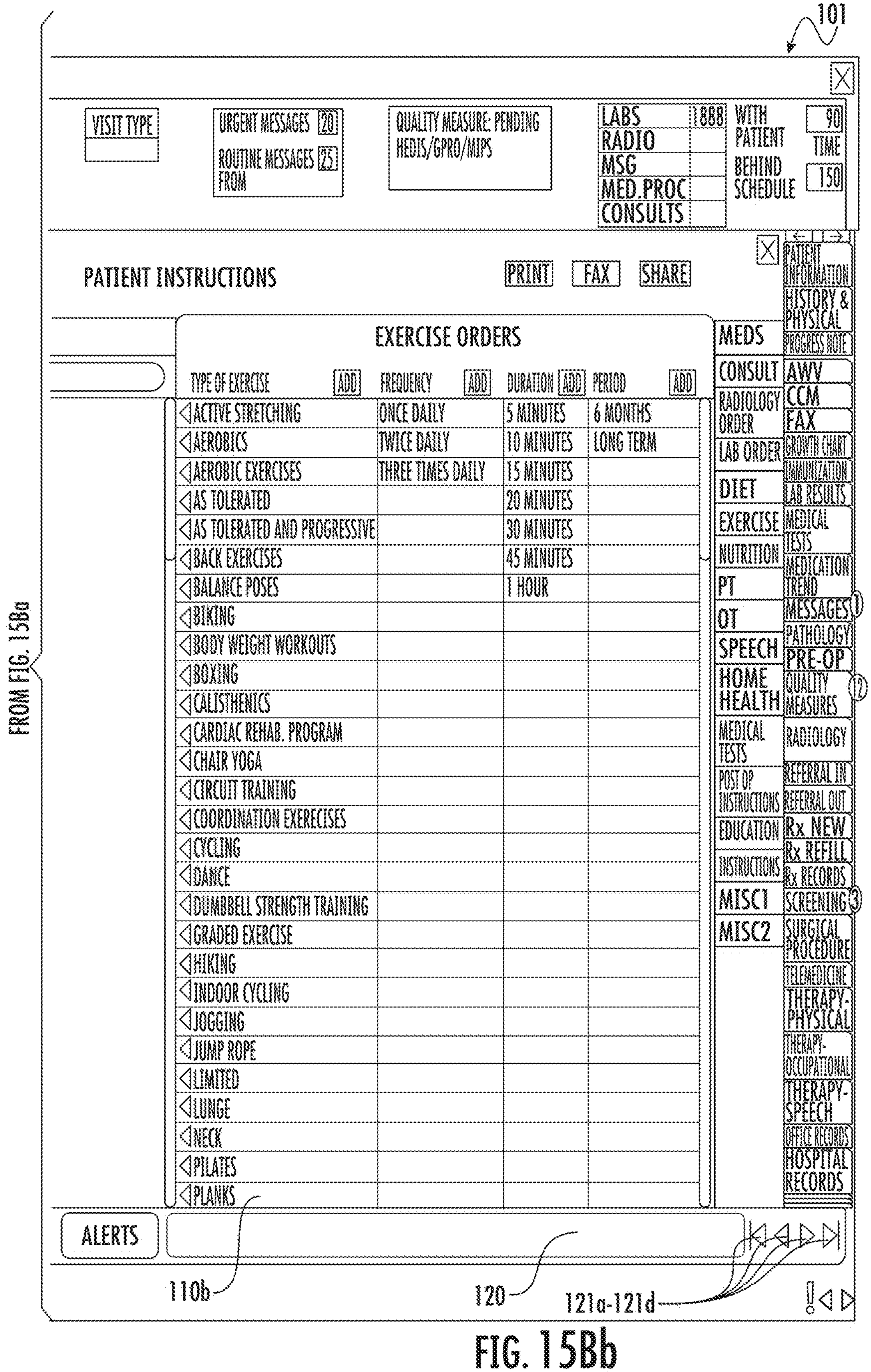

As seen in FIGS. 15Aa-15Bb, the plurality of EHR functions illustratively comprises an assessment and plan function permitting the medical professional to provide the patient orders for future healthcare. For example, the assessment and plan function illustratively includes exercise orders and patient instructions. Miscellaneous tabs 1 and 2 are to cater to evolving medicine and health care industry changes.

Another aspect is directed to a non-transitory computer-readable medium for an EHR system 100 comprising a display 102. The EHR system 100 provides an EHR GUI 101. The non-transitory computer-readable medium has computer-executable instructions for causing the EHR system 100 to perform steps comprising storing an EHR database 105 for a plurality of patients, and rendering the EHR GUI 101 on the display 102 for accessing given patient data related to a given patient within the EHR database. The EHR GUI 101 comprises a switchable interface area 106 configured to switch between a plurality of EHR functions. Each EHR function is to provide access to a respective different type of information from the given patient data in the EHR database 105. The EHR GUI 101 comprises a navigation tab menu 111 adjacent to a first side 107*a* of the switchable interface area 106 and comprising a plurality of navigation tabs 112*a*-112*n* for accessing the plurality of EHR functions within the switchable interface area, and a patient history tab menu 113 adjacent to a second side 107*b* of the switchable interface area. As noted hereinabove, each of the plurality of navigation tabs 112*a*-112*n* may comprise a visual indicator for a number of notifications within the respective EHR function. The second side 107*b* is opposite the first side 107*a*. The patient history tab menu 113 comprises a plurality of patient history tabs 114*a*-114*e* for accessing different types of historical patient data from the given patient data in the EHR database 105. The EHR GUI 101 comprises an alert footer menu 116 below the switchable interface area 106, the alert footer menu comprising a plurality of potential medical alert display windows 117, 120 for the given patient, and a specialist footer menu 122 adjacent to the alert footer menu and comprising a plurality of potential specialist notifications 123*a*-123*f*.

Yet another aspect is directed to a method for operating an EHR system 100 comprising a display 102, the EHR system providing an EHR GUI 101. The method comprises storing an EHR database 105 for a plurality of patients, and rendering the EHR GUI 101 on the display 102 for accessing given patient data related to a given patient within the EHR database. The EHR GUI 101 comprises a switchable interface area 106 configured to switch between a plurality of EHR functions. Each EHR function is to provide access to a respective different type of information from the given patient data in the EHR database 105. The EHR GUI 101 comprises a navigation tab menu 111 adjacent to a first side 107*a* of the switchable interface area 106 and comprising a plurality of navigation tabs 112*a*-112*n* for accessing the plurality of EHR functions within the switchable interface area, and a patient history tab menu 113 adjacent to a second side 107*b* of the switchable interface area. In some embodiments, the plurality of navigation tabs 112*a*-112*n* may comprise a visual indicator for a number of notifications within the plurality of EHR functions.

The second side 107*b* is opposite the first side 107*a*. The patient history tab menu 113 comprises a plurality of patient history tabs 114*a*-114*e* for accessing different types of historical patient data from the given patient data in the EHR database 105. The EHR GUI 101 comprises an alert footer menu 116 below the switchable interface area 106, the alert footer menu comprising a plurality of potential medical alert display windows 117, 120 for the given patient, and a specialist footer menu 122 adjacent to the alert footer menu and comprising a plurality of potential specialist notifications 123*a*-123*f*.

As seen in FIGS. 13Aa-13Bb, the plurality of EHR functions illustratively comprises a laboratory ordering function permitting the medical professional to order laboratory testing for the given patient.

Figure 16A:
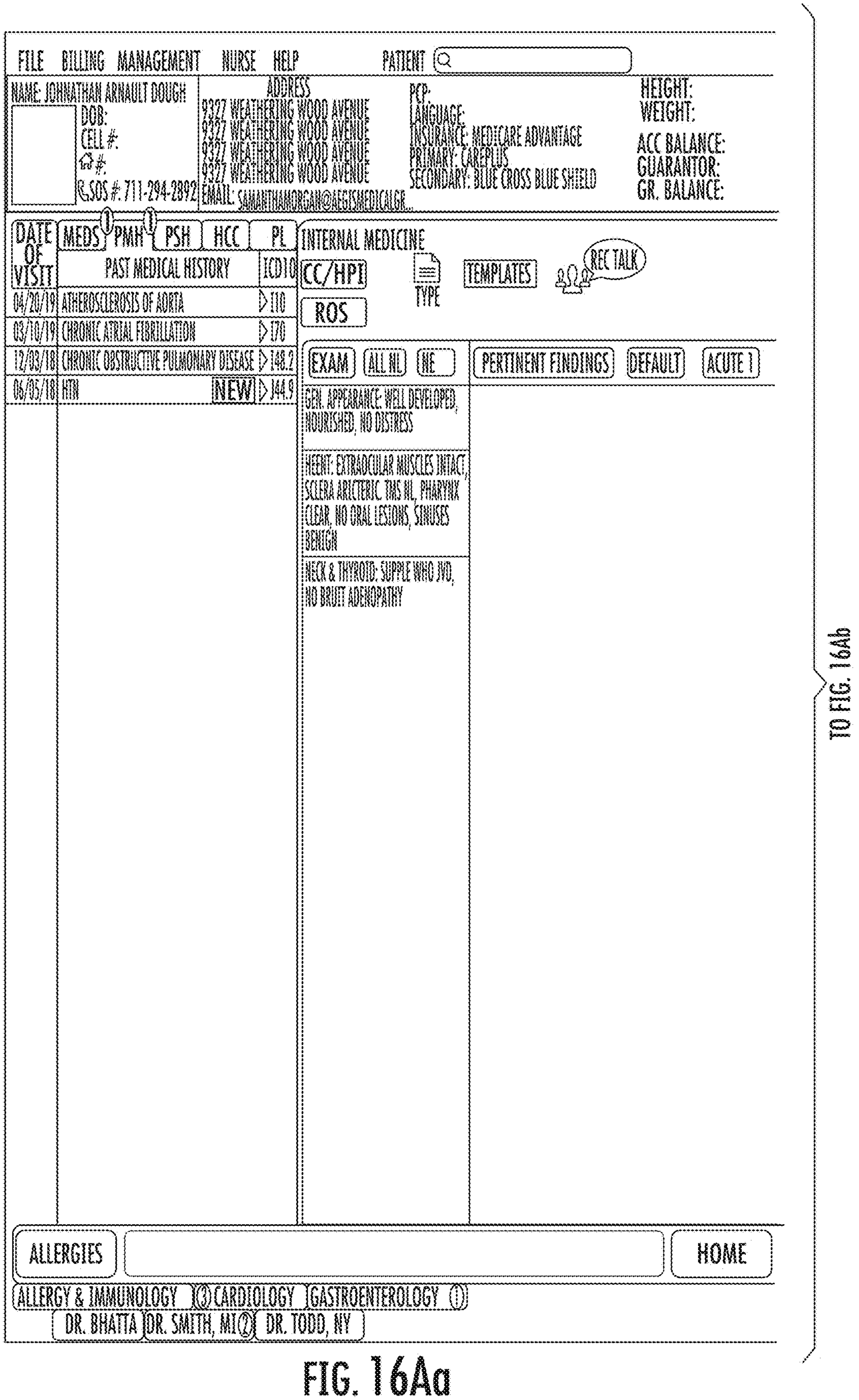
FIGS. 16Aa-16Pb are screenshots of an example embodiment of a progress note assessment and plan-prescription writing function of the EHR GUI from the EHR system of FIG. 1.
Figure 16A:
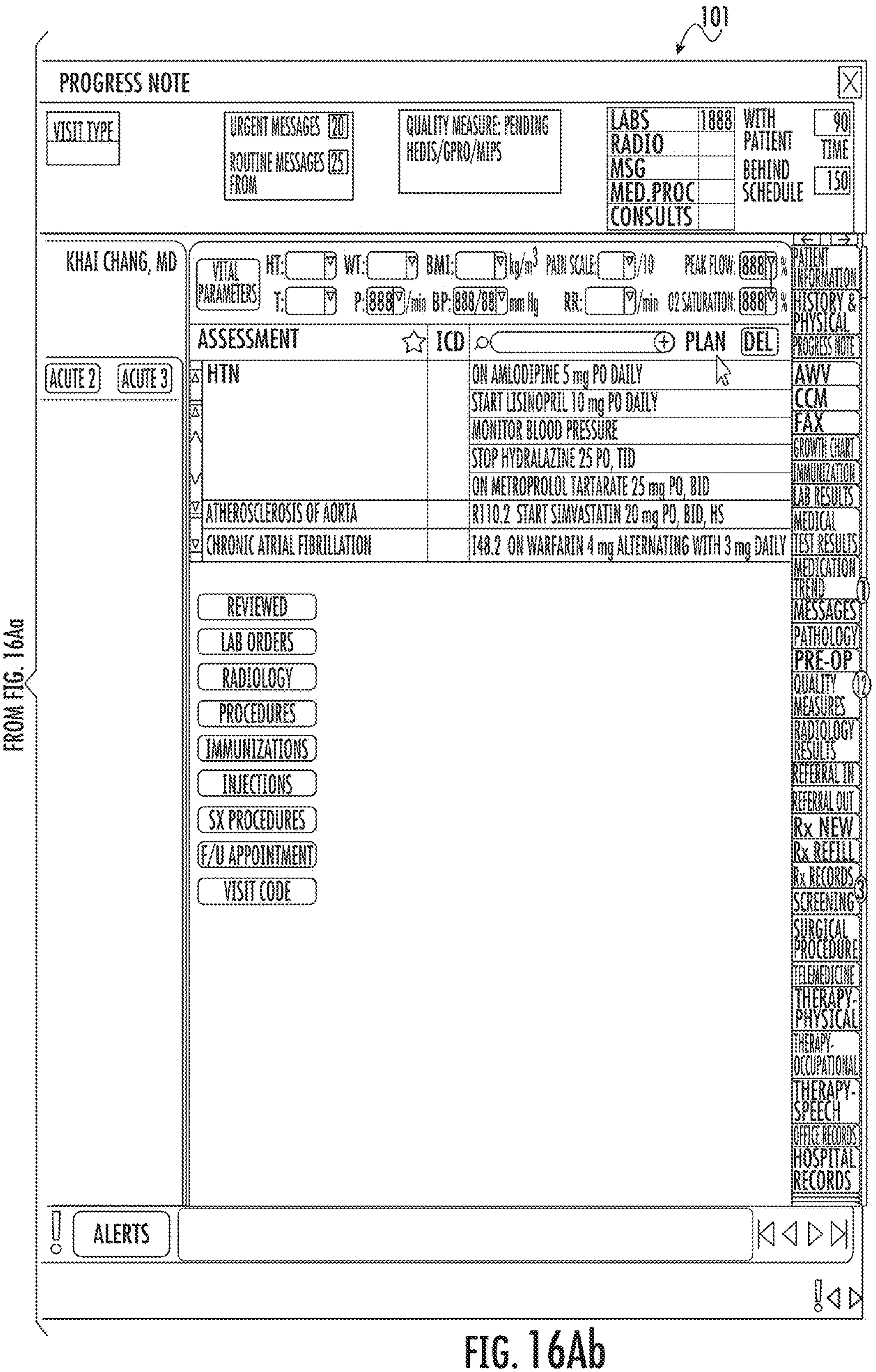
Figure 16B:
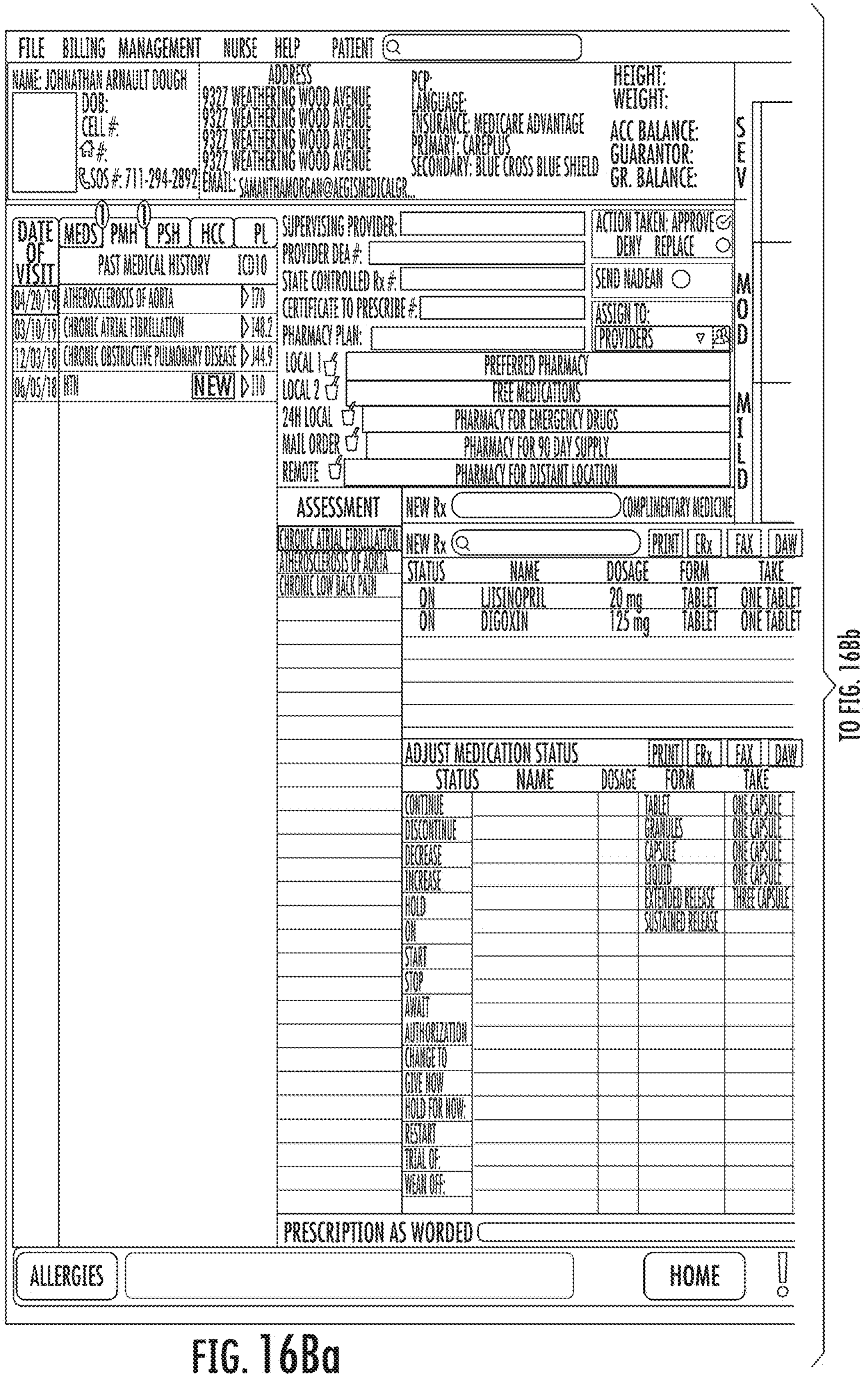
Figure 16B:
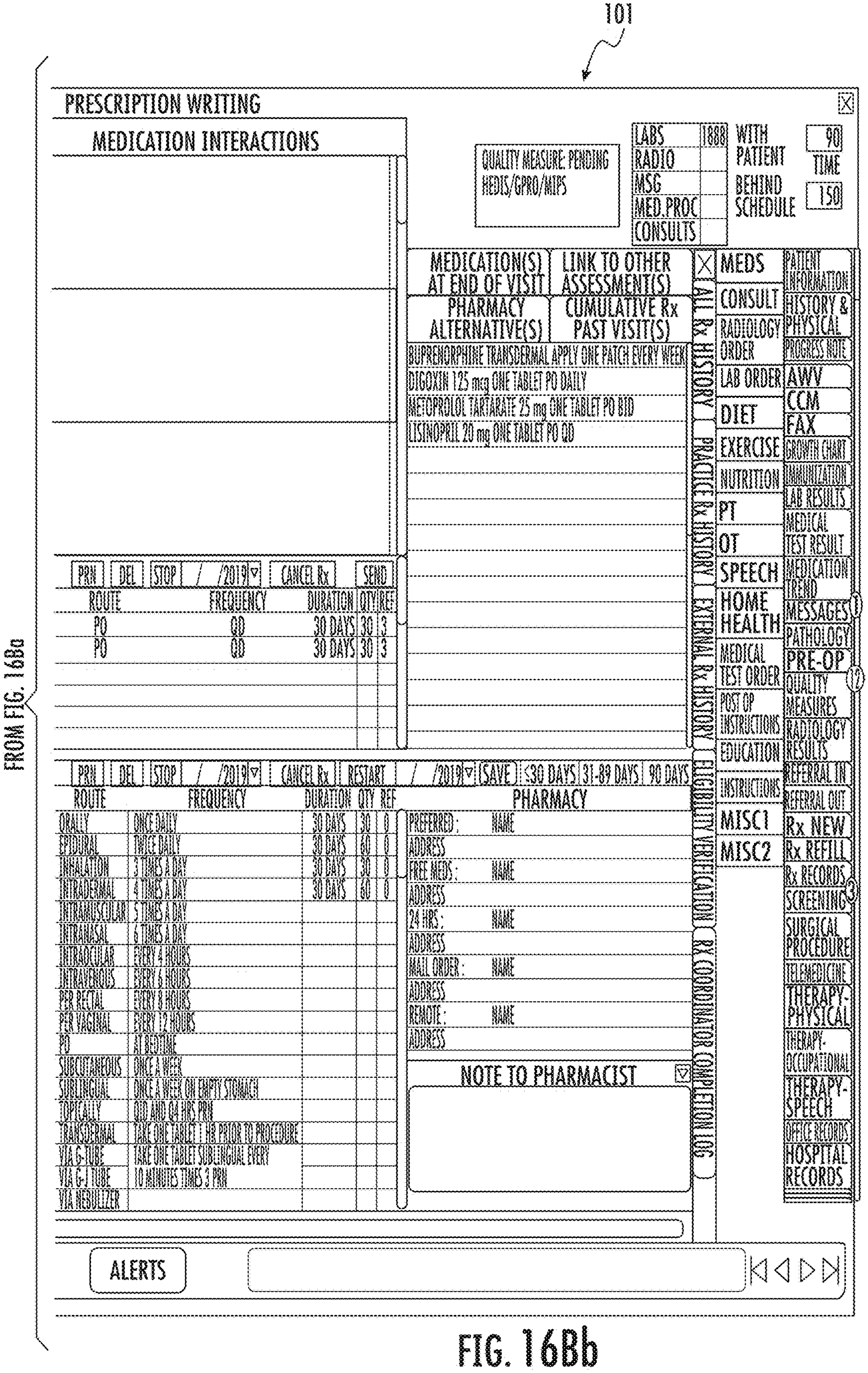
Figure 16C:
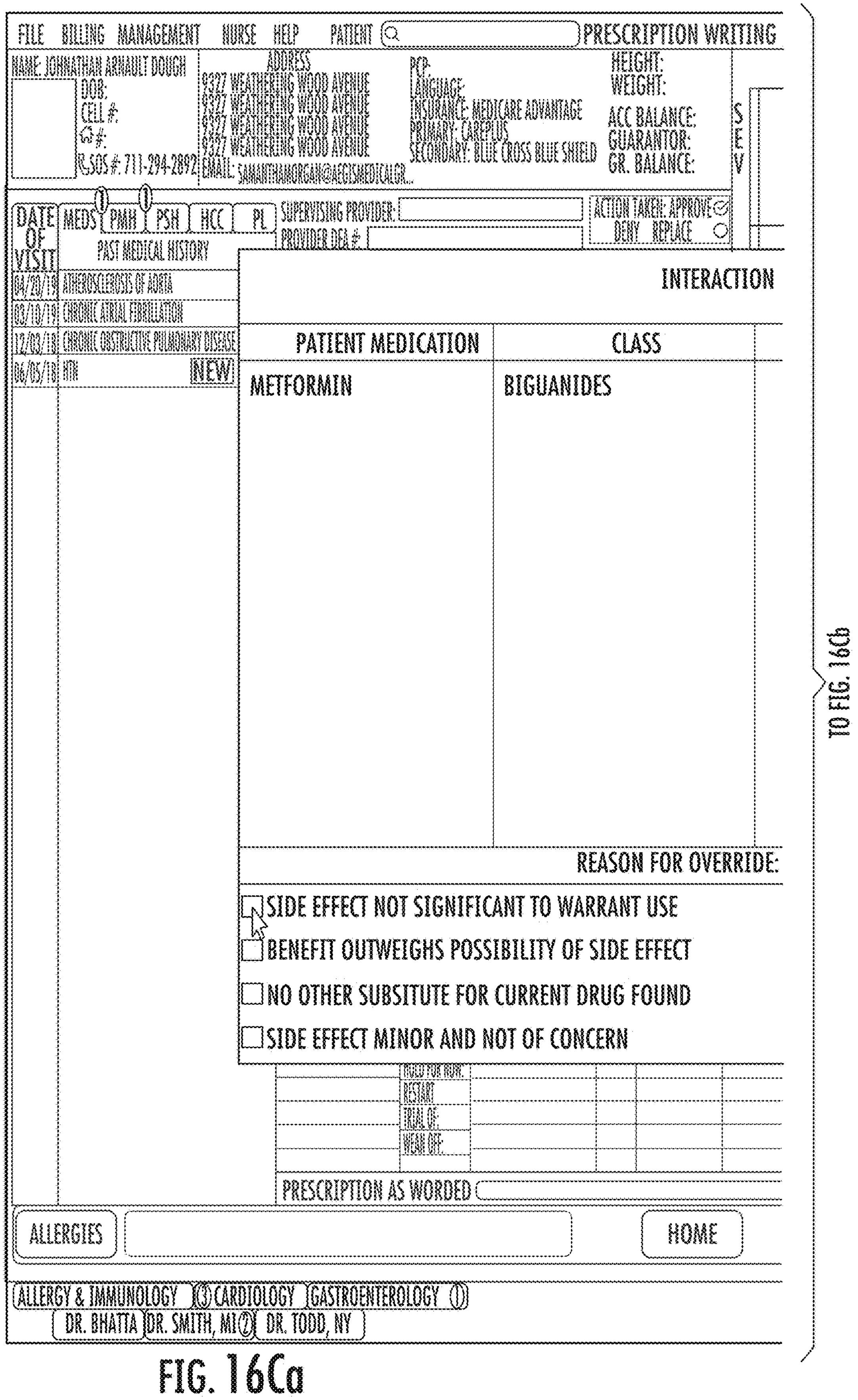
Figure 16C:
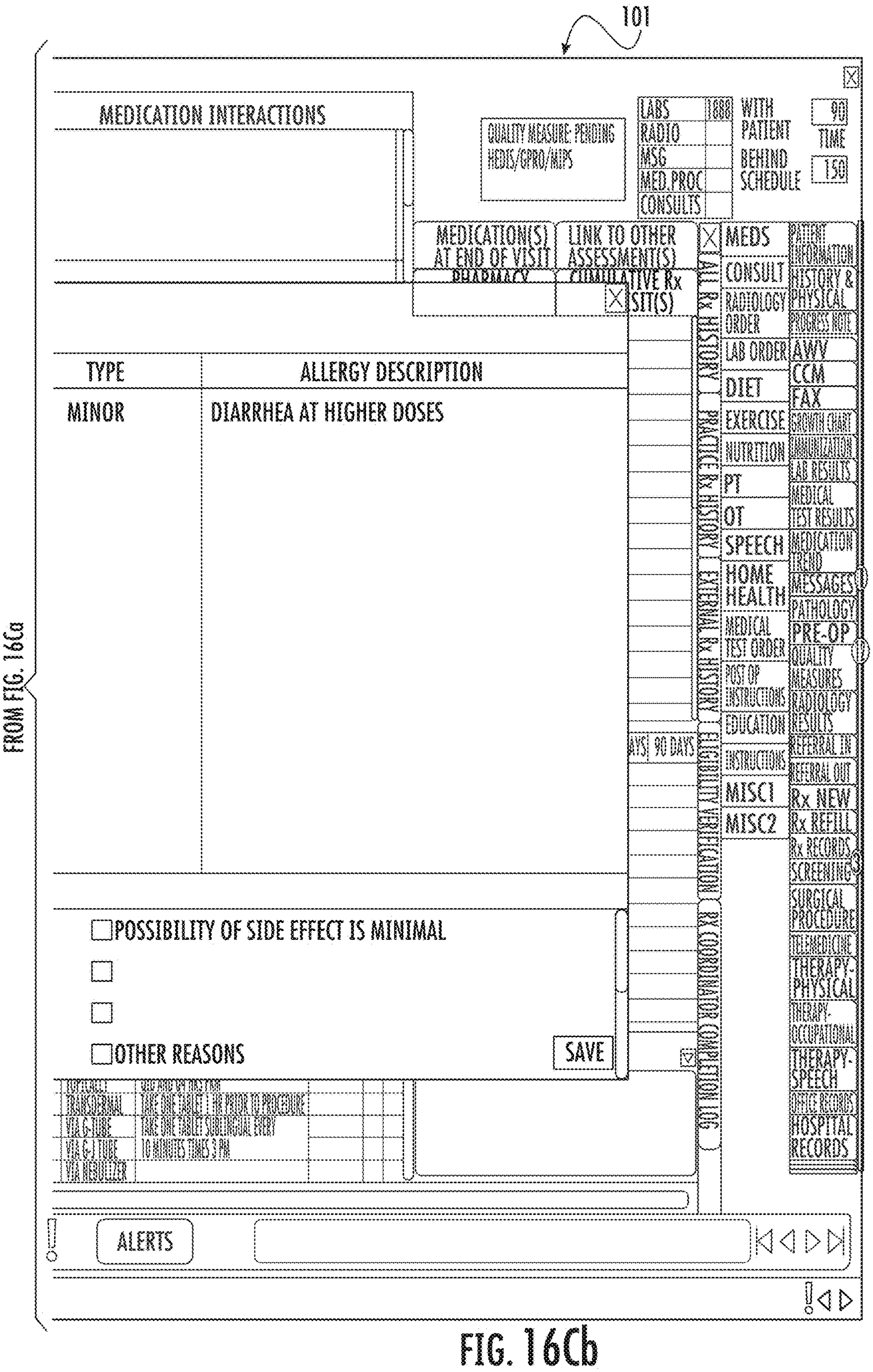
Figure 16D:
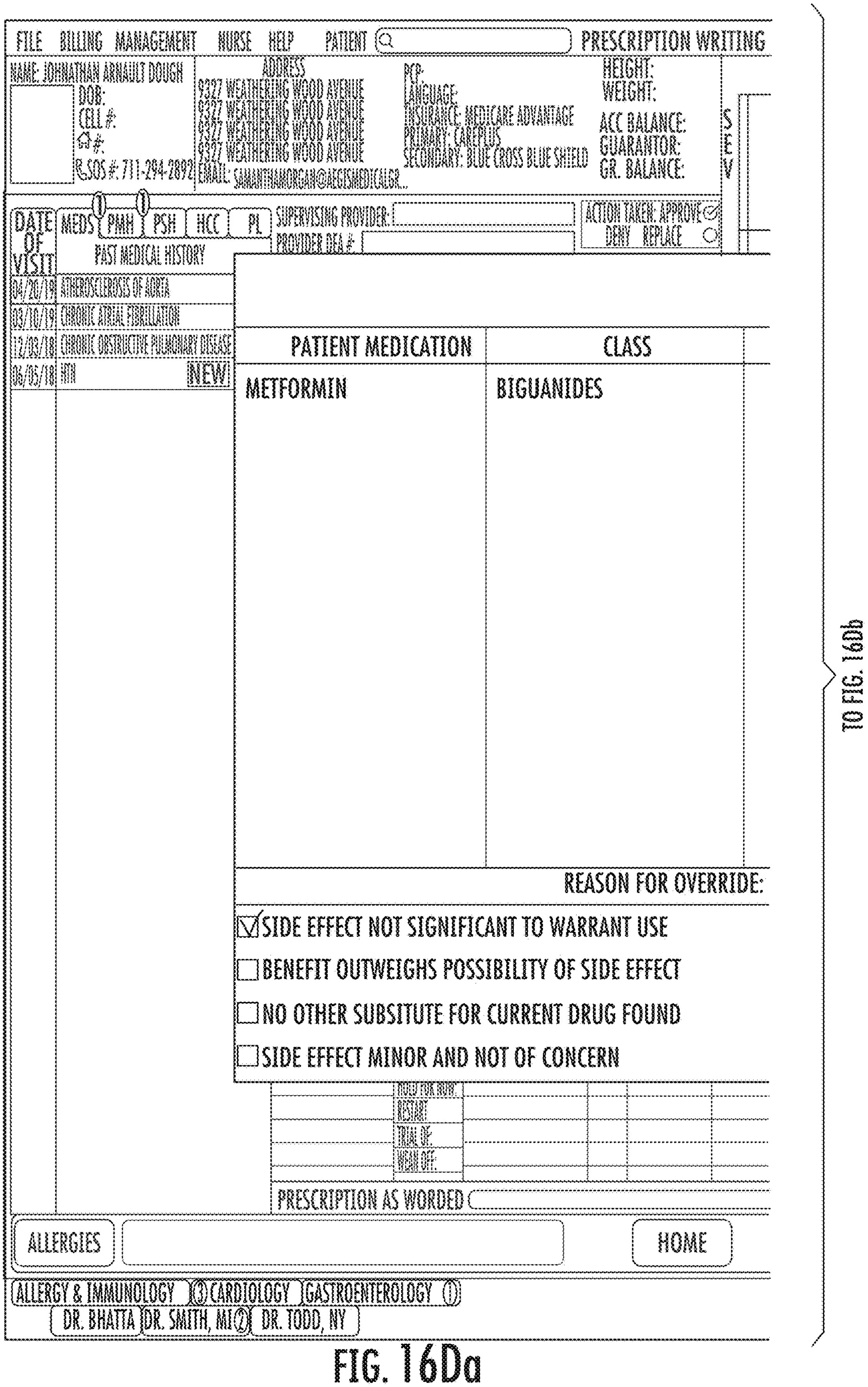
Figure 16D:
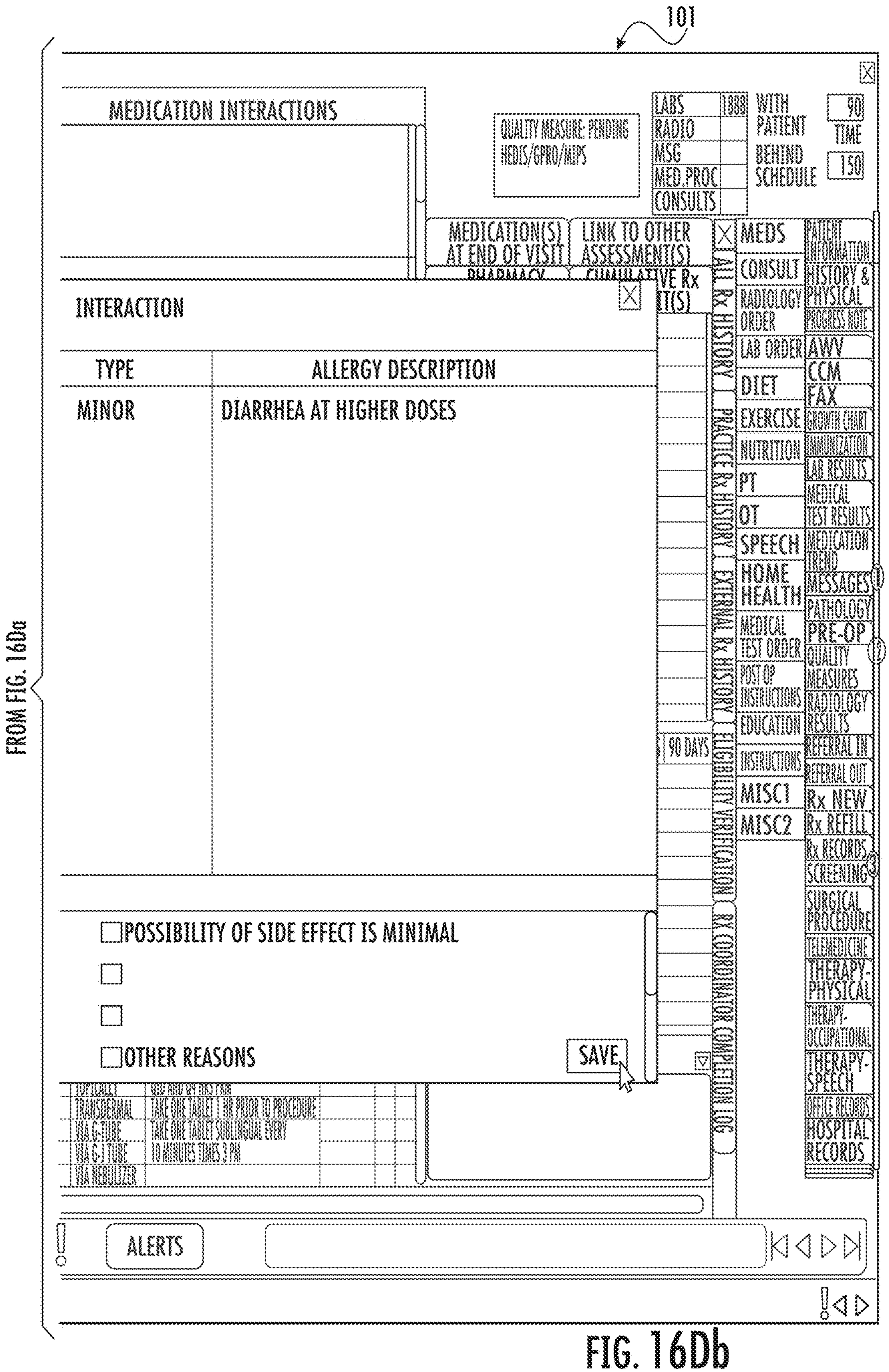
Figure 16E:
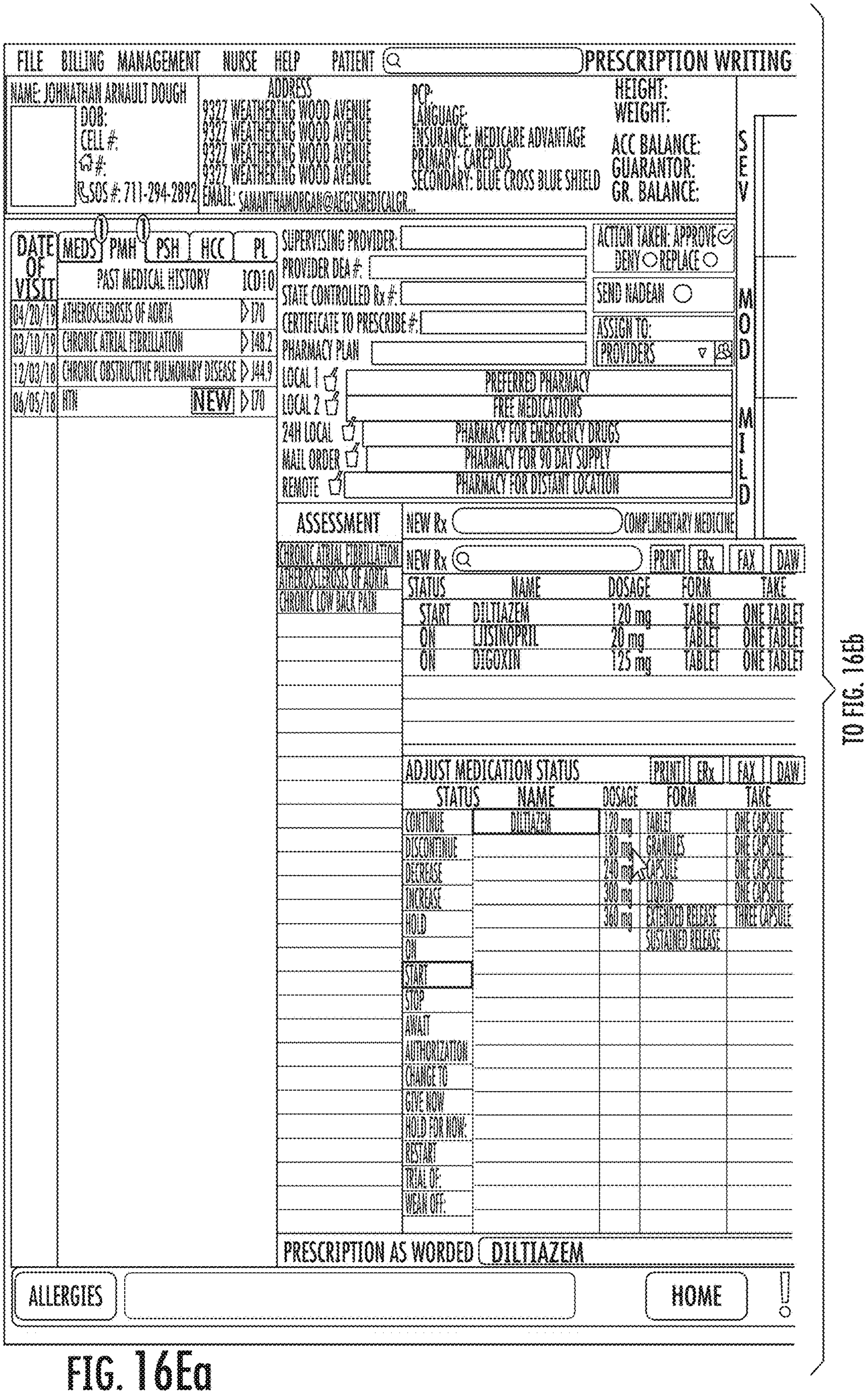
Figure 16E:
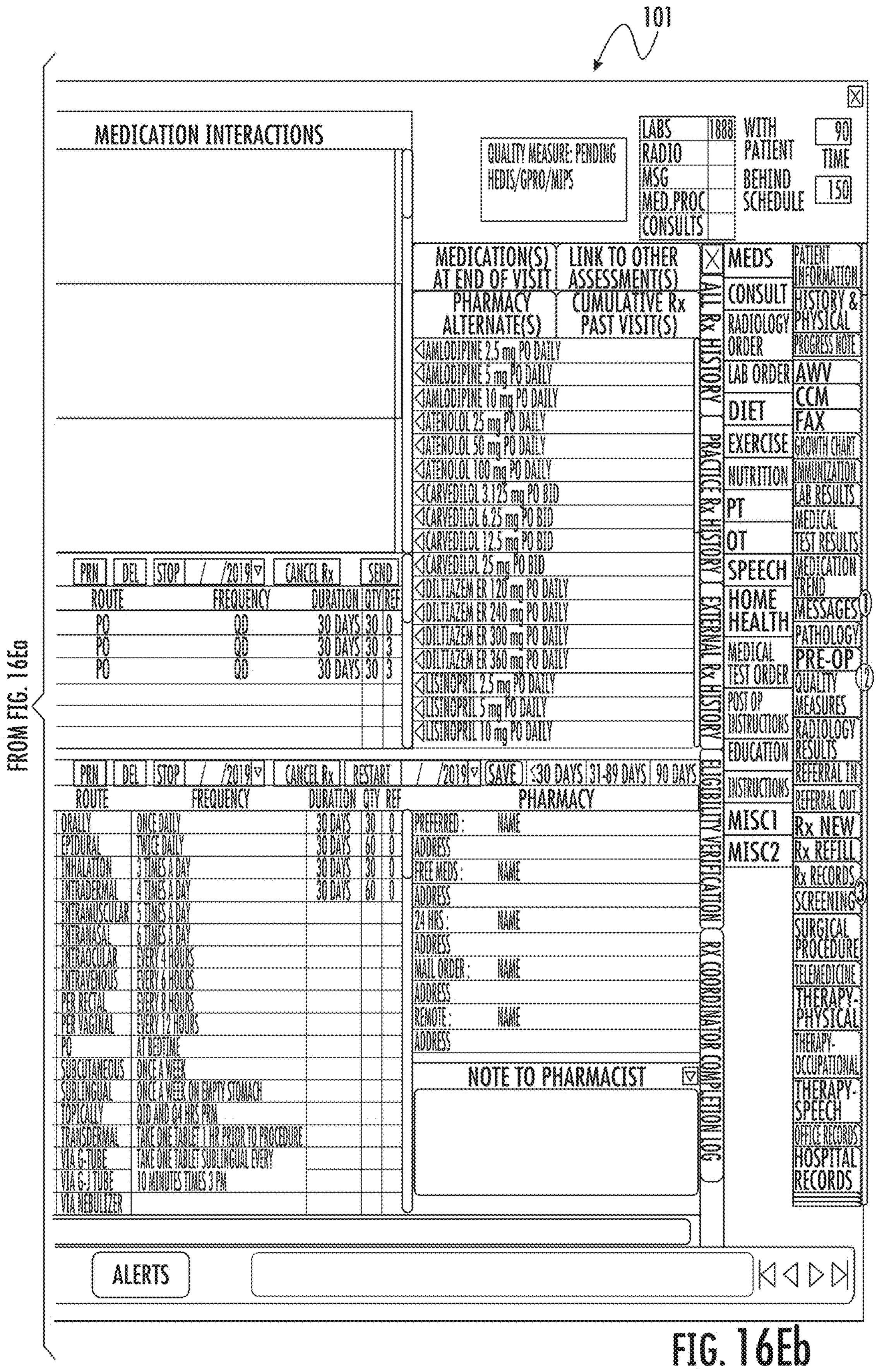
Figure 16F:
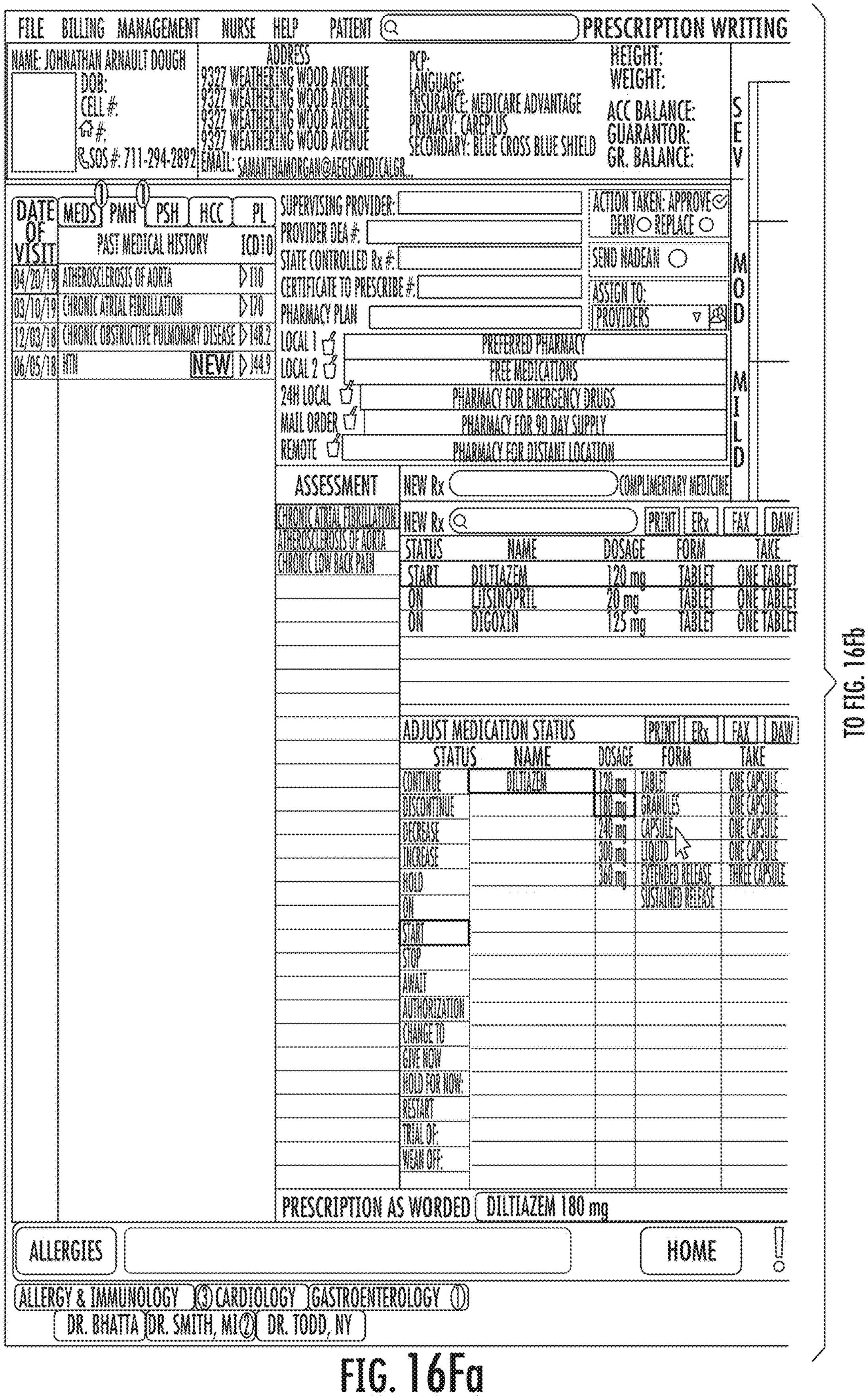
Figure 16F:
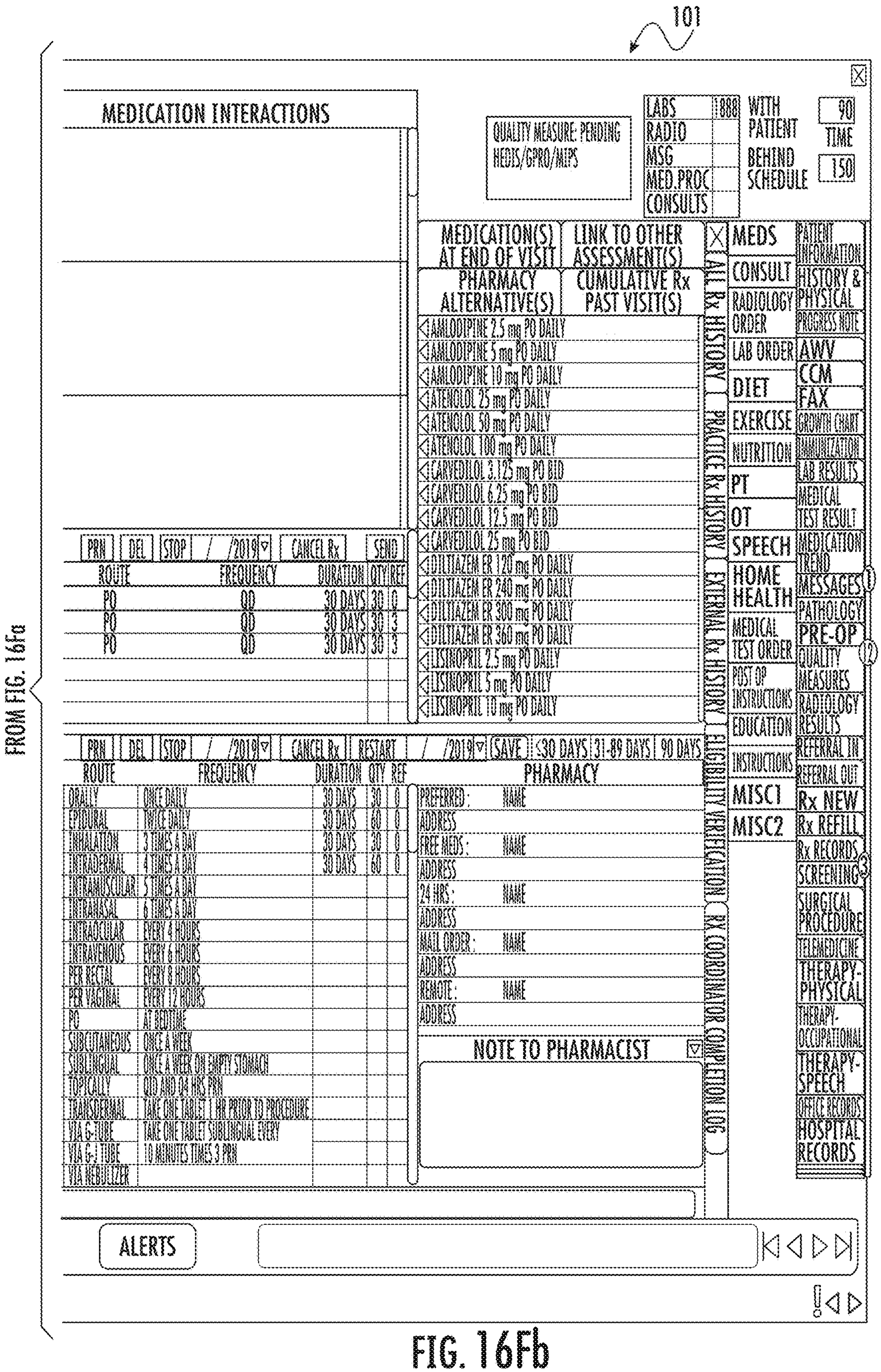
Figure 16G:
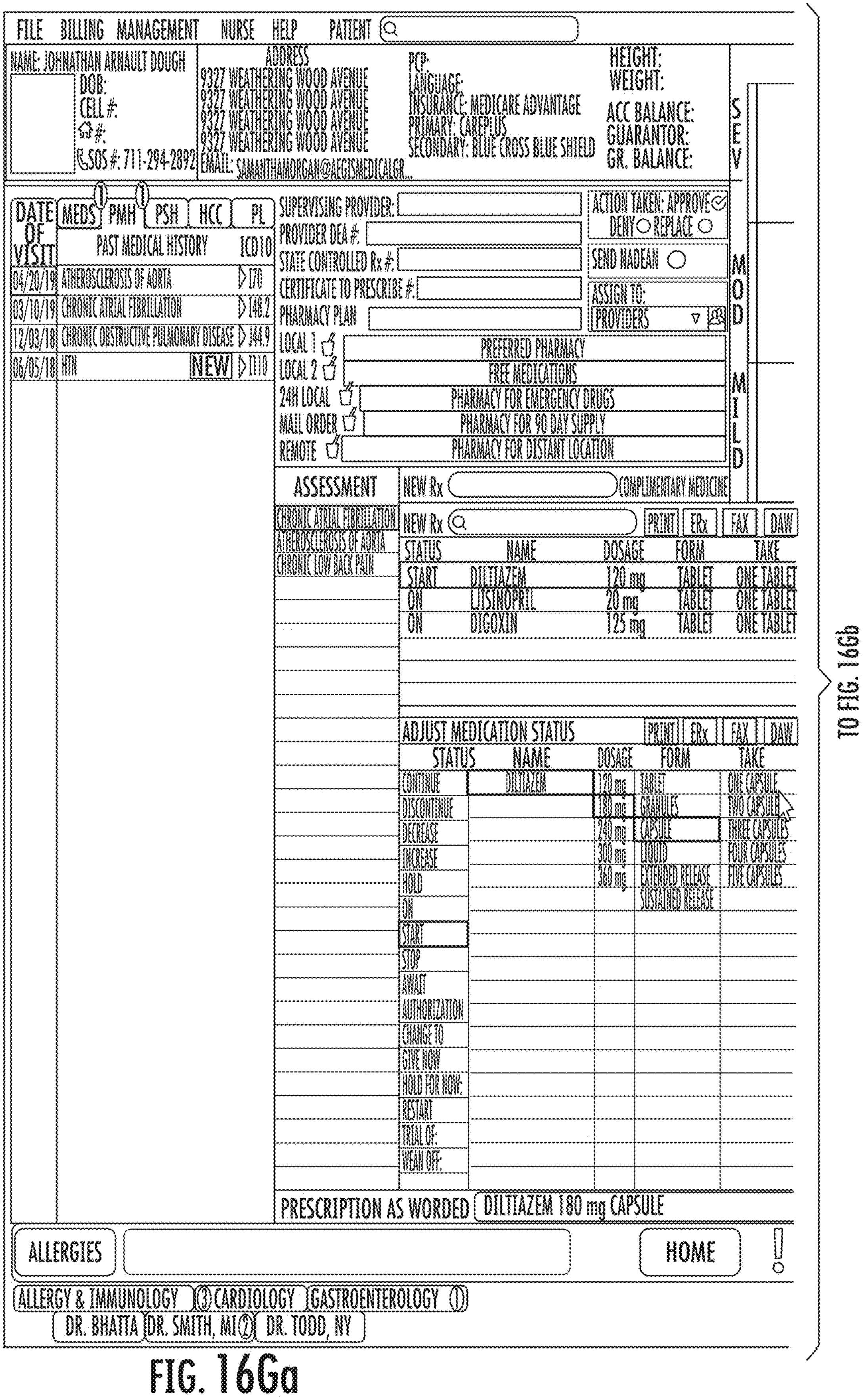
Figure 16G:
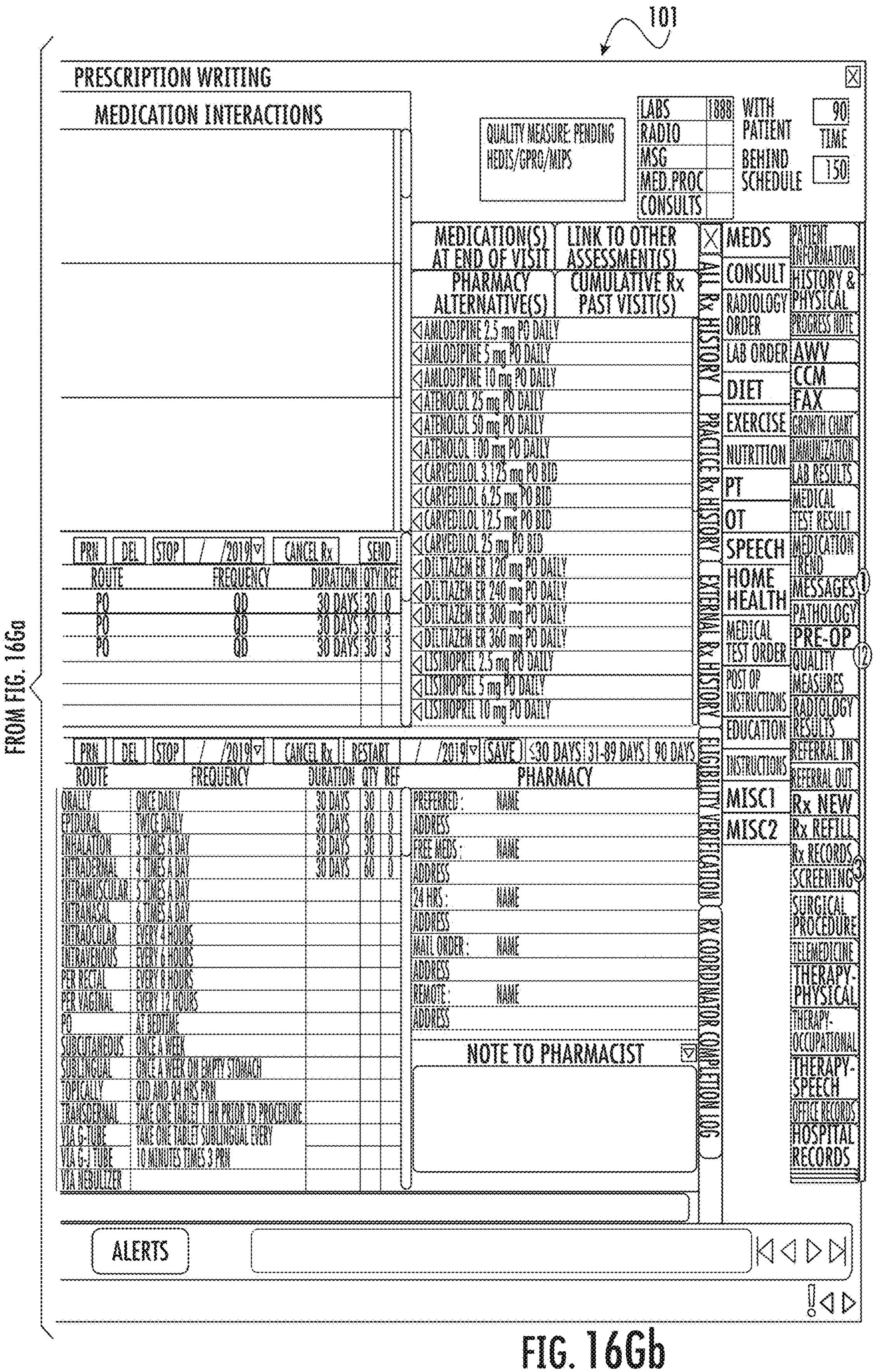
Figure 16H:
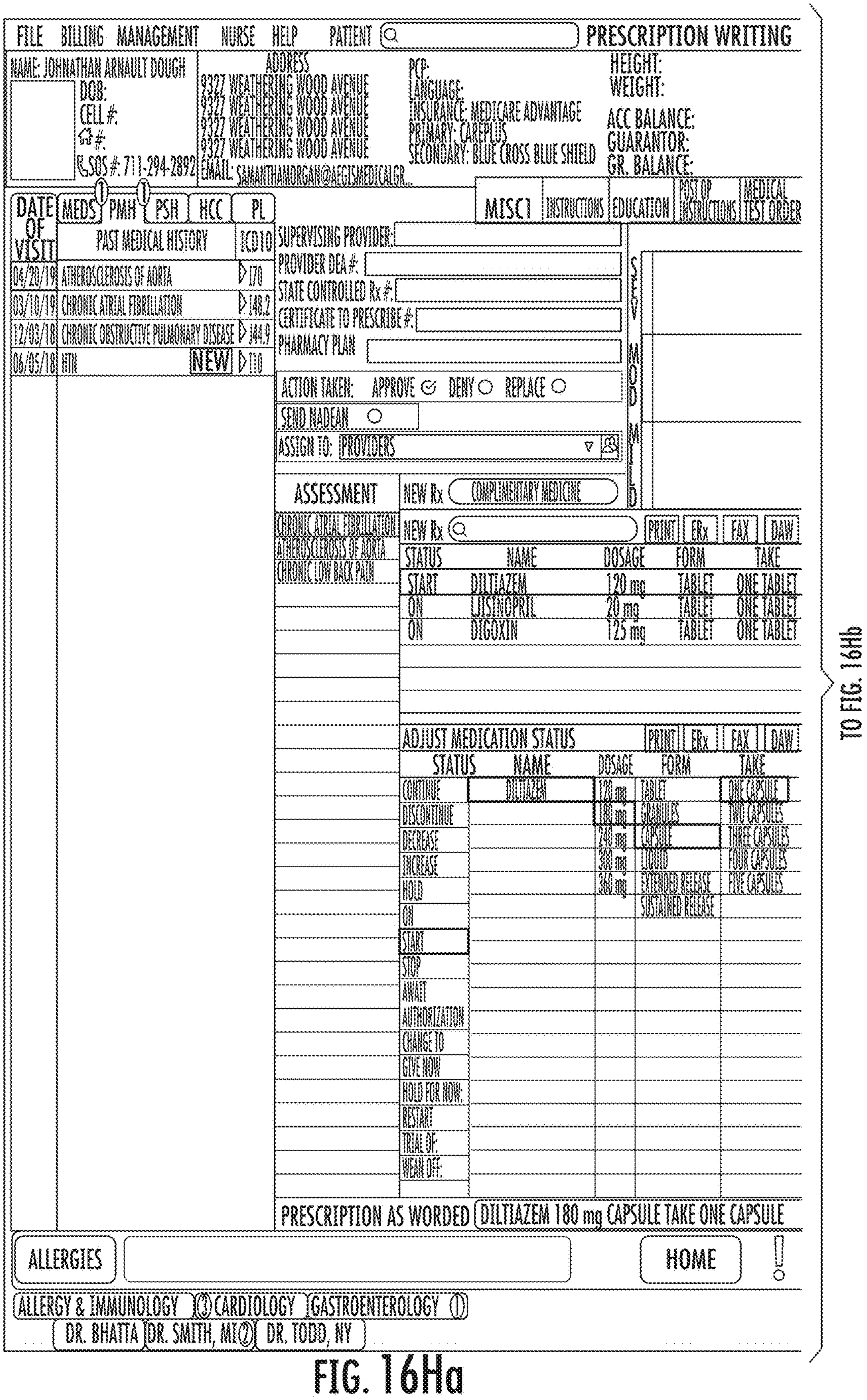
Figure 16H:
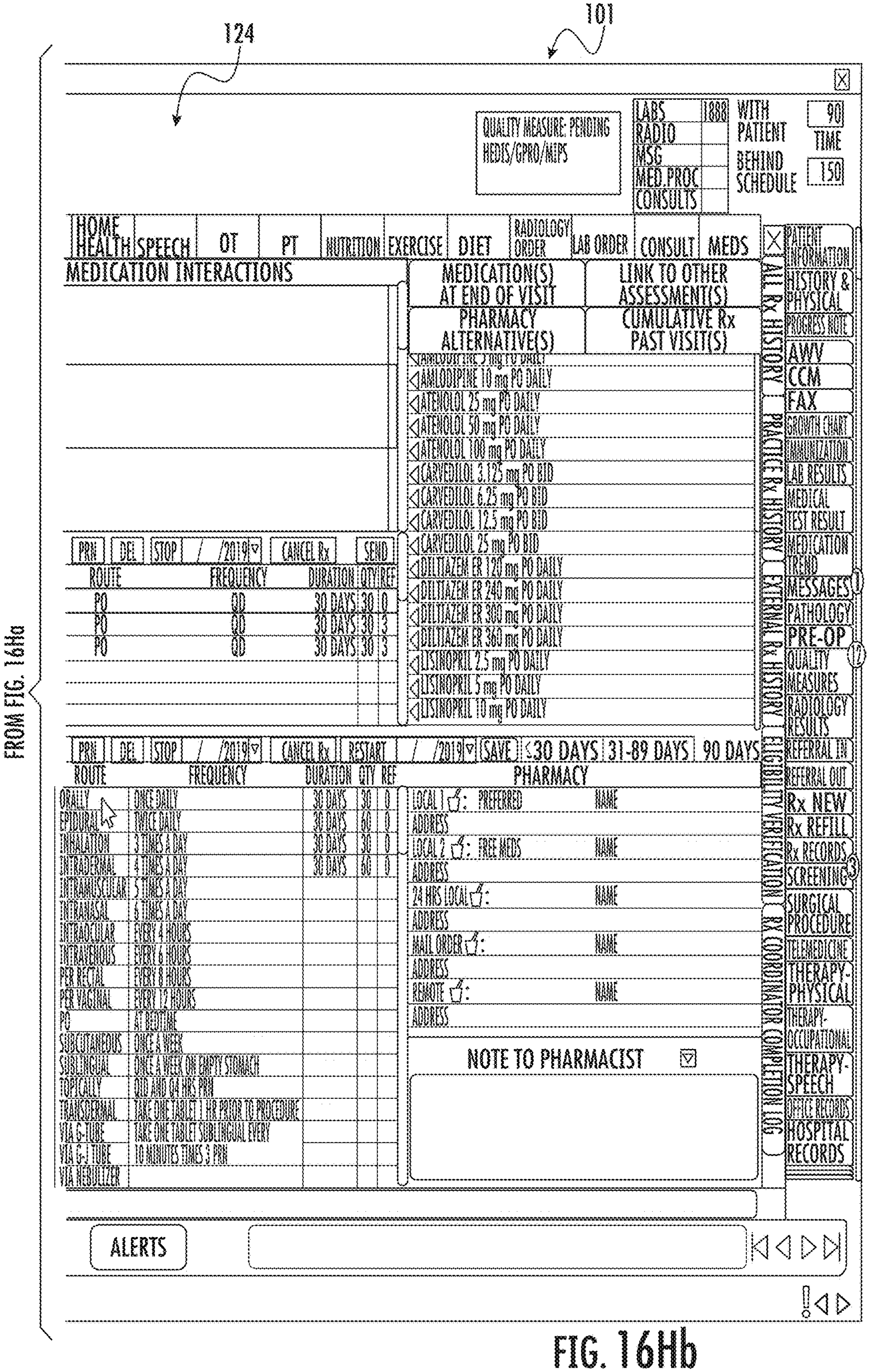
Figure 16I:
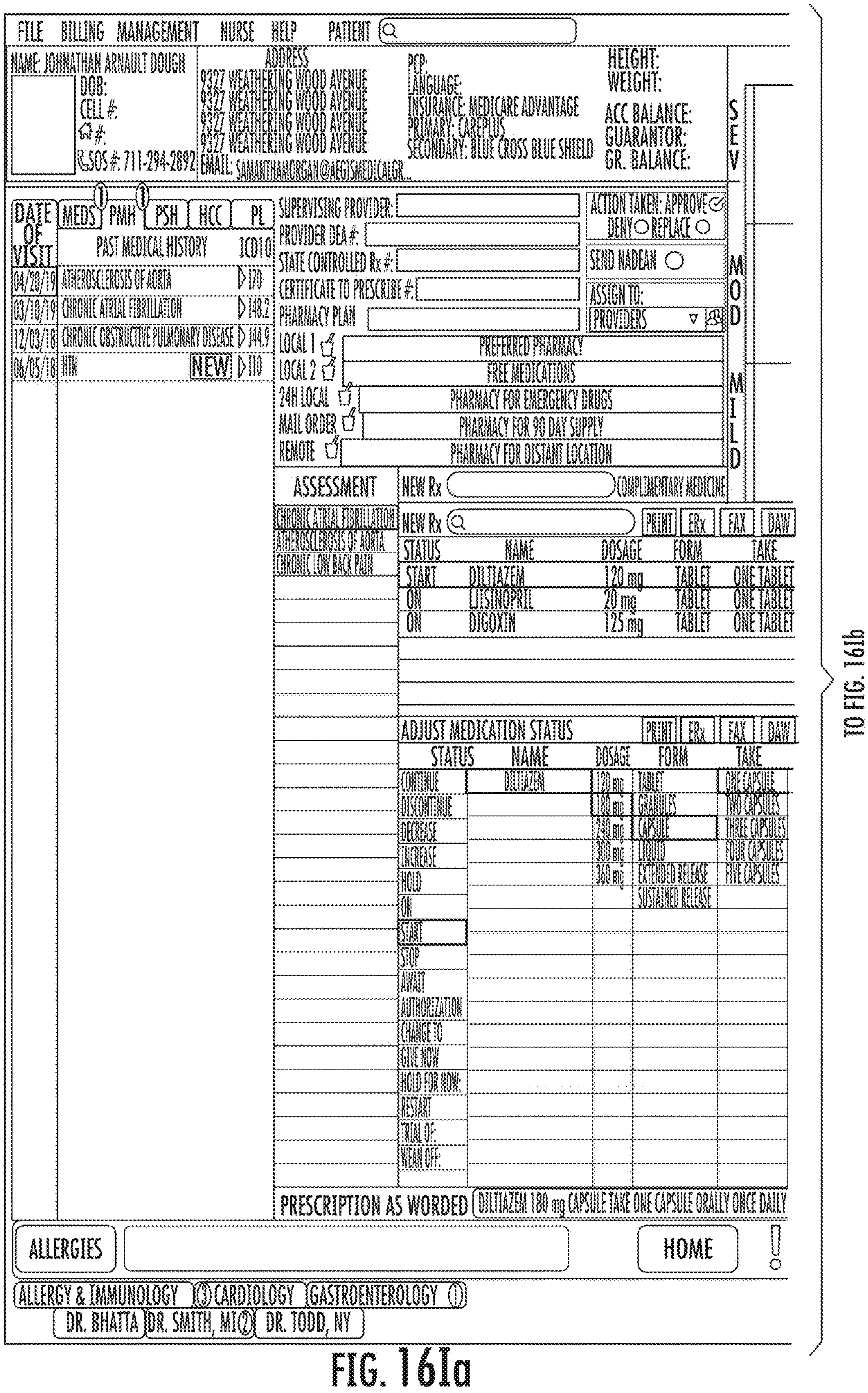
Figure 16I:
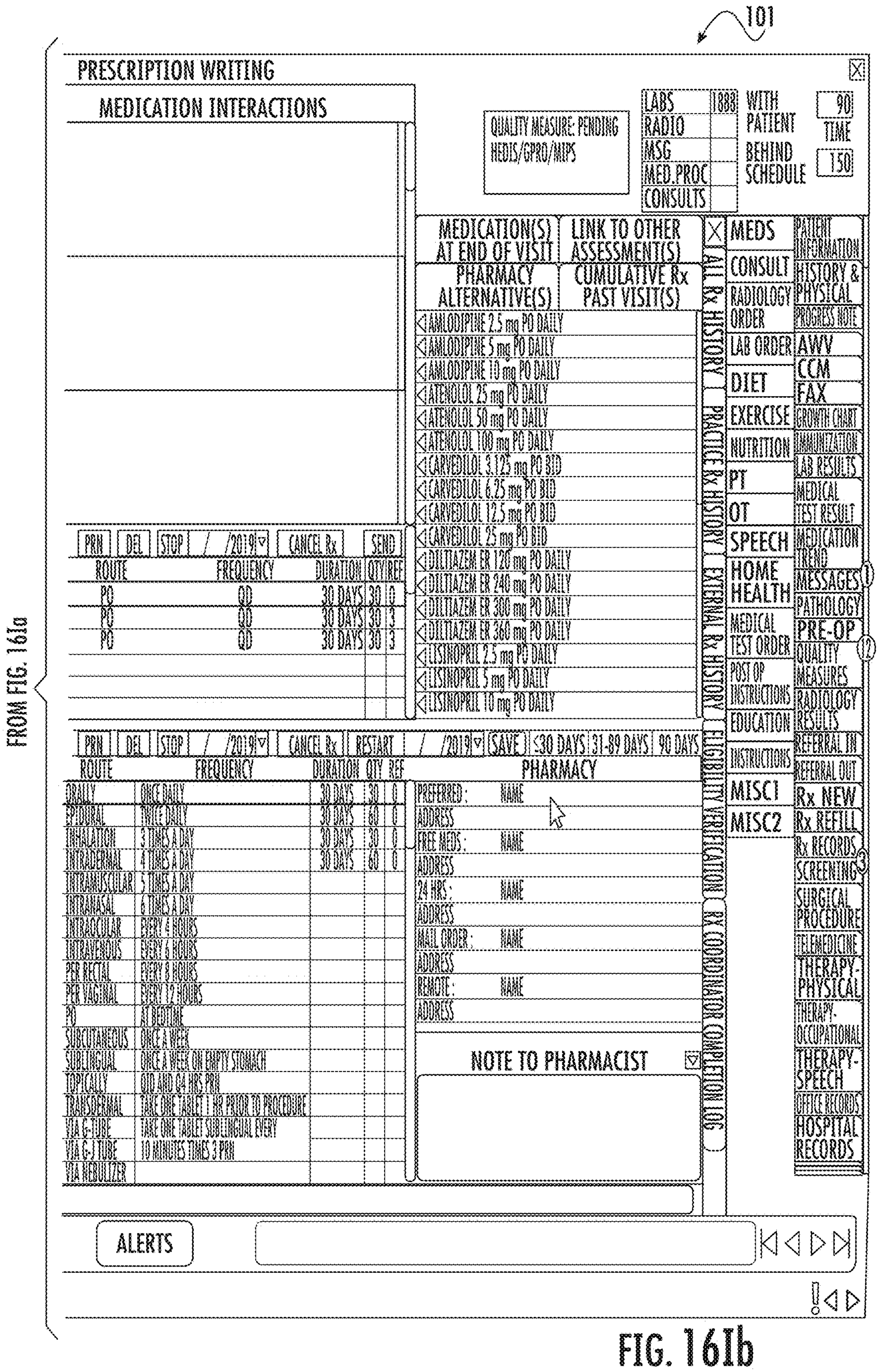
Figure 16J:
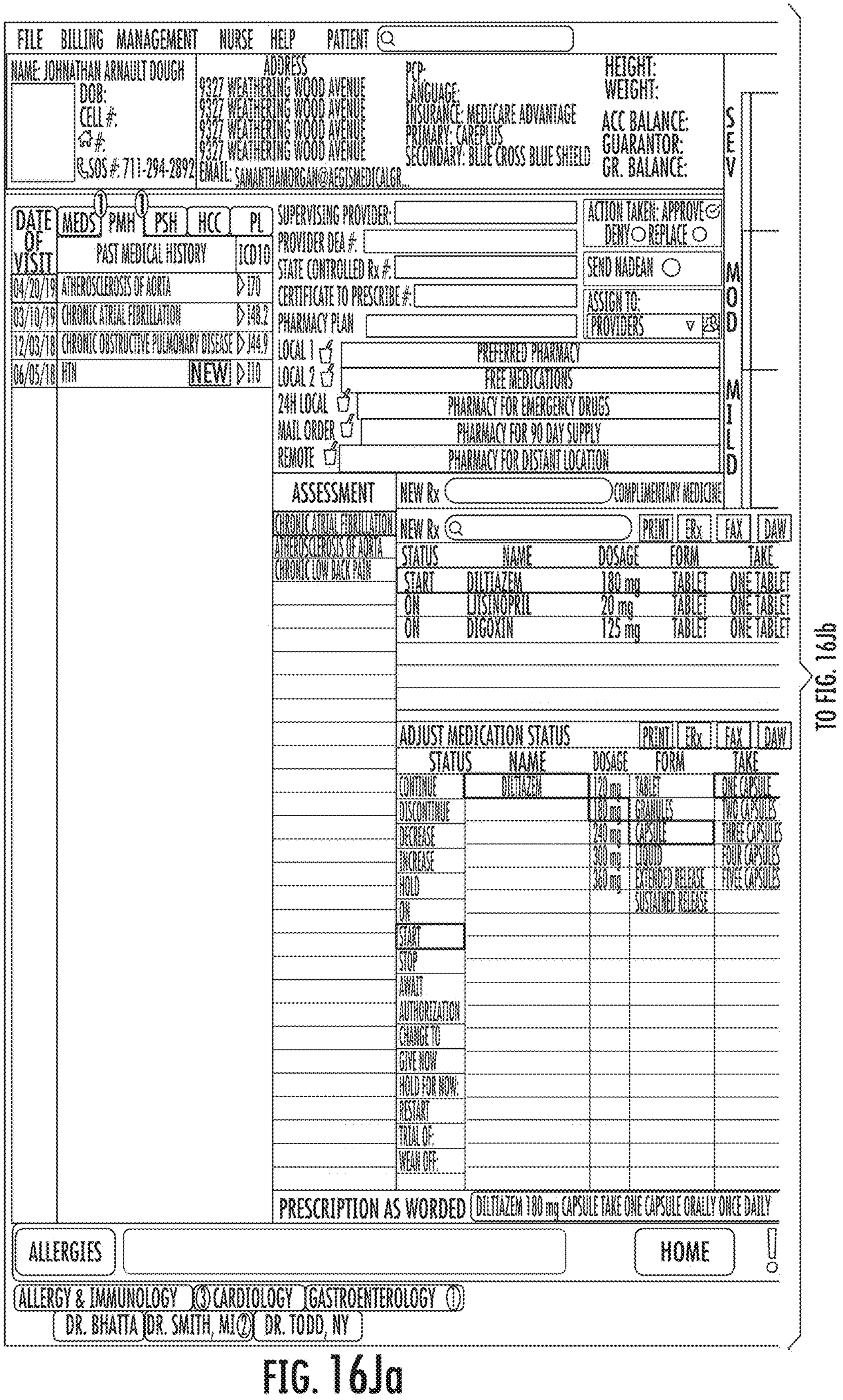
Figure 16J:
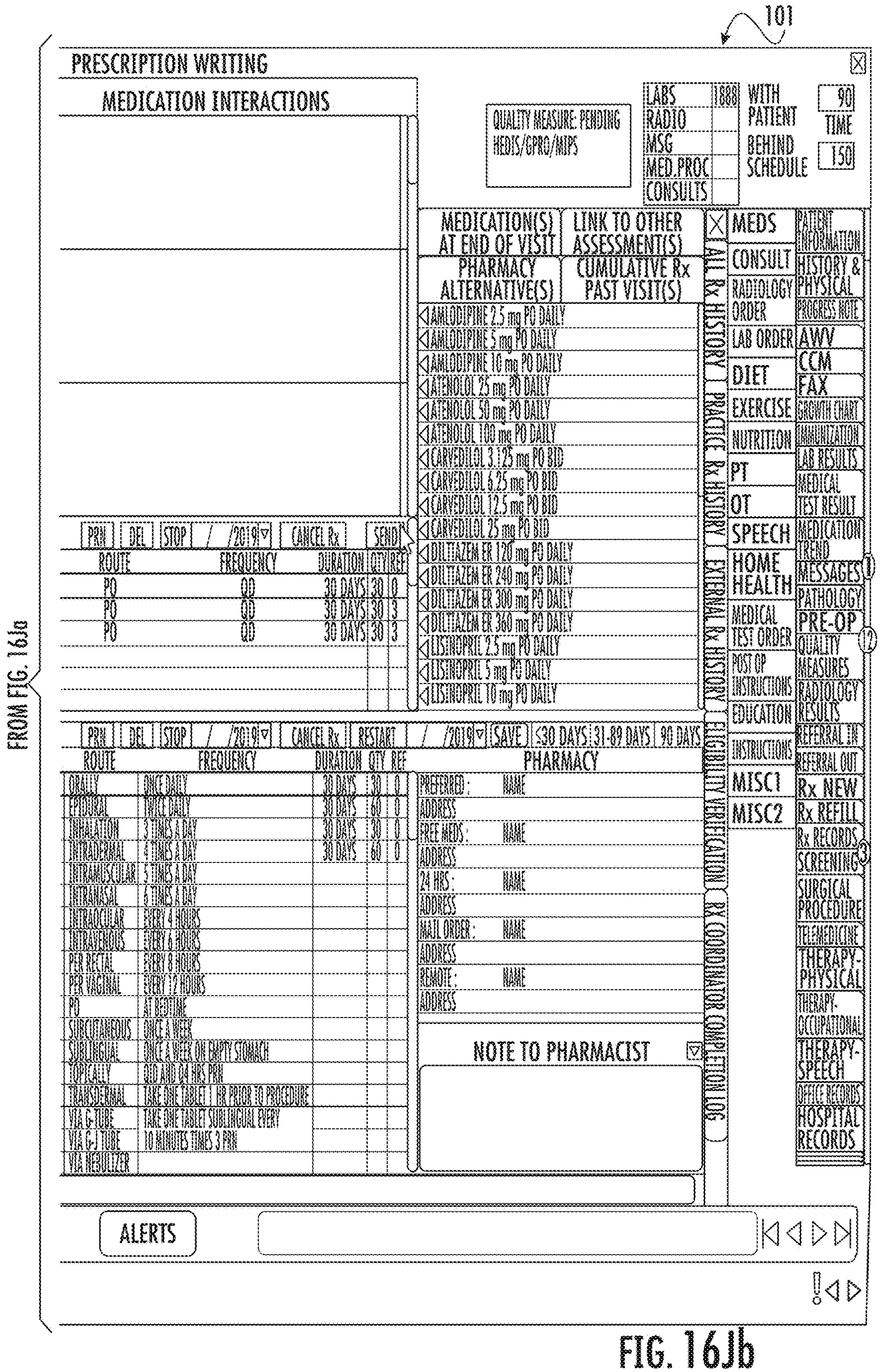
Figure 16K:
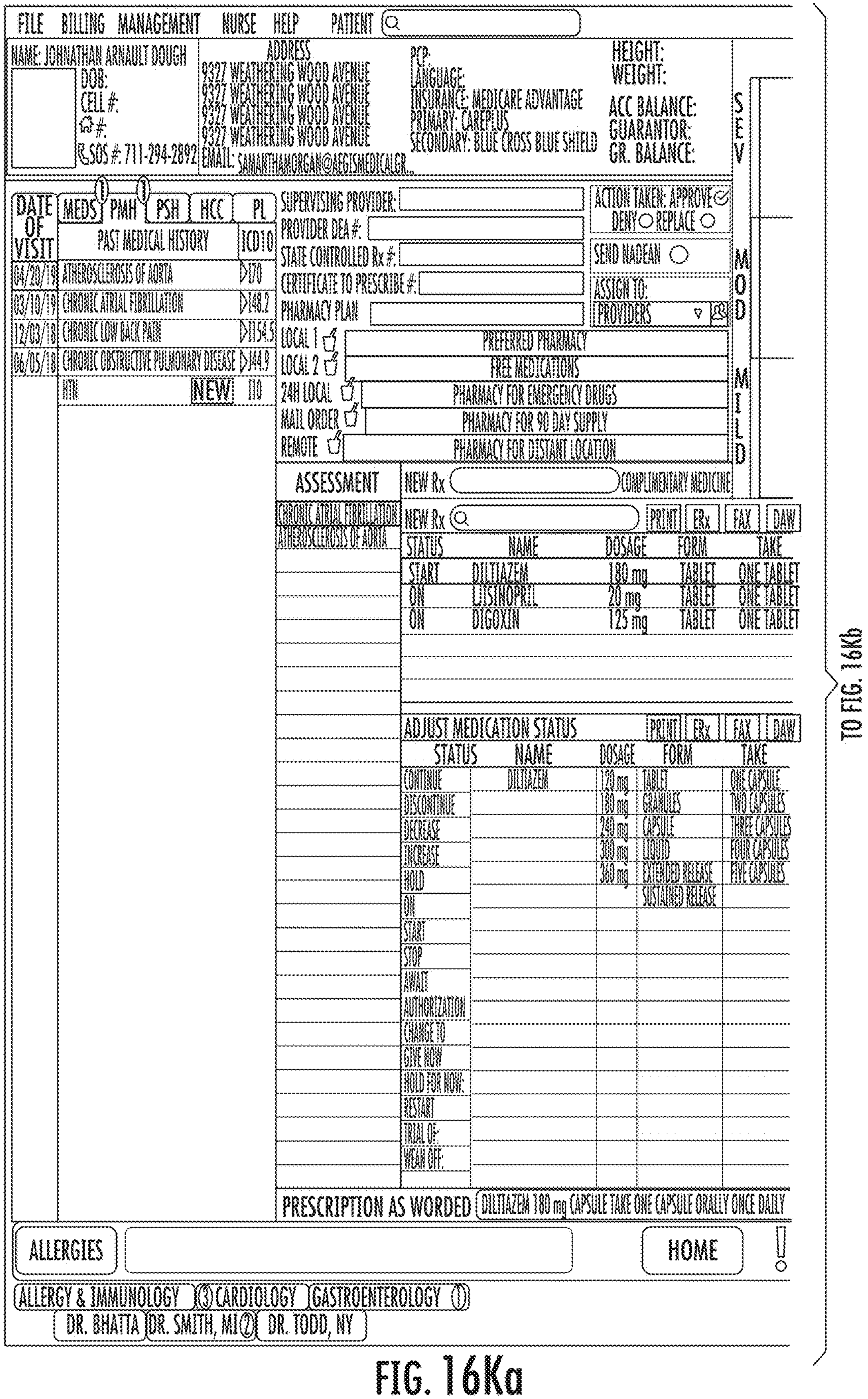
Figure 16K:
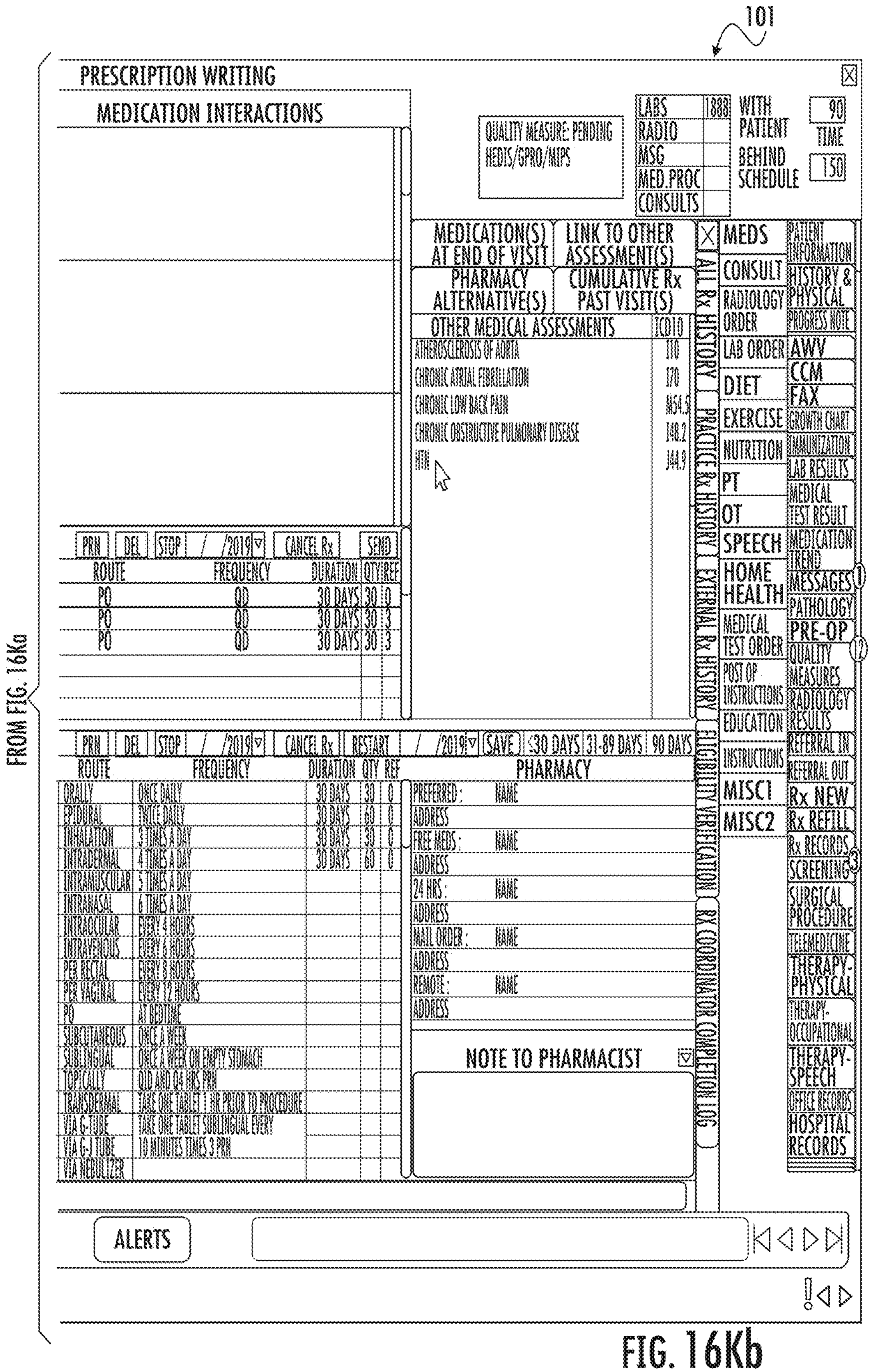
Figure 16L:
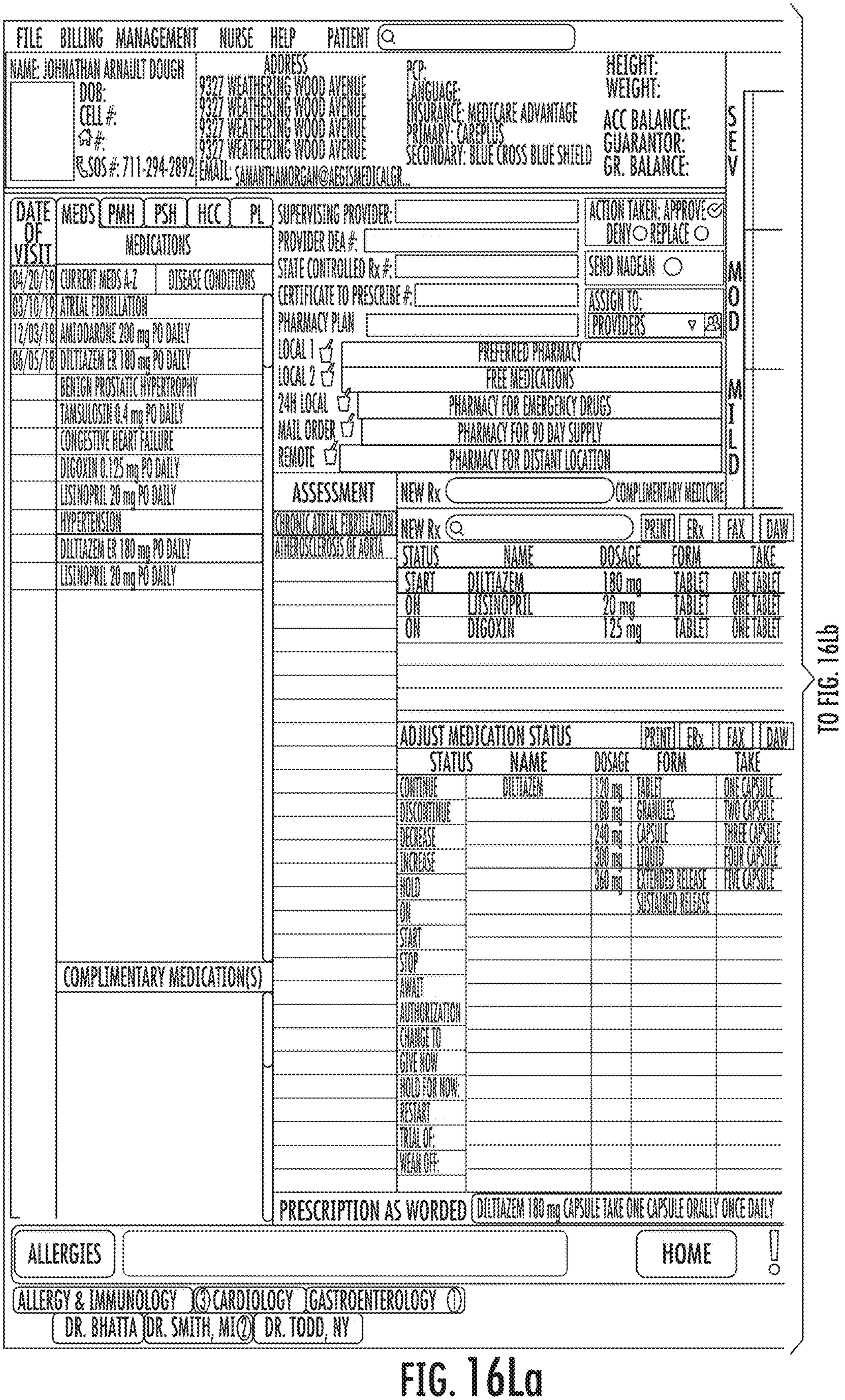
Figure 16L:
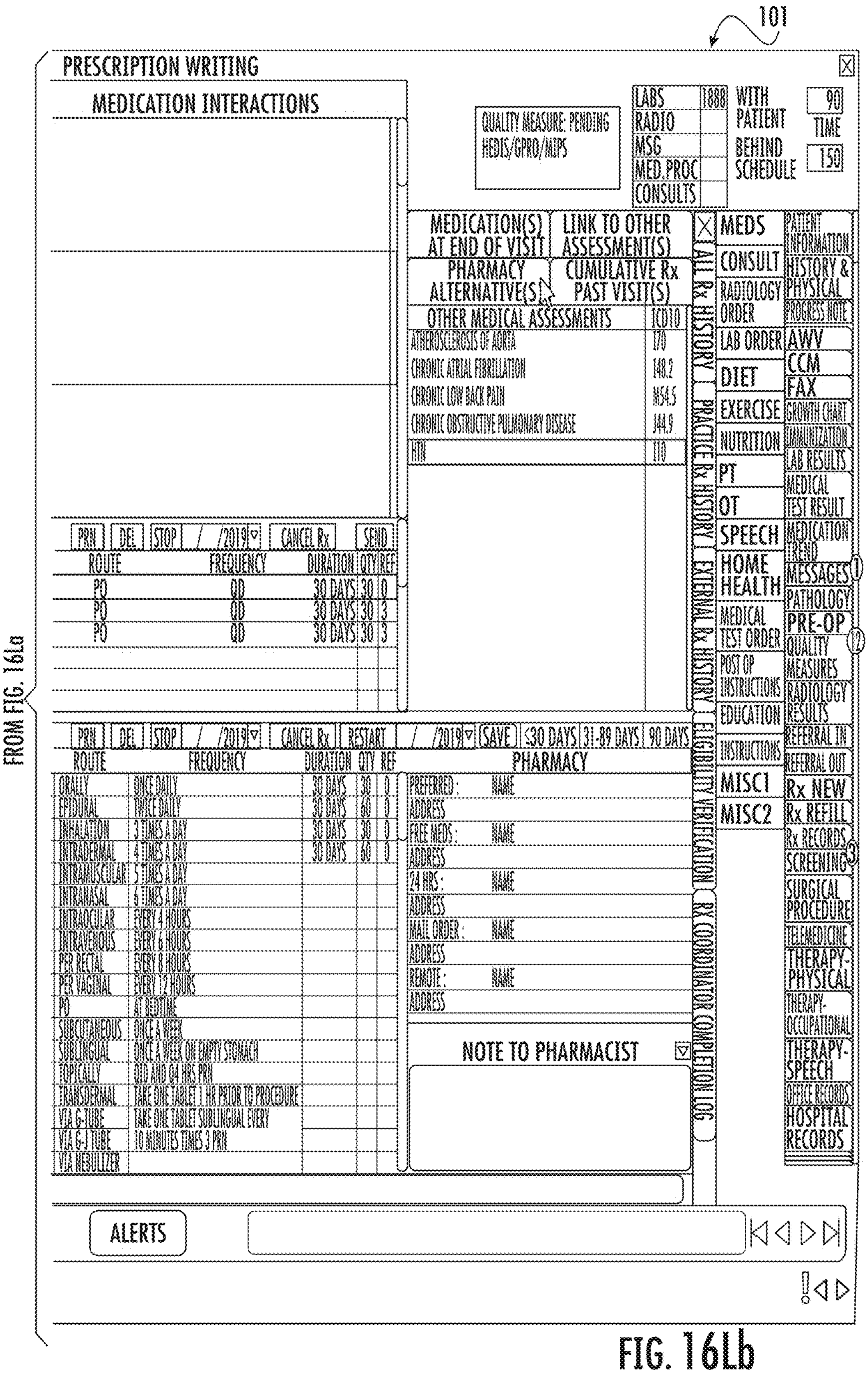
Figure 16M:
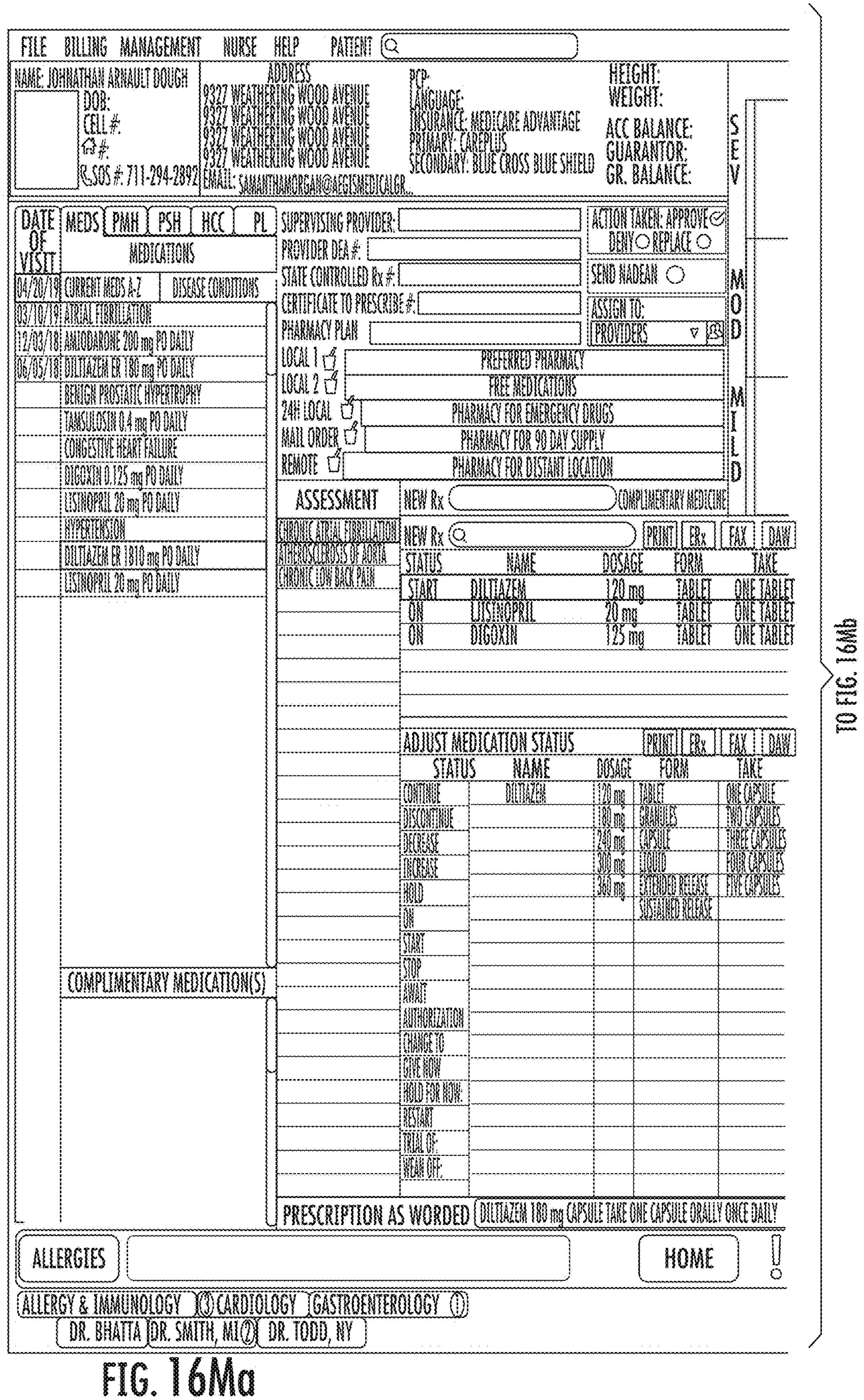
Figure 16M:
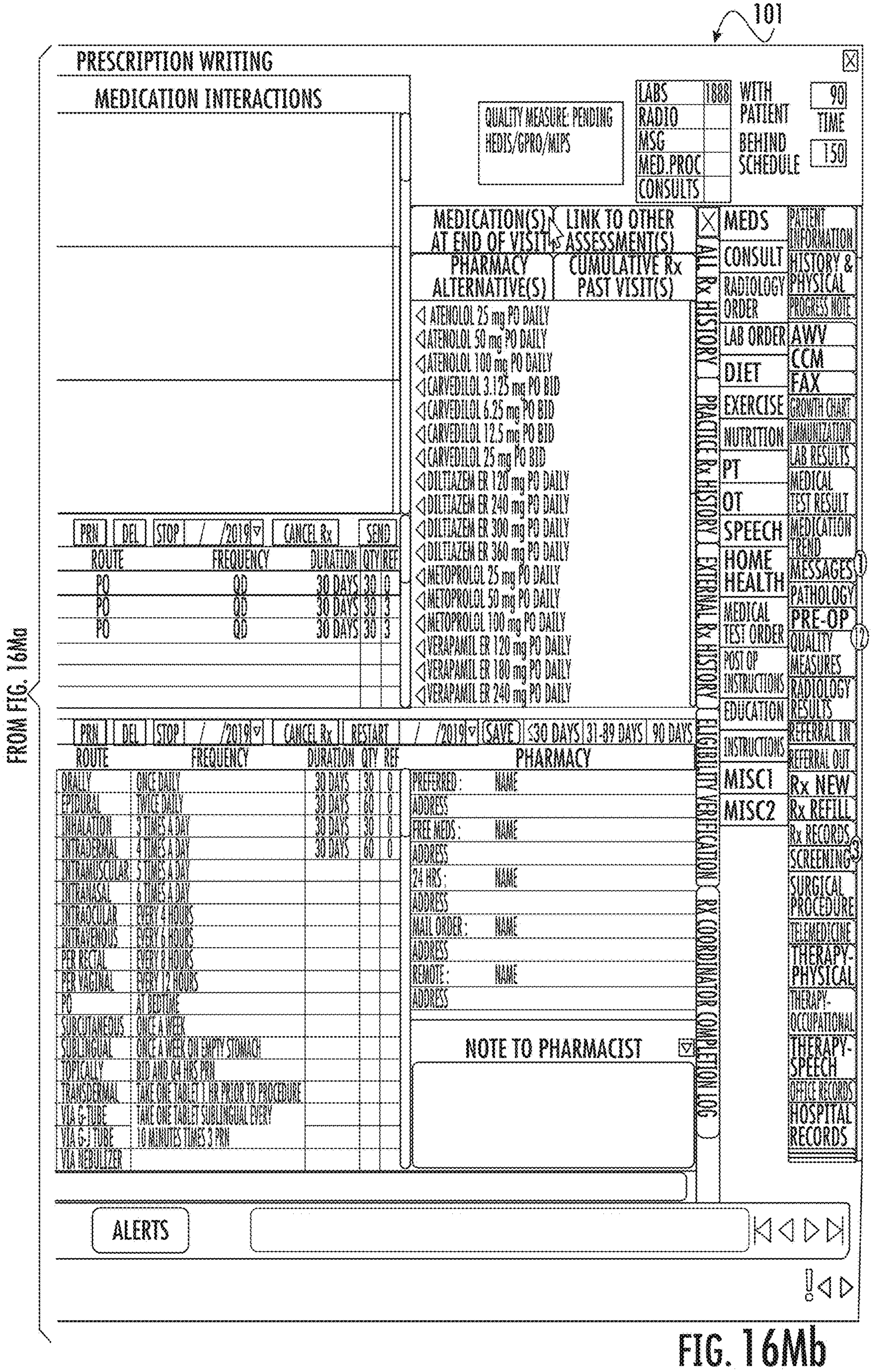
Figure 16N:
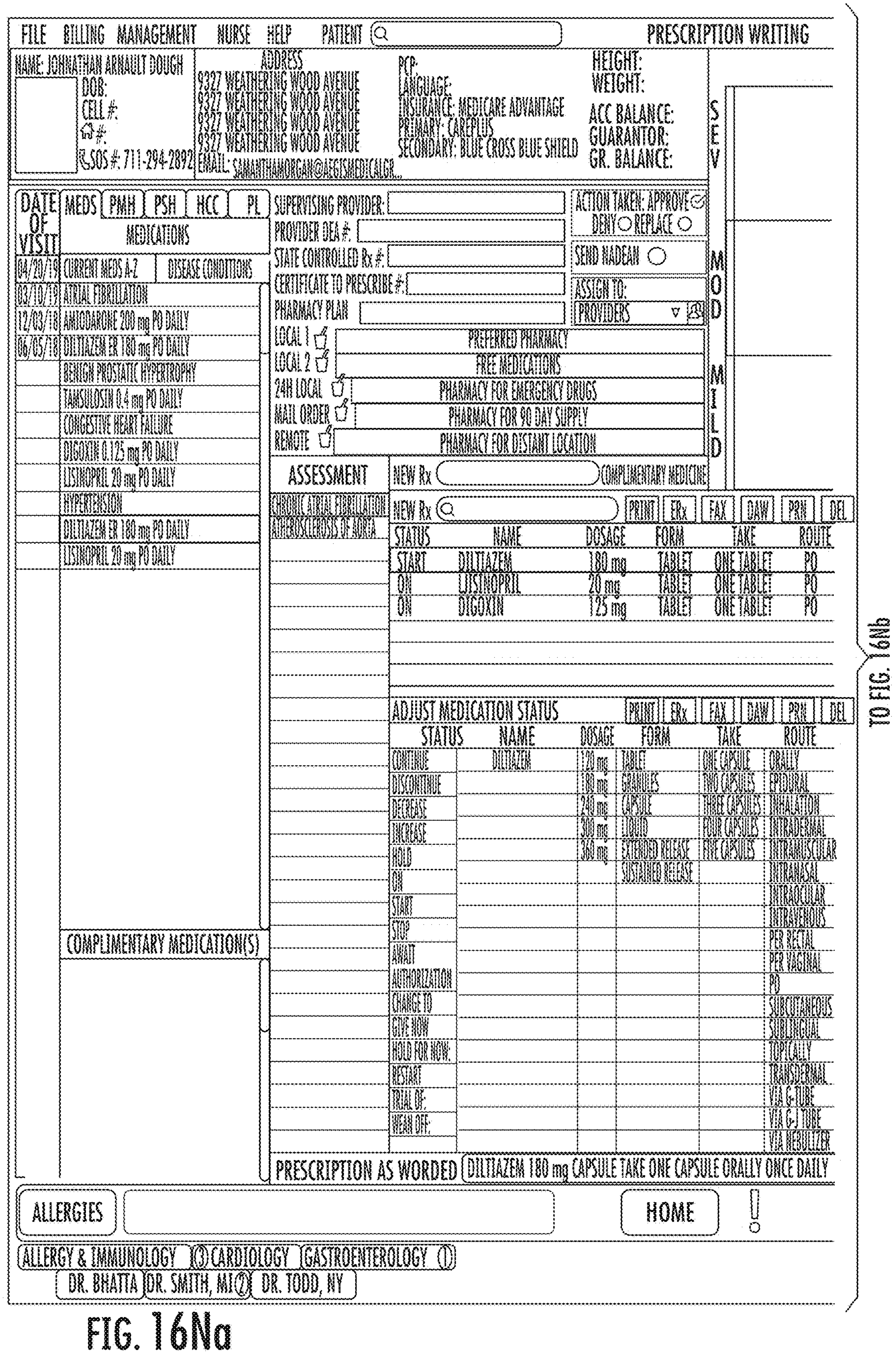
Figure 16N:
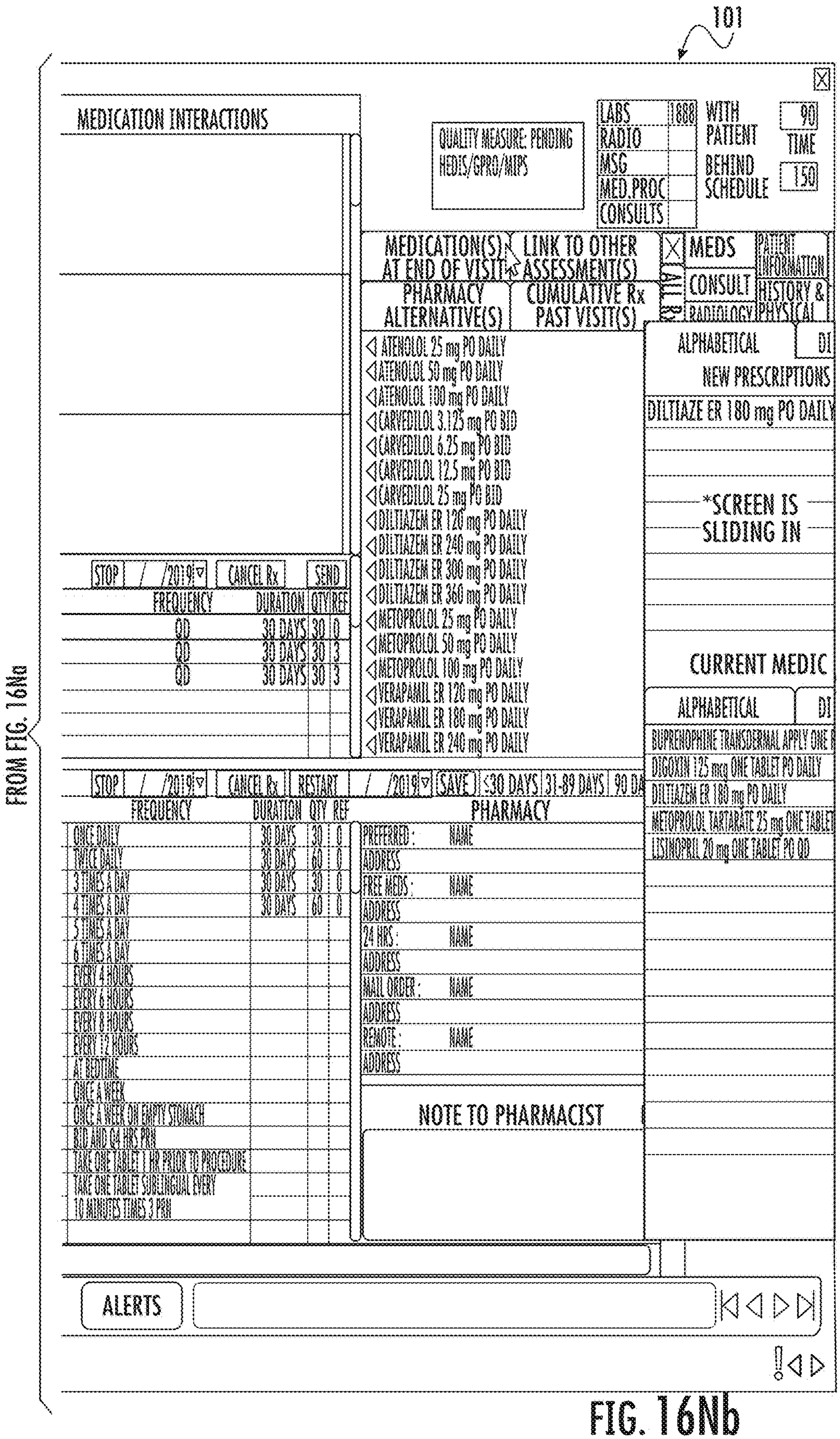
Figure 160A:
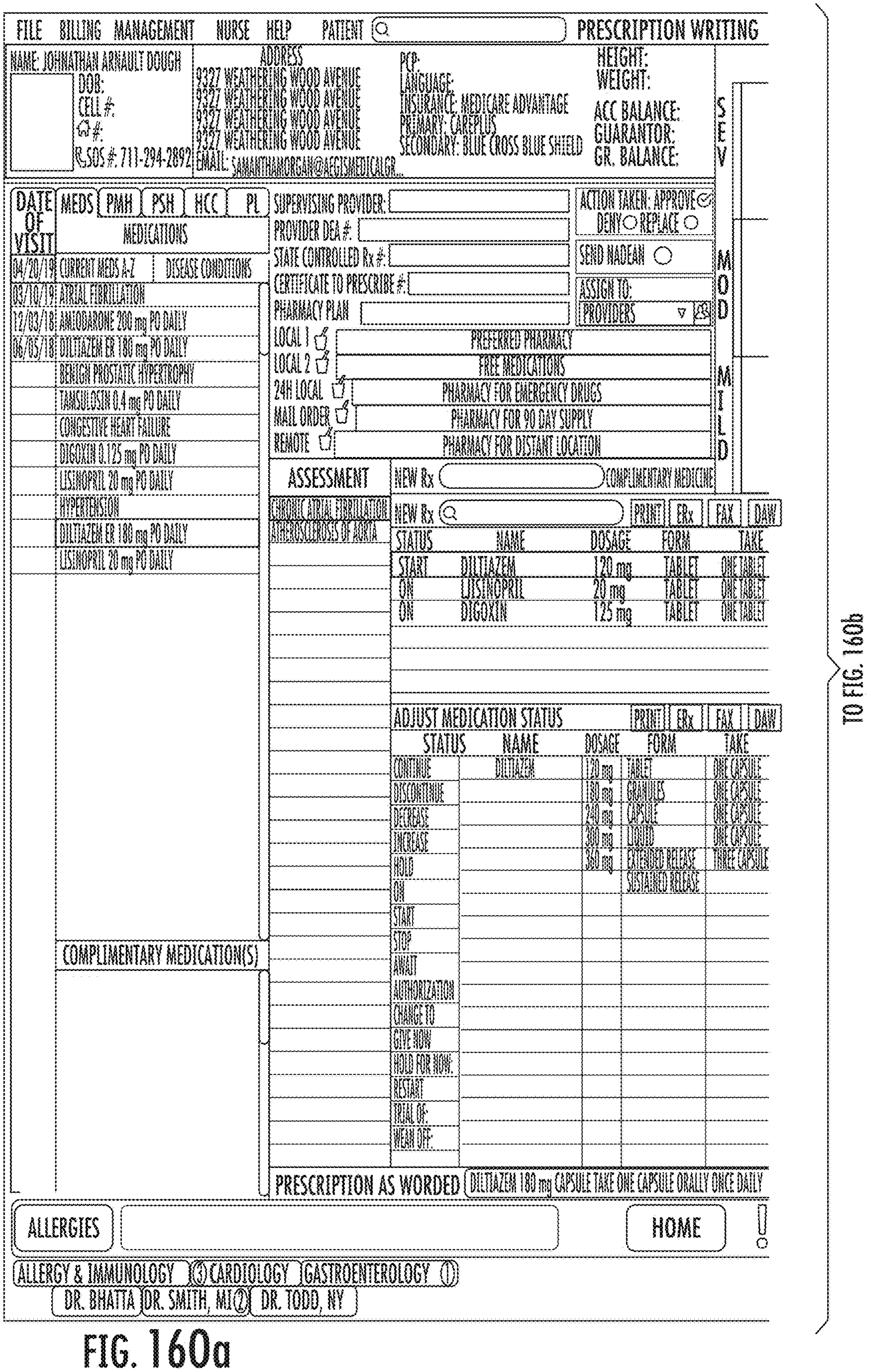
Figure 160B:
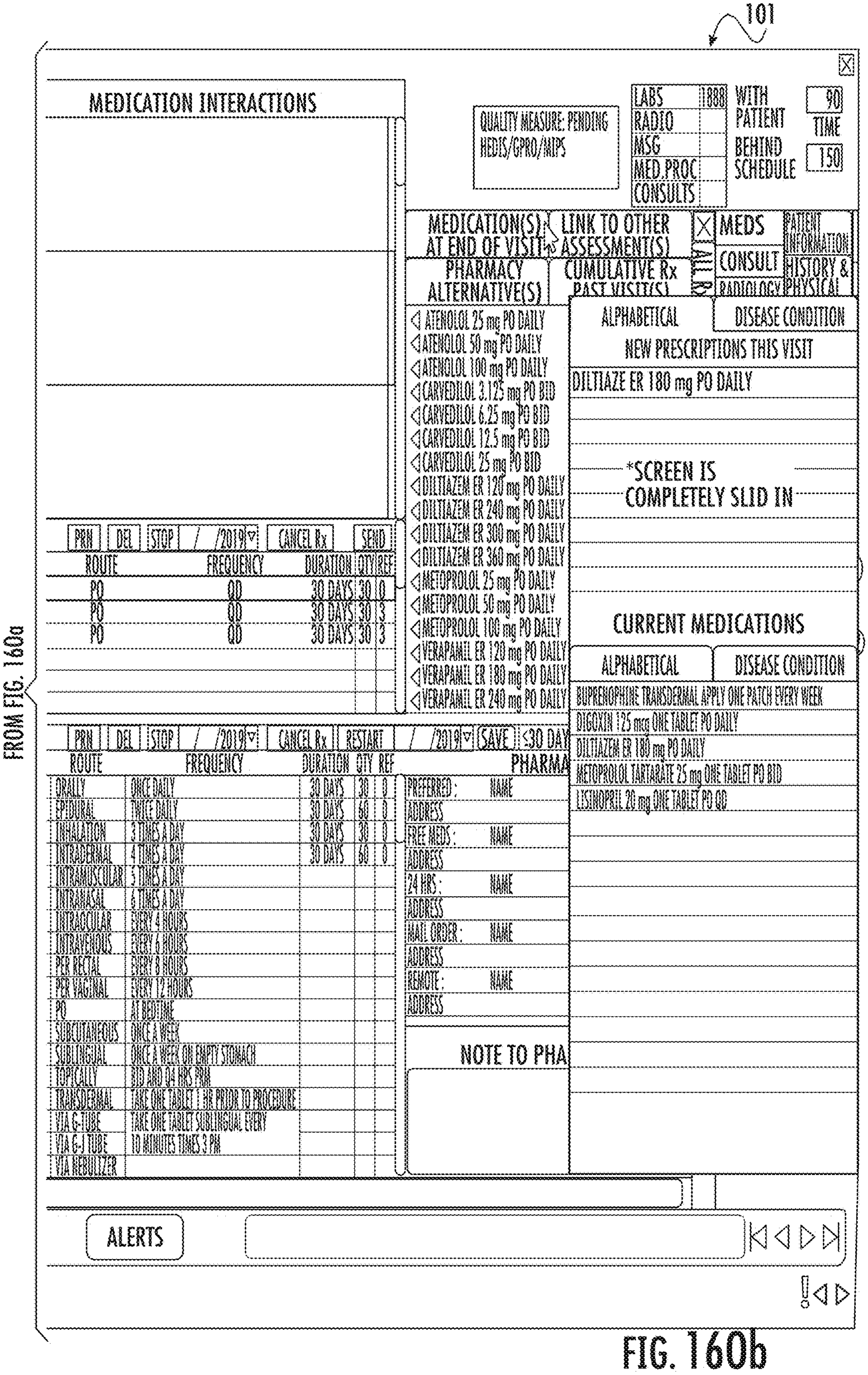
Figure 16P:
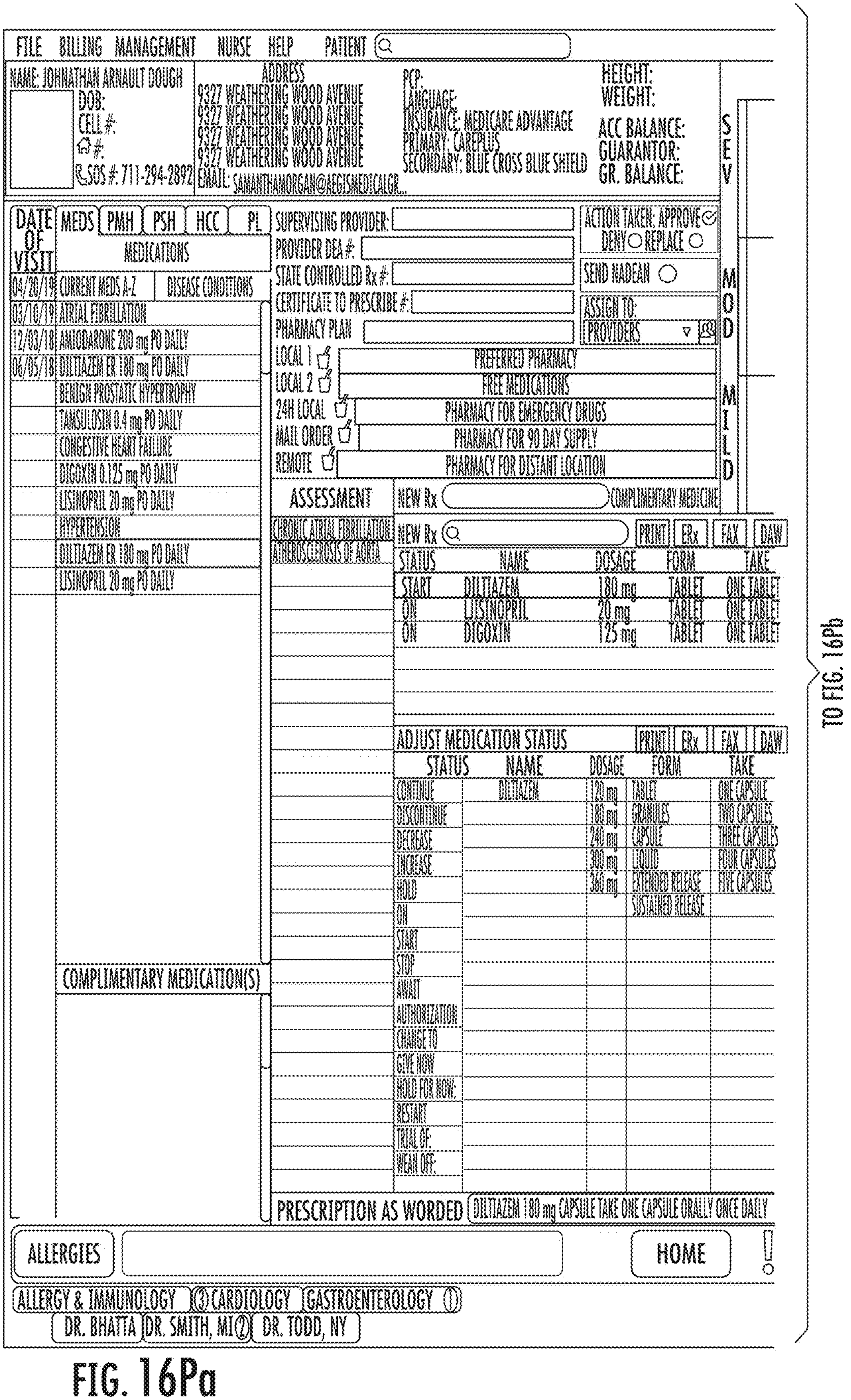
Figure 16P:
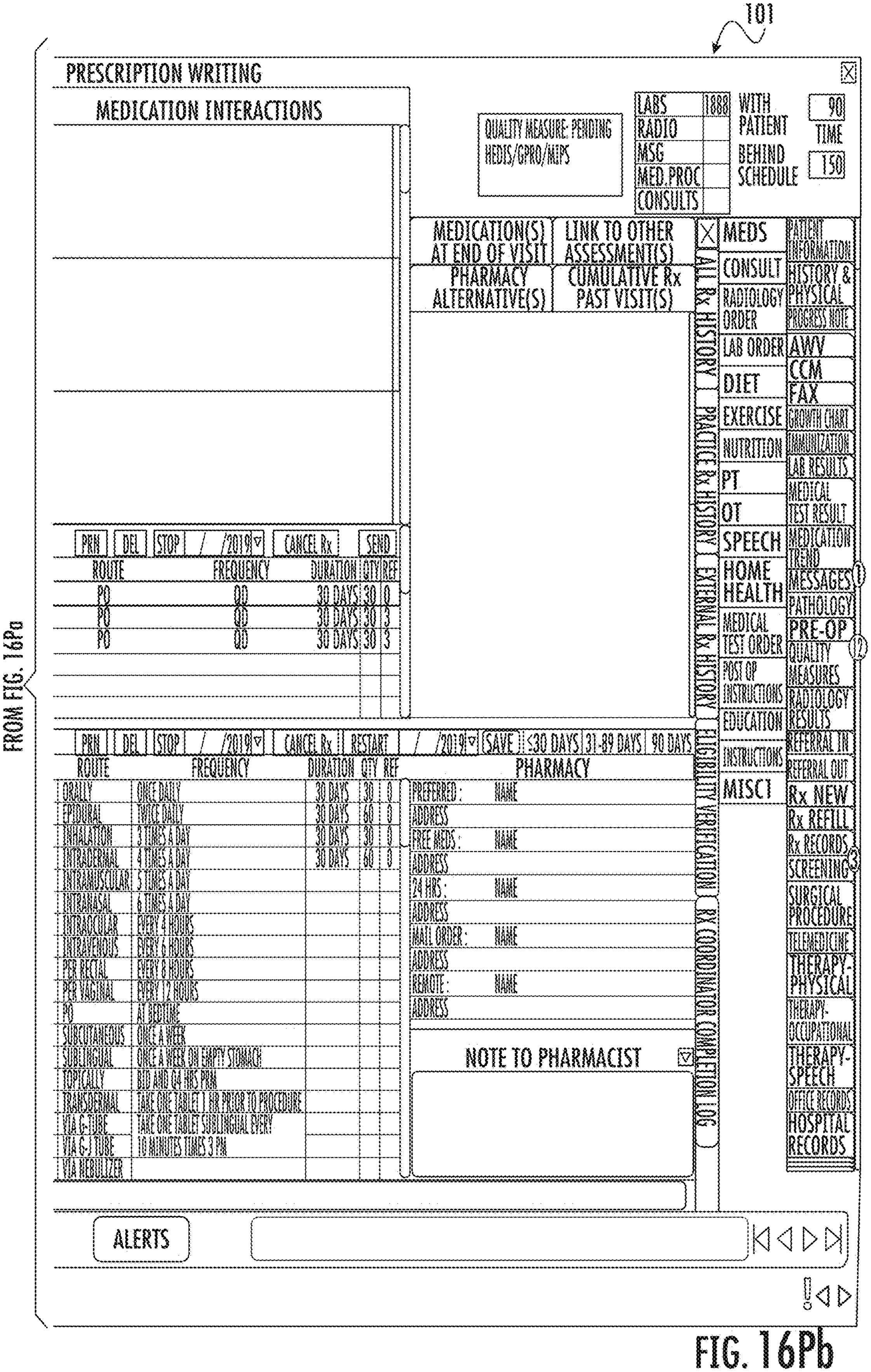

Referring now to FIGS. 16Aa-16Pb, the progress note function is discussed in detail. When the patient's chart is opened from the provider's schedule for the day. It will open the progress note function when it is a "routine follow up" visit. When the assessment and plan bar on the right hand page is clicked on, it will open the "assessment and plan" template. All the tabs to work on the assessment and plan template will be performed by clicking on the second column of tabs from the extreme right hand side of the screen. These active tabs are highlighted in black for illustrative clarity. By default, the active tab will be medication (i.e., meds). This active medication prescription and adjustment function allows the provider to prescribe new medications, increase, decrease, stop, hold, and make all kinds of necessary changes to an existing medication the patient is taking for a particular assessment.

Referring now to FIGS. 16Aa-16Pb, the progress note function is now described with reference to patient assessment and plan medication orders. When the assessment and plan horizontal bar of the progress note function is pressed, it will take the provider to a new "assessment and plan" screen, which defaults to "medication(s)" as the active screens. On this "assessment and plan" template, there will be multiple tabs including the following: medications, consult, radiology order, lab order, diet, exercise, nutrition, PT, OT, speech therapy, home health, medical tests, post operative instructions, education, instructions, and miscellaneous tabs for future use. The "meds" tab (i.e., medication tab) is highlighted in black by default and will be the active tab; this is due to medication(s) being commonly used in typical applications. On the left side will be the "date of the visit" column and next to it will be the patient history tabs 114*a*-114*e*. From these tabs, the assessments applicable for the visits can be pulled into the assessment column. This includes the medications, PMH, PSH, HCC and PL tab. Each of these subsequent assessments can be individually highlighted.

All the assessments put in the progress note second page will show up here too. Any assessments not pulled in from the progress note can always be put in as required, based on the patient's medical issues from the patient history tabs 114*a*-114*e* on the left side of the screen. Any highlighted assessment from the progress note function of FIGS. 2A-2B, will be automatically highlighted here also. If another assessment is highlighted, the previous one will turn to normal. All the current medications for the new assessment will now populate under "name" just below the "new Rx" search box on the headings bar. The status for all current medication the patient is on will show "on." On the top right upper hand tabs include cumulative Rx past visits, link to other assessment(s), pharmacy alternatives and medications at the end of the visit.

Cumulative Rx Past Visit(s): Will display when clicked, all medications prescribed and used for any specific assessment in the past, in alphabetical order. This list will have been saved automatically to a database from past prescriptions, e-prescribed for that assessment. All prescriptions will show incremental strength going downwards and in increasing frequency of administration for that medication. The arrow to the left of a medication can be clicked to bring it into the plan for a particular assessment which is highlighted. If there is any medication interaction it will display that, and will not allow the medication to be brought in. A box will show up "override drug interaction" in which a drop down box must be checked or filled/typed out, as to why it can still be prescribed. Then the arrow can be clicked again to bring the medication in.

Link to Other assessment(s): tab is toward the right upper hand corner of the template also. It will have all the diagnoses/assessment, from the past medical history of the patient. Any new medication prescribed can be linked to other assessment(s) if it is being used for multiple diagnoses on the patient, if it is not already linked to it in the past. Pharmacy Alternatives: When this tab is clicked, it will highlight the alternative for any medication which is not preferred by the prescription plan. The medication alternatives will be in alphabetical order and with incremental dosage increases noted. Medication(s) at end of Visit: This is the last tab which when clicked will show two sections underneath.

"New prescriptions this visit": This column will list all the new medications prescribed at this visit, for all the different assessments in alphabetical order. "Current Medications": will list the total of all the new and previous medications (i.e., the dosage of which may or may not have been changed) that the patient will be leaving the office at the end of the visit. Come midnight, this will then become the default list of the patient's medications. A template will slide in from the right side of the screen, to show the new prescriptions and current medication when this tab is clicked. When the tab is unclicked or another tab is clicked, then this screen will slide back to the right and go into hiding. The allergy and alert row at the bottom will display any possible reason(s) as to why the prescription can or cannot be given to the patient.

New Medication: "new Rx," Search can be instituted for any medication for the assessment that is highlighted. When the medication name starts to be typed in then all the preparations for that medication will start populating right below the Search box in a dropdown box. The applicable preparation with the correct dosage can then be clicked on and highlighted. It will put it on the top row under the "name" of the medication.

Also, any new medication can also be pulled in by clicking on the "top right upper hand tabs," on the "cumulative Rx past visit(s)." All previous medications prescribed for that assessment will be populated here in alphabetical order and in incremental dosage formulation from the top towards the bottom. The correct name with formulation can be brought in by clicking on the arrow to the left of it. Any medication which is populated after a new search or brought in from the cumulative Rx past visit besides showing up in the new Rx in the section at center of the screen, will also show up in the "medication adjustment status" screen in the center of the screen in the lower part. Any previous medication that the patient has been taking and in front of which it says "on" can also highlighted and it will show up in the "medication adjustment status" screen. Here, any necessary changes or adjustments can be made and saved. It will reflect this change in the section above where the medication was first highlighted. The status will also reflect the change from "on" to the new change in status.

Any new medication which populates will have "start" under the status column for that new medication. All previous medication for that assessment which populates the template and has "on" as its status, will be pushed down, to accommodate the addition of the new medication(s) on the top. Any "medication interactions" will display on the upper part of the template, right of the midline. The severe interactions will be at the top and below it the moderate and then the mild. If there is any medication interaction then it will show on the medication interaction section with the severe interactions, followed by the moderate and mild towards the bottom. A scroll bar is present to scroll through the list if it is long. If there is a significant interaction then, a box will pop up "override drug interaction" in which a dropdown box must be checked or filled/typed out, as to why it can still be prescribed. Then the arrow can be clicked again to bring the medication in.

Any new medication prescribed, when highlighted can be linked to other assessment by clicking on the "link to other assessment(s)" tab which is toward the right upper hand corner. It is possible to link it to multiple assessments. complimentary/alternative medication: any complimentary or alternative medication can be searched in the search box right above the search for the "new Rx" and is to the right of the "assessment" heading.

Dose Adjustment: To adjust the dose of a previously prescribed medication: 1) the medication can be pulled in from the medication list by clicking it under the medication tab, under which it is listed. When this happens, then all the assessments listed under will now show up under the assessment column. 2) If an assessment is pulled in by clicking on the arrow to the right of it under the "assessment" column from the past medical history, HCC tab or PL then it can be clicked on, to highlight it. This will bring up the name of all the medications that have been prescribed in the past for that medication, below the "new Rx" under "name." The status will default to "on." When any of these medications are clicked to highlight it, then it will show the medication now under the "adjust medication status" section, on the topmost row, with "on" showing as the default current status to the left of it. Only one medication can have dosage adjustment performed at any time.

Now any of the buttons under the status column can be checked to change its status. Dosage, form, amount to take, route, frequency, duration, quantity, and refills can all be adjusted to suit the patient's needs. Thereafter, the pharmacy where it needs to be sent, is chosen from the choices on the extreme right side of the "adjust medication status". Then, the save button can be pressed to save the changes and the medication will disappear from the "adjust medication status" and repopulate on the box above under "new Rx" with the appropriate changes as instituted. The status will show depending on what the change was. If the dose was increased, then it will show "increase" as the new status.

Prescription as Worded: At the very bottom will type out the medication as the options are being adjusted by clicking on them to ensure that it is exactly the way that the provider wants it to be or if any new medication is being prescribed and adjustments being made to the dosage, form, frequency or any other instructions. Provider details and Pharmacies: On the top part of the template to the left of the midline, there is the details of the provider related to prescribing. Pharmacy plan is listed if the patient has one. There are five pharmacies which will be listed: First: is the local pharmacy that the patient prefers; Second: is a local pharmacy which provides some free drugs; Third: Is pharmacy which is open late hours close to the patient residence; Fourth: Mail order pharmacy for long term prescriptions; and Fifth: Remote pharmacy when the patient is at his second home and needs something called in for emergency or for his long term medications.

All Rx History: This will have the prescriptions given by other providers who are using this EHR but outside the practice. Practice Rx History: Will have all the prescriptions sent electronically by all the providers in the same practice, under the same specialty (single specialty practice) as well as different specialties (Multispecialty practice). External Rx history: This will have the prescriptions written by other providers who are taking care of the patient who are using a different EHR if down the road interoperability allows that to happen. Eligibility verification: This is to verify the eligibility for the prescription. Rx Coordinator Completion Log: This will show the log for all the Rx coordinators for each financial year, month, and date and how many prescriptions were sent by each one of them on a day-to-day basis.

Referring now to FIGS. 13Aa-13Bb, the laboratory (lab) order function is described in detail (i.e., EHR patient text explanation for assessment and plan-laboratory orders). When the "assessment and plan" bar is pressed on the second page, a template will open which will have all tabs related to further orders show up on the side like medications, radiology, laboratory (Lab), PT, OT and ST, etc. By clicking the "lab order" tab on the right hand side, another template will open which will be for the Lab orders to be put in. On the left hand side will be the standard tabs which will include medications, PMH, PSH, PL and HCC tab. From this PMH tab, all the medical diagnosis which are relevant for that particular visit, can be pulled into the assessment by clicking on the different "diagnoses" under the PMH, which is the second column from the left hand side. Any new assessments can also be added under the assessments column, by searching for a diagnosis not in the past medical history, using the search button.

Whenever an assessment is clicked on, it will highlight it, into a different "active color" and labs pertaining to that assessment can now be added into the lab section to the right of it, which could be related to an acute visit, say an a) Upper respiratory Infection or 2) Acute Diverticulitis. Labs can also be added for routine visits, and the diagnoses codes along with the ICD codes can be added next to it from the PMH, which has the diagnoses with the ICD 10 code attached with it.

At the top of the space for the Lab orders are going to be 3 buttons 1) Today 2) Calendar and 3) Routine. Today: When the button for "today" is clicked it will create a bar below in the lab column with today's date on it and Lab orders can now be pulled in from the left side of it, for the labs to be drawn the same day of the patient visit. This is usually for "acute visits" when there is an acute problem, for which labs need to be drawn the same day.

Calendar Button: When there is a desire for a lab to be ordered any time period with no specificity then the calendar button can be opened to choose any date or week(s) to be created, so that labs can be added to have it drawn by the phlebotomist in that time frame when it is required. For example, a patient is started on a statin drug and needs a lab (Liver function test) drawn in two months to ensure that the medication is not affecting the liver. The calendar can be used to create a date for two months from the date of the visit and the required blood test (liver function test) can be ordered under that date.

Routine: This button is to order routine labs for the patient prior to his visit to see the doctor which is usually a couple of weeks prior to the visit, which could be anywhere from 3-6 months' time in general. If for example, the patient is being seen in 4½ months, then the lab can be ordered for 4 months. The routine button can be programmed for 4 months by "right" clicking on it and a box will open up which will have different time frame already prepopulated on it like 2, 2½, 3, 3½, 4, 4½ months etc. The provider can pick and choose the time frame he wants to use and then click the "save" button to save it for that time frame. When the provider clicks on the routine button in the future, it will automatically create a bar with a working date for 4 months. Now since it was just created it will by default be active and now Lab orders can be added under that date from the "test menu" either as "individual" labs or can be brought in from the "group" lab.

Any lab order created by mistake under a particular "heading" can be highlighted and be deleted by clicking on the "DEL" (Delete) button on the heading bar. Any "individual" lab under a heading, can be deleted by clicking on the negative (−) round button to the right of it. All pending tests: All lab tests ordered by any provider including specialists for any future dates will be displayed under the "all pending tests" bar. This is to prevent ordered or same lab tests too close to each other and prevent duplication and prevent wastage of resources.

Test Menu: Providers can create a test menu based on the specialty. It can be created under individual as "individual labs test" or as a group of lab tests for certain conditions under a second column labelled as "group lab tests". There is a scroll bar for each "individual" and "group" column.

Individual Bar: The (+) button is to add individual test under the individual column and the (−) button is to delete any test which was ordered by mistake, or the user decides to delete it for any reason. Group Bar: The (+) button is to add a group bar under the group column. Different headings for groups can be created by clicking on this plus button which can then be labeled, and then individual lab tests can be added under each heading by using the plus button on that individual heading bar which was created. The (−) button is to delete a group bar and any individual labs added underneath it, which was created in the past, by highlighting the bar and then clicking the (−) button.

Completed Tests: When the "completed tests" button is pressed it will display all the individual and group lab tests done in the recent past going into the remote past (in descending order), along with the dates and who it was ordered by. All Cancelled Tests: This heading in the lower half of the screen (Completed Tests) will display all the tests cancelled in the past. When the button with the double (++) sign is clicked, it should show who was the provider responsible for cancelling the test.

Specialty: This will display all the different specialties tabs. If there is any test which the provider cannot remember for a particular assessment, help can be sought by clicking on the specialty tab related to that assessment. It will then display all the tests which was ordered by the specialists in that field for that diagnosis (assessment). This is a functionality which no other EHR has and can be very helpful. It will hasten the care of the patient by having all the requisite lab reports available even before the patient sees the specialist. It will save unnecessary repetitive visits to the specialists since what the specialist wanted is already available. Hence, cutting specialist waiting time by preventing redundant specialist visits; and this will help primary care providers improve patient care by opening specialist input (i.e., special lab test ordering availability) to the Primary care physician and widening their knowledge base.

This screen is important for the flow and minimal number of clicks. The provider never has to move outside the screen. All the lab orders created under "individual tests" and all "group headings" once created with multiple labs orders under it, is saved to a data base and will be retrieved and stay on the right side of the screen for future use and with one click on the arrow it can be brought in as an order for the staff to carry out and the patient can be called and instructed to come in as per the dates of the required lab orders.

Figure 18A:
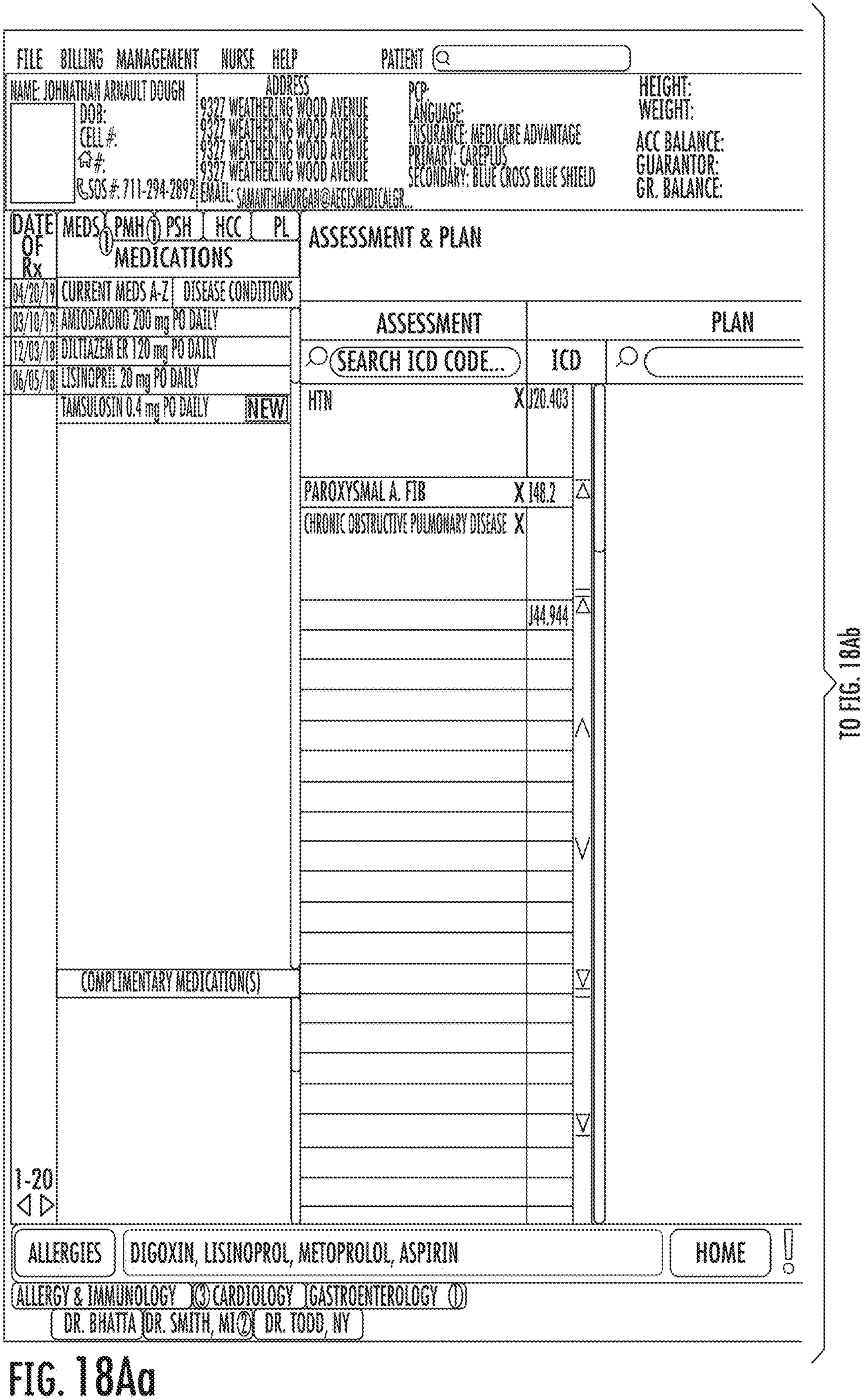
FIGS. 18Aa-18Db are screenshots of an example embodiment of a progress note assessment and plan-diet, home health, post operative instructions function of the EHR GUI from the EHR system of FIG. 1.
Figure 18A:
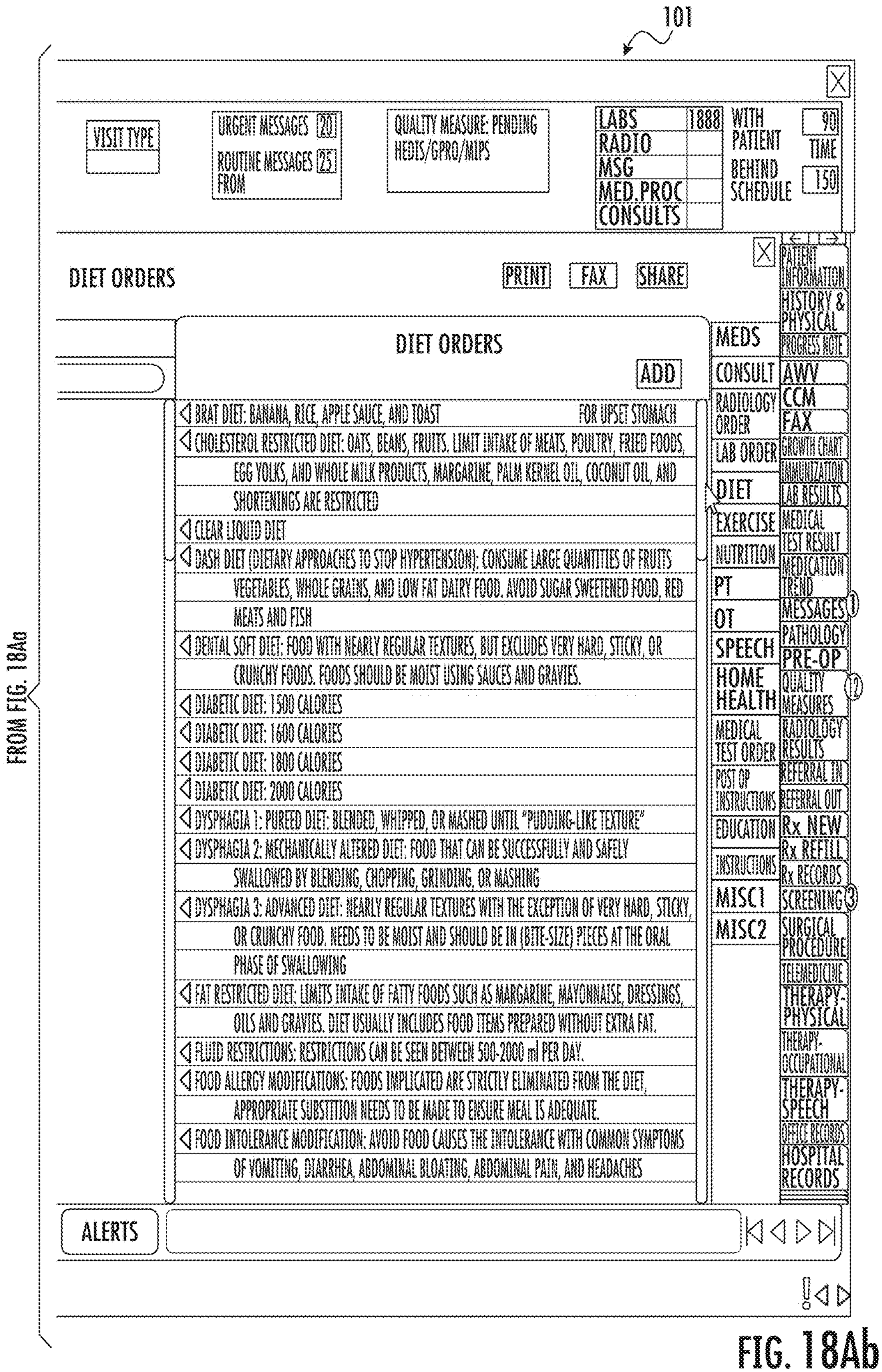
Figure 18B:
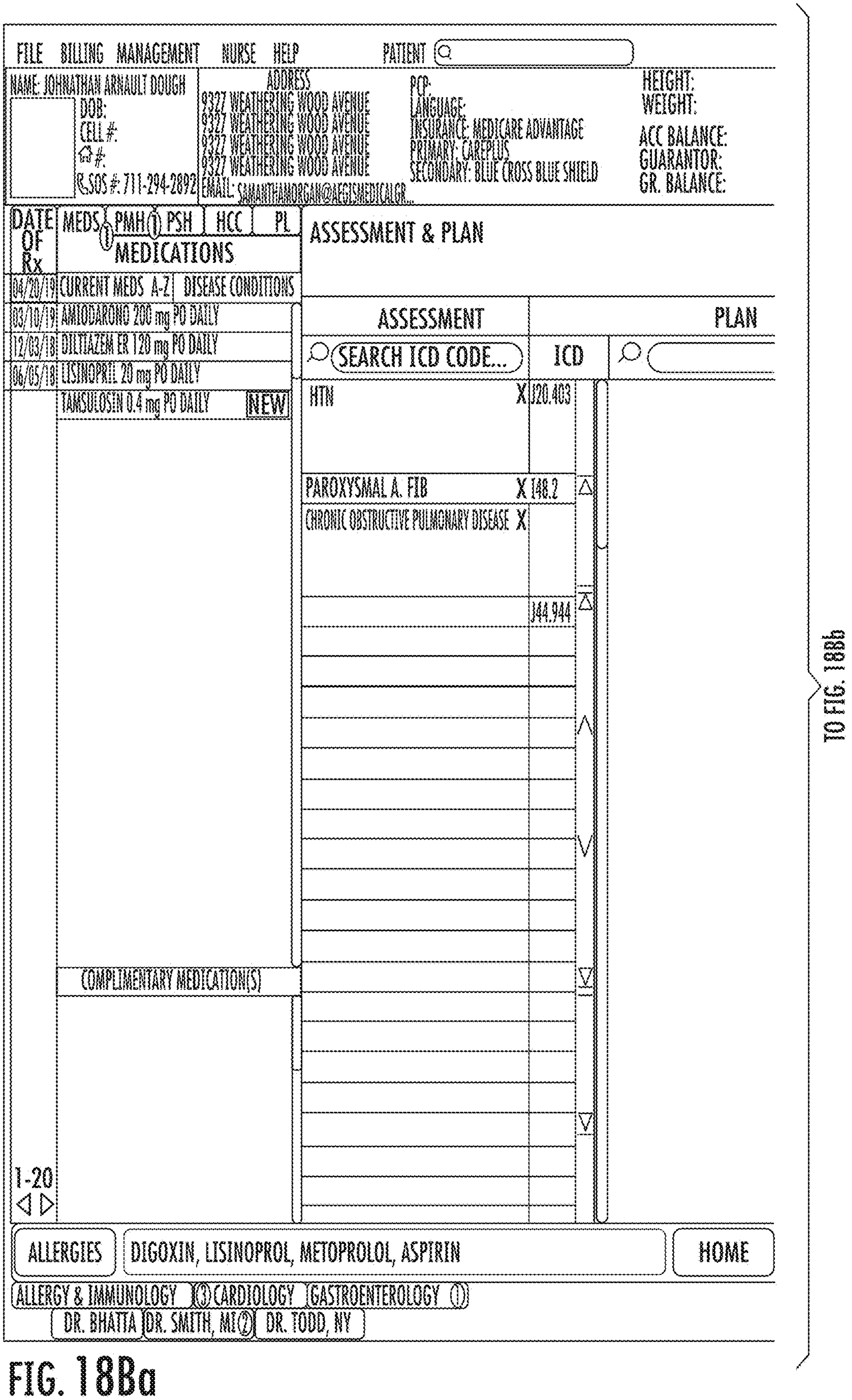
Figure 18B:
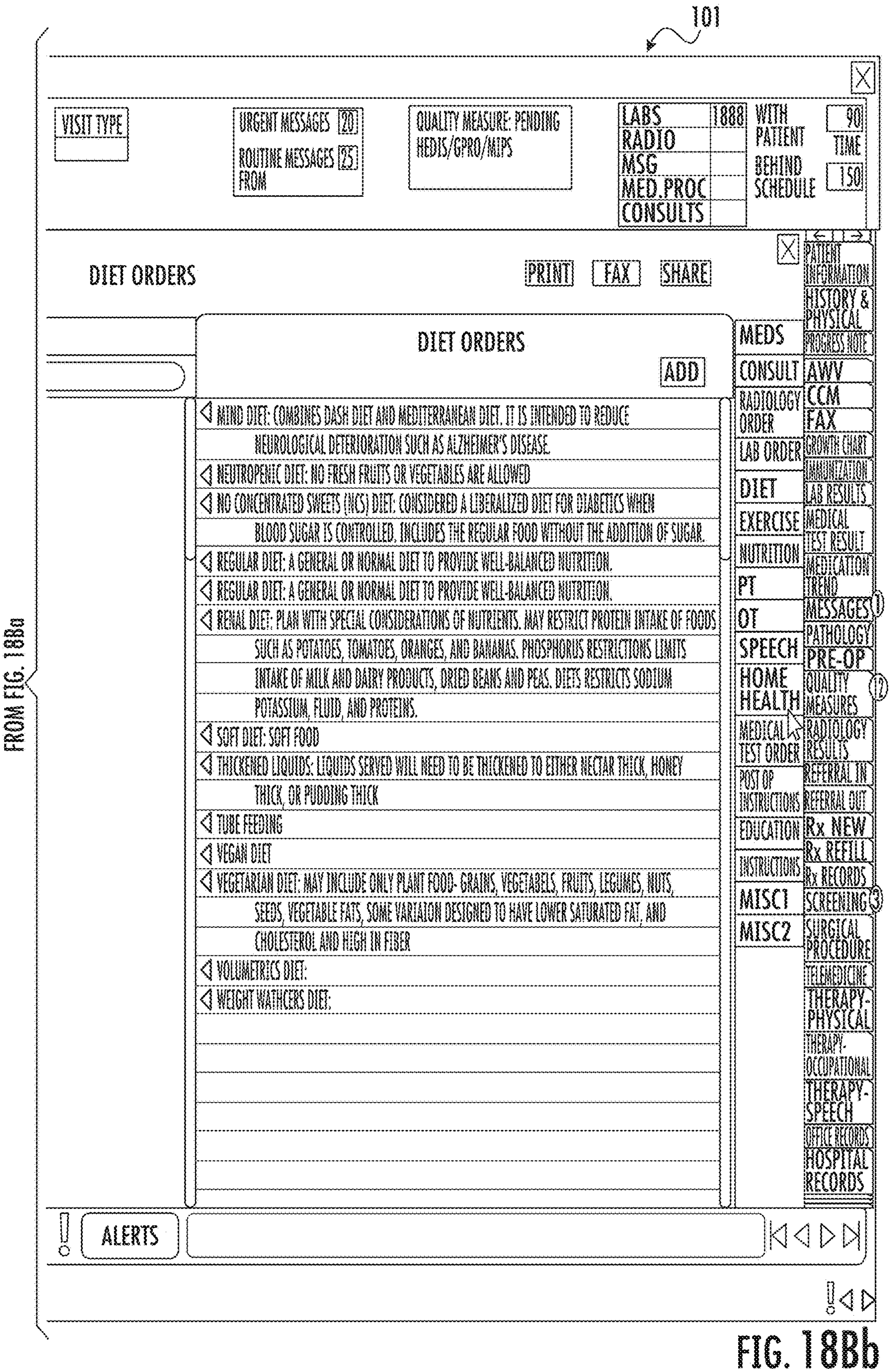
Figure 18C:
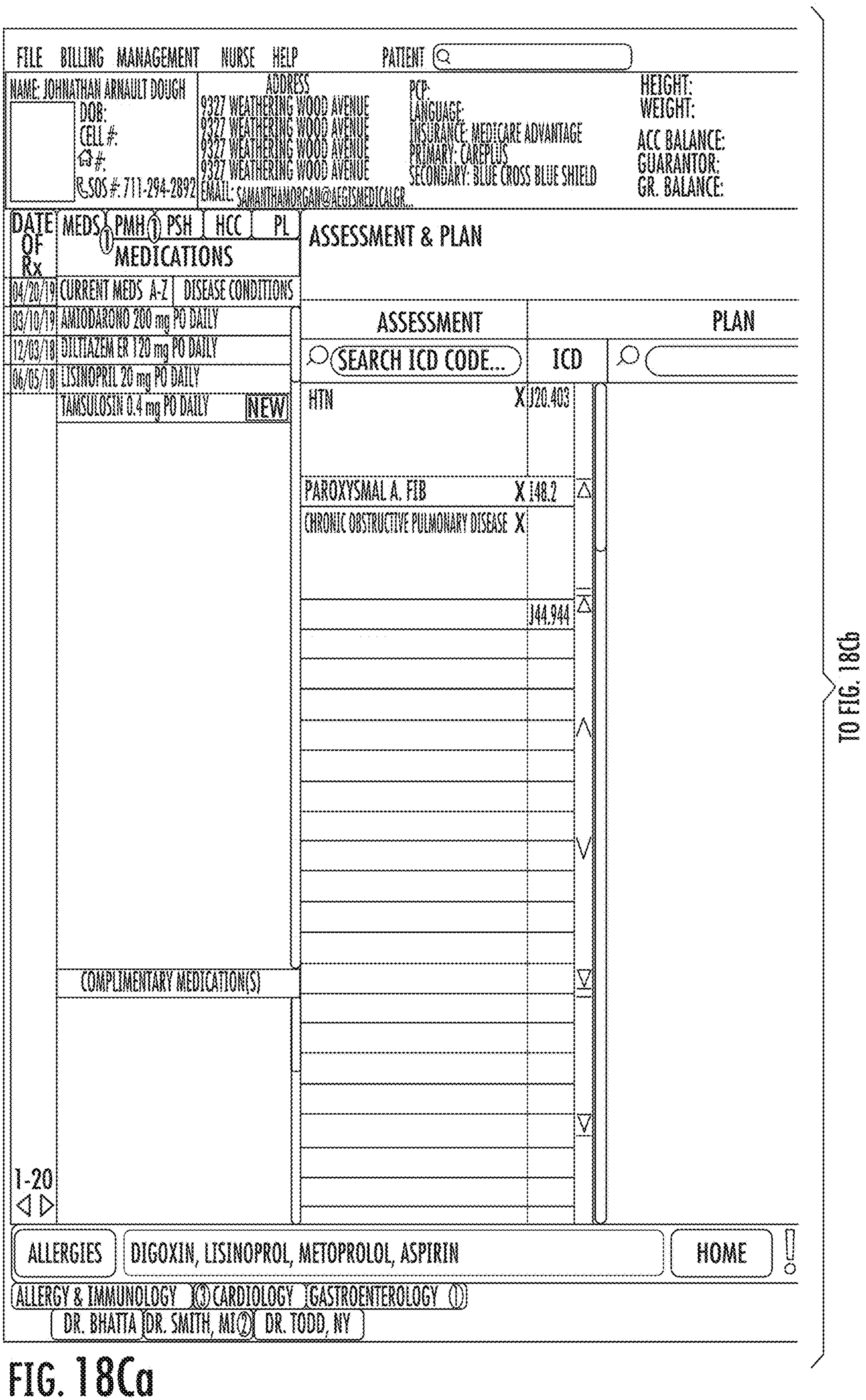
Figure 18C:
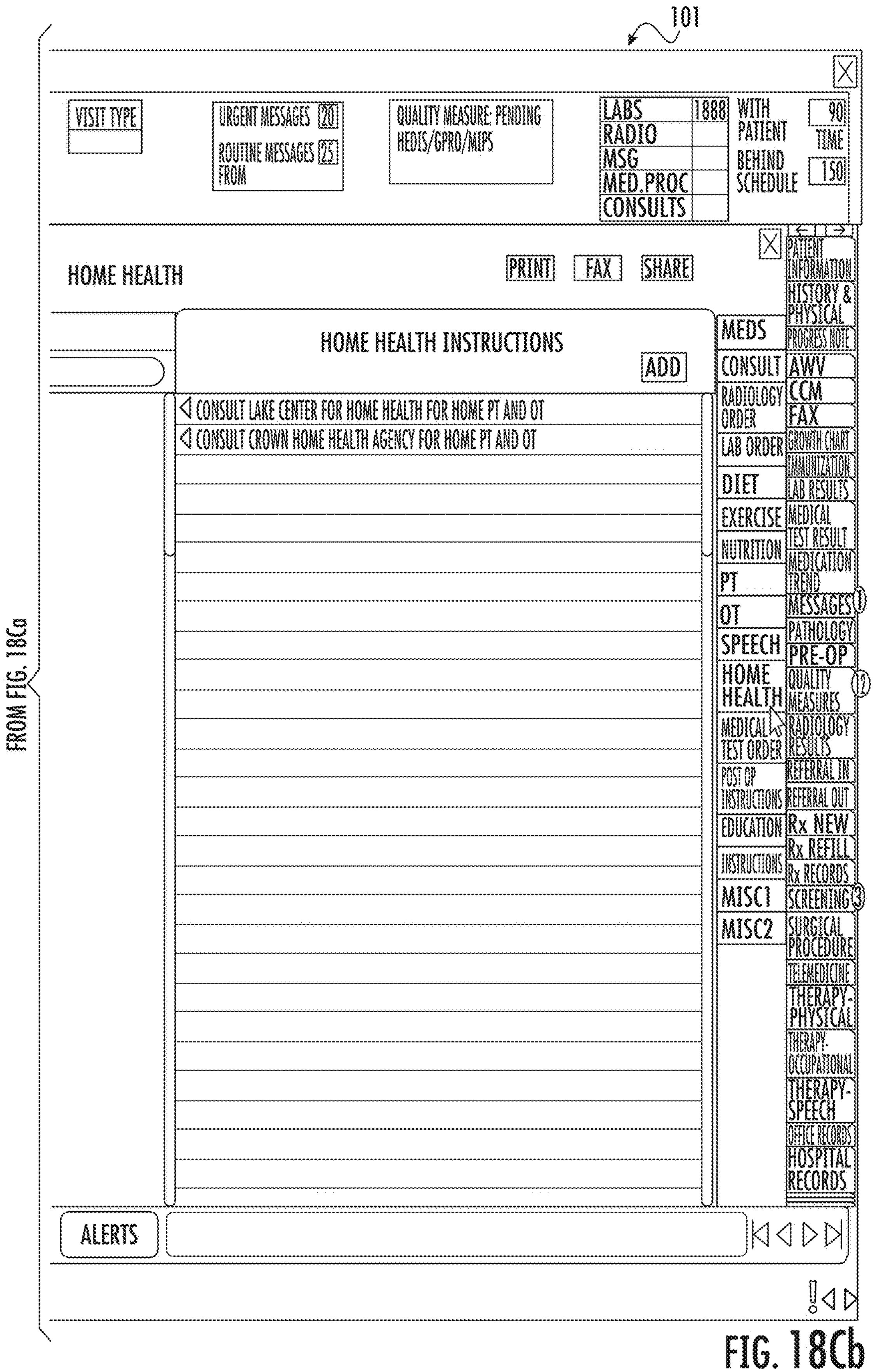
Figure 18D:
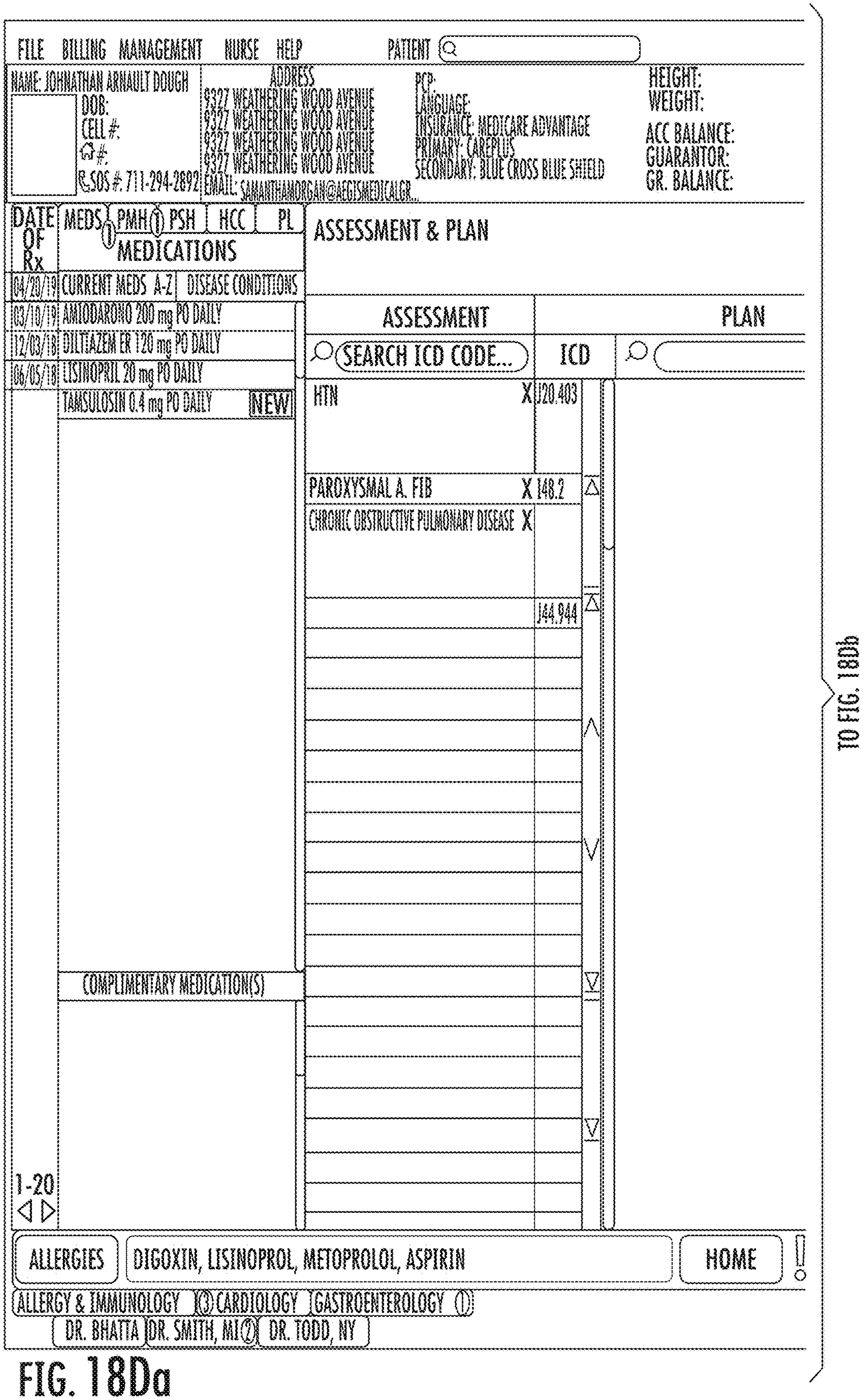
Figure 18D:
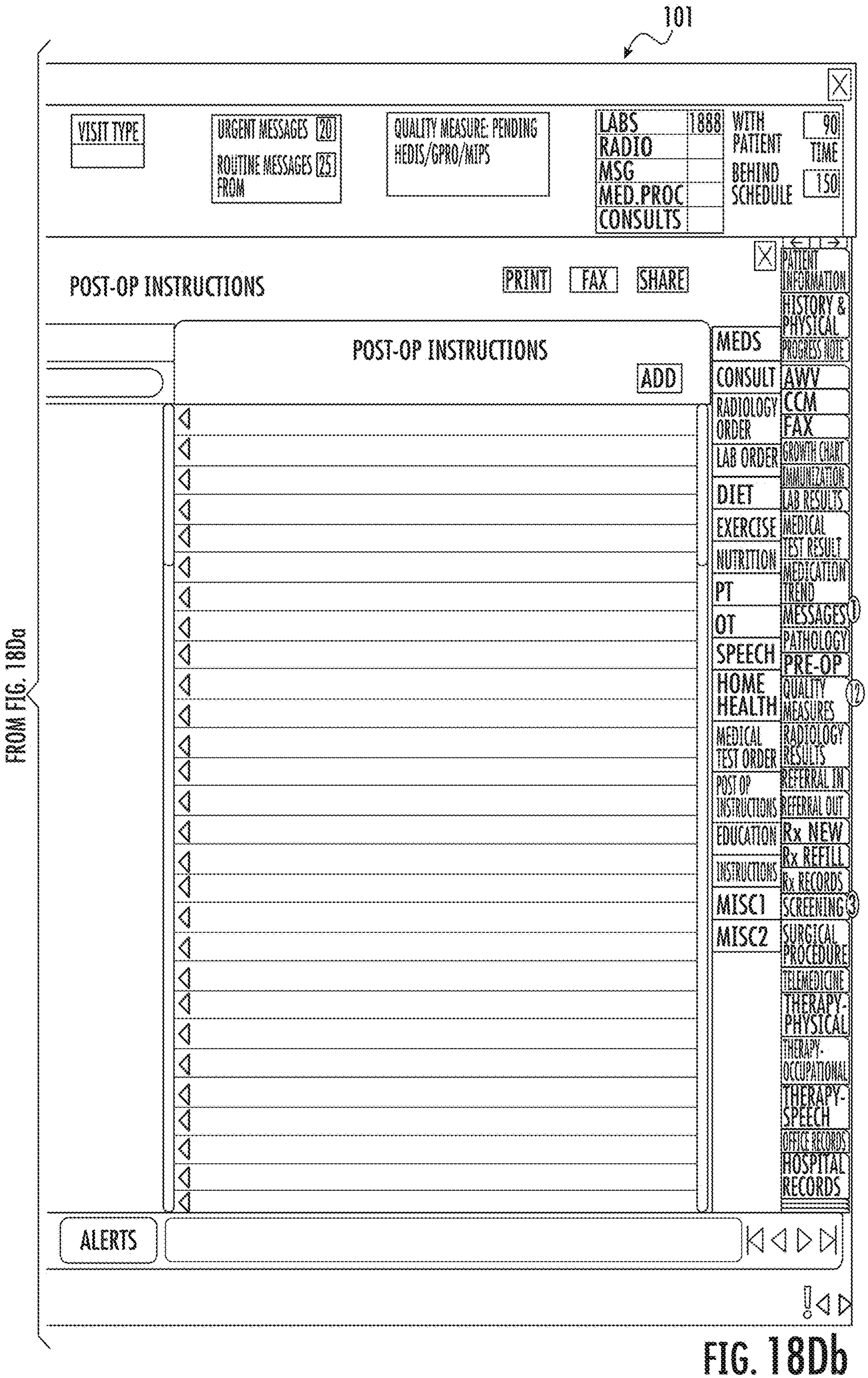

Referring to FIGS. 18Aa-18Db, the assessment and plan diet, home health and post operation instructions functions are shown. The orders/instructions will be pre-populated, or orders can be added by the providers and by clicking on the arrows next to it they can be brought into the Plan.

Figure 19A:
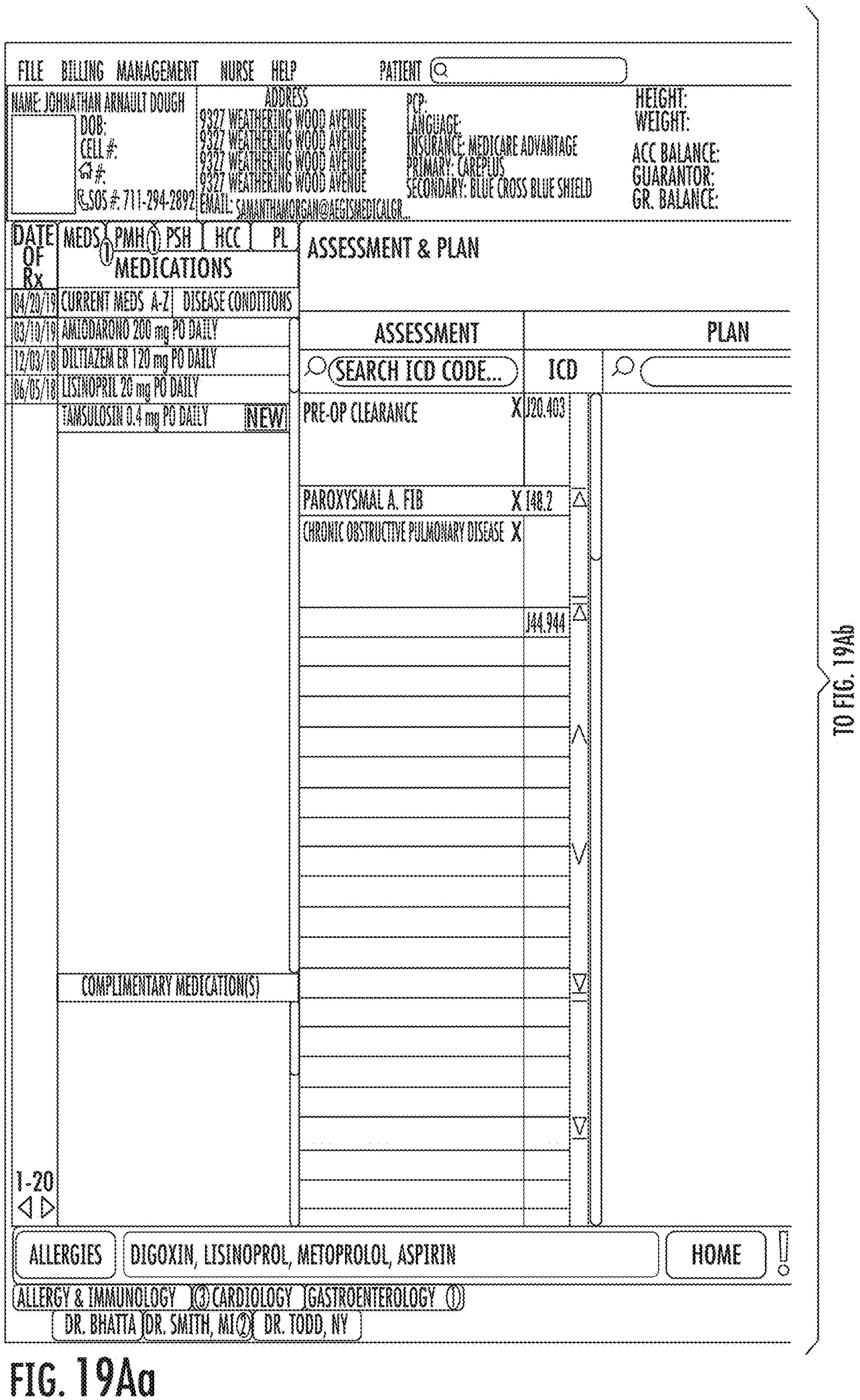
FIGS. 19Aa-19Gb are screenshots of an example embodiment of a progress note assessment and plan-instructions and consult function of the EHR GUI from the EHR system of FIG. 1.
Figure 19A:
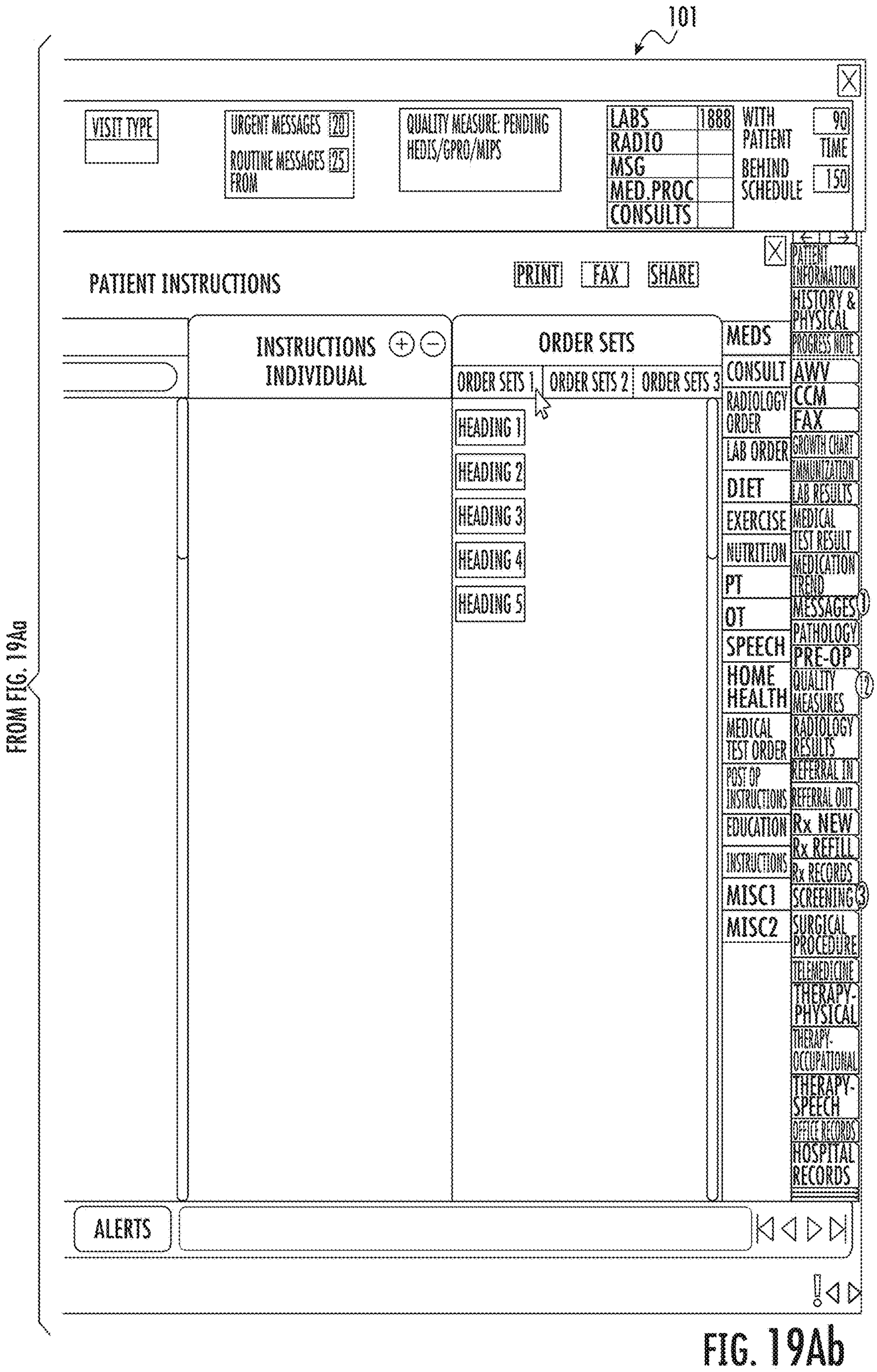
Figure 19B:
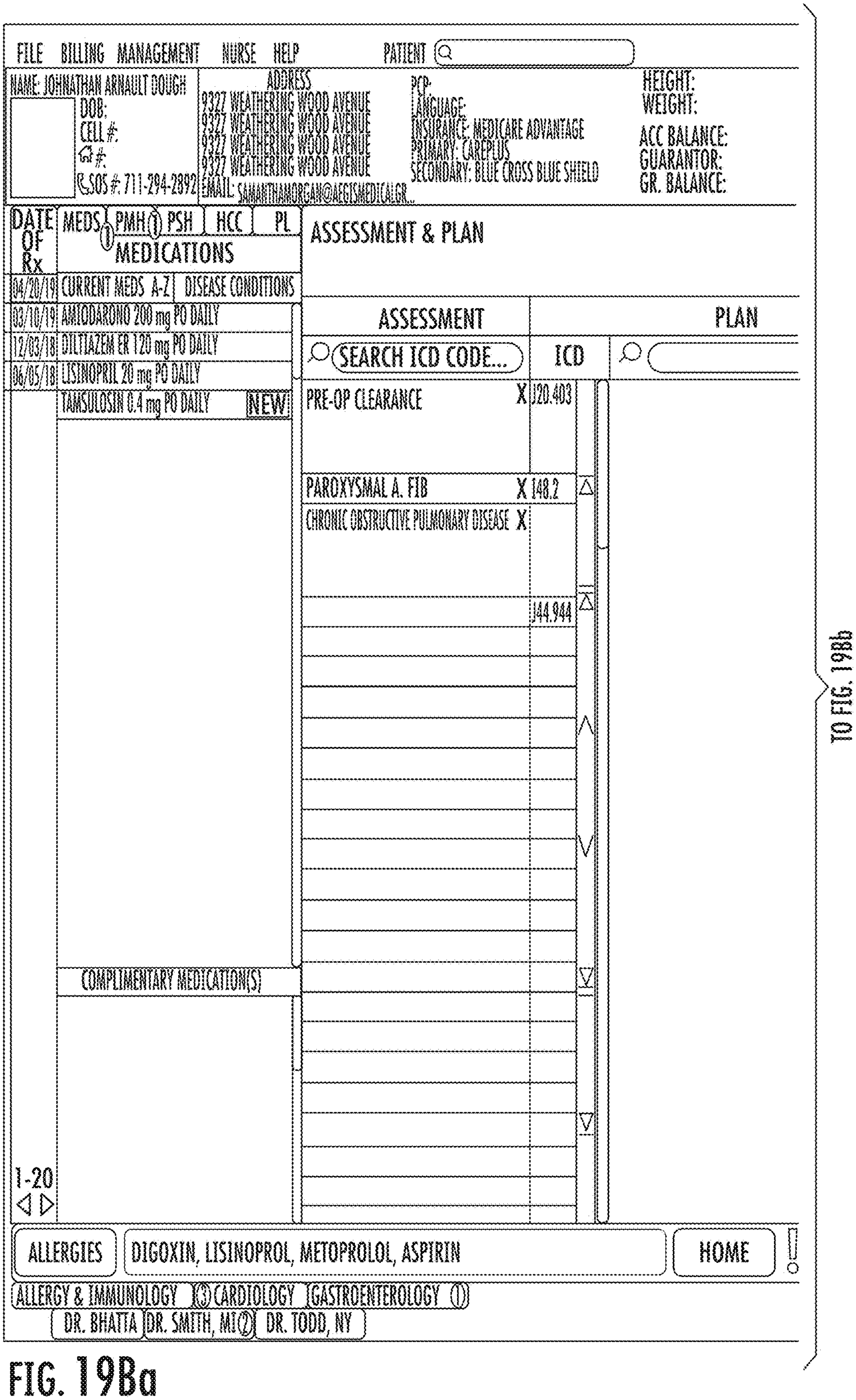
Figure 19B:
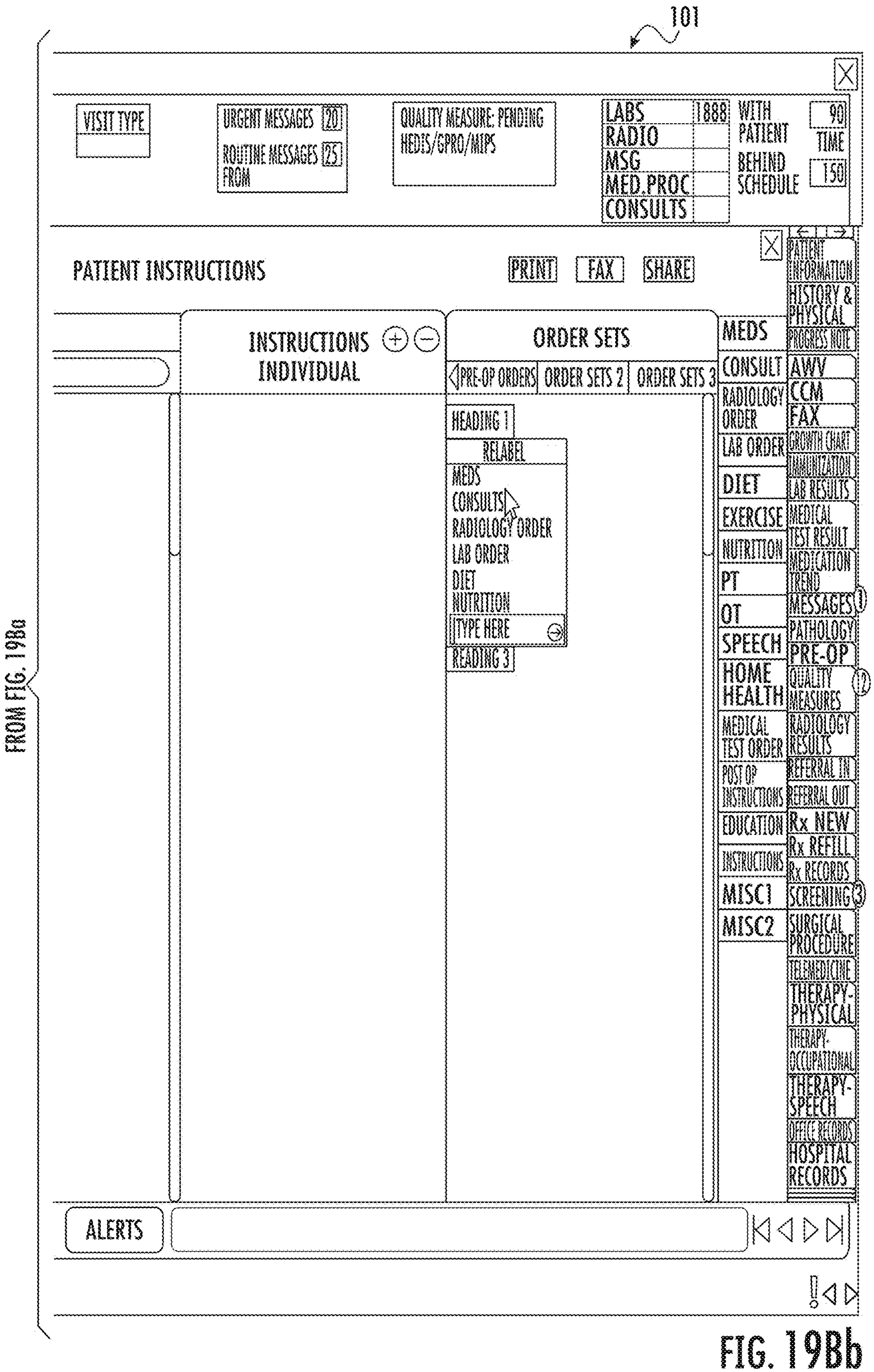
Figure 19C:
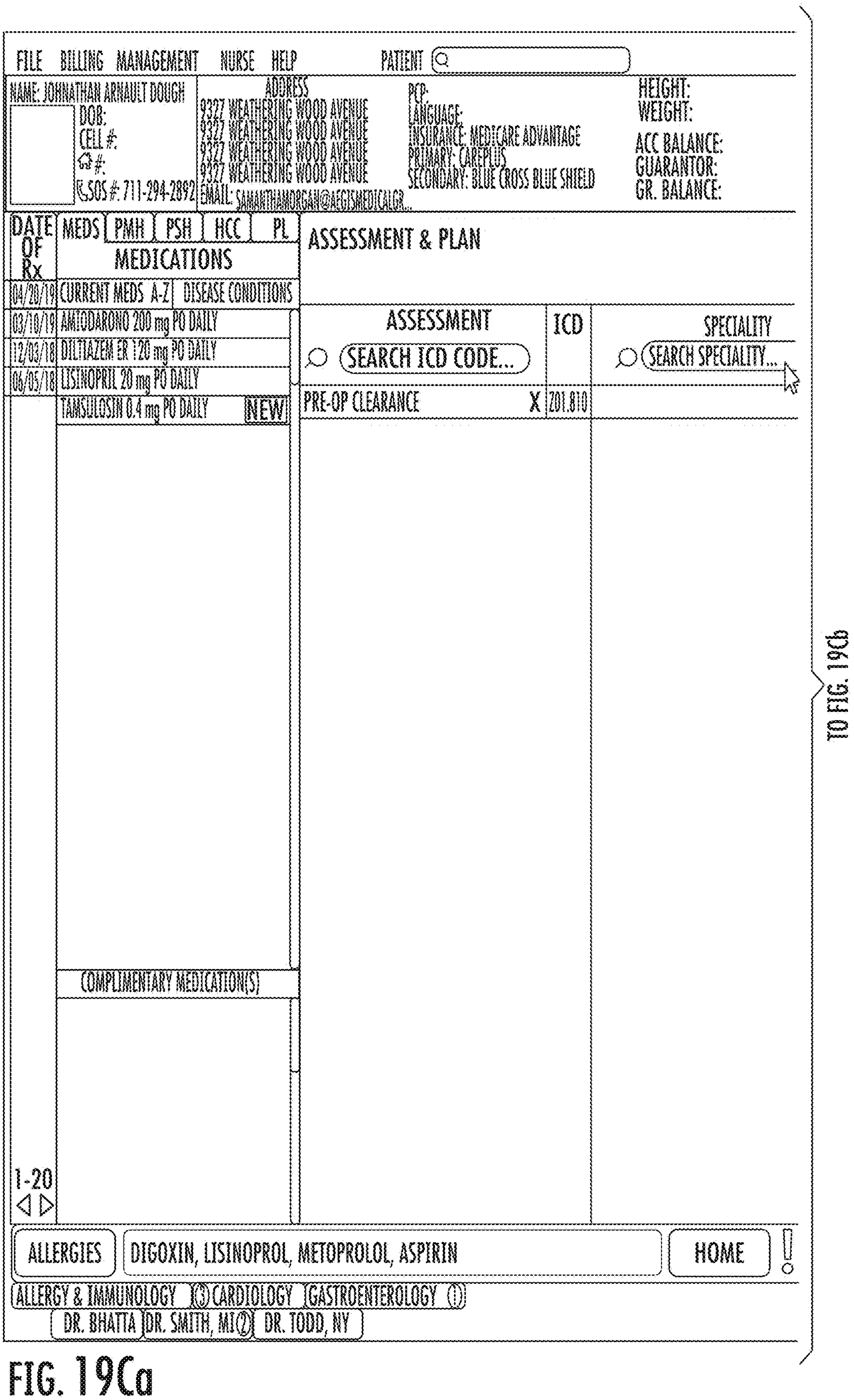
Figure 19C:
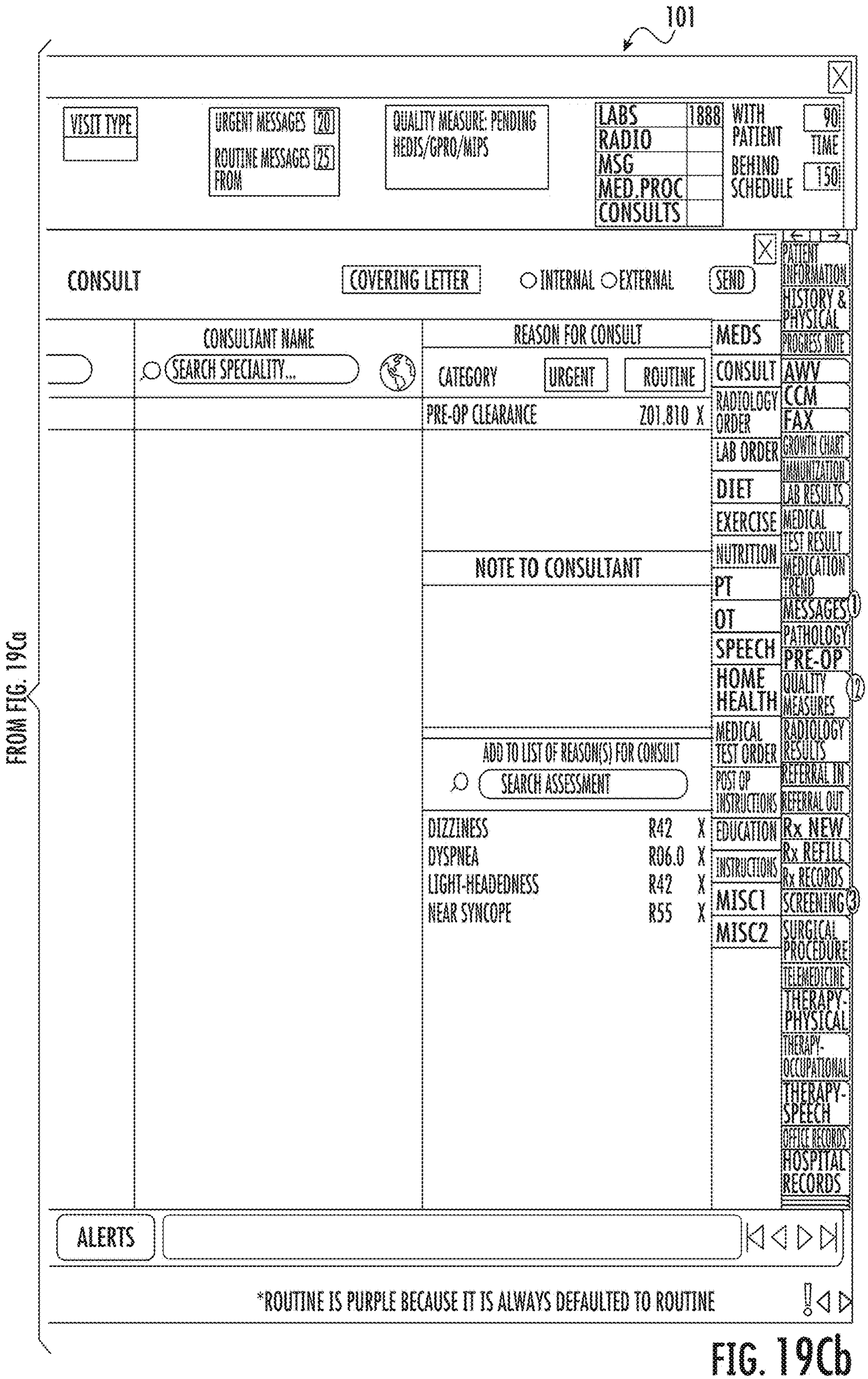
Figure 19D:
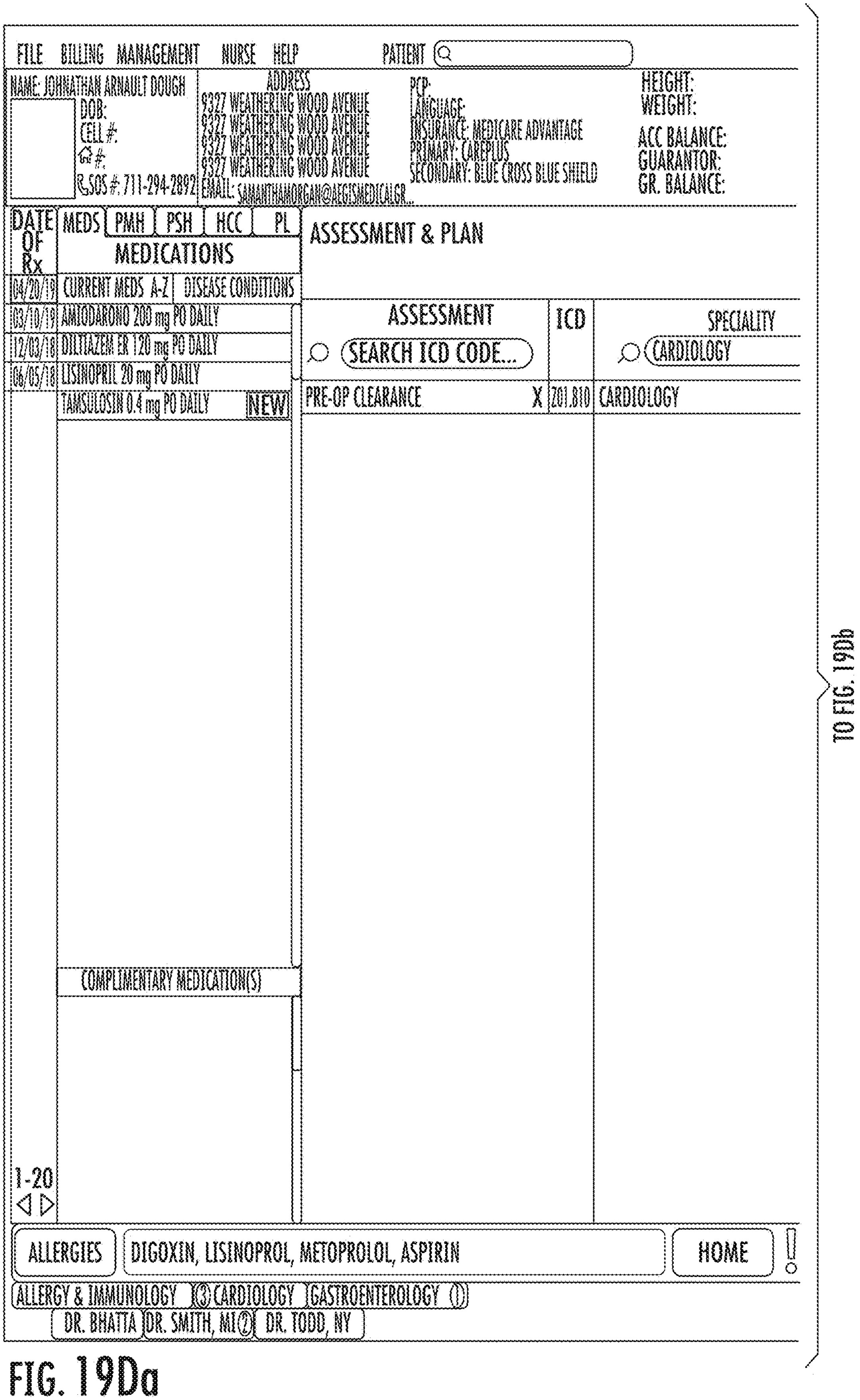
Figure 19D:
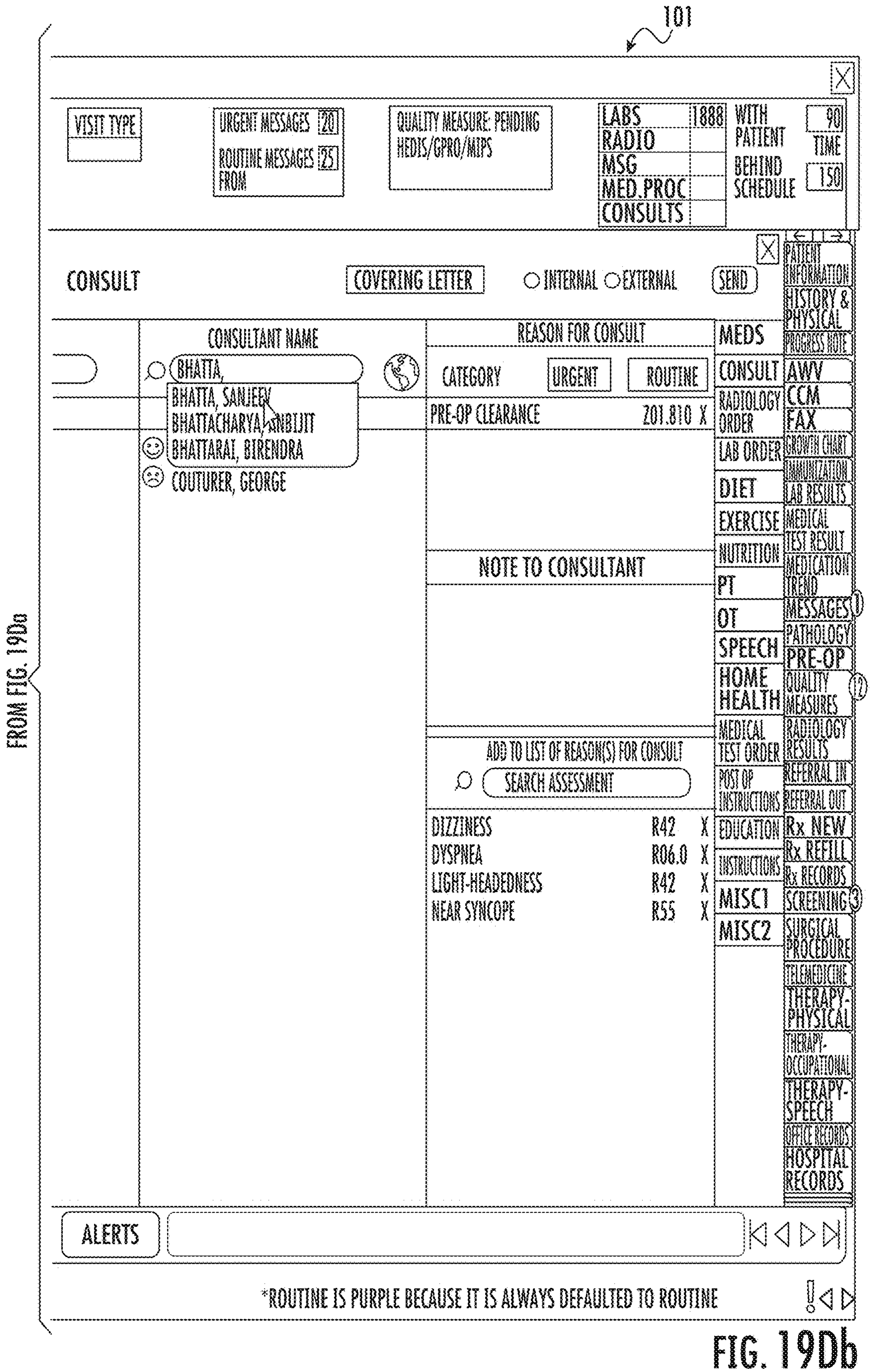
Figure 19E:
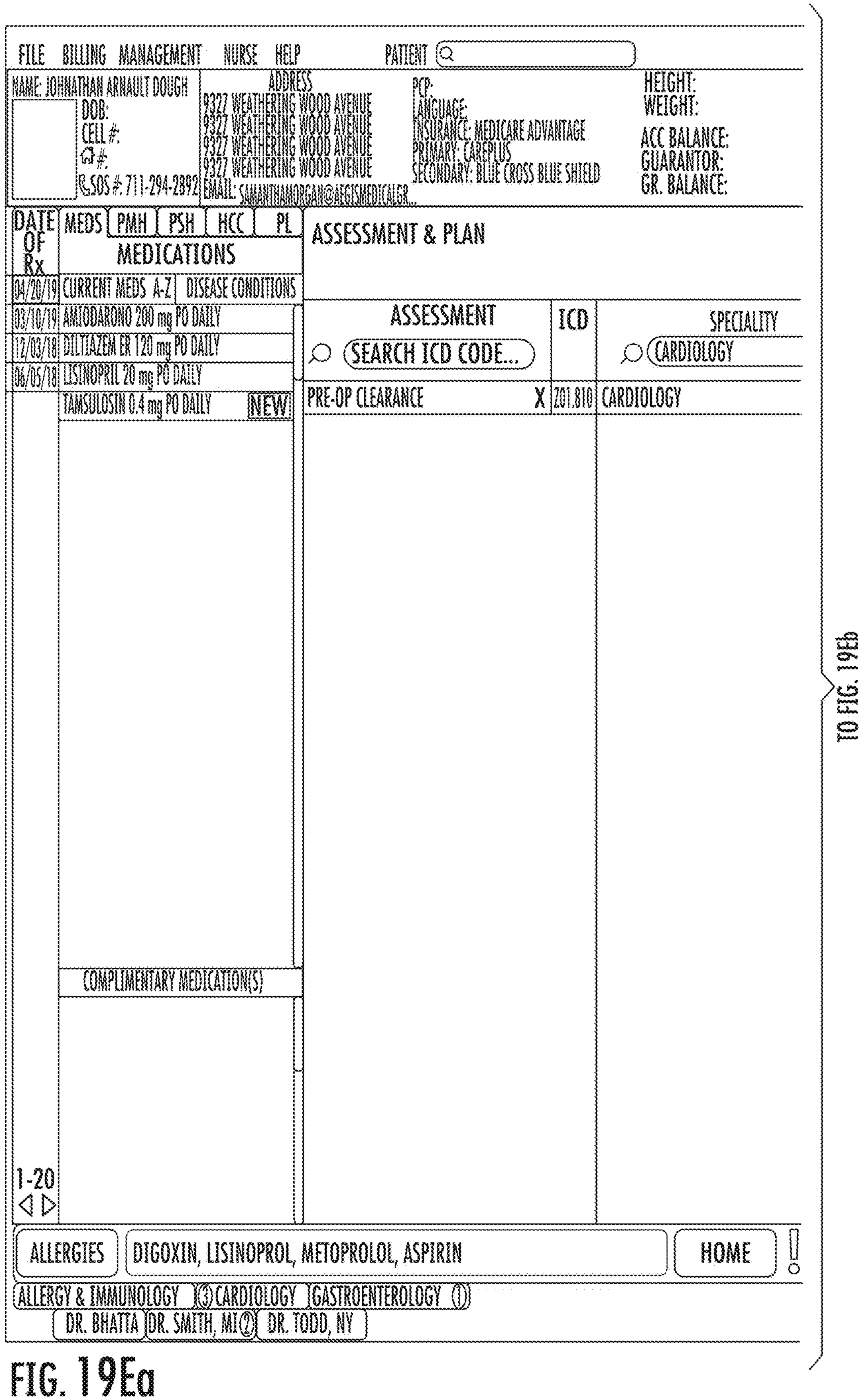
Figure 19E:
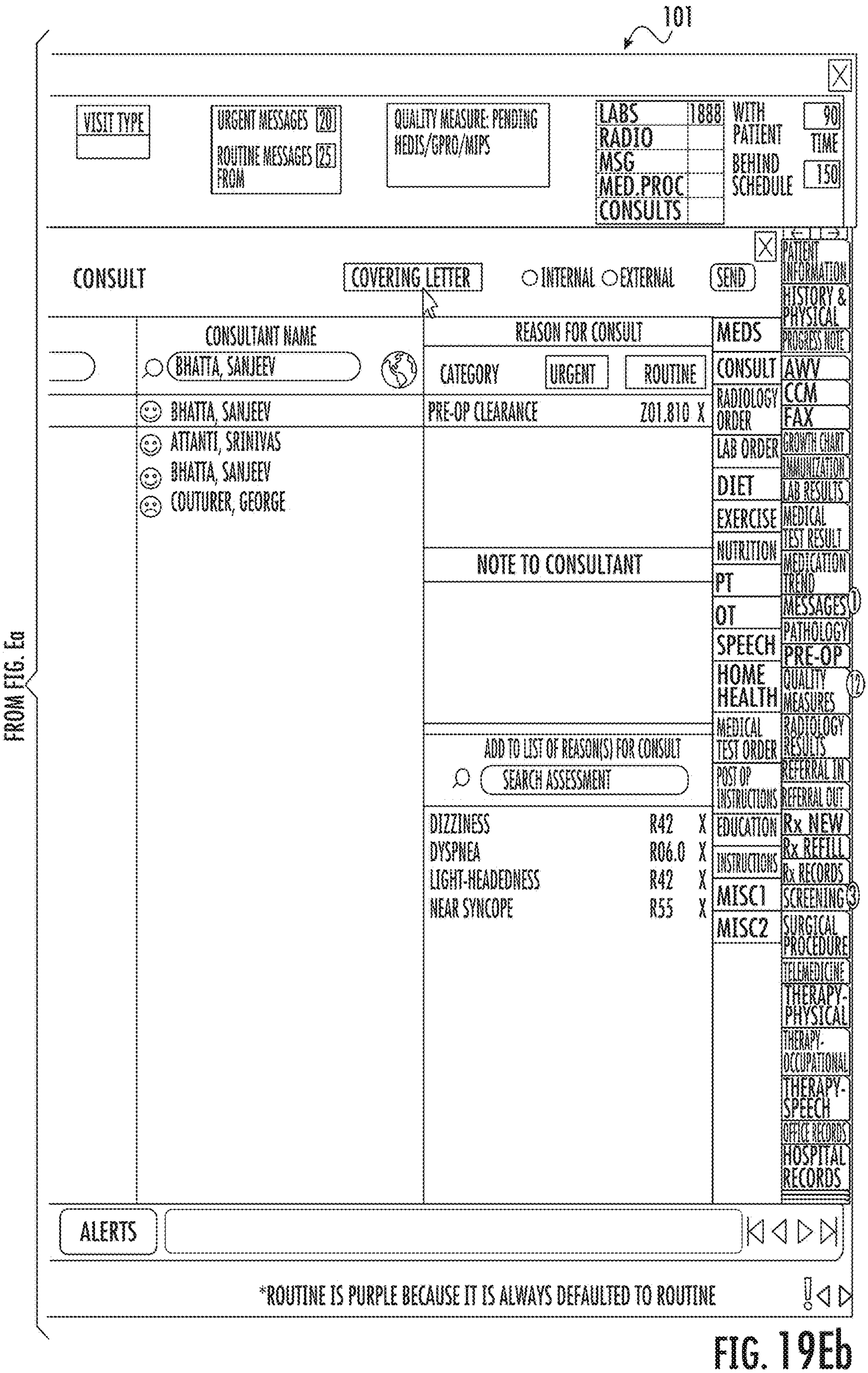
Figure 19F:
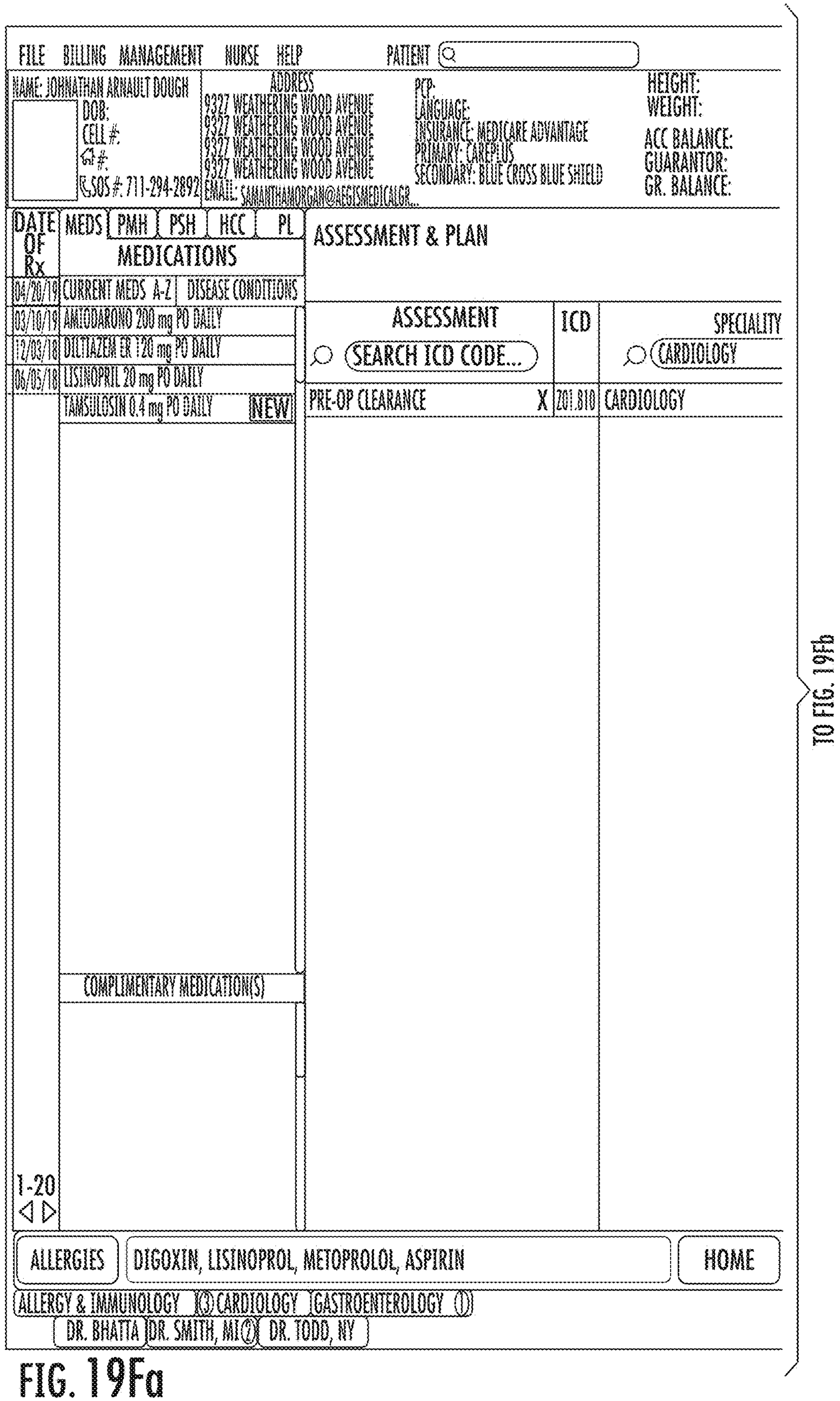
Figure 19F:
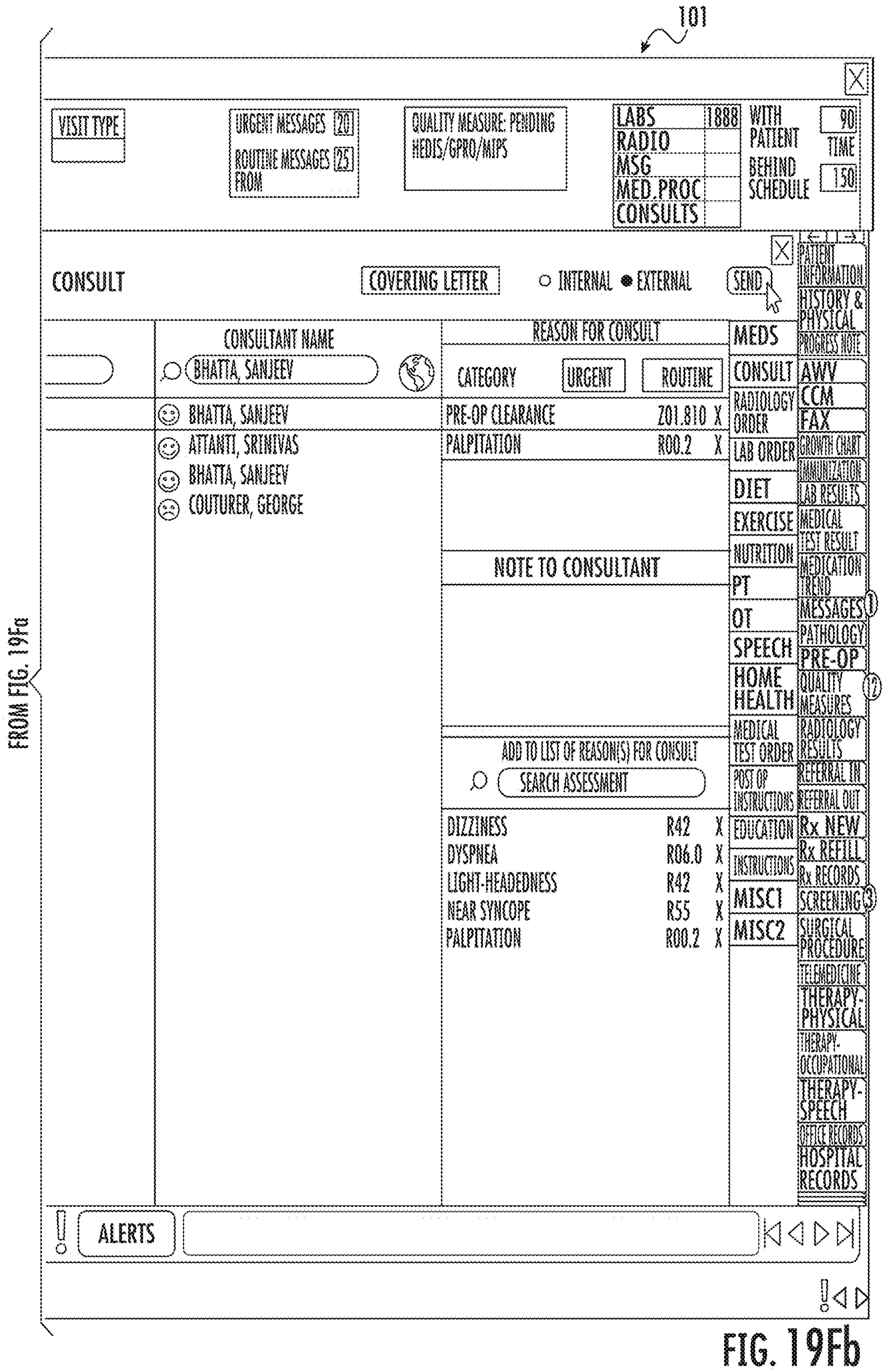
Figure 19G:
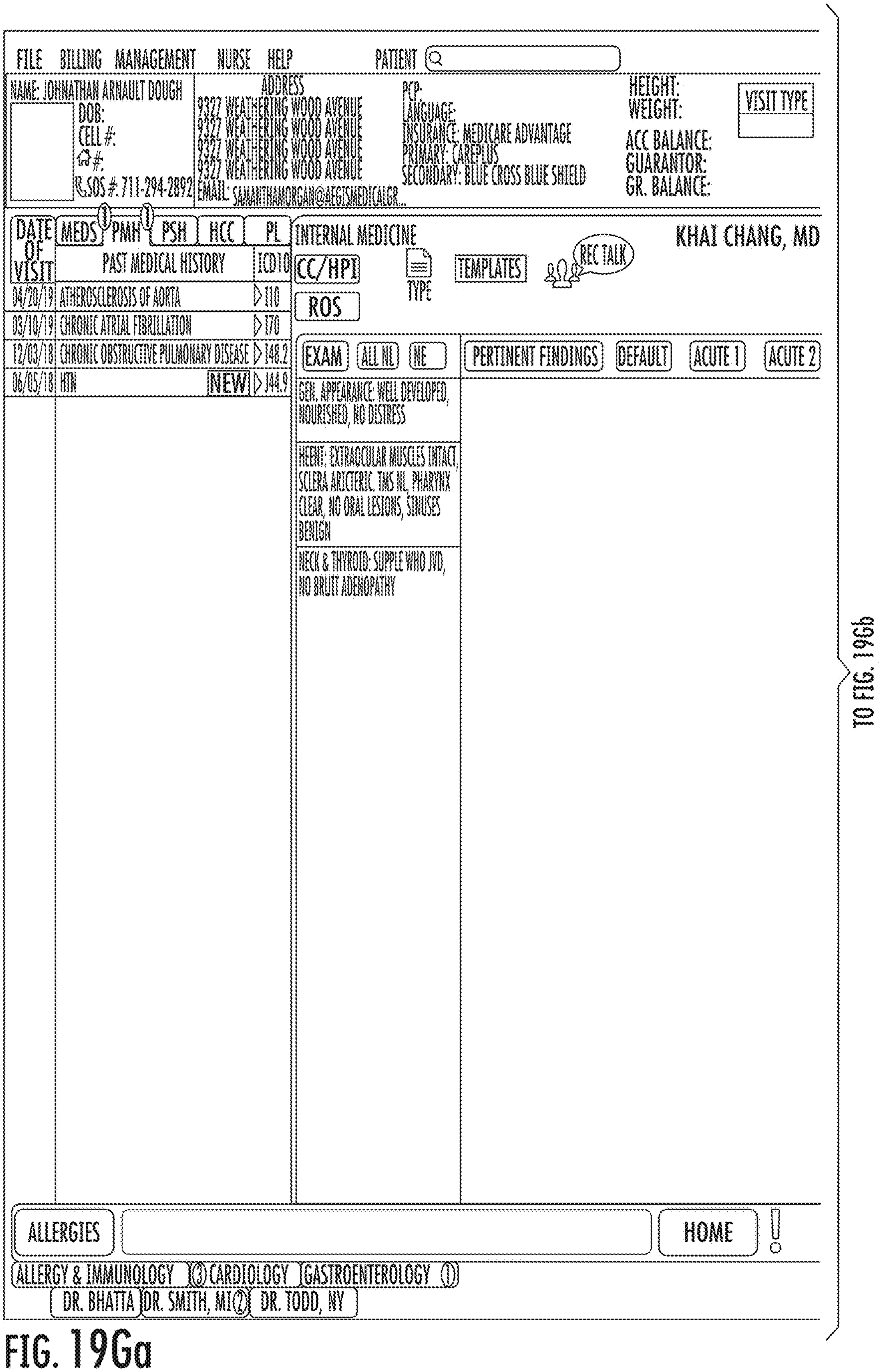
Figure 19G:
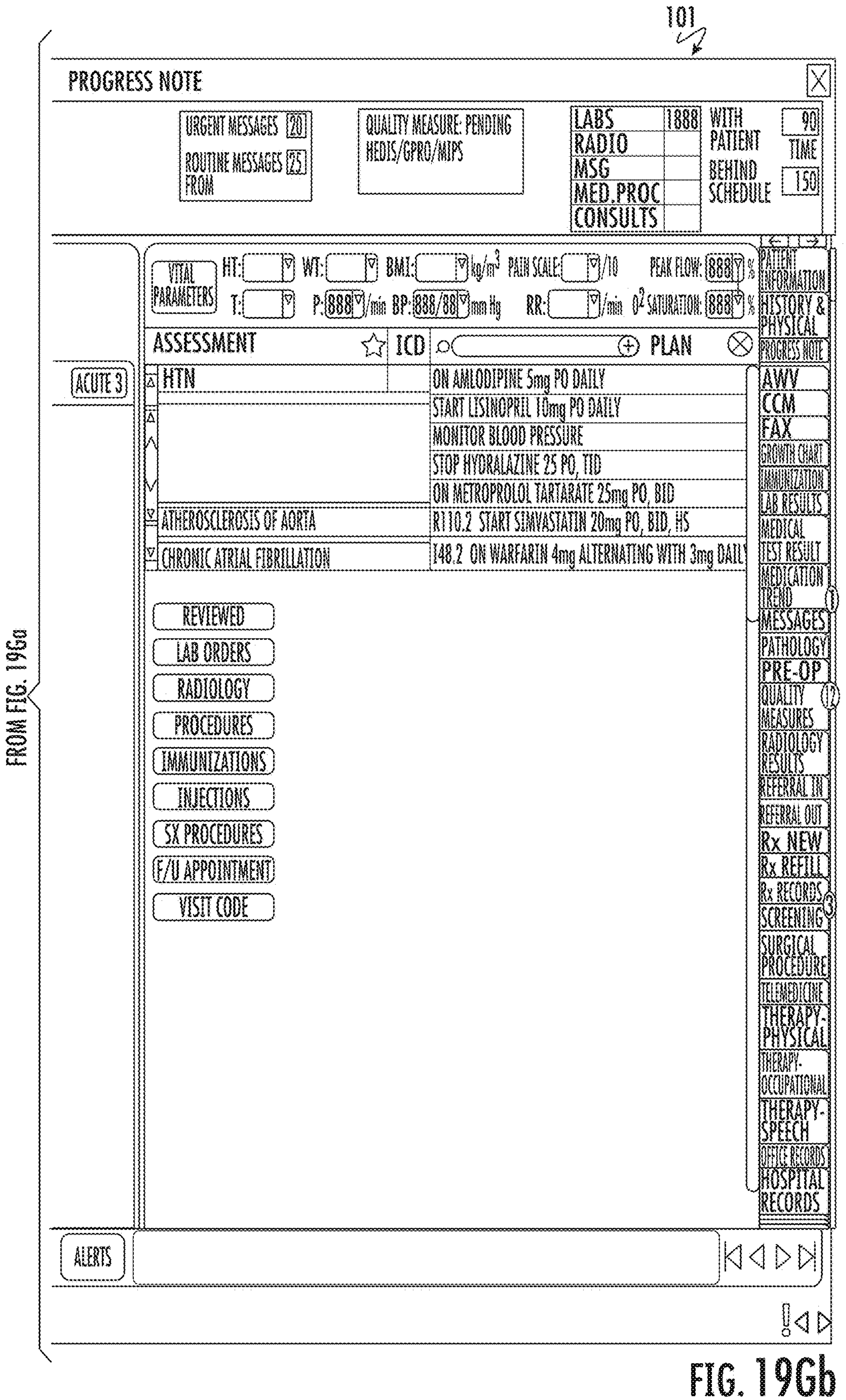

Referring to FIGS. 19Aa-19Gb, any orders except what has already been covered under all the other tabs on the right side of the assessment and plan template (i.e., the second row of vertical tabs from the extreme right hand side of the progress note of the patient chart). This could be any order not covered under the other tabs.

This could be "individual instructions", which will be available immediately to the right of the plan column, for example, the "flutter valve breathing exercises" for an assessment of "COPD", "decrease fluid intake" for an assessment of "congestive heart failure", "decrease salt intake" for assessment of "congestive heart failure", or "take stool softener docusate sodium OTC, if constipated from taking Iron tablet" for assessment of "Iron deficiency anemia". It also could be "order sets" where a group of orders can be created beforehand under different headings and the saved under one order set. This column will be to the extreme right of the template. When the arrow for the order set has been created, which will have multiple orders created under multiple different headings, a single click will then bring it into the Plan hence saving time and effort. Similarly, different kinds of order sets could be created for different circumstances and saved for future use depending on those circumstances.

The key functionality is that: All instructions will be related to the assessment and created for each individual assessment. All the instructions created will be saved under this tab for future use, and will automatically be displayed whenever that assessment is populated under the assessment (diagnoses) heading. So, as more and more new instructions are being created, for a particular assessment, a compendium of instructions will be created over a period, for that assessment. Thereafter, all the provider needs to do in the future is to click on the arrow(s) to the left of those instruction(s) either individual or multiple instructions created under order sets, to bring it into the Plan for that assessment. Therefore, typing and searching may be reduced in the long run.

Figure 20A:
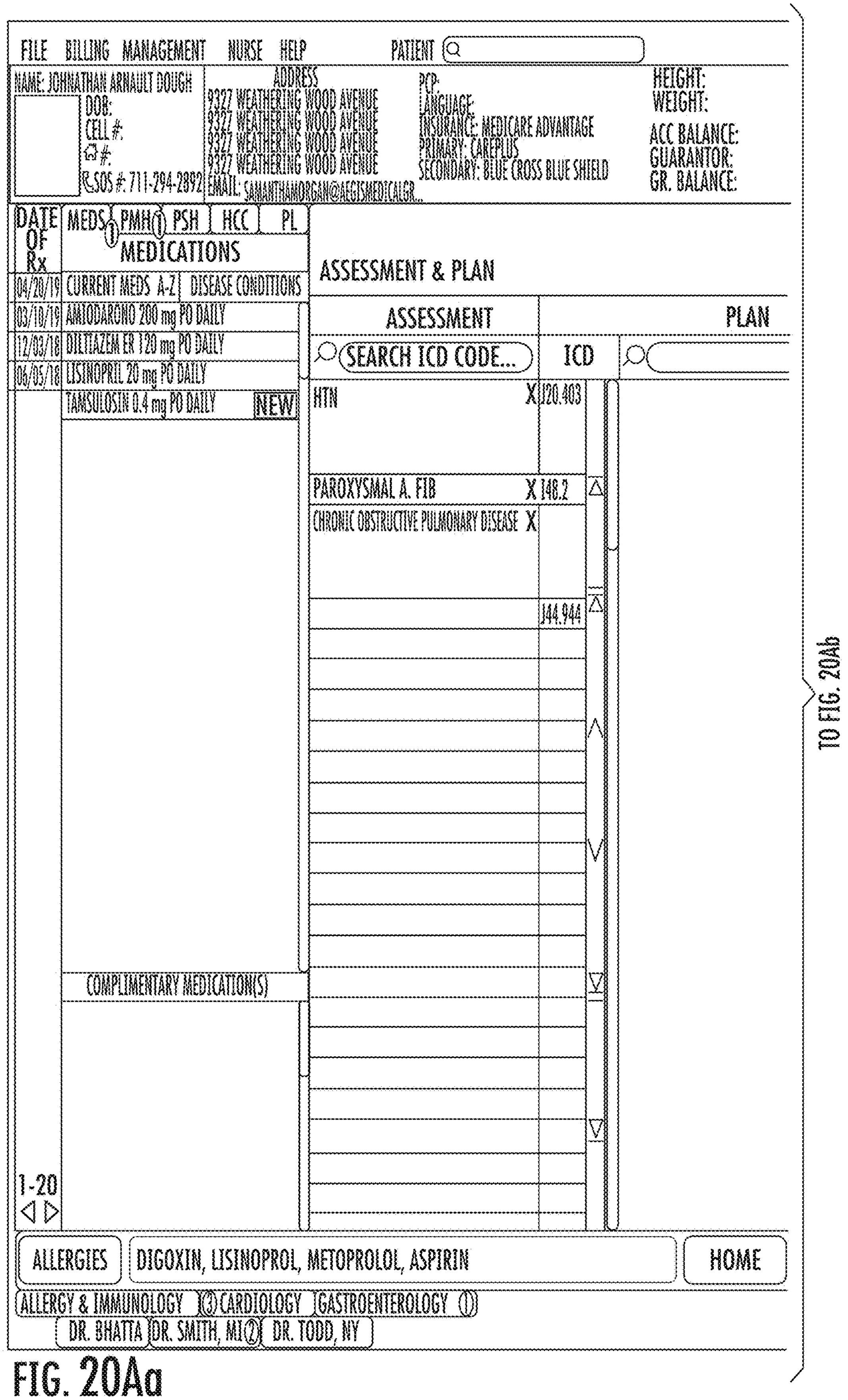
FIGS. 20Aa-20Cb are screenshots of an example embodiment of a progress note assessment and plan-physical therapy, occupational therapy, and speech therapy function of the EHR GUI from the EHR system of FIG. 1.
Figure 20A:
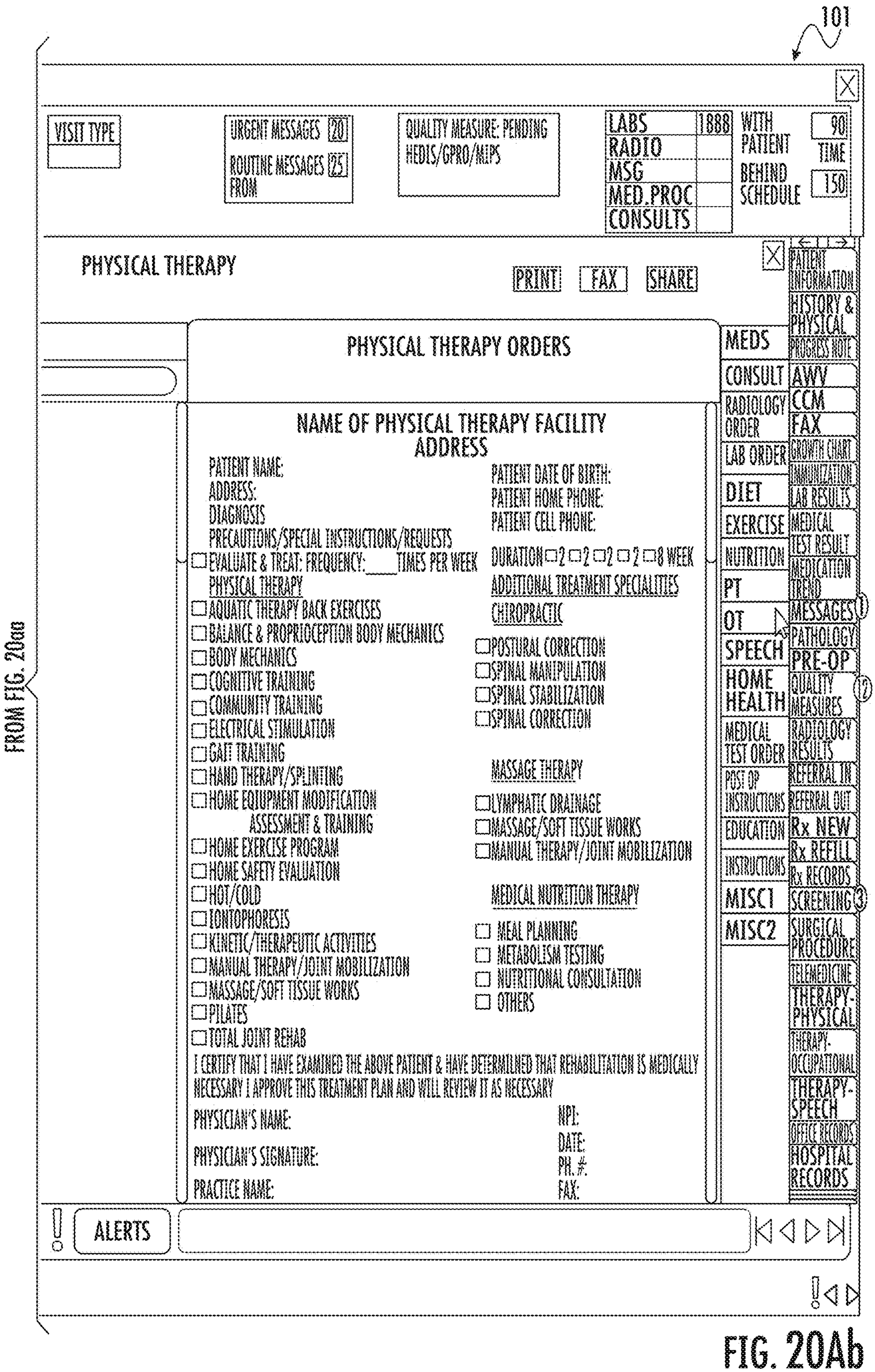
Figure 20B:
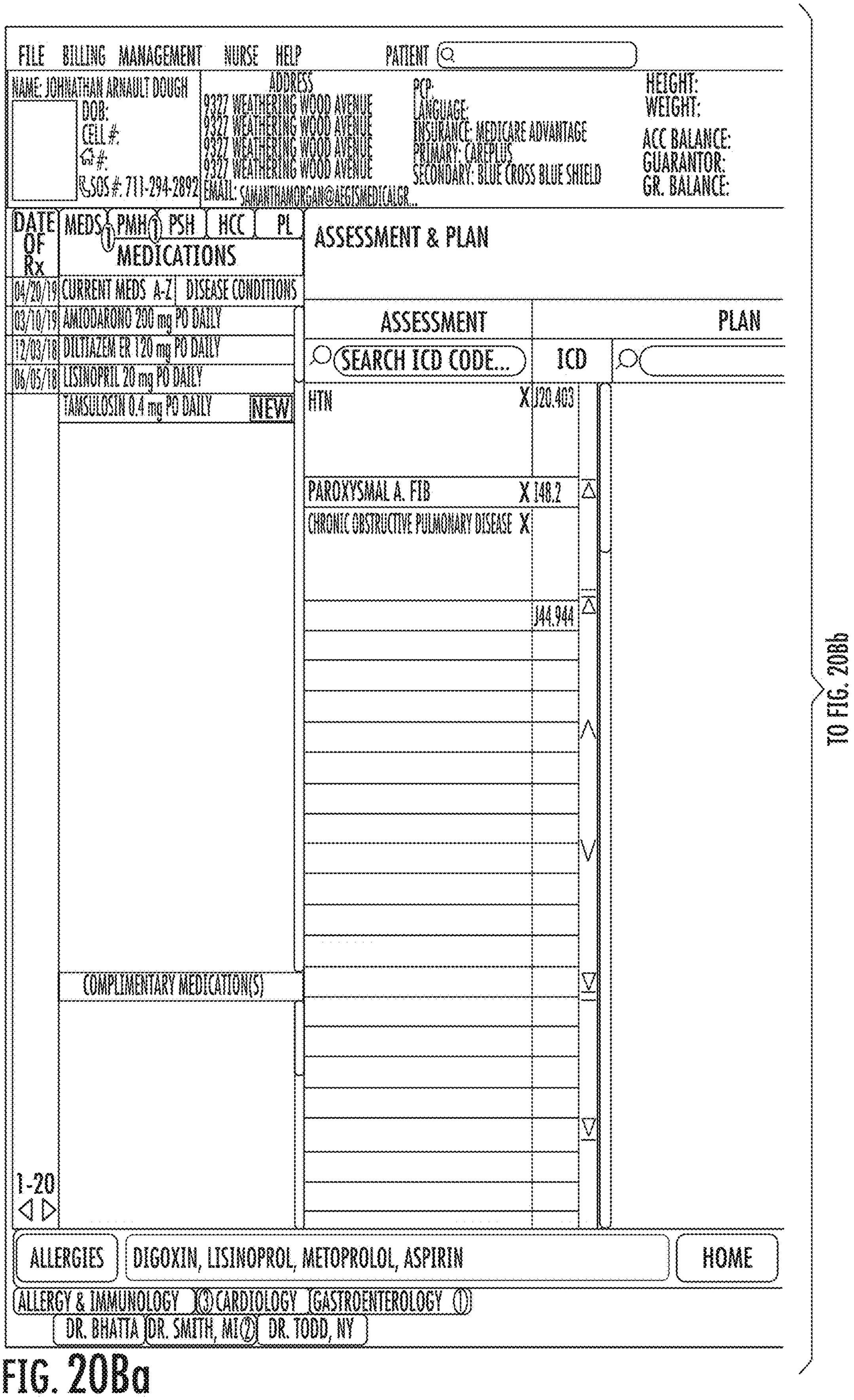
Figure 20B:
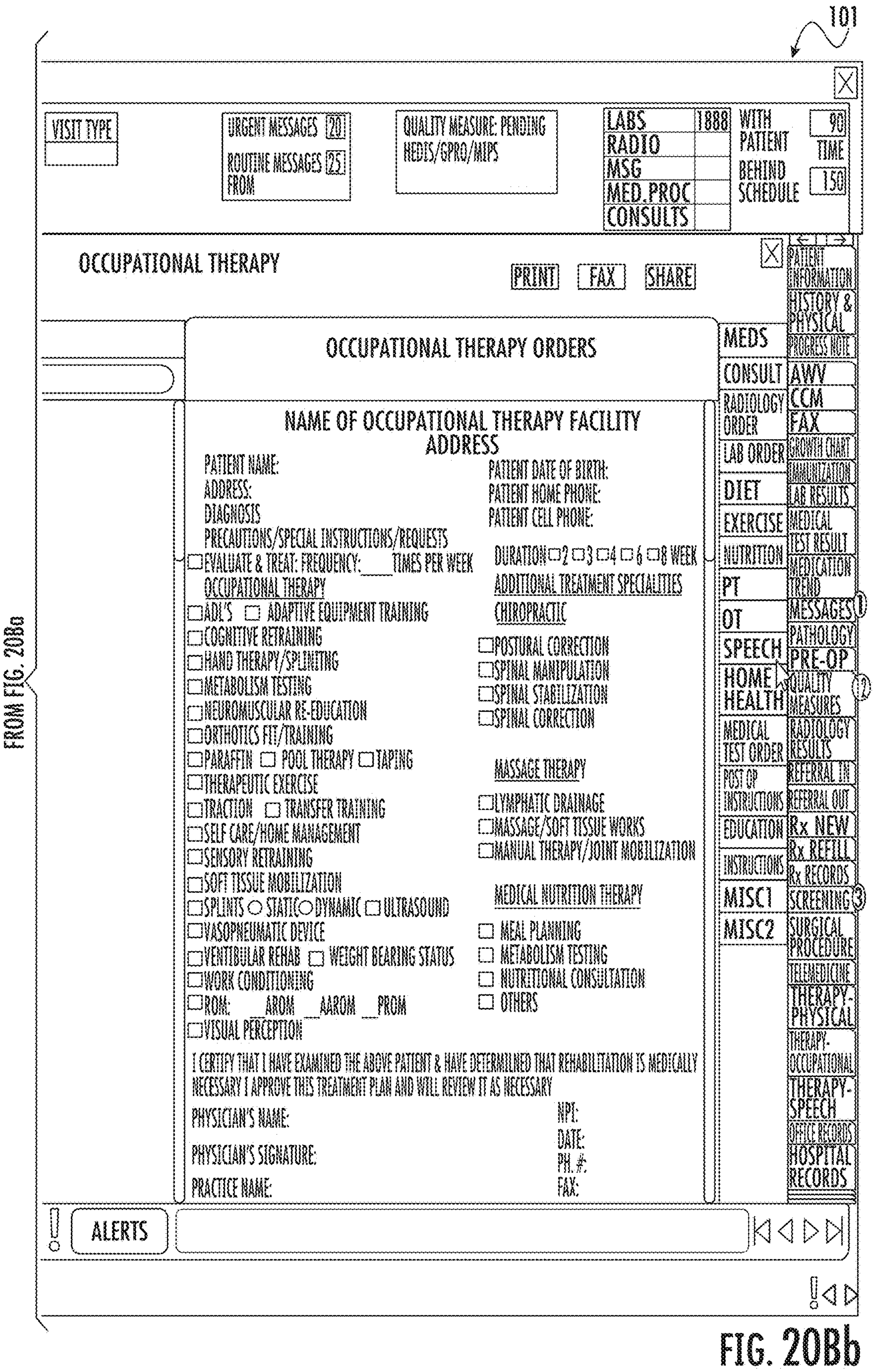
Figure 20C:
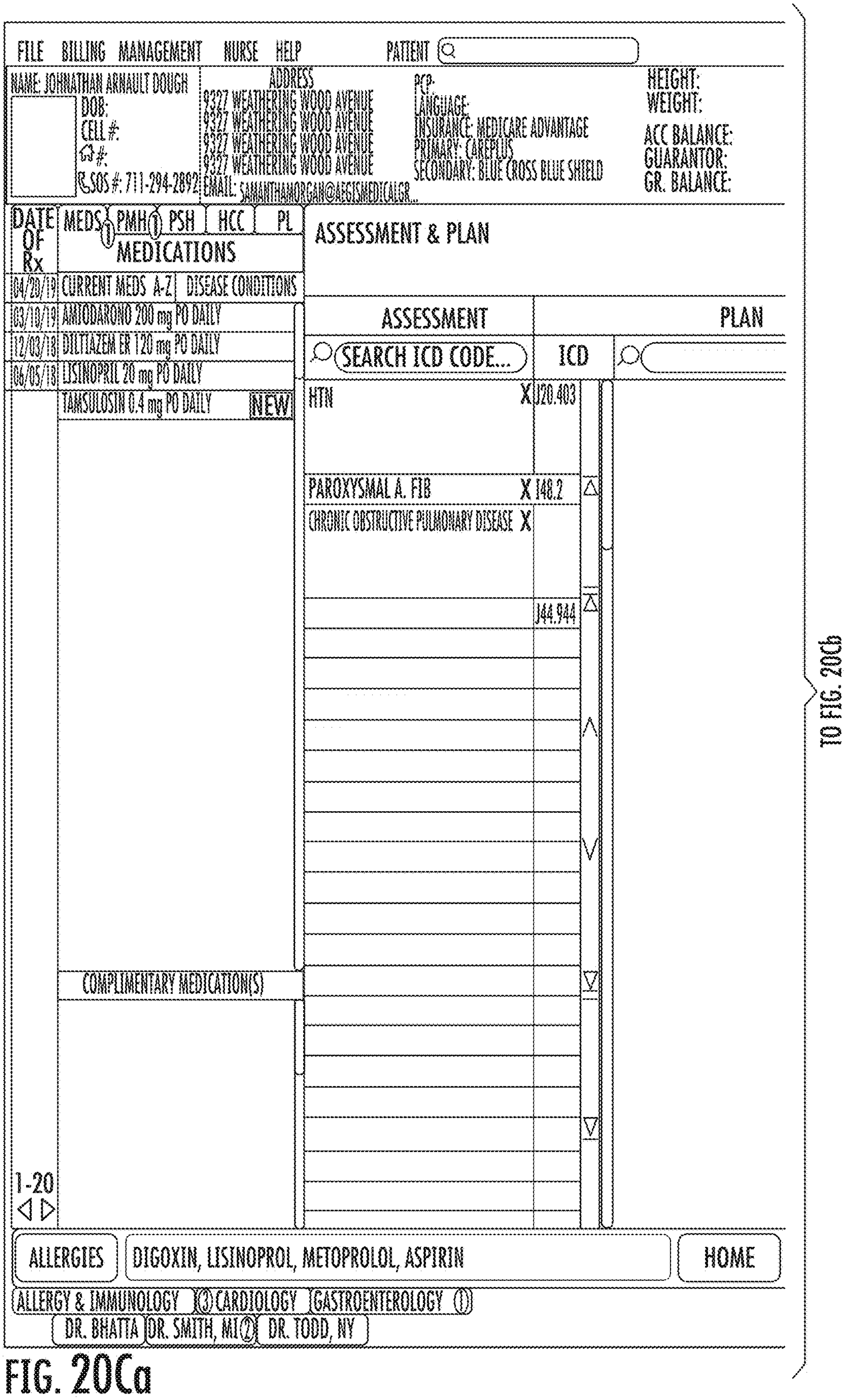
Figure 20C:
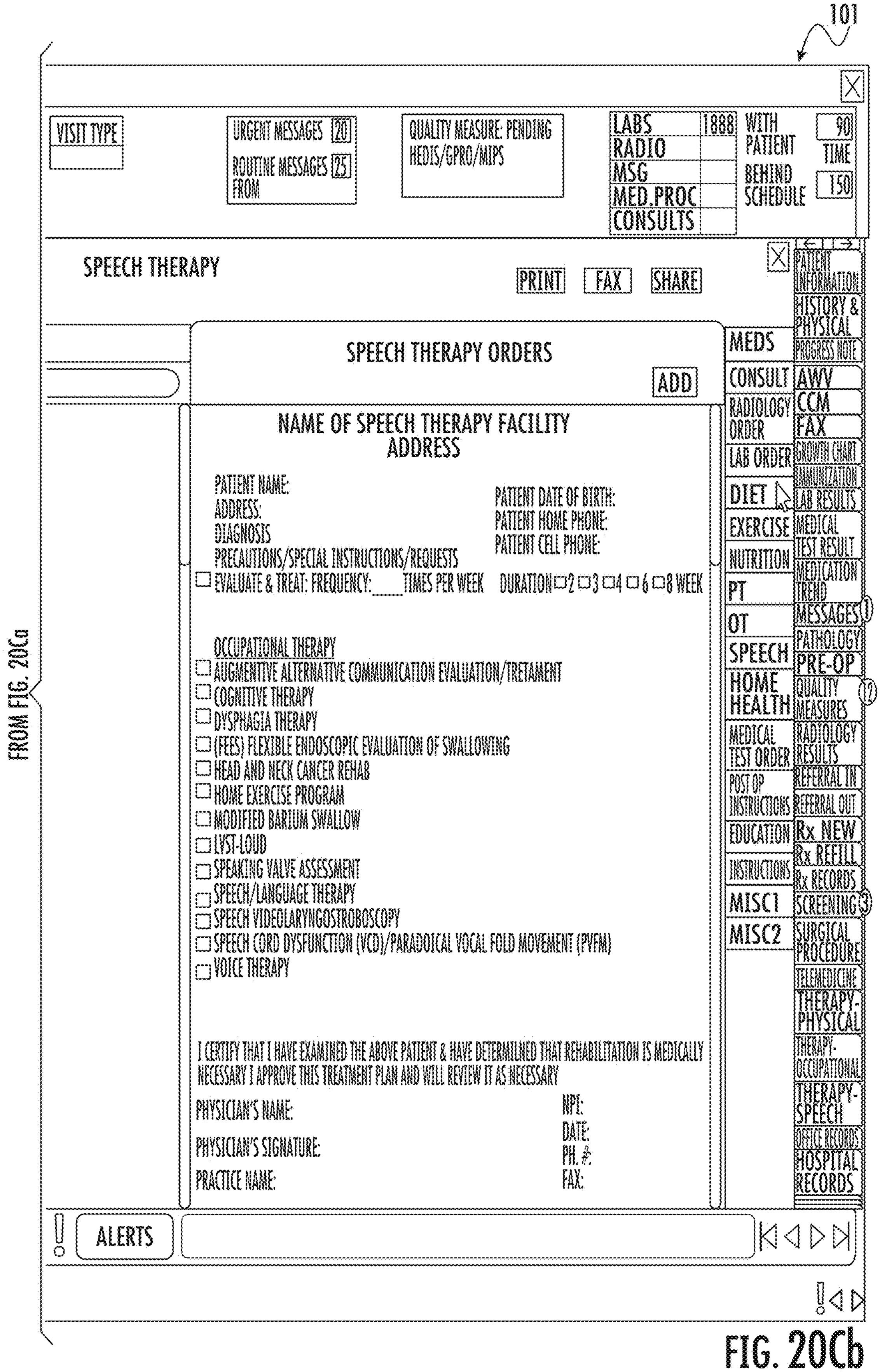

Referring to FIGS. 20Aa-20Cb, in these screenshots, when the tabs are clicked, this will upload a prescription for these modalities of therapy. It will already have all the possible treatment modalities prepopulated with a check box in front of it. The provider will need to choose the template he needs to use based on the patient needs and will then click on the "search" button for the company or facility that he wants the patient to go to and then it will populate the name of the company or facility on the plan. The provider can then choose the kind of therapy, frequency, and the duration which the patient needs, and this can be checked or typed in. It will have all the patient details on the prescription. This will allow the facility to call the patient and set up the appointment for the therapy. The provider's name and details and signature space will be at the bottom of the prescription. It will be populated automatically from the EHR database including the signature, and this can be faxed or printed and given to the patient.

Figure 17A:
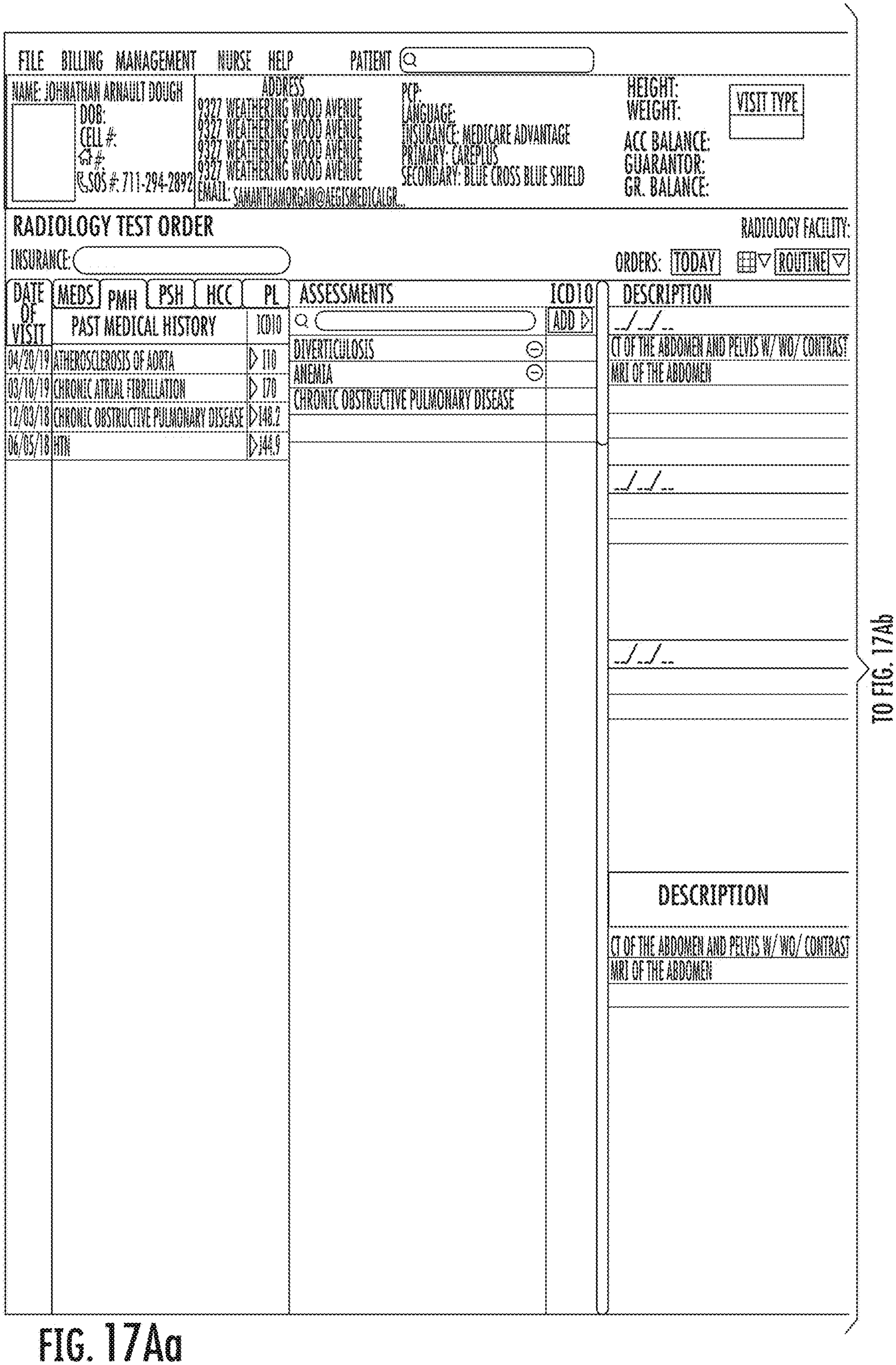
FIGS. 17Aa-17Db are screenshots of an example embodiment of a progress note assessment and plan-radiology order function of the EHR GUI from the EHR system of FIG. 1.
Figure 17A:
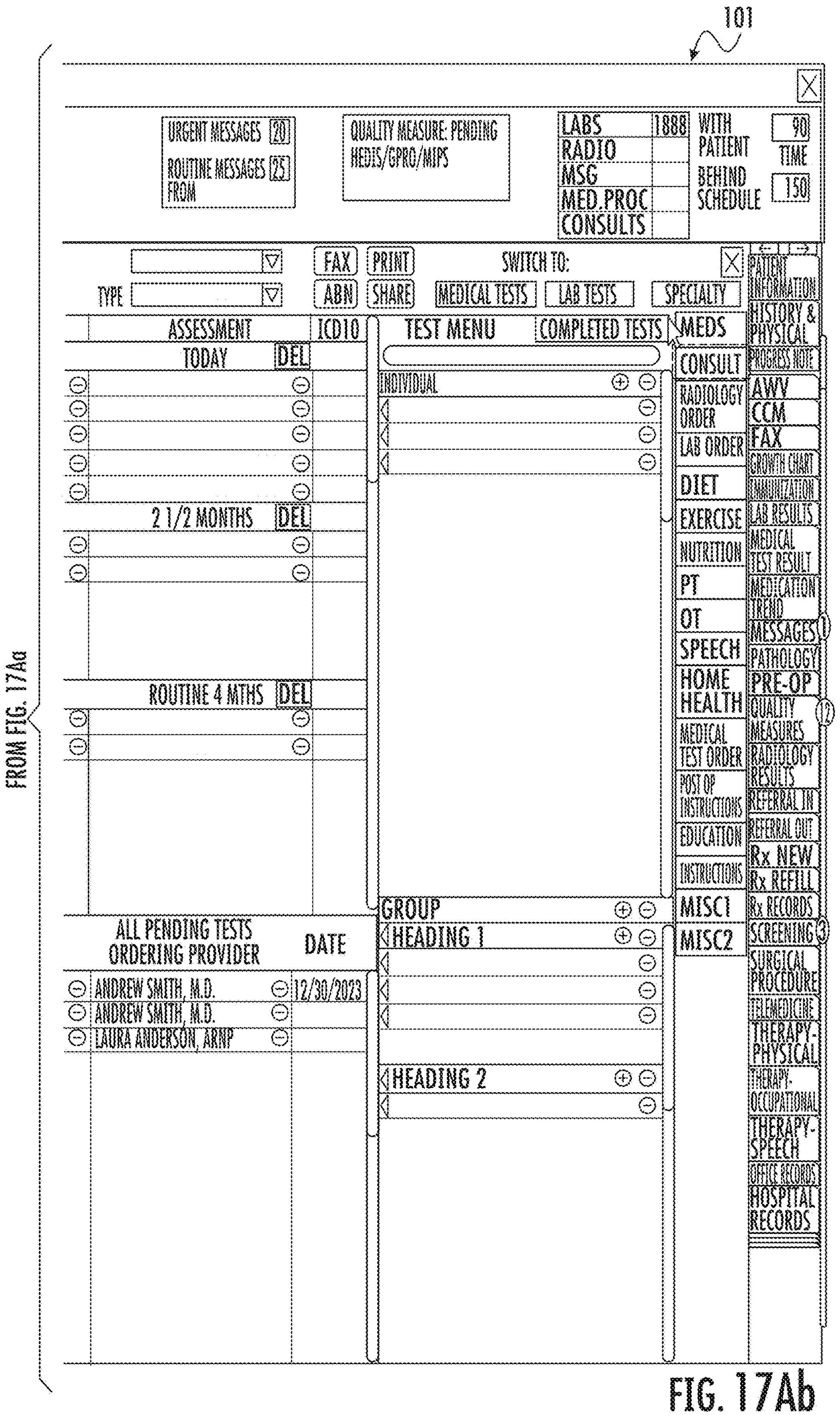
Figure 17B:
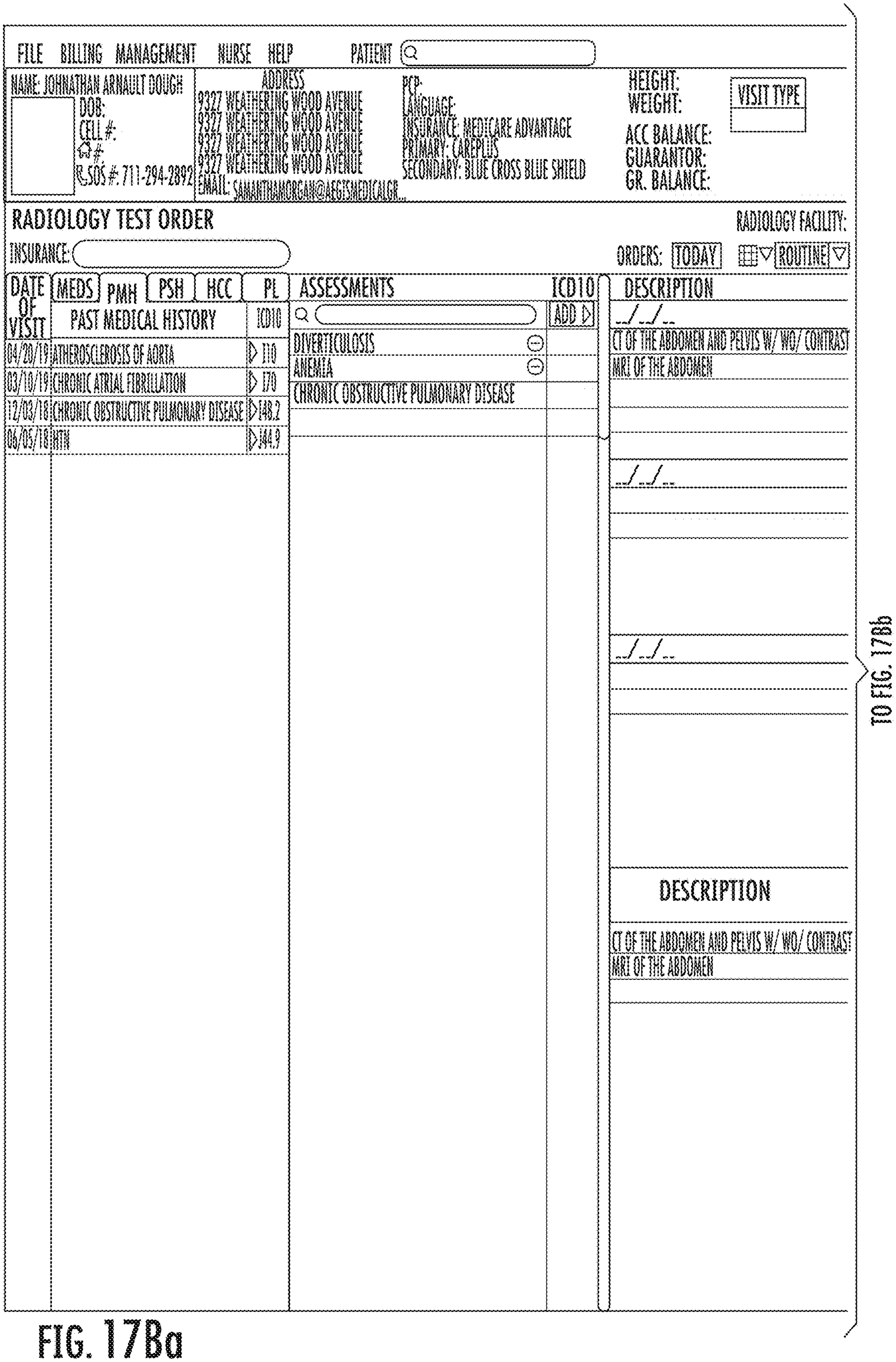
Figure 17B:
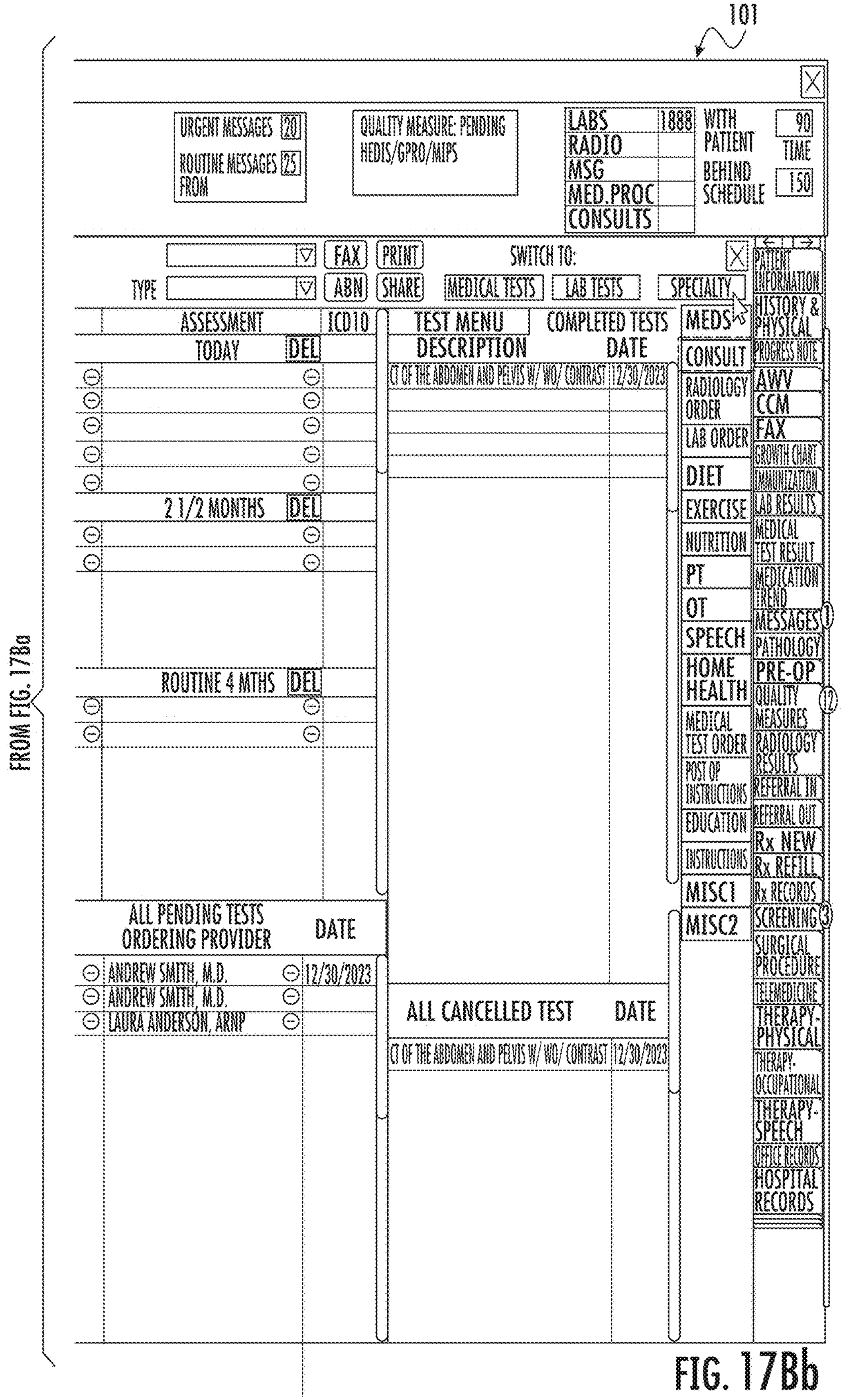
Figure 17C:
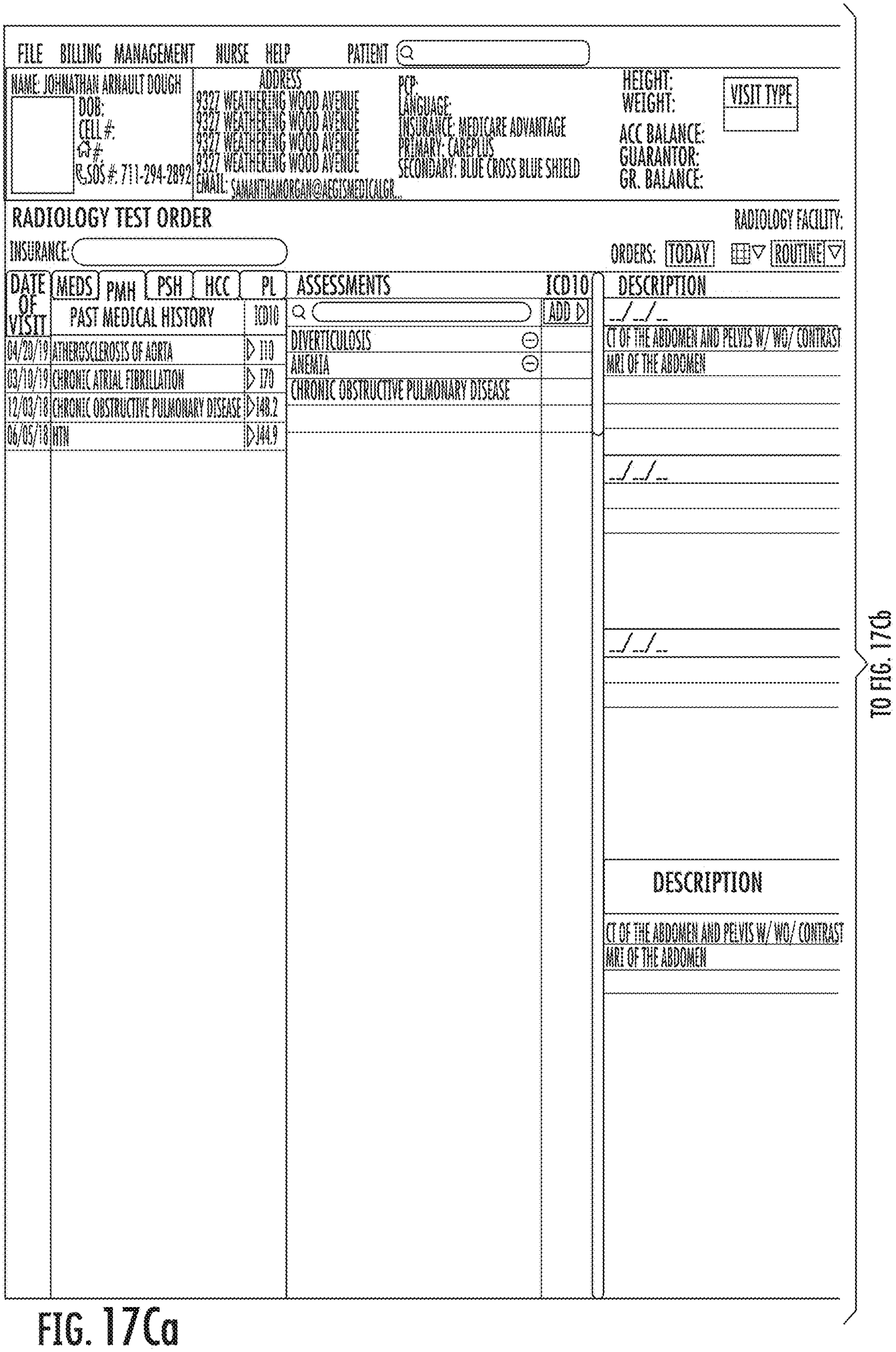
Figure 17C:
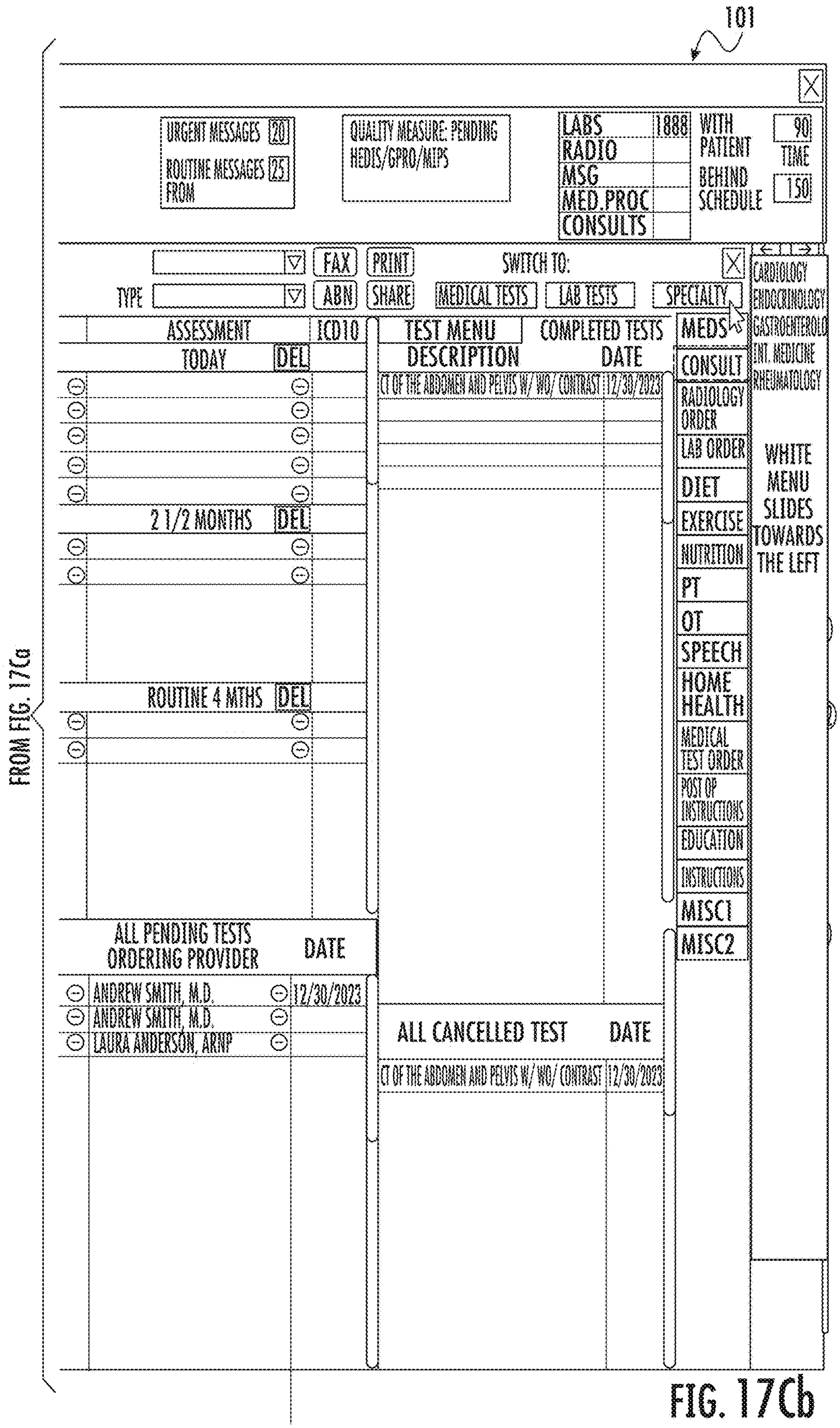
Figure 17D:
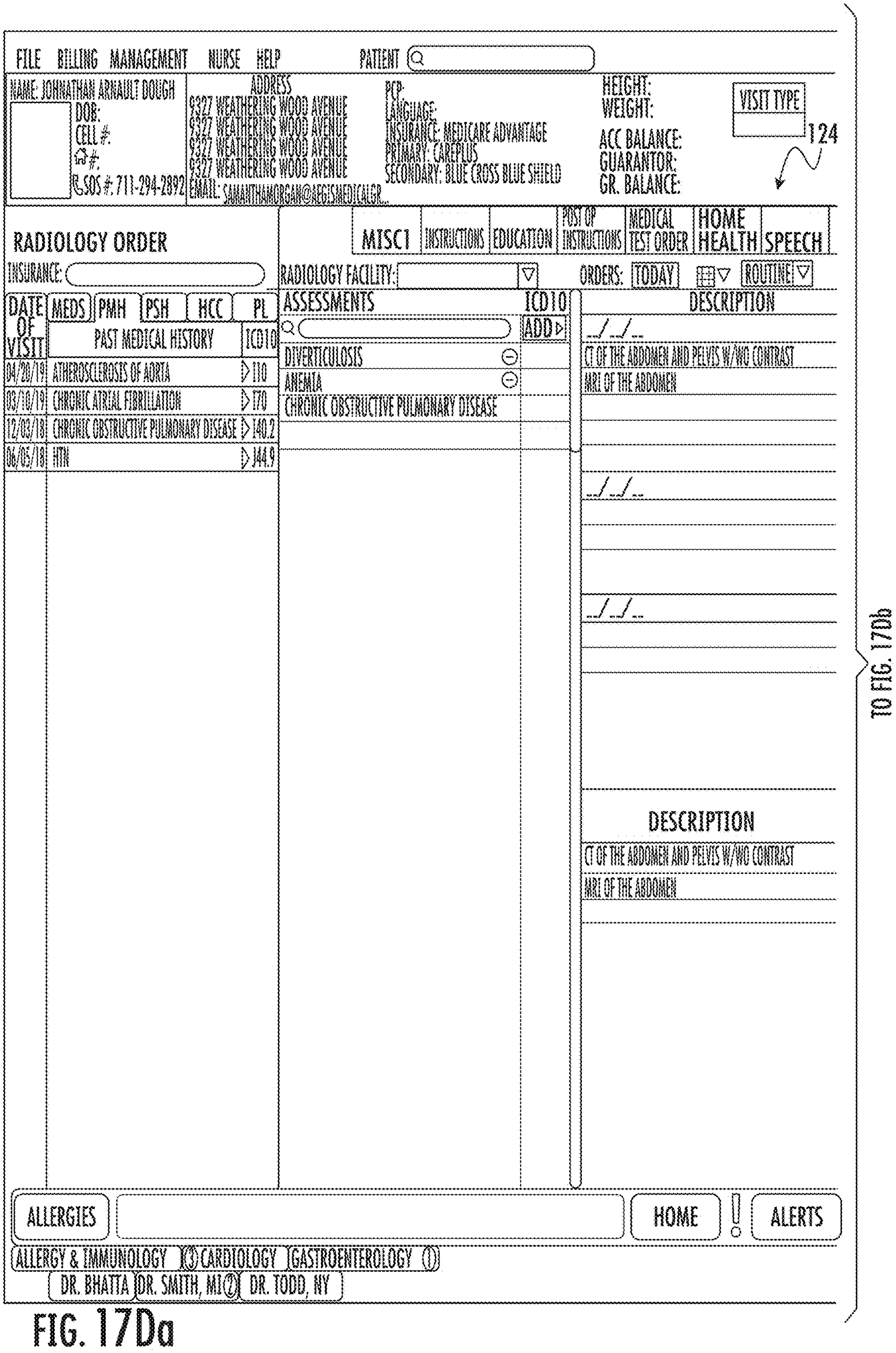
Figure 17D:
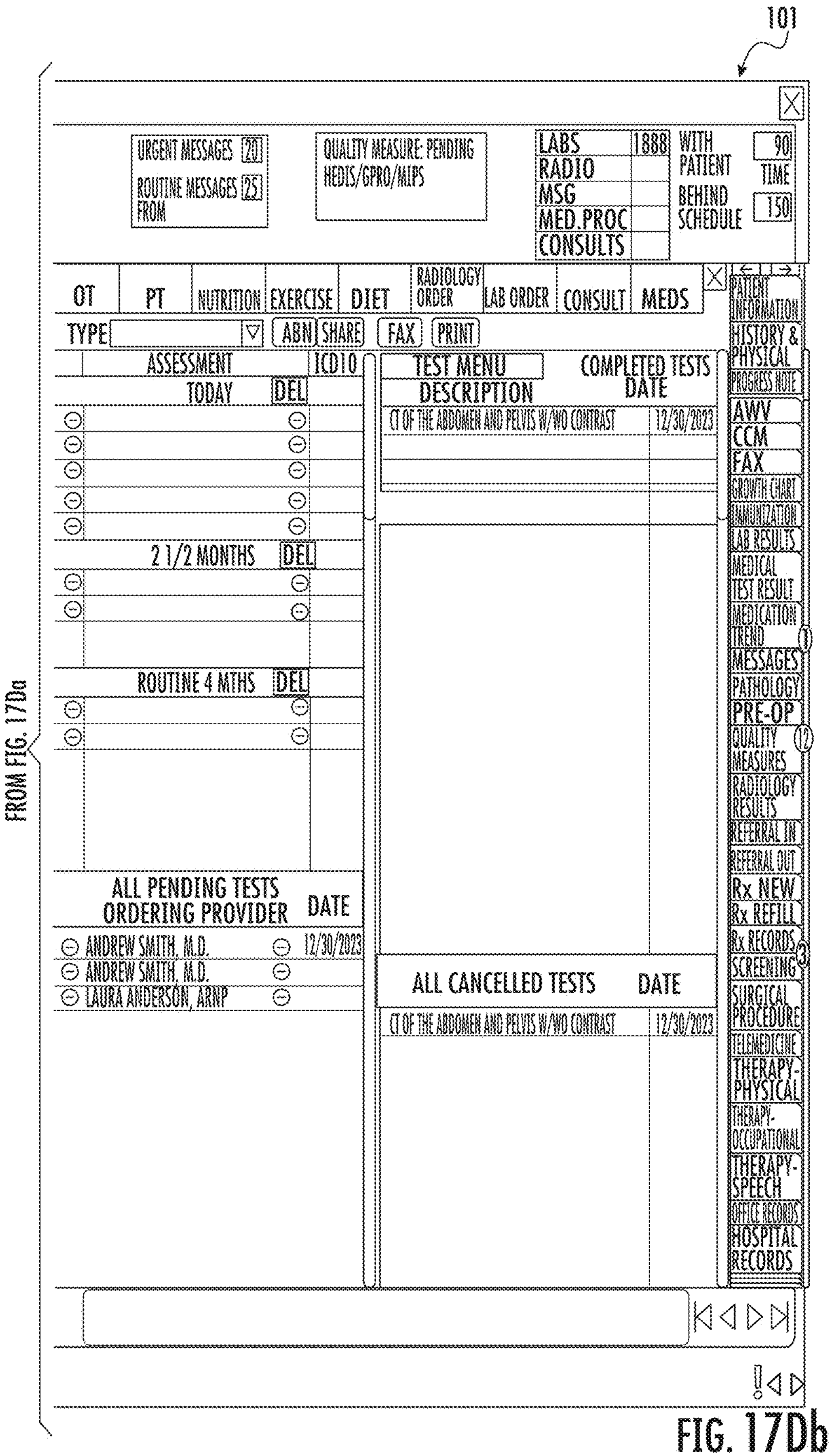

Referring to FIGS. 17Aa-17Db, the radiology order function is now described. When the "assessment and plan" bar is pressed on the progress note second page, a template will open which will have all tabs related to further orders show up on the side like medications, radiology order, lab order, PT, OT, and speech therapy, etc. By clicking the "radiology order" tab on the right hand side, another template will open which will be for the radiology orders to be put in.

On the left hand side will be the standard tabs which will include medications, PMH, PSH, PL and HCC tab. From this PMH tab all the medical diagnosis which are relevant for that particular visit, can be pulled into the assessment by clicking on the different "diagnoses" under the PMH which is the second column from the left hand side. Any new assessments can also be added under the assessments column, by searching for a diagnosis not in the past medical history, using the search button.

Whenever an assessment is clicked on, it will highlight it, into a different "active color" and radiology order pertaining to that assessment can now be added into the radiology section to the right of it, which could be related to an acute visit, say an 1) Upper respiratory Infection needing a Chest X-Ray or 2) Acute Diverticulitis needing a CT scan of the abdomen.

Radiology orders can also be added for certain routine tests on a yearly basis, for example, Meningioma a brain tumor follow up or any other time frame as deemed appropriate based on the diagnosis, and the diagnoses codes along with the ICD codes can be added next to it from the PMH or PL which has the diagnoses with the ICD 10 code attached with it. On the top of the space for the radiology orders are going to be 3 buttons 1) Today 2) Calendar and 3) Routine. Today: When the button for "today" is clicked, it will create a bar below in the radiology column with today's date on it and radiology orders can now be pulled in from the left side of it, for the radiology test to be performed on the same day of the patient visit. This is usually for "acute visits" when this is usually required.

Calendar Button: When there is a desire for a radiology test to be ordered for a particular time frame with no specificity then the calendar button can be opened to choose any date, week(s) or month(s) to be created, so that test can be ordered to have it performed in that particular time frame when it is required. For example, when the patient has an abnormal mammogram and needs a repeat in say 6 months, the calendar can be used to create a date for six months from the date of the previous mammogram. The order can then be automatically faxed to the radiology facility a couple of months prior to the test so that it can be scheduled for the patient.

Routine: This button is to order routine radiology for the patient. Say a patient has been a heavy smoker and needs a low dose CT Chest for lung cancer screening, the routine button can be programmed for 1 year by "right" clicking on it and a box will open up which will have different time frame already prepopulated on it like 2, 2½, 3, 3½, 4, 4½ months etc. up to a year on it and the provider can pick and choose the time frame he wants to use and then click the "save" button to save it for that time frame. When he clicks on the routine button in the future, it will automatically create a bar with a working date for one year. Now since it was just created it will by default be active and now radiology orders can be added under that date from the "test menu" either as "individual" or can be brought in from the "group" test(s). Any radiology order created by mistake under a particular "heading" can be highlighted and be deleted by clicking on the "DEL" (Delete) button on the heading bar.

Any "individual" radiology test under a heading, can be deleted by clicking on the Negative (−) round button to the right of it. All Pending Tests: All radiology tests ordered by any provider including specialists for any future dates will be displayed under the "all pending tests" bar. This is to prevent ordered or same radiology tests too close to each other and prevent duplication and prevent wastage of resources.

Test Menu: Providers can create a test menu based on their specialty. It can be created under Individual as "individual radiology test" or as a "group" of radiological test for certain conditions under a second column labelled as "group tests". There is a scroll bar for each "individual" and "group" column. Individual Bar: the (+) button is to add an individual test under the individual column and the (−) button is to delete any test that was ordered by mistake, or the user decides to delete it for any reason. Group Bar: the (+) button is to add a group bar under the group column. Different headings for groups can be created by clicking on this plus button which can then be labeled, and then individual lab tests can be added under each heading by using the plus button on that individual heading bar which was created. The (−) button is to delete a group bar and any individual labs added underneath it, which was created in the past, by highlighting the bar and then clicking the (−) button.

Completed Tests: When the "completed tests" button is pressed, it will display all the individual and group radiology tests done in the recent past going into the remote past (i.e., in descending order), along with the dates and who ordered it. All Canceled Tests: This heading in the lower half of the screen (Completed Tests) will display all the tests cancelled in the past. When the button with the double (++) sign is clicked it should show who was the provider responsible for cancelling the test. Specialty: When this tab is clicked on then the column with all the specialties will slide in from the right side of the screen. This will display all the different specialties under one column. If there is any test which the provider cannot remember for a particular assessment, help can be sought by clicking on the specialty related to that assessment. It will then display all the tests which was ordered by the specialists in that field for that diagnosis (i.e., assessment). Then the provider can click on it to bring that test into the description column from the specialist test menu. This is a functionality which no other EHR has and can be helpful. It will hasten the care of the patient by having all the requisite lab reports available even before the patient sees the specialist. It will save unnecessary repetitive visits to the specialists since what the specialist wanted is already available. Hence, this will cutt specialist waiting time by preventing redundant specialist visits and help primary care providers improve patient care by opening specialist input (special lab test ordering availability) to the primary care physician and widening their knowledge base.

Figure 21A:
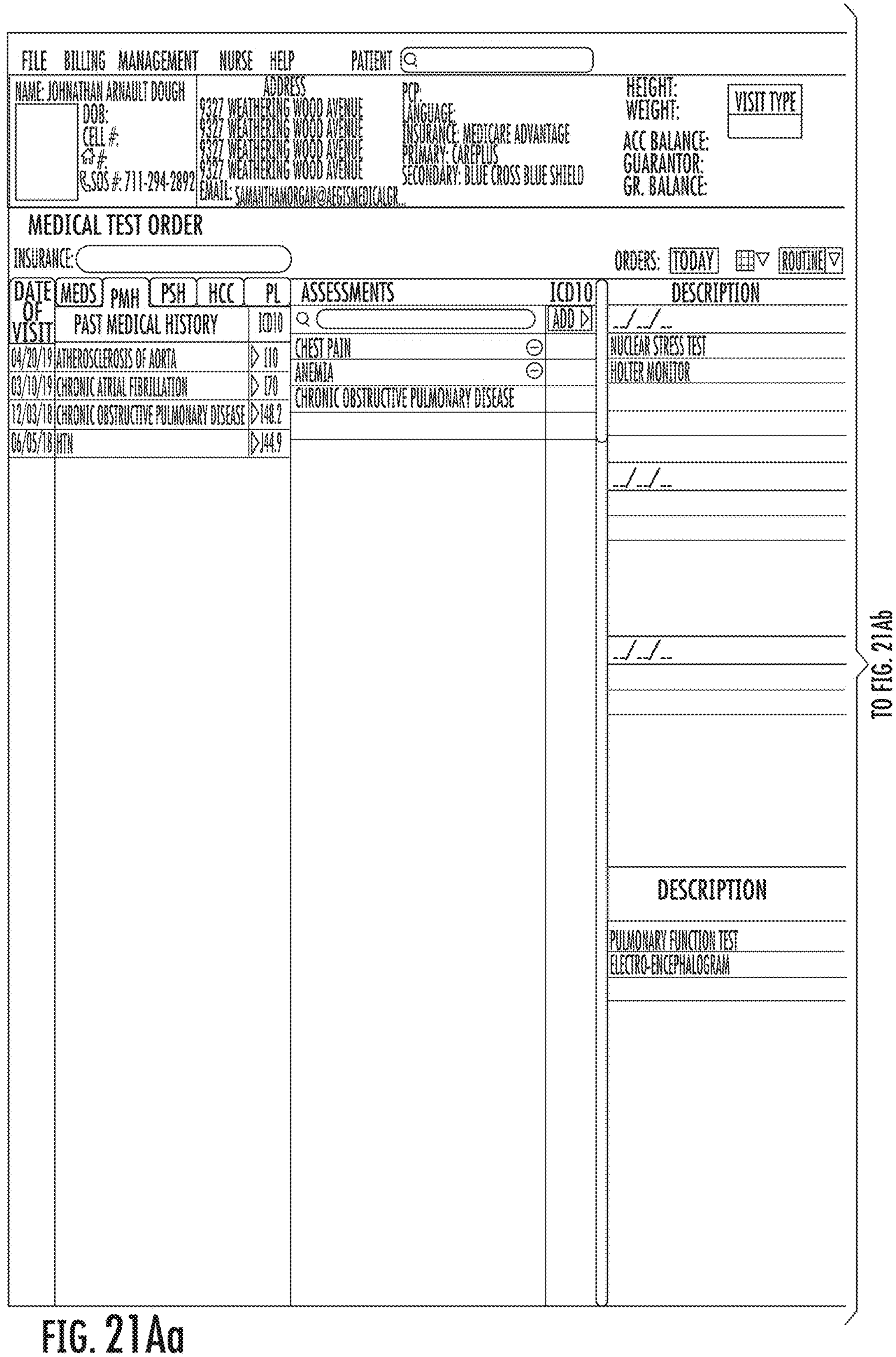
FIGS. 21Aa-21Cb are screenshots of an example embodiment of a progress note assessment and plan-medical test order function of the EHR GUI from the EHR system of FIG. 1.
Figure 21A:
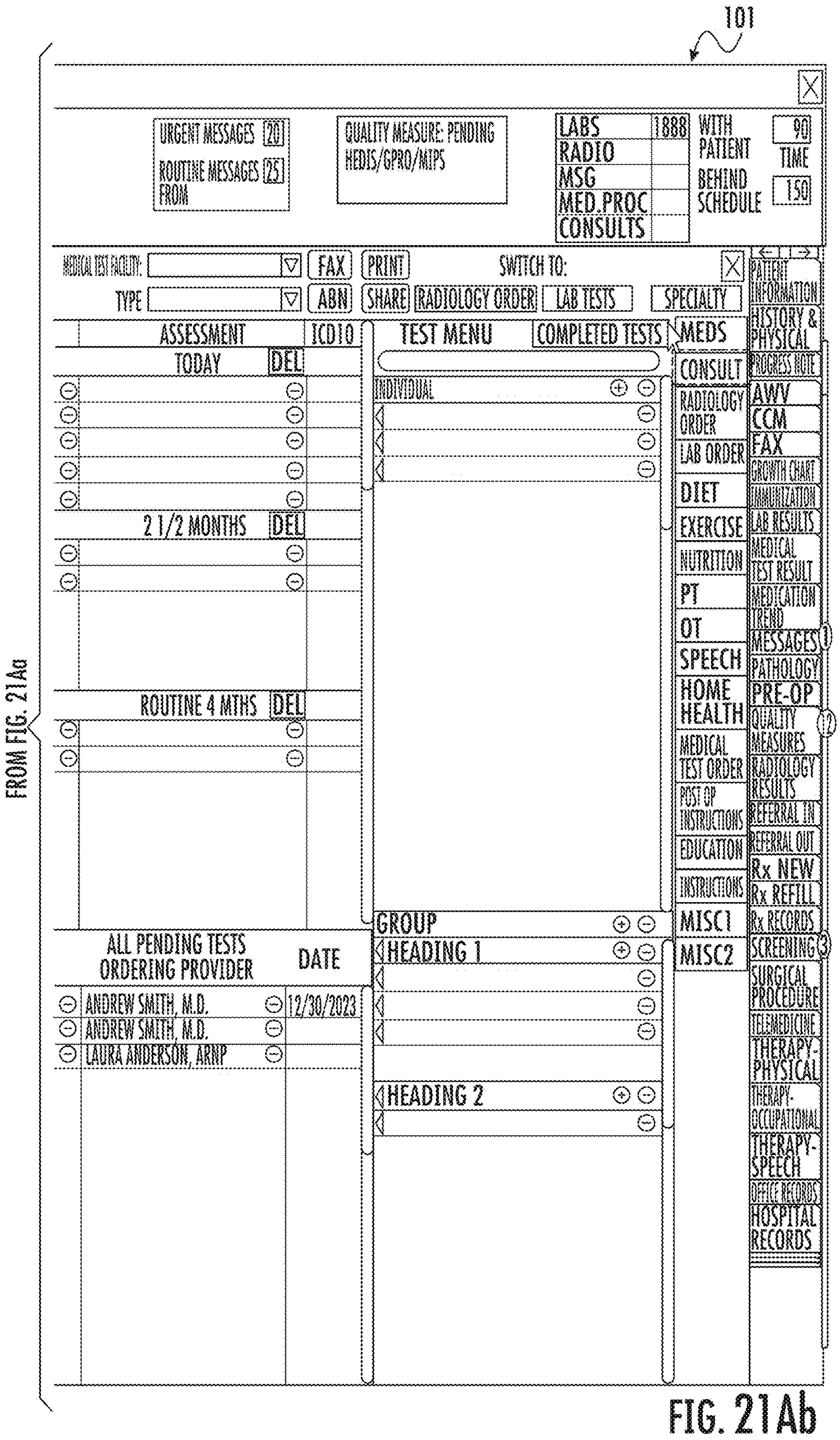
Figure 21B:
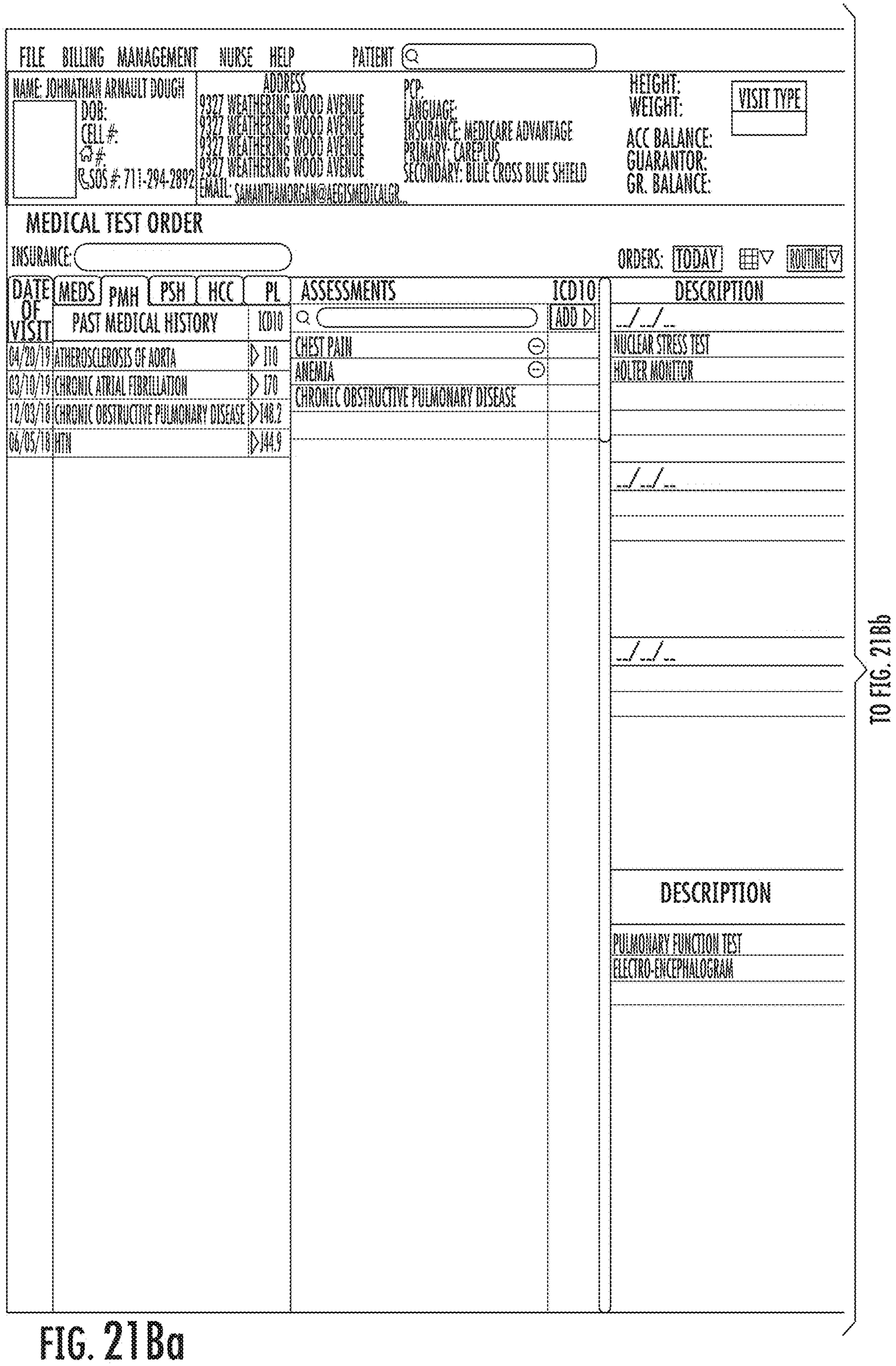
Figure 21B:
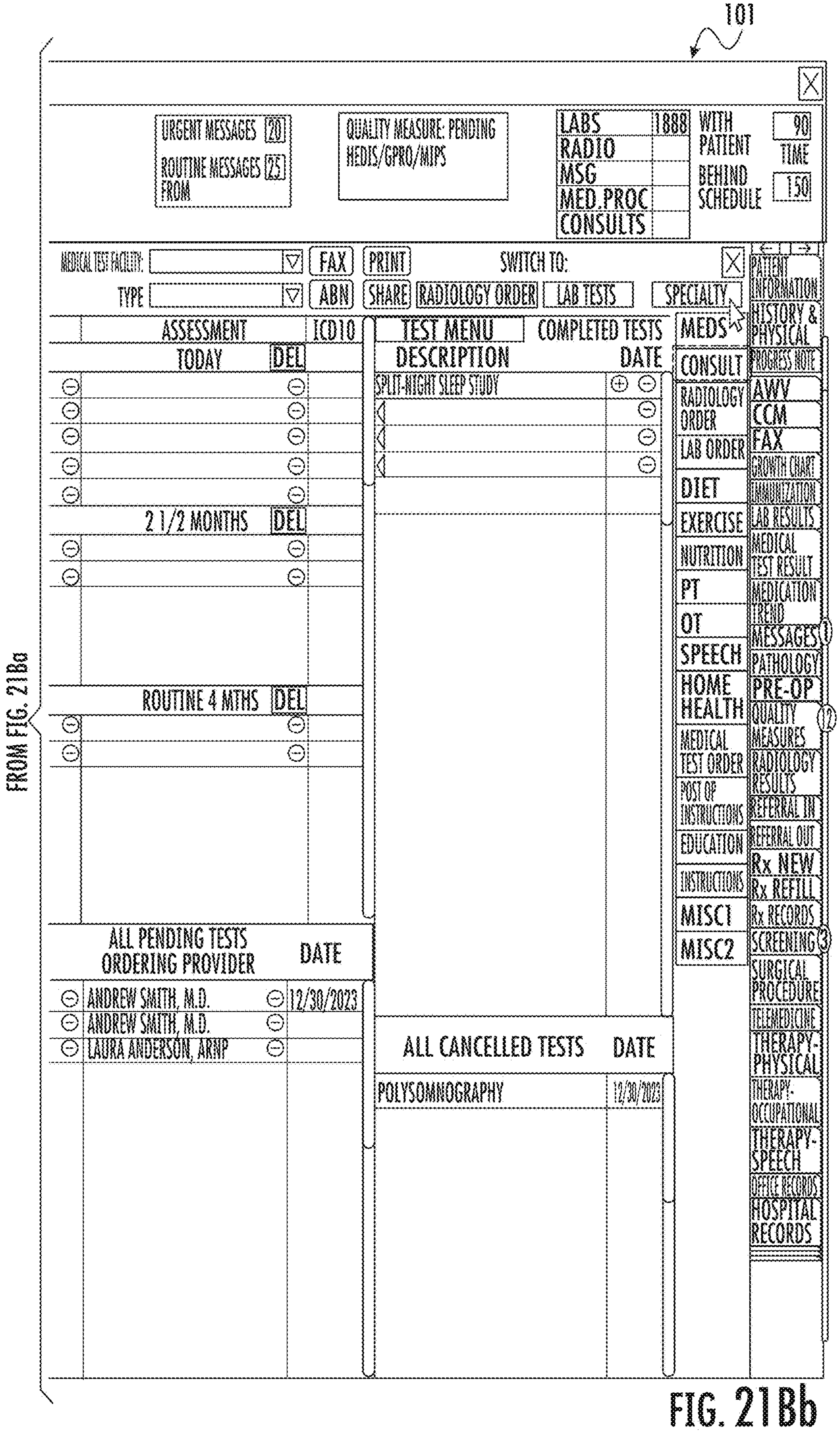
Figure 21C:
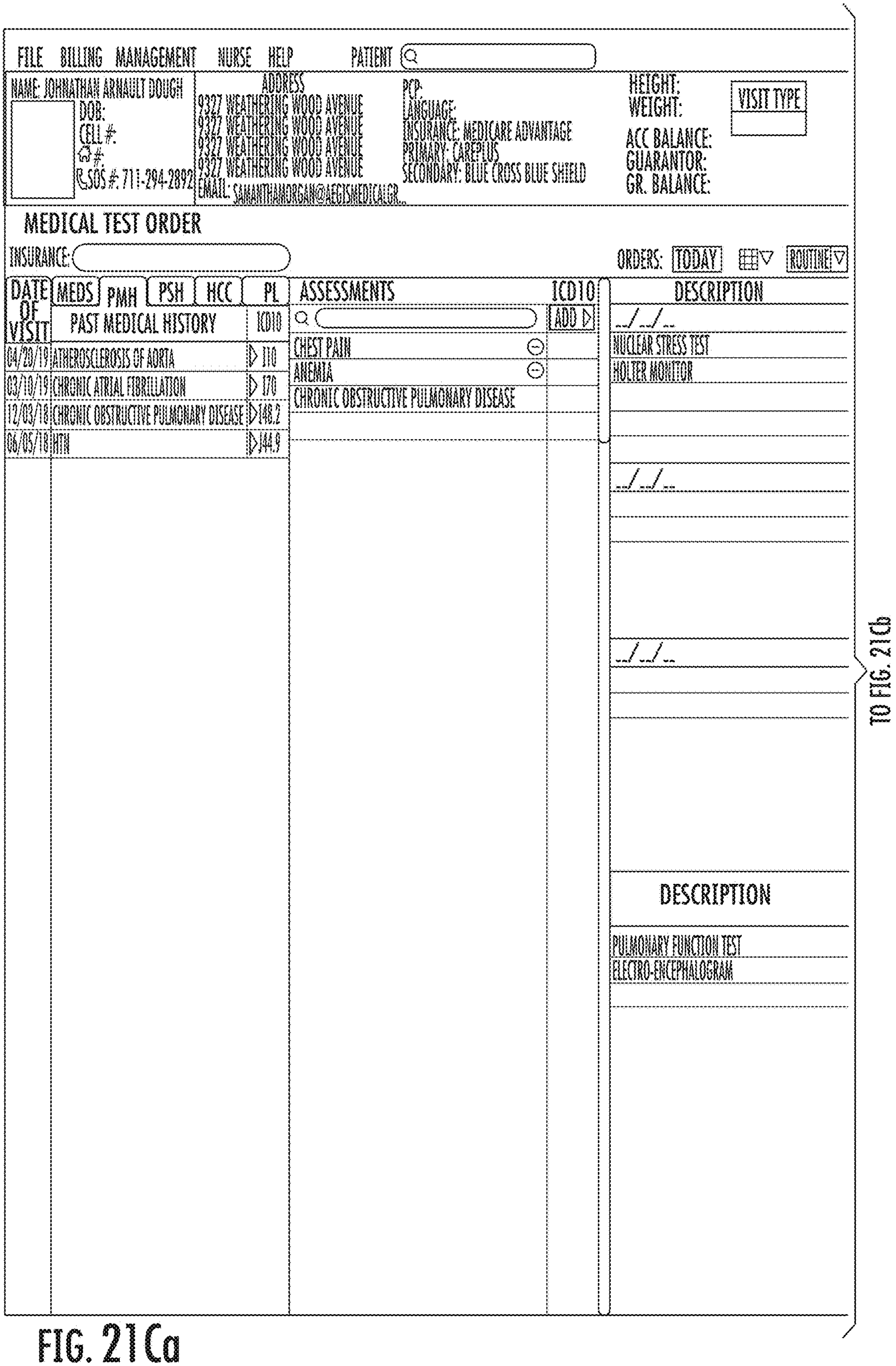
Figure 21C:
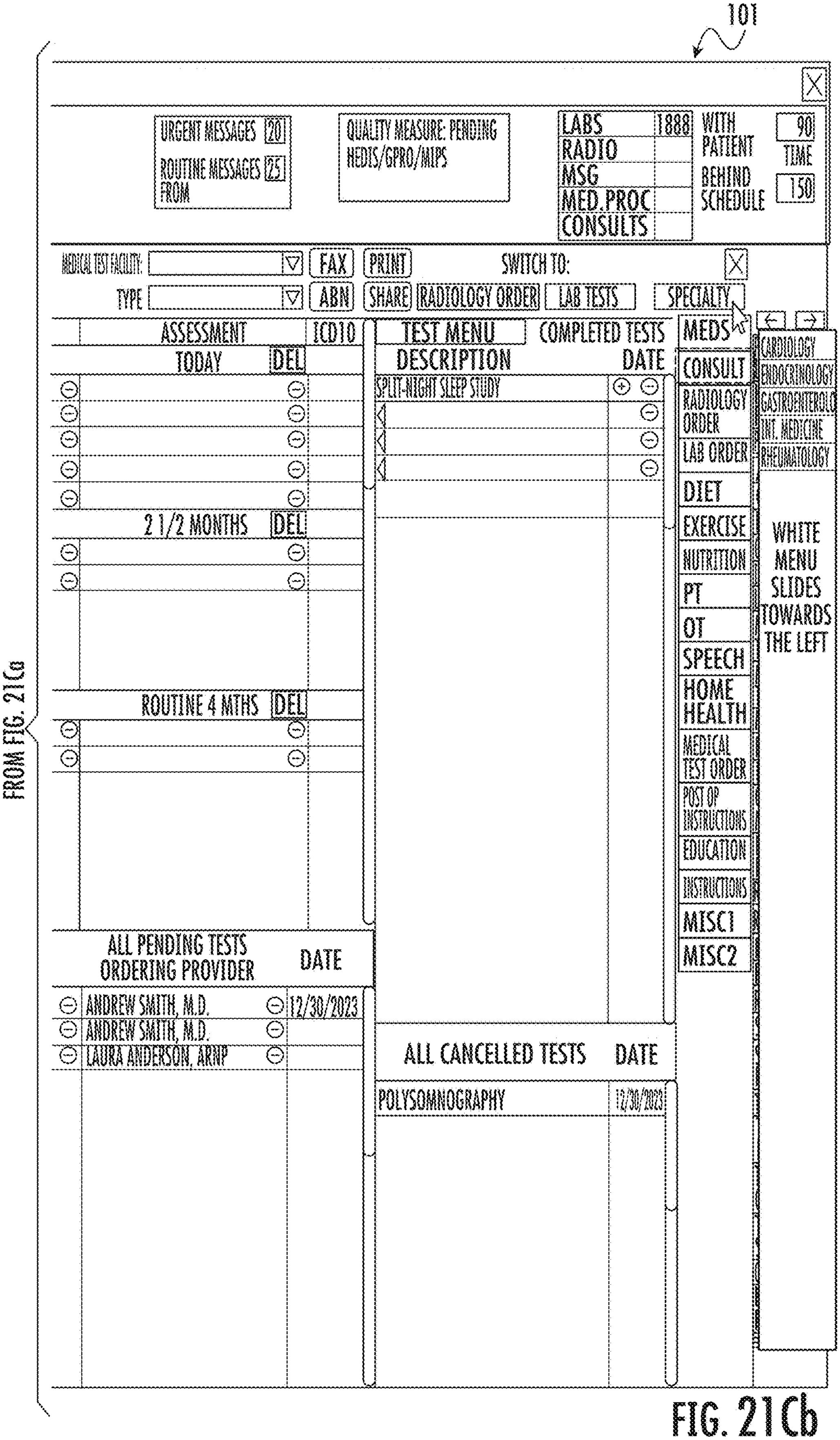

Referring to FIGS. 21Aa-21Cb, the medical test order function is now described. When the "assessment and plan" bar is pressed on the progress note second page, a template will open which will have all tabs related to further orders show up on the side like medications, radiology order, lab order, PT, OT and speech therapy, medical test order, etc.

By clicking the "medical test order" tab on the right hand side, another template will open which will be for the medical test orders to be put in. On the left hand side will be the standard tabs which will include medications, PMH, PSH, PL & HCC tab. From this PMH tab all the medical diagnosis which are relevant for that particular visit, can be pulled into the assessment by clicking on the different "diagnoses" under the past medical history, which is the second column from the left hand side. Any new assessments can also be added under the assessments column, by searching for a diagnosis not in the past medical history, using the search button.

Whenever an assessment is clicked on, it will highlight it, into a different "active color" and medical test order pertaining to that assessment can now be added into the medical test section to the right of it, which could be related to an acute visit, say an a) Chest Pain needing a nuclear stress test and Holter monitor. Medical test orders can also be added for certain routine tests on a yearly basis if needed. On the top of the space for the radiology orders are going to be 3 buttons 1) Today 2) Calendar and 3) Routine. TODAY: When the button for "today" is clicked it will create a bar below in the medical test column with today's date on it and radiology orders can now be pulled in from the left side of it, for the medical test to be performed on the same day of the patient visit. This is usually for "acute visits" when this is usually required.

Calendar Button: When there is a desire for a medical test to be ordered for a particular time frame with no specificity then the calendar button can be opened to choose any date, week(s) or month(s) to be created, so that test can be ordered to have it performed in that particular time frame when it is required. For example, if the patient had an abnormal medical test and needs a repeat in say 6 months, the calendar can be used to create a date for six months from the date of the previous medical test. The order can automatically be faxed to the radiology facility a couple of months prior to the test so that it can be scheduled for the patient.

Routine: This button is to order routine medical test for the patient. The routine button can be programmed for 1 year by "right" clicking on it and a box will open up which will have different time frame already prepopulated on it like 2, 2½, 3, 3½, 4, 4½ months etc., up to a year on it; and the provider can pick and choose the time frame he wants to use and then click the "save" button to save it for that time frame. When he clicks on the routine button in the future, it will automatically create a bar with a working date for one year. Now since it was just created it will by default be active and now medical test orders can be added under that date from the "test menu" either as "individual" or can be brought in from the "group" test(s). Any medical test order created by mistake under a particular "heading" can be highlighted and be deleted by clicking on the "DEL" (Delete) button on the heading bar. Any "individual" medical test under a heading, can be deleted by clicking on the Negative (–) round button to the right of it.

All Pending Tests: All Medical tests ordered by any provider including specialists for any future dates will be displayed under the "all pending tests" bar. This is to prevent ordered or same radiology tests too close to each other and prevent duplication and prevent wastage of resources. Test Menu: Providers can create a test menu based upon the specialty. It can be created under individual as "individual radiology test" or as a "group" of radiological test for certain conditions under a second column labelled as "group tests". There is a scroll bar for each "individual" and "group" column. Individual Bar: the (+) button is to add individual test under the individual column and the (–) button is to delete any test which was ordered by mistake, or the user decides to delete it for any reason.

Group Bar: the (+) button is to add a group bar under the group column. Different headings for groups can be created by clicking on this plus button which can then be labeled, and then individual lab tests can be added under each heading by using the plus button on that individual heading bar which was created. The (–) button is to delete a group bar and any individual labs added underneath it, which was created in the past, by highlighting the bar and then clicking the (–) button.

Completed Tests: When the "completed tests" button is pressed it will display all the individual and group medical tests done in the recent past going into the remote past (in descending order), along with the dates and who it was ordered by when the cursor is hovered on the cancelled test. All Cancelled Tests: This heading in the lower half of the screen (Completed Tests) will display all the tests cancelled in the past. When the button with the double (++) sign is clicked it should show who was the provider responsible for cancelling the test when the cursor is hovered on the cancelled test.

Specialty: When this tab is clicked on then the column with all the specialties will "slide in" from the right side of the screen. This will display all the different specialties under one column. If there is any test which the provider cannot remember for a particular assessment, help can be sought by clicking on the specialty related to that assessment. It will then display all the tests which was ordered by the specialists in that field for that diagnosis (assessment). Then the provider can click on it to bring that test into the description column from the specialist "test menu." When the specialty button is unchecked then the column with all the specialties listed will slide out of view to the right and disappear. This is a functionality which no other EHR has and can be helpful. It will hasten the care of the patient by having all the requisite medical test reports available even before the patient sees the specialist. It will save unnecessary repetitive visits to the specialists since what the specialist wanted is already available.

Figure 22A:
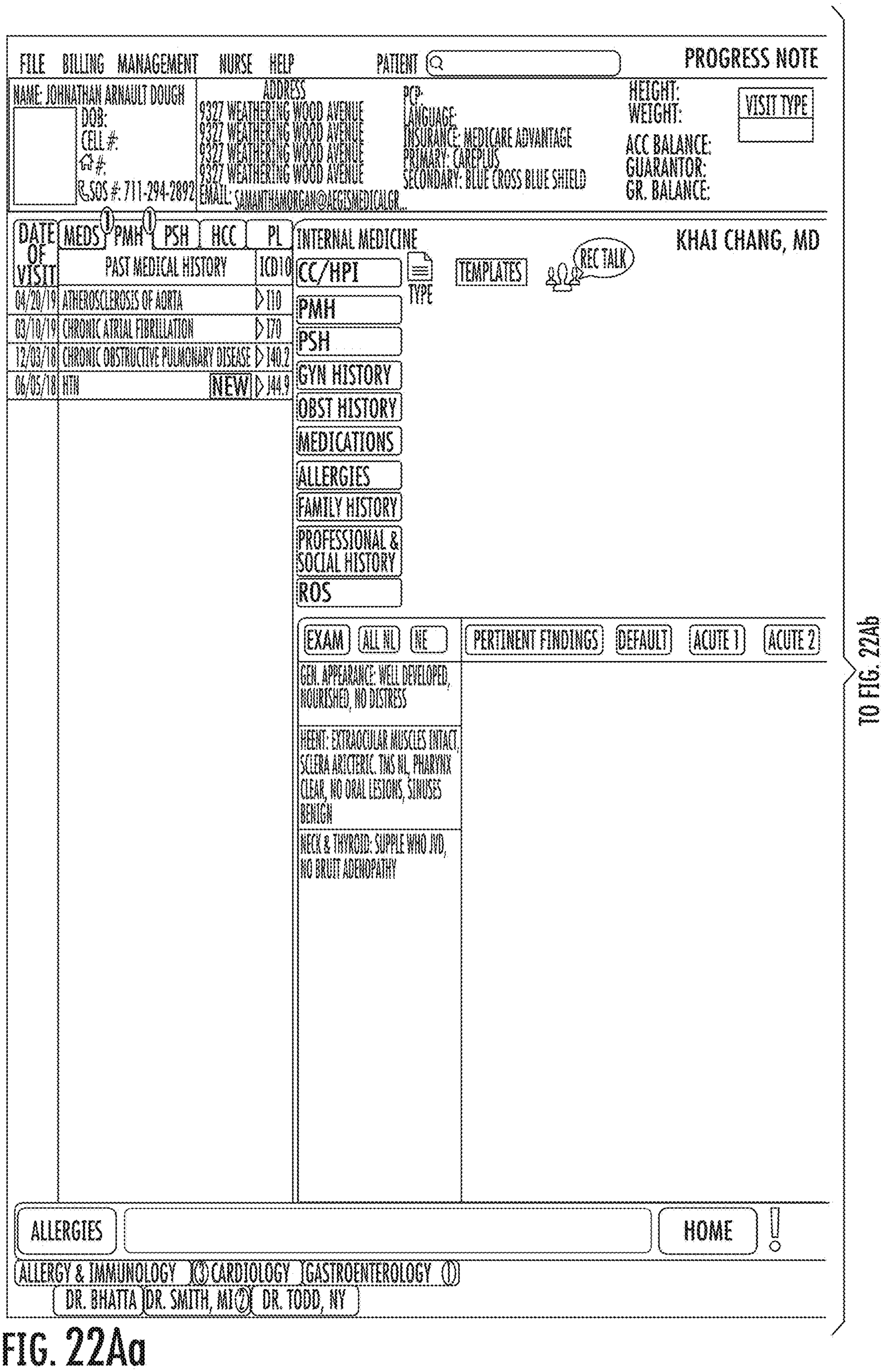
FIGS. 22Aa-22Jb are screenshots of navigation flow in an example embodiment of the history and physical and progress note function from the EHR GUI from the EHR system of FIG. 1.
Figure 22A:
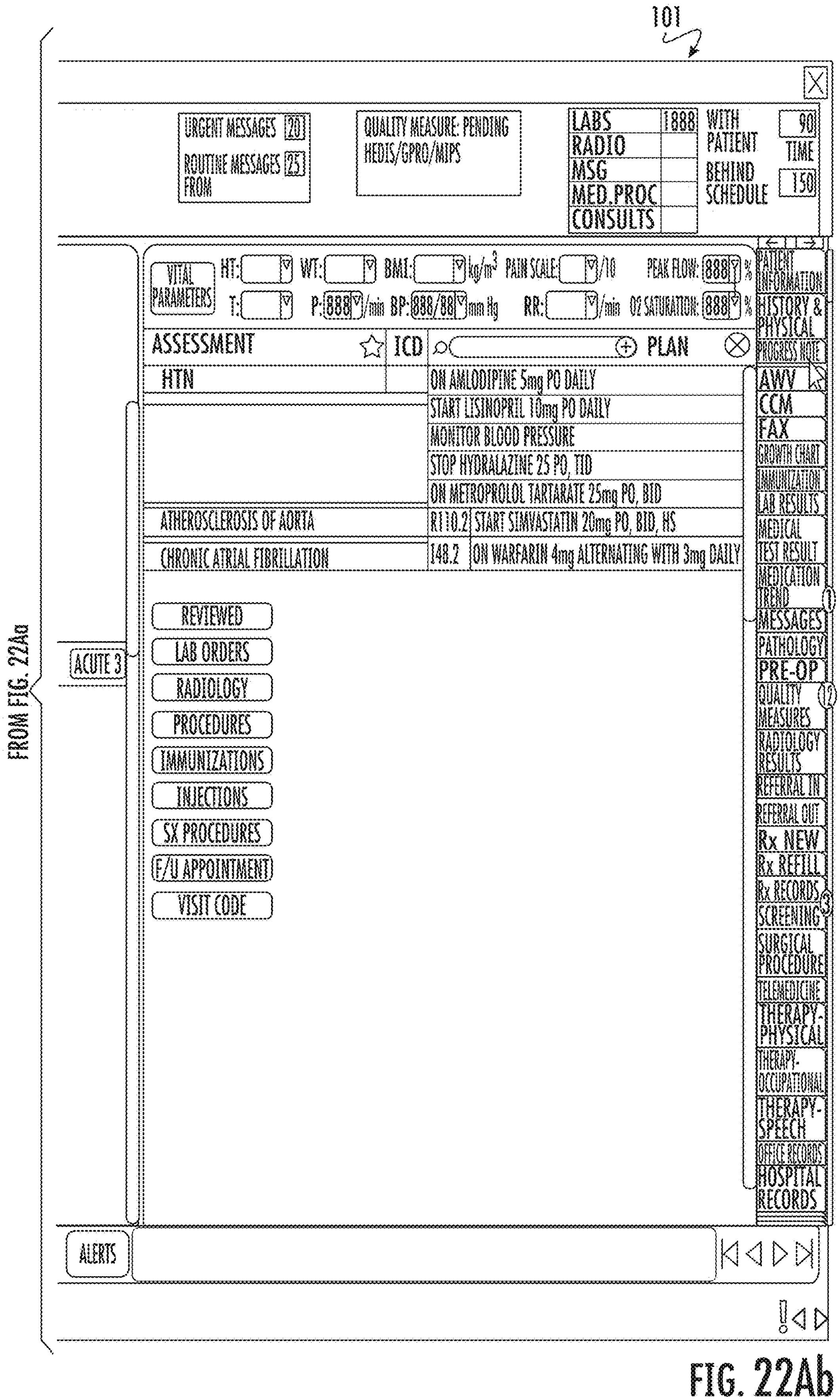
Figure 22B:
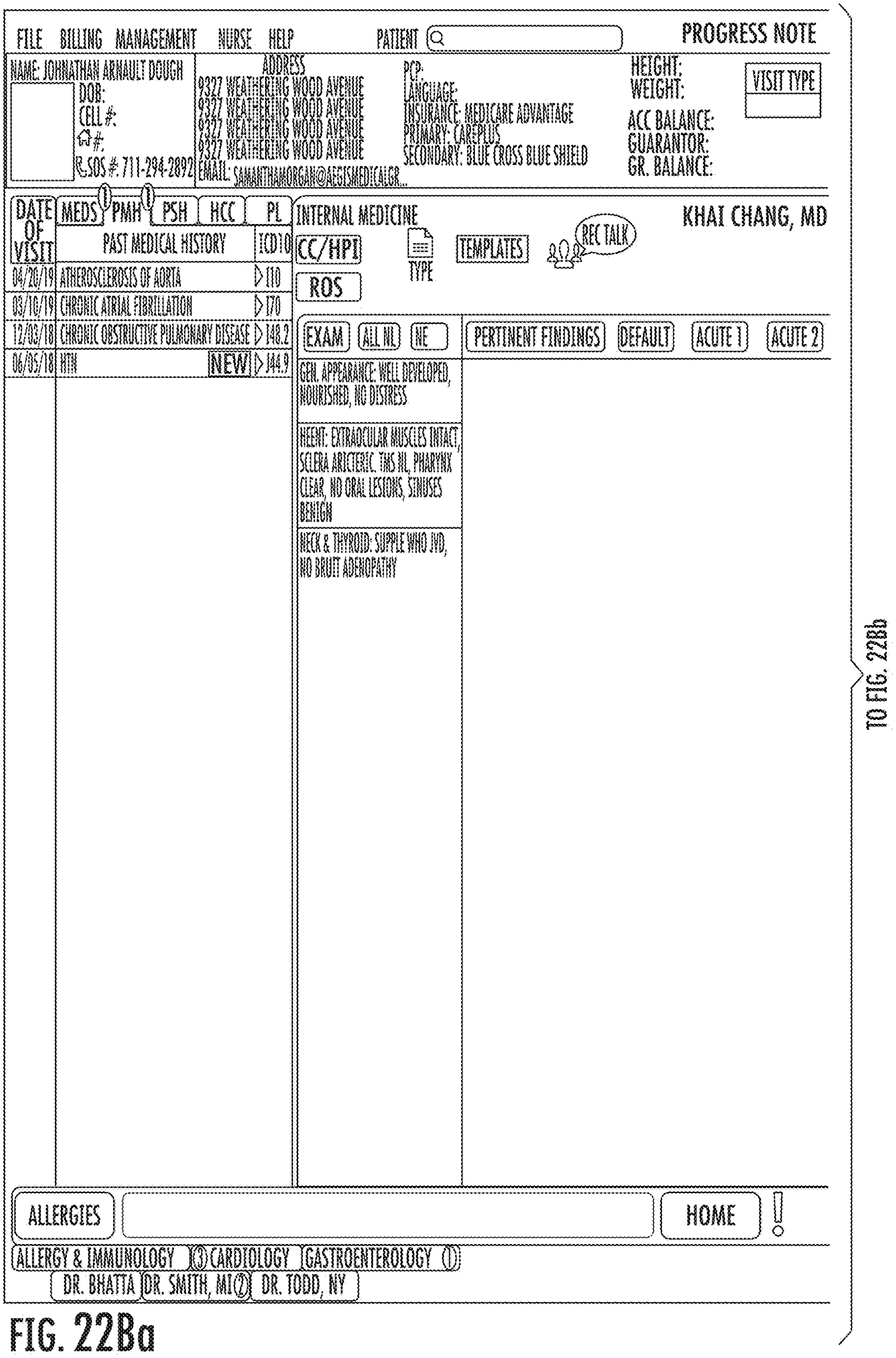
Figure 22B:
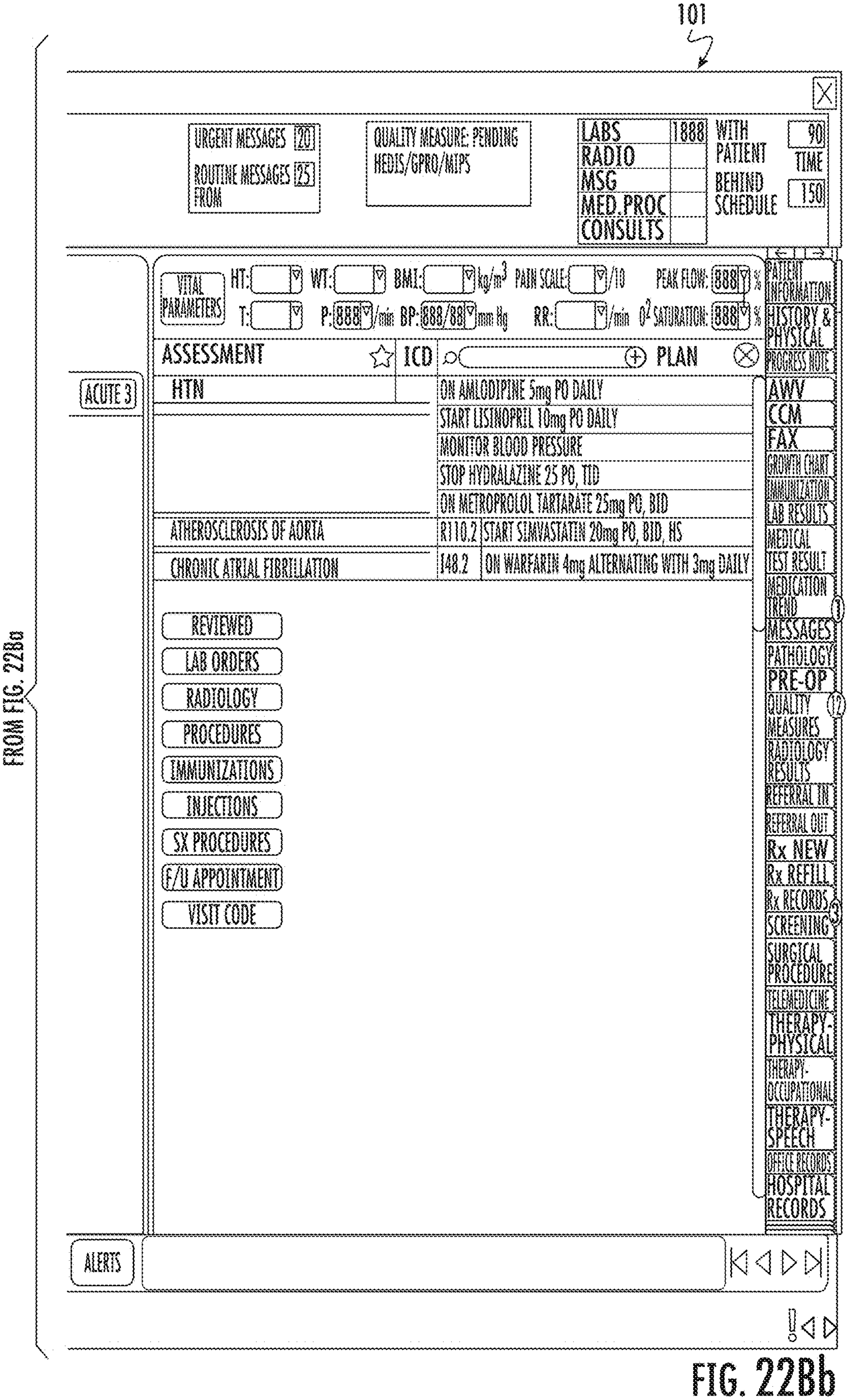

Referring to FIGS. 22Aa-22Gb, the history and physical function, the progress note function, the lab result function, the medical test report result, the message's function, the quality measure's function, and the immunization function are now described. The "history or physical" tab when the patient is seen as a new patient or when the patient has not been seen for the last three years. This tab is on the extreme right hand side towards the top. "Progress note" tab where 80% or more of the charting will be done subsequently after the patient has established with the doctor. This is a Note created at each visit.

Figure 22C:
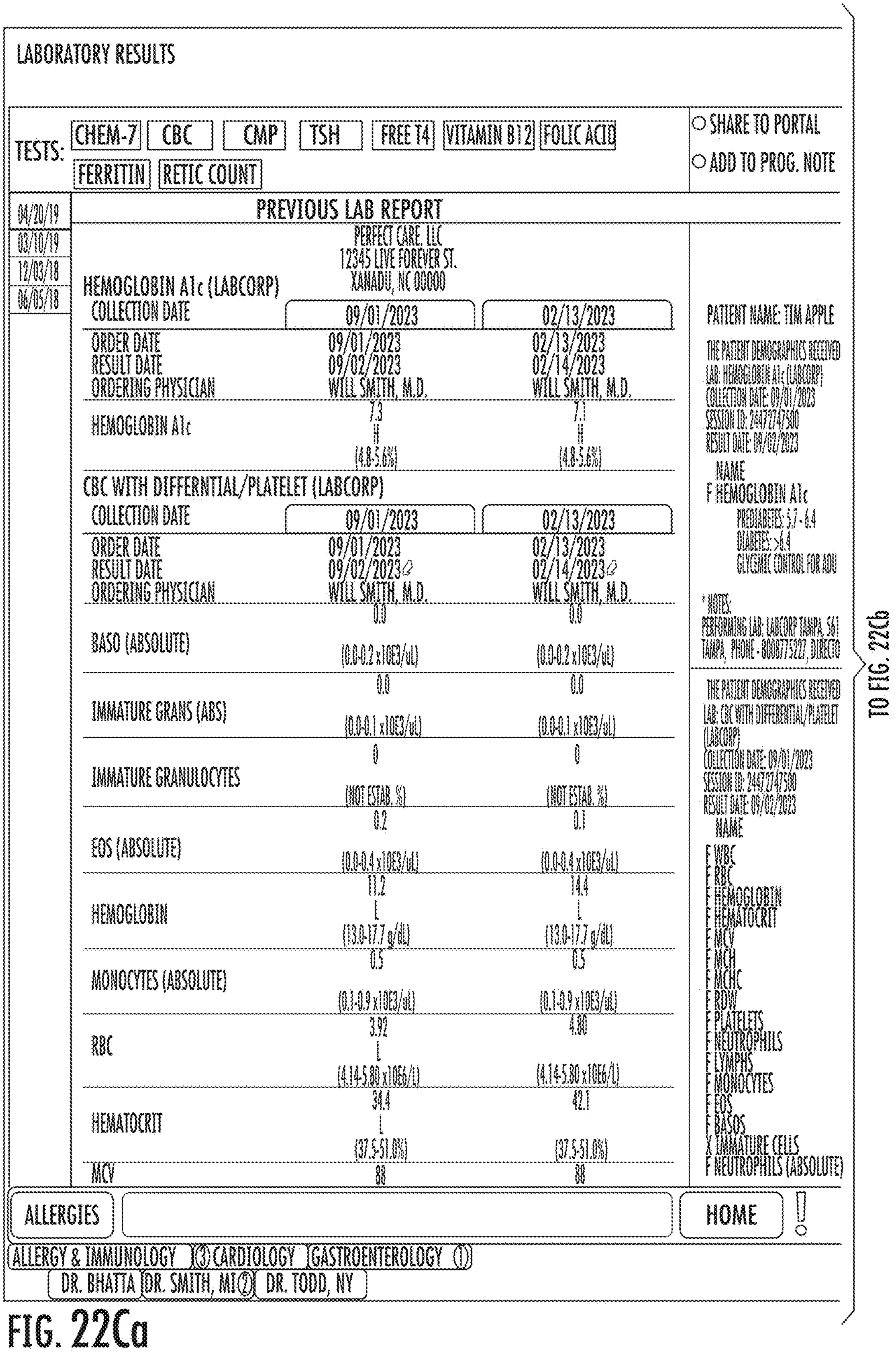
Figure 22C:
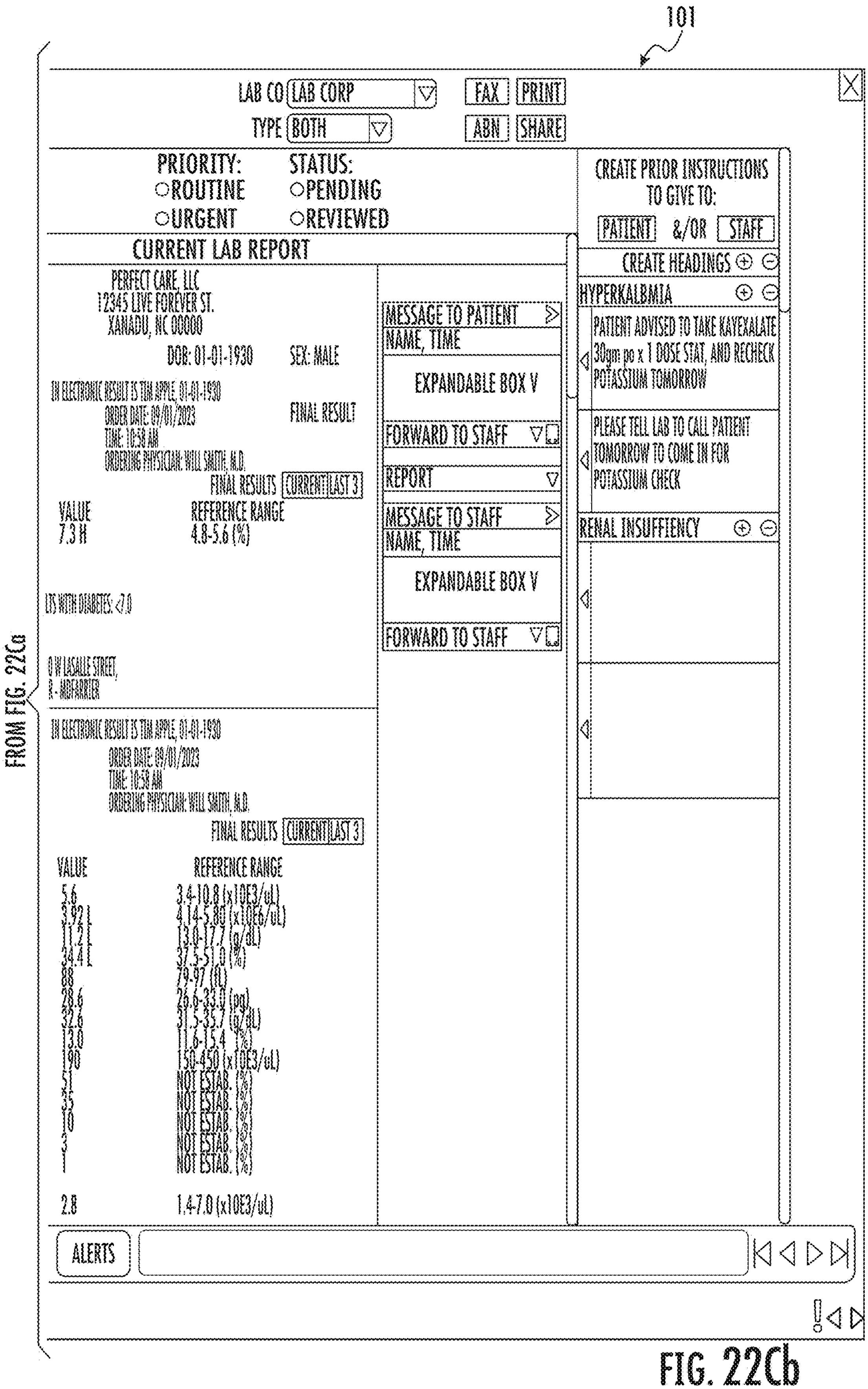

For the lab result function in FIGS. 22Ca-22Cb, the lab result template will display the date on the extreme left side of the screen. The latest test date for the result will be on the top and the previous lab test dates will be receding into the past in descending order. By default, the most recent test date will be highlighted, and the latest available lab results available will be openly displayed. One page will display the latest lab results and the second page will display the previous three to four previous lab results for the same lab test (for comparison purposes).

On the very top of the left hand page will be displayed all the lab tests which were ordered and now displayed here for that particular date. The lab results which are available will be highlighted in a different color and any pending lab results which was transmitted to the lab, but the result of which has not been received will be displayed in a different color.

Functionality: The scroll bar will display the individual test results in the order as shown on the top left hand page going from left to right here shown as: Chem-7, CBC, CMP, TSH, Vitamin B12, Folic acid and Retic count. At the same time, if the CBC is being displayed on the second right hand page, then in the "test" menu displayed on the left upper hand above the "previous lab report" the CBC button will be highlighted. Instant comparison: As the scroll is moved down and a new lab test result hits the top of the page under the "current lab report," the previous 3-4 lab test result for that same test will pop up on the left hand side screen for comparison purposes. This will continue until all the test results have been scrolled through by the provider.

Patient Instructions: Patient instructions can be created for each lab result. Under the "create headings" when the "patient" button above the create heading is activated by clicking on it, and the (+) button on the create heading bar is clicked, then 2 template boxes will pop up one above the other on top of this screen. The top one will have a different background (here shown in green). A heading can be assigned to it and instructions for that heading can be populated beneath it. This can then be saved by clicking on the "save" button. Thereafter, the screen with the boxes will disappear and instructions will be saved. This will create a heading and instructions below it in a box with a green background for patient instructions.

Staff Instructions: Similarly, staff instructions can be created for each lab result. Under the "create headings" when the "staff" button above the create heading is activated by clicking on it, and the (+) button on the create heading bar is clicked, then 2 template boxes will pop up one above the other on top of this screen. The bottom one will have a different background (here shown in white). A heading can be assigned to it and instructions for that heading can be populated beneath it. This can then be saved by clicking on the "save" button. Thereafter, the screen with the boxes will disappear and instructions will be saved. This will create a heading and instructions below it in a box with a white background for staff instructions.

Once saved the instructions will then populate on the extreme right hand column of the screen. There will be an arrow to the left of the instruction box to move it into the patient instructions box in the box on the current lab report. The background color will match to tell the provider which box the instructions will move to. Here, it is depicted that that instructions saved into the green background will move to the patient instruction box which also has a green background. The instruction in the box with the white background will be for the staff, and when the arrow next to it is clicked on that box, it will move the instructions into the staff instruction box, which also has a white background. Alternatively, the instructions (message) for patient and instructions (message) for patient can be populated below the pages, similar to the medical test report depicted in FIGS. 22Da-22Db.

Share to Portal: when checked, allows the lab results to be displayed on the portal for the patient to view. Add to progress note: Will allow all the lab results for that date to be pulled into the progress note of the patient created for that day's visit. Priority: will show whether the lab needs to be reviewed right away or can be done at leisure for the provider and the staff both when that button is checked. STATUS: will show if the lab is "pending" for review or it has been "reviewed."

For the radiology report (results) function in FIGS. 7*a*-7*b*, the template will display the date on the extreme left hand side column, with the most recent date on the top, and it will be highlighted. The second column from the left will display the categories of different tests under radiology, for example, X-Rays, ultrasounds, nuclear medicine etc. Under these categories will have subcategories of tests listed, for example, X-ray of hip, X-ray of left shoulder, X-ray of right hip and X-Ray chest etc.

The center part of the screen will have two large pages. This will display the latest result of the test ordered and any previous result of the same test if it was performed in the past. If multiple tests were performed in the past, then it will display the second last one for comparison purposes. The results will come under this tab either from a fax received from the radiology office or directly if performed within the office from the device itself, if it is integrated with the software. It can also be scanned if the patient bring a paper hard copy of the result.

Instant comparison: The previous and current report both have a scroll bar on the right for reviewing the full report. As the scroll is moved down the results from the current and the last test report performed can be compared side by side.

The dot indicator: The dot on the test report indicates that there is another report which still has not been reviewed by the provider (i.e., a notification indicator). So, when the current report is viewed and when the provider has put in the instructions for the patient regarding the test and sent it to the staff the dot next to that test will disappear. Therefore, now the provider can now click on the bar with the second tab on it which in this case is the X-Ray Chest. This will again bring the last comparative report for comparison purposes and once the instructions for the patient are sent for the staff to call the second dot will also disappear. Radiology Result tab Notification: Once the provider now has reviewed all the radiology results which were pending and the instructions for the patients have been sent, the "notification" on the "radiology results" tab will also disappear.

Patient Instructions: Patient instructions can be created for a radiology result. Under the "create headings", when the "patient" button above the create heading is activated by clicking on it, and the (+) button on the create heading bar is clicked, then 2 template boxes will pop up one above the other on top of this screen. The top one will have a different background (here shown in green). A heading can be assigned to it and instructions for that heading can be populated beneath it. This can then be saved by clicking on the "save" button. Thereafter, the screen with the boxes will disappear and instructions will be saved. This will create a heading and instructions below it in a box with a green background for patient instructions.

Staff Instructions: Similarly, staff instructions can be created for the radiology result. Under the "create headings", when the "staff" button above the create heading is activated by clicking on it, and the (+) button on the create heading bar is clicked, then 2 template boxes will pop up one above the other on top of this screen. The bottom one will have a different background (here shown in white). A heading can be assigned to it and instructions for that heading can be populated beneath it. This can then be saved by clicking on the "save" button. Thereafter, the screen with the boxes will disappear and instructions will be saved. This will create a heading and instructions below it in a box with a White background for Staff instructions.

Auto save: Once saved the instructions will then populate on the extreme right hand column of the screen. There will be an arrow to the left of the instruction box to move it into the patient instructions box in the box on the current radiology report. The background color will match to tell the provider which box the instructions will move to. Here, it is depicted that the Instructions saved into the "green" background will move to the patient instruction box which also has a green background. The instruction in the box with the "white" background will be for the staff, and when the arrow next to it is clicked on that box, it will move the instructions into the staff instruction box, which also has a white background. To summarize, all instructions will be linked to the test ordered.

Cumulative Patient and Staff Instructions: All the instructions created for the Patient and Staff will be saved into a database for that test result. In the future if any "CTA of the carotid" result is displayed, all the Patient and Staff instructions will now auto populate on the right hand side. The same will happen for the "X-ray chest" result also.

Share to Portal: when checked, allows the radiology results to be displayed on the portal for the patient to view. Priority: will show whether the report needs to be reviewed right away or can be done at leisure for the provider and the staff both, when that button is checked. Status: will show if the lab is "pending" for review or it has been "reviewed." Facility: will show where the test was performed.

Figure 22D:
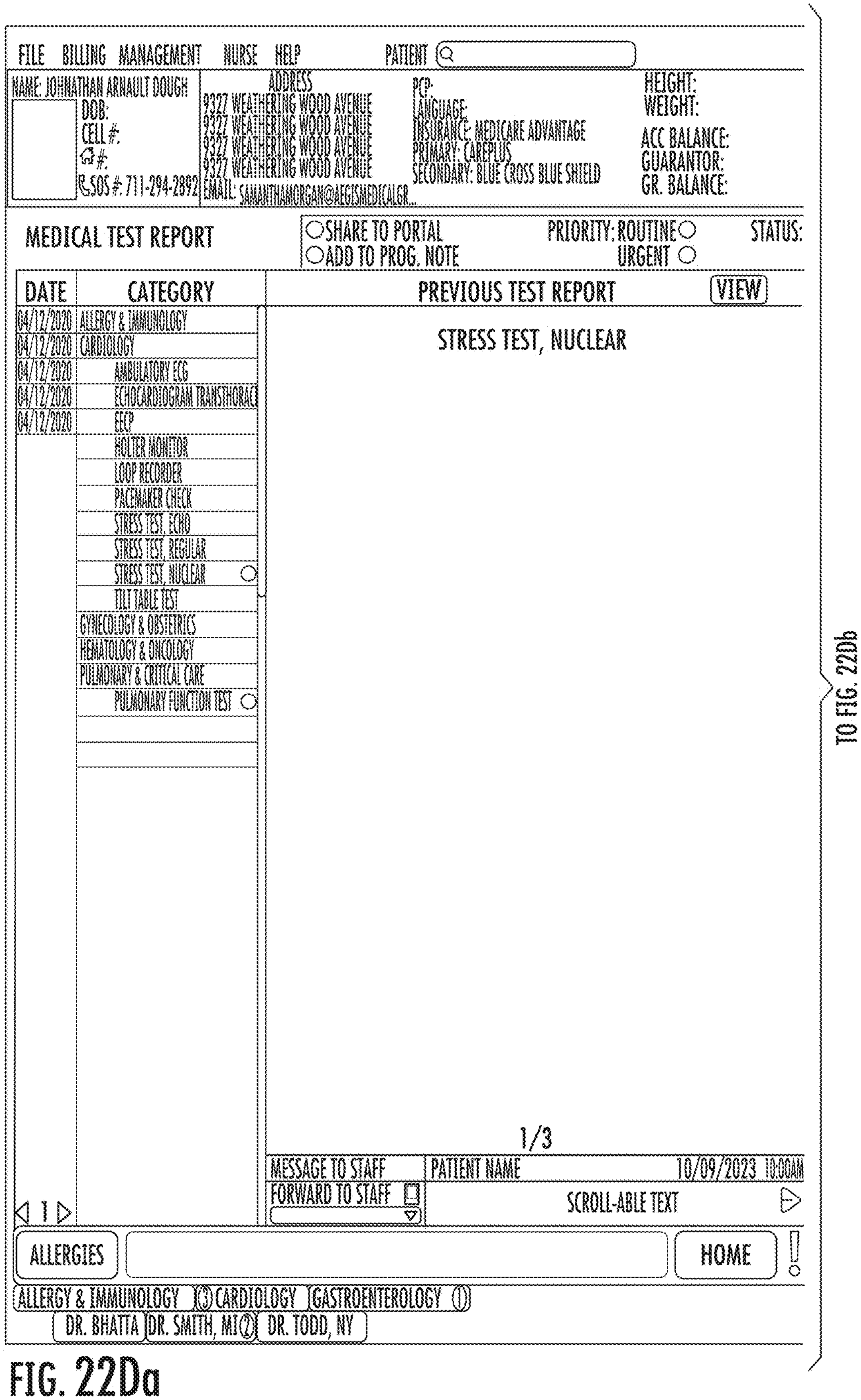
Figure 22D:
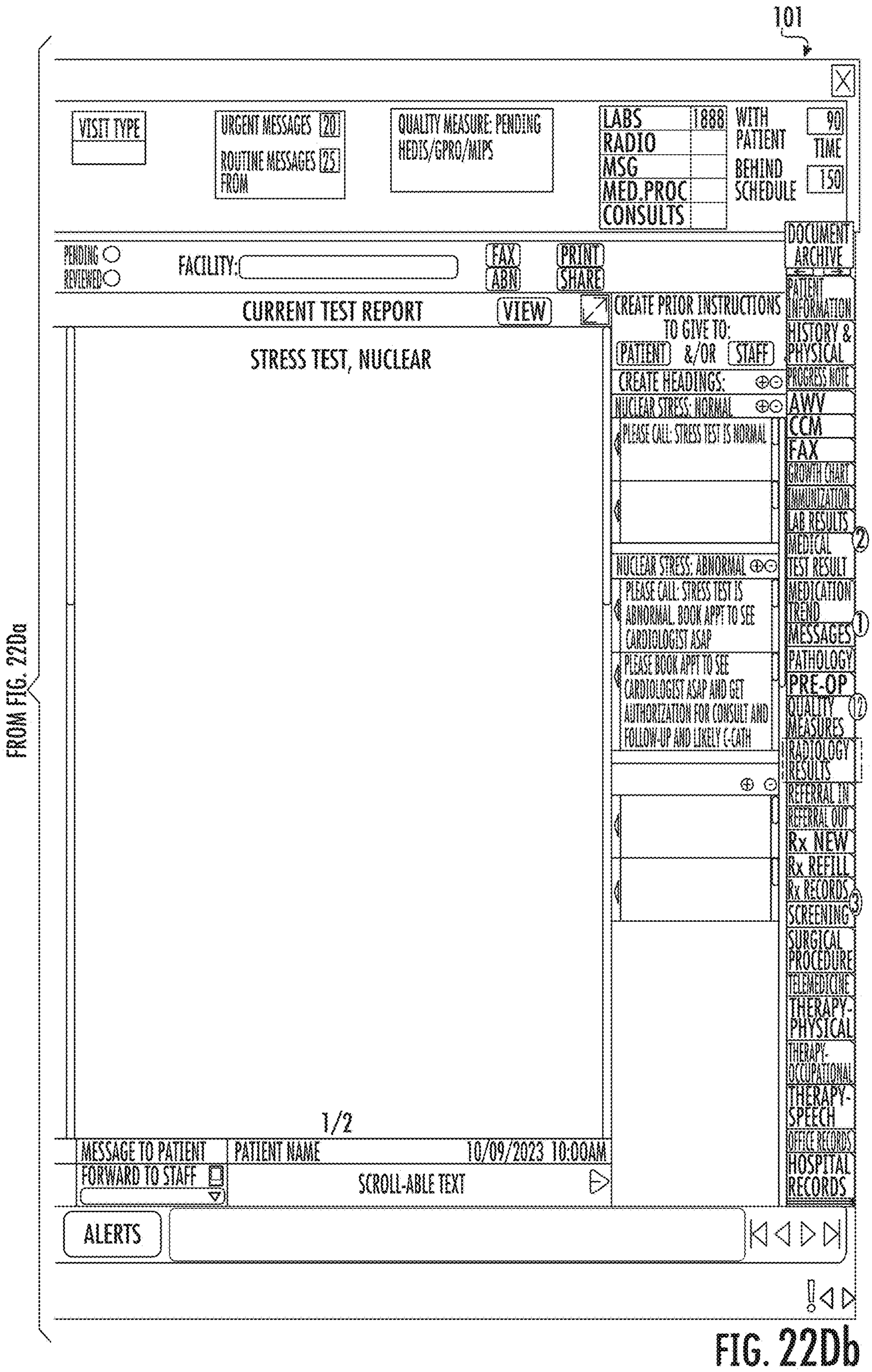

For the medical test report function in FIGS. 22Da-22Db, the template will display the date on the extreme left hand side column, with the most recent date on the top, and it will be highlighted. The second column from the left will display the Categories of different tests except what is already covered under radiology and labs. Under these categories will have subcategories of tests listed under each "specialty." So, the second column will display the specialties and all tests under that specialty as a subcategory. The center part of the screen will have two large pages. This will display the latest result of the test ordered and any previous result of the same test if it was performed in the past. If multiple tests were performed in the past, then it will display the second last one for comparison purposes. The results will come under this tab either from a fax received from the specialist's office or directly if performed within the office from the device itself if it is integrated with the software. It can also be scanned if the patient brings a paper hard copy of the result.

Instant comparison: The previous and current report both have a scroll bar on the right for reviewing the full report. As the scroll is moved down the results from the current and the last test report performed can be compared side by side. Dot Indicator: The dot on the test report indicates that there is another report which still has not been reviewed by the provider. So, when the current report "stress test, nuclear" is viewed and when the provider has put in the instructions for the patient regarding the test and sent it to the staff the dot next to that test will disappear. Therefore, now the provider can now click on the bar with the second tab on it which in this case is the pulmonary function test. This will again bring the last comparative report for comparison purposes and once the instructions for the patient are sent for the staff to call the patient, the second dot will also disappear.

Medical Test Result Tab Notification: Once the provider now has reviewed all the medical test results which were pending and the instructions for the patients have been sent to the staff to instruct the patient, the "notification" on the "medical test results" tab will disappear. Patient Instructions: patient instructions can be created for medical test results. Under the "create headings" when the "patient" button above the Create Heading is activated by clicking on it, and the (+) button on the Create Heading bar is clicked, then 2 template boxes will pop up one above the other on top of this screen. The top one will have a different background (here shown in Green). A heading can be assigned to it and instructions for that heading can be populated beneath it. This can then be saved by clicking on the "save" button. Thereafter, the screen with the boxes will disappear and instructions will be saved. This will create a heading and instructions below it in a box with a green background for patient instructions.

Staff Instructions: Similarly, staff instructions can be created for the medical test result. Under the "create headings" when the "staff" button above the create heading is activated by clicking on it, and the (+) button on the create heading bar is clicked, then 2 template boxes will pop up one above the other on top of this screen. The bottom one will have a different background (here shown in white). A heading can be assigned to it and instructions for that heading can be populated beneath it. This can then be saved by clicking on the "save" button. Thereafter, the screen with the boxes will disappear and instructions will be saved. This will create a heading and instructions below the result, in a box with a White background for Staff instructions.

Auto save: Once saved the Instructions will then populate on the extreme right hand column of the screen. There will be an arrow to the left of the instruction box to move it into the patient instructions box in the box on the current lab report. The background color will match to tell the provider which box the instructions will move to. Here, it is depicted that the instructions saved into the "green" background will move to the patient instruction box which also has a green background. The instruction in the box with the "white" background will be for the staff, and when the arrow next to it is clicked on that box, it will move the instructions into the Staff Instruction box, which also has a white background. To summarize, all instructions will be linked to the test ordered.

Cumulative Patient and Staff Instructions: All the instructions created for the patient and staff will be saved into a database for that test result. In the future, if any "stress test, nuclear" result is displayed, all the Patient and Staff instructions will now auto populate on the right hand side. Similarly, if the Pulmonary Function Test (PFT) bar under Pulmonary and Critical Care is clicked on, then it will display all the Patient and Staff instructions for PFT which was created and saved in the past on the right hand side. Share to Portal: when checked, allows the medical test result (report) to be displayed on the portal for the patient to view. Priority: will show whether the report needs to be reviewed right away or can be done at leisure for the provider and the staff both, when that button is checked. Status: will show if the medical test result is "pending" for review or it has been "reviewed." Facility: will show where the test was performed.

Figure 22E:
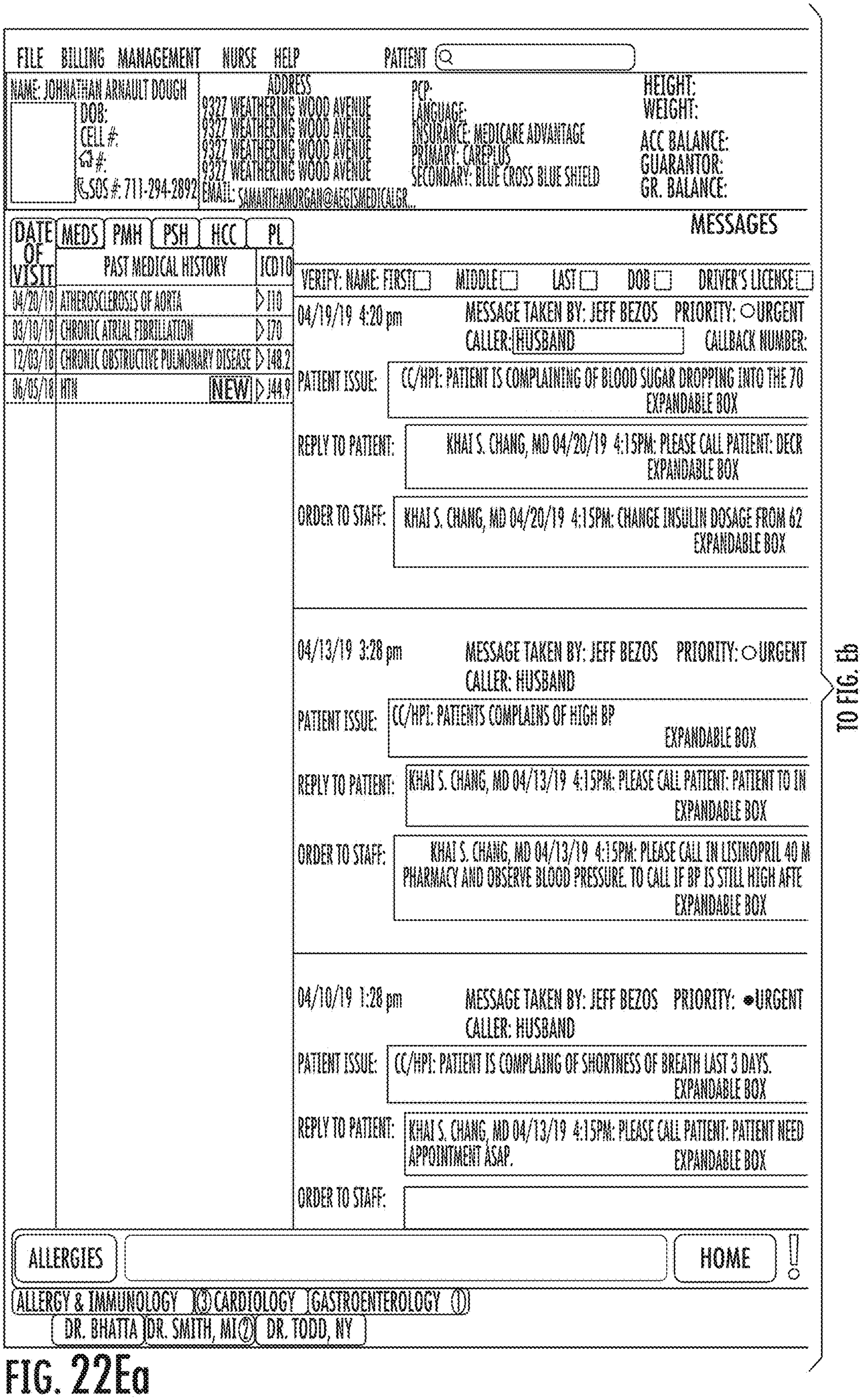
Figure 22E:
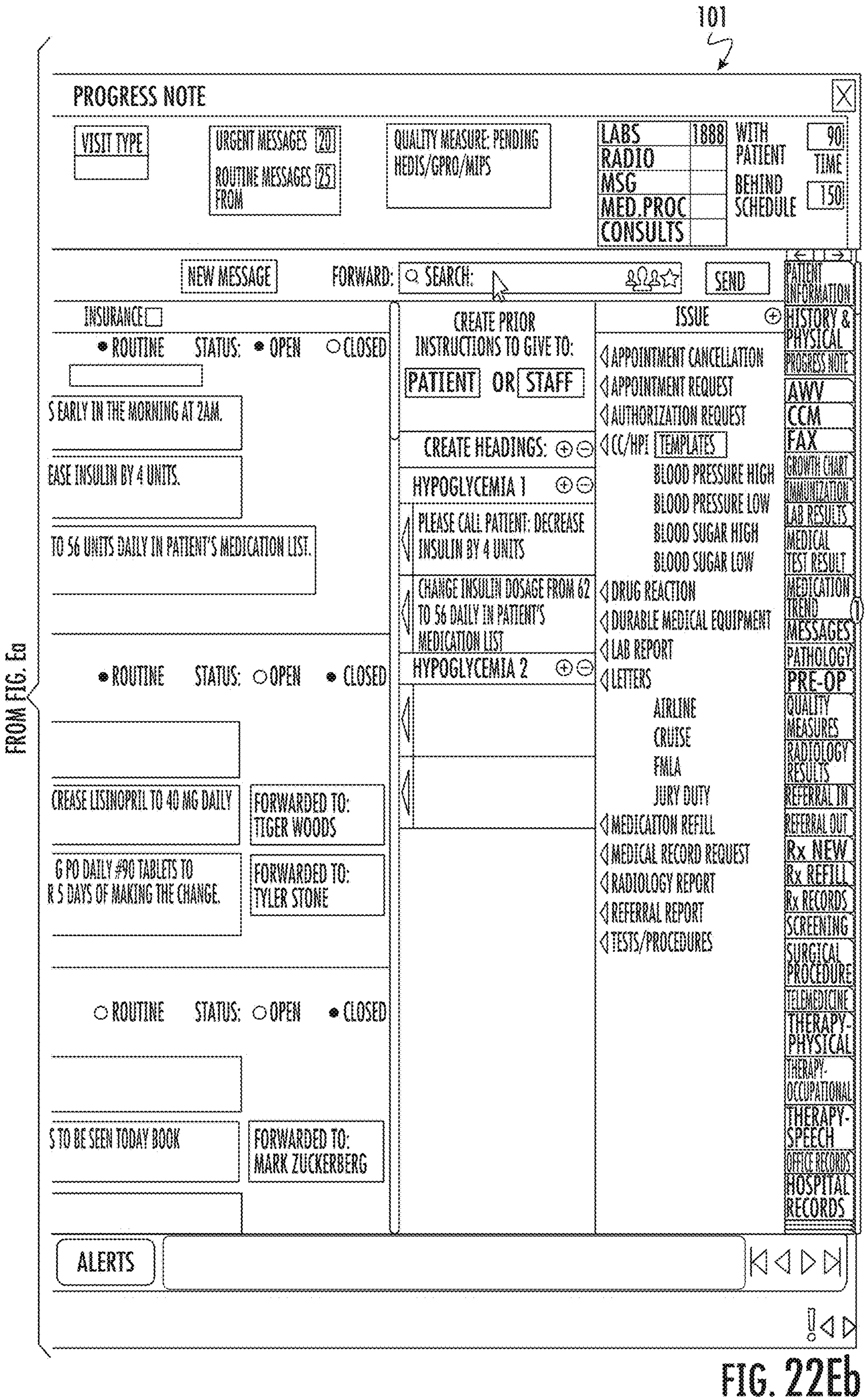

For the messages function in FIGS. 22Ea-22Eb, the text messaging template will have the screen where all the details regarding the issue described by either the patient or the caller will be noted and then forwarded to the relevant staff for the necessary action to be taken. All documentation will be typed and saved. There will be option of time stamp manually or in the practice management it can be set to "automated" so that as soon as the cursor is inserted into the message box to type, it will automatically insert the name, designation, date and time. On the right hand side will be the common issues which are dealt with by the office staff, and these issues come from the patients or relatives calling the office.

The create "patient instructions" and "staff instructions" will only be for providers to create and use. This will only be linked to when the CC/HPI Template is used, then this section will be activated and allow providers to create instructions for both the patient and staff which will be saved to a database for future use.

Once the instructions are brought into the colored boxes, then the boxes can be highlighted by clicking on it and then search can be activated to look for the staff who it needs to be forwarded to. Whenever a particular staff is regularly being used it will add a numerical one to that name so that it stays on top, to automatically populate the search box, so that down the road, only the "send" button must be clicked to forward the message to that staff. There will be an "X" on the right hand side of the favorite name popping up in the search box. If say the staff leaves or is no longer with the practice, then the "X" button can be right clicked to show the "deactivate" button. Once this button is clicked, that staff member's name will then drop to the bottom of the list and will be grayed out. If say the staff returns to the practice again in the future, then his name again can be reactivated by right clicking on it at the bottom of the list and "activate" button can be clicked to reactivate that staff again. The numerical value will remain attached to his name where he left off, and it will bring his name again towards the top depending on what numerical value he left the practice at. The instruction could flow either up or down depending on what the practice prefers; this can be configured in the background.

Figure 22F:
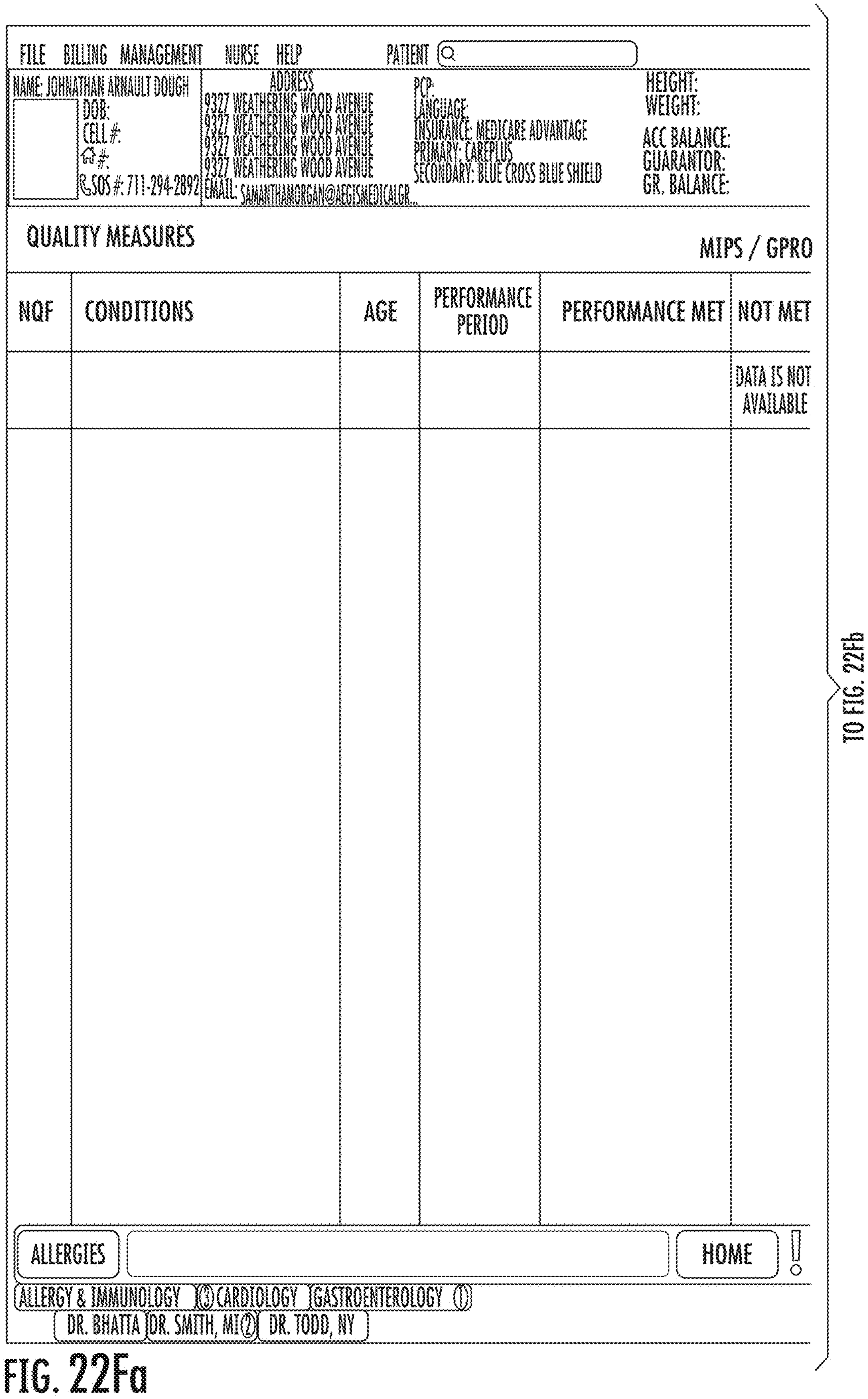
Figure 22F:
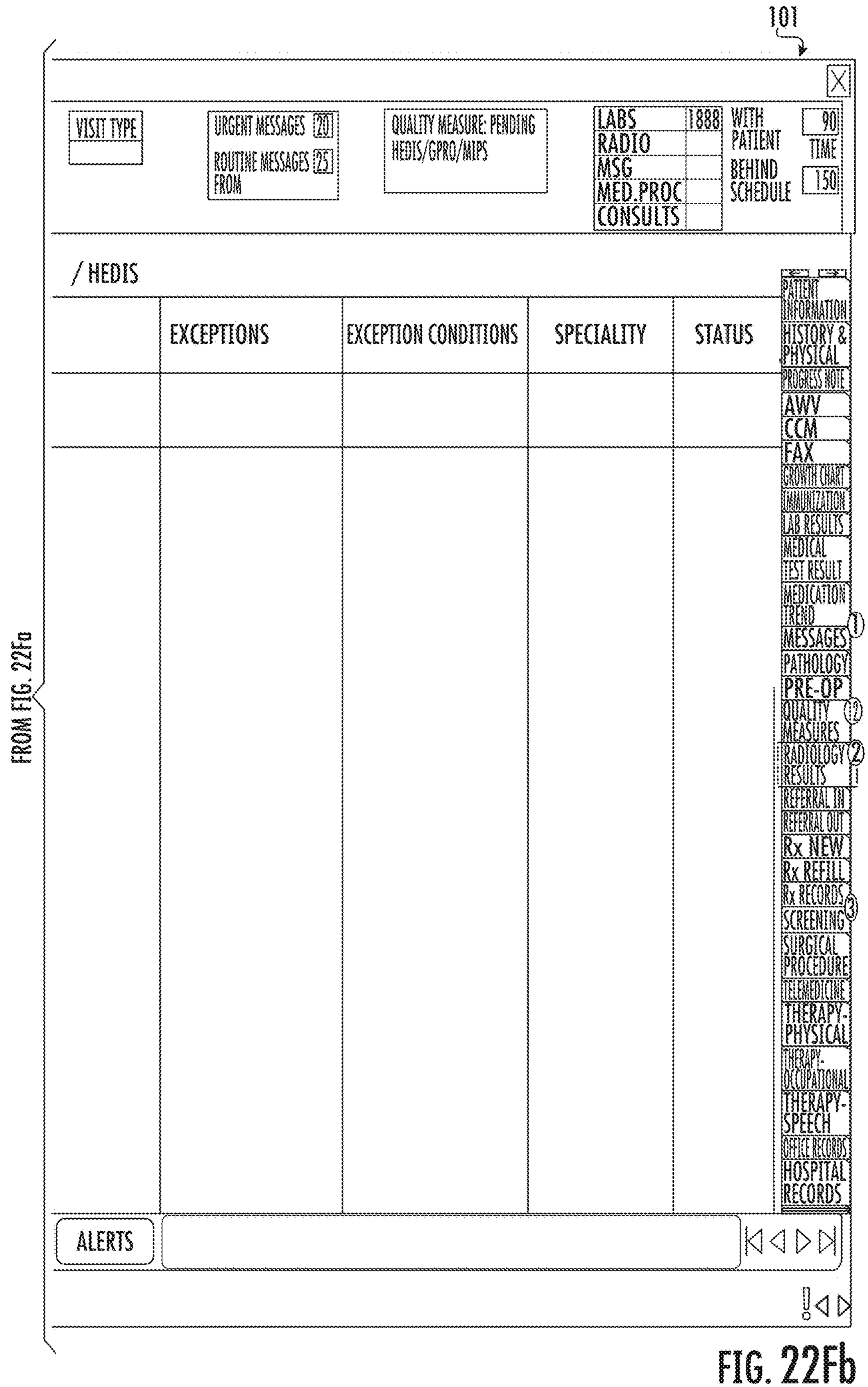

For the quality measures function in FIGS. 22Fa-22Fb, the quality measures for a particular year are going to be populated. Most measures don't change, but some measures do change every year. The changes the determined by the government and the Insurance companies changes every year. The different columns are to follow and track the measures which are pending or not completed. Once they are completed, then they will drop down to the very bottom of the screen. So only those measures which are not completed will stay on the top and they will show as the number on the notification on the tab for "quality measures" tab. Also, in the practice management, there will be a dashboard, which will show the patient's name and demographics. Patients with the maximum number of incomplete measures will be at the very top. Then in descending order, it will have the list of patients who will have lesser quality measures incomplete.

Figure 22G:
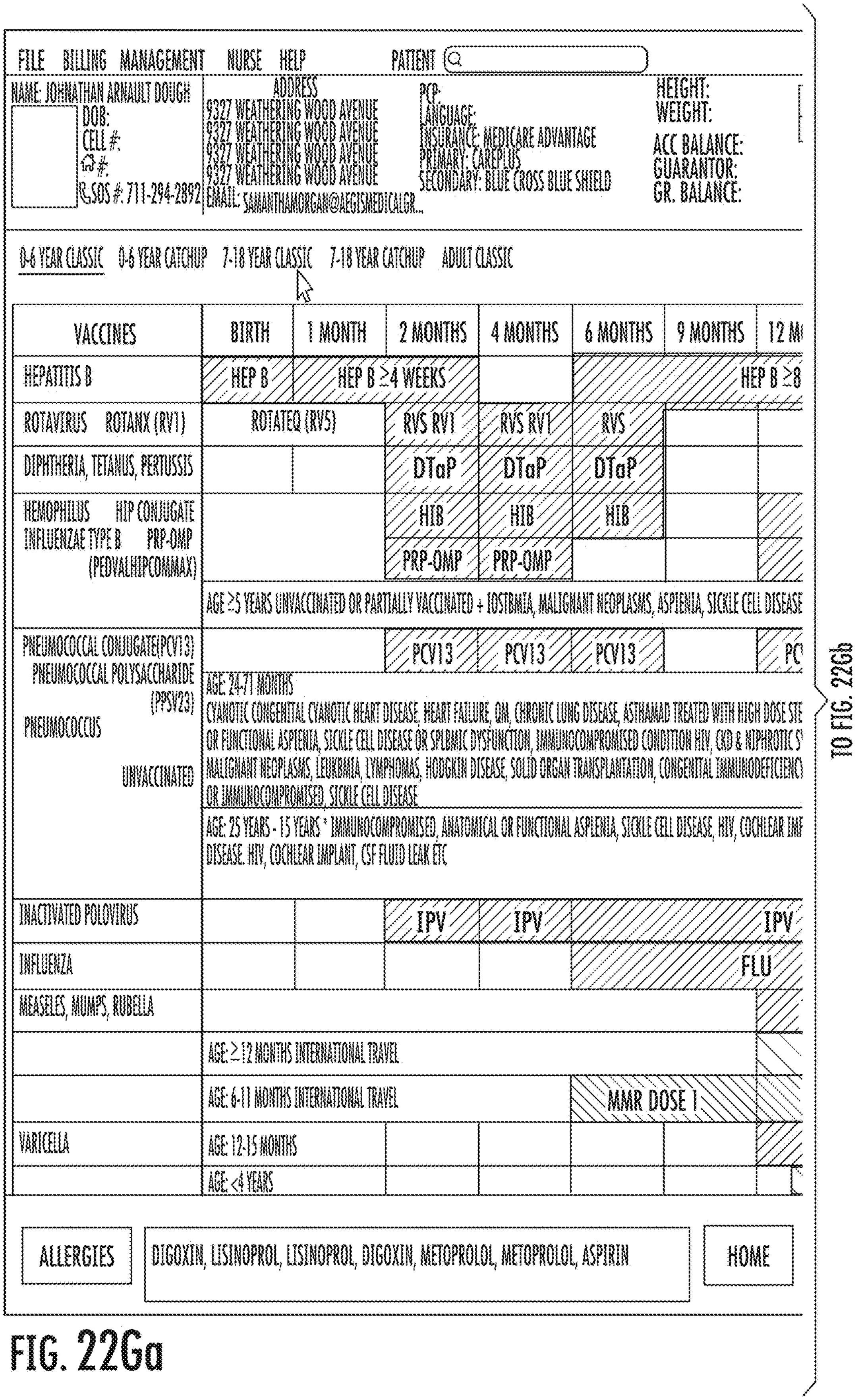
Figure 22G:
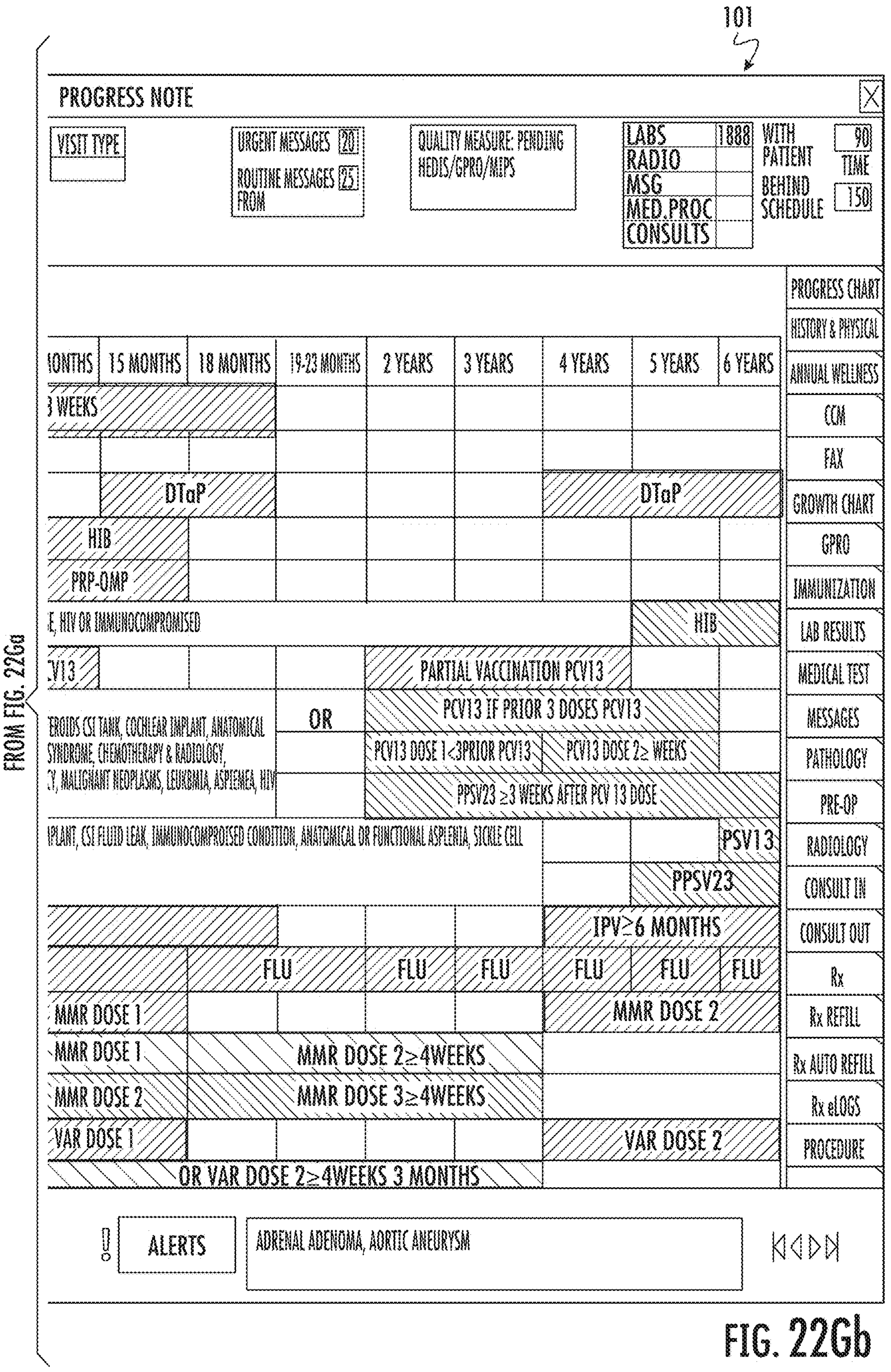
Figure 22H:
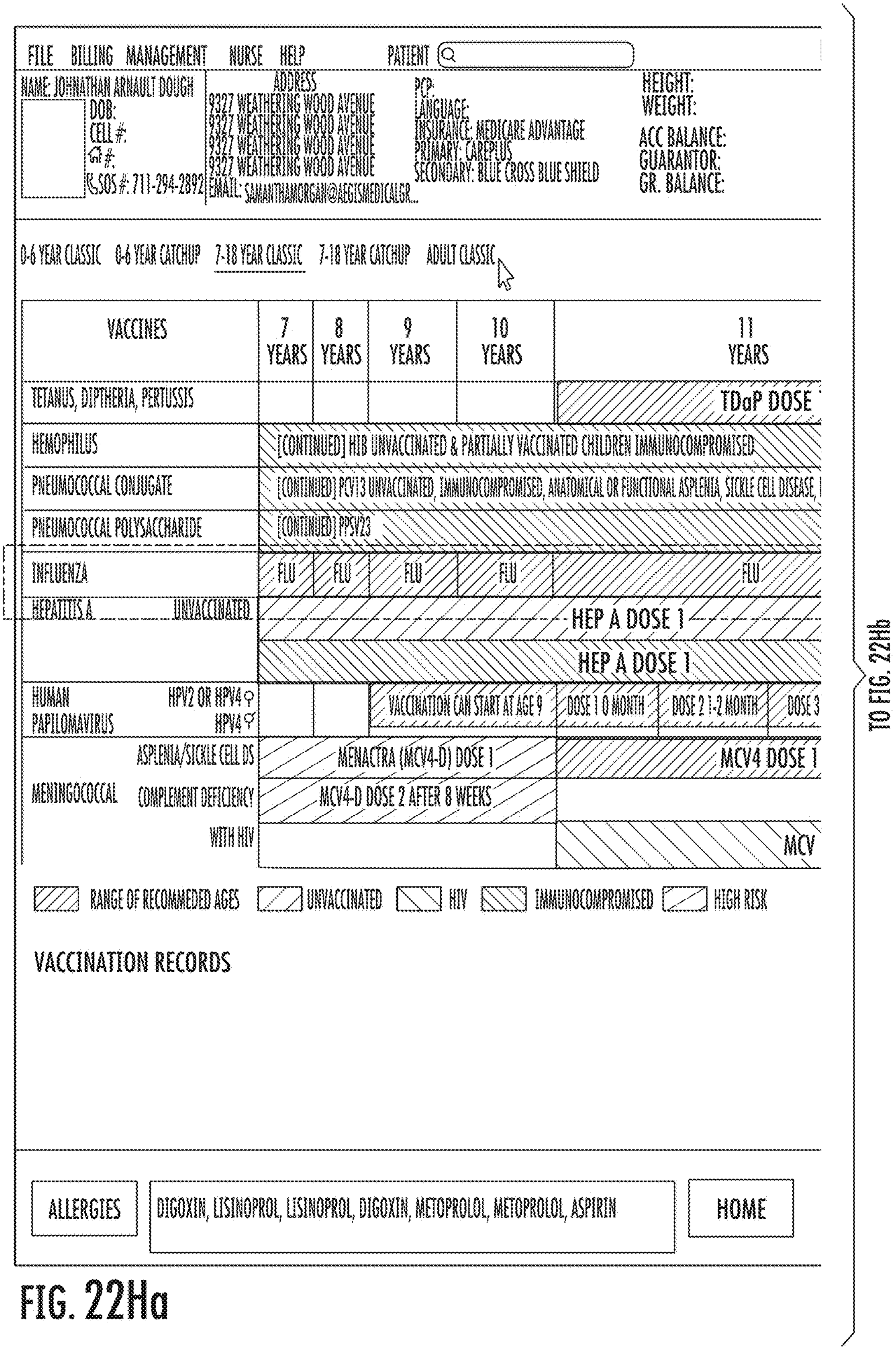
Figure 22H:
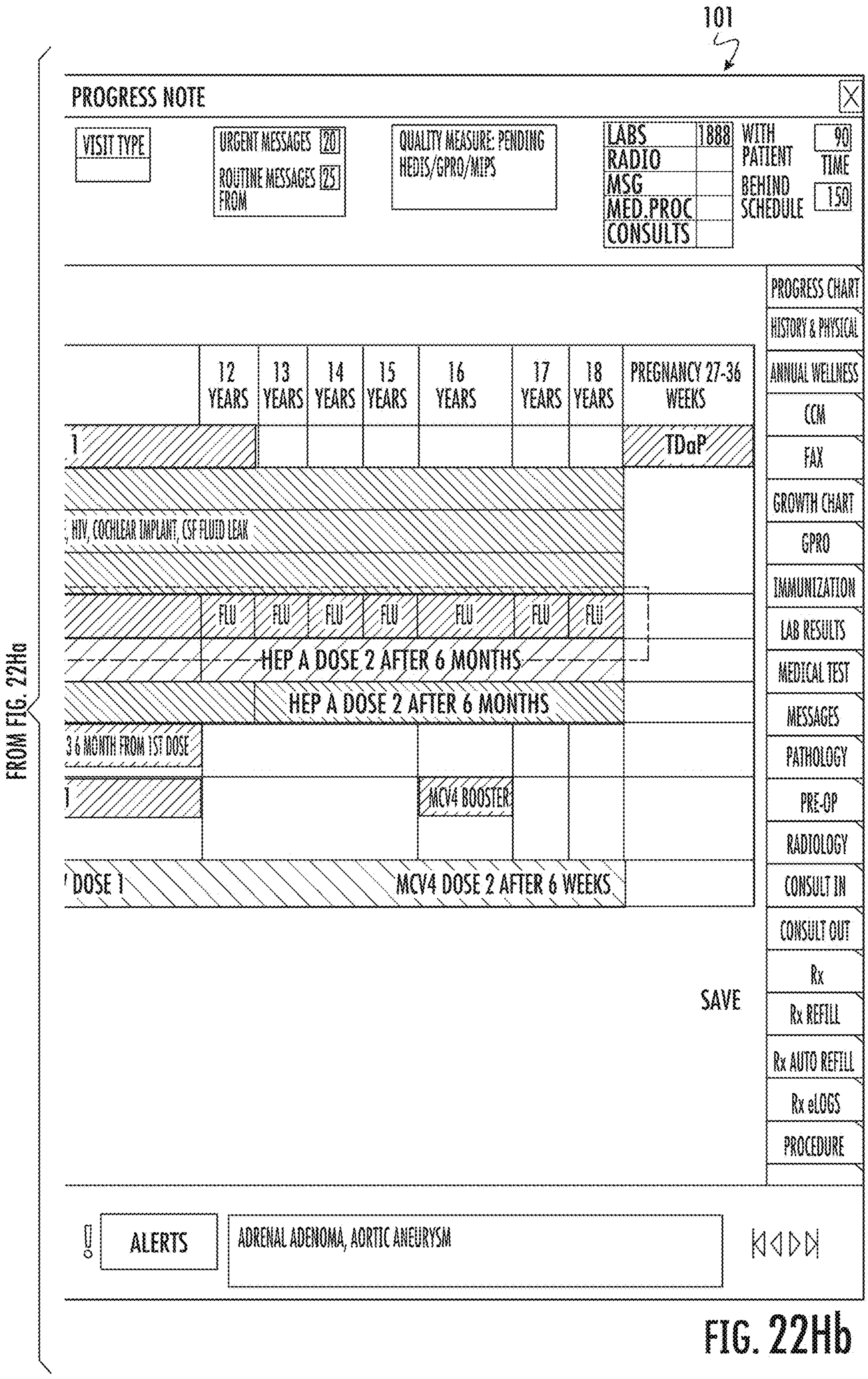
Figure 22I:
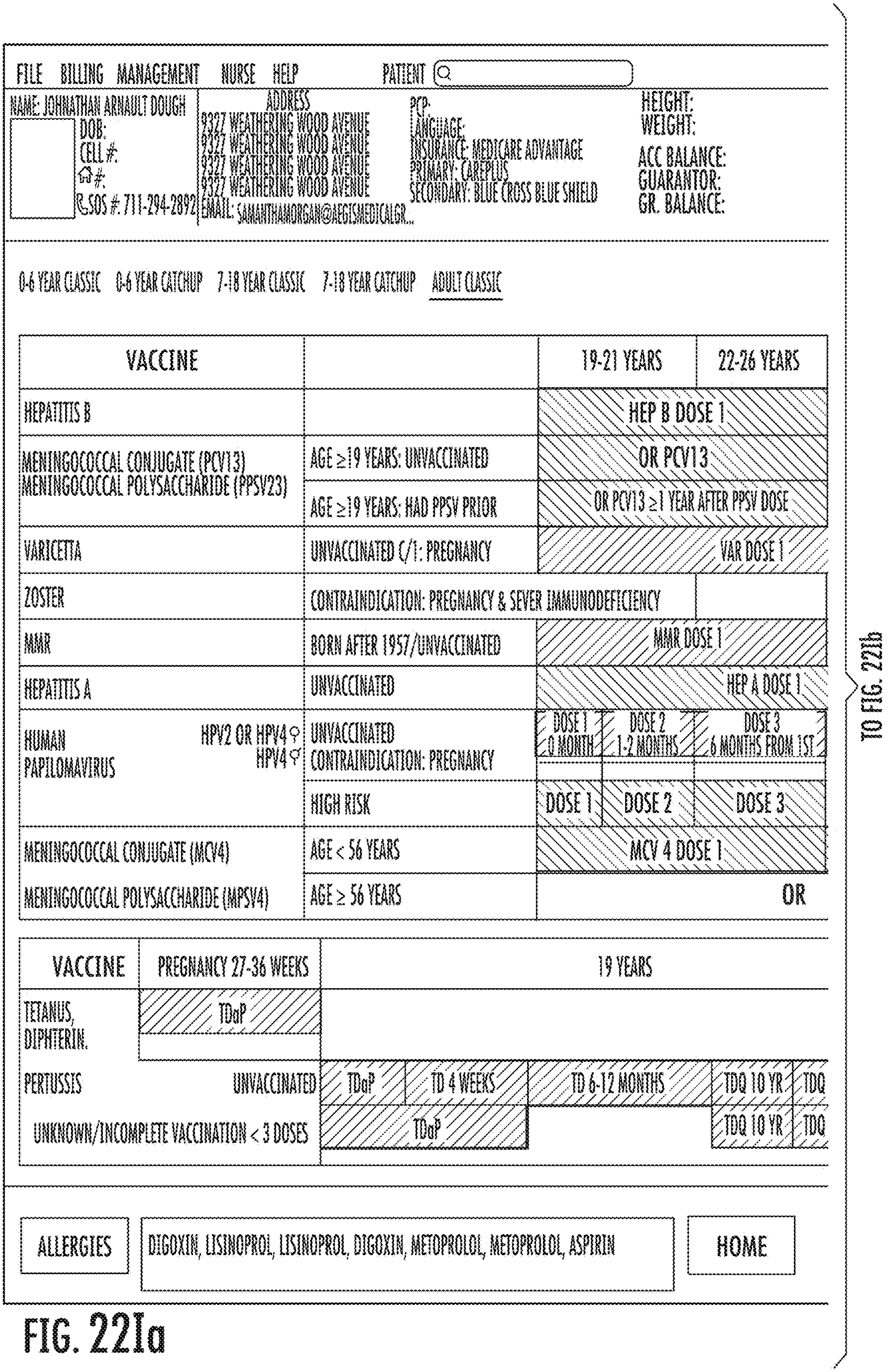
Figure 22I:
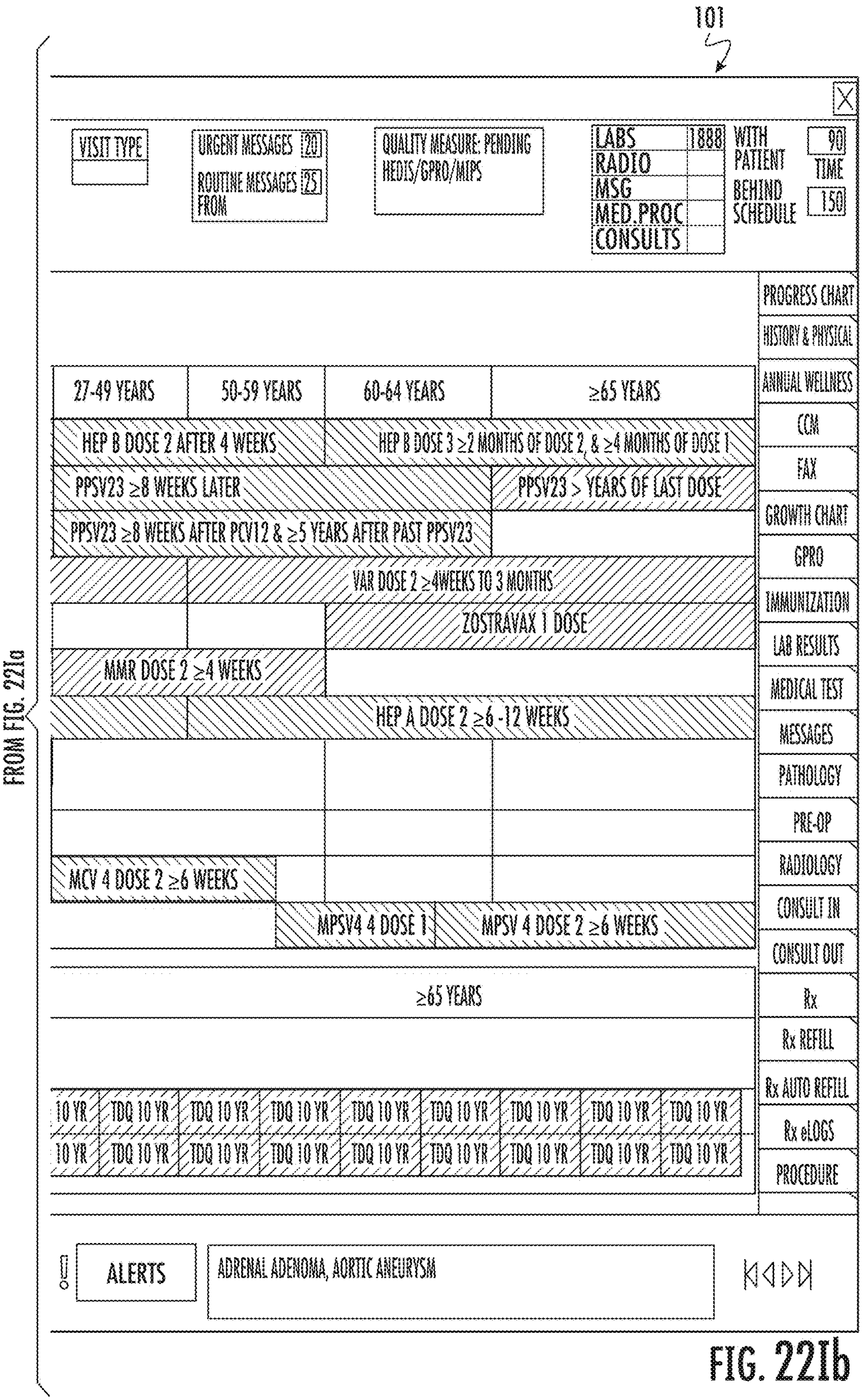

For the immunization function in FIGS. 22Ga-22Jb, the immunization function is designed like a brick wall. The age at which it should be given is given at the top. Whenever a vaccine for that age is needed, the template will send a text reminder to the patient and an email to remind the patient or the mother if the patient is an infant or a child. When the rectangular bar representing the vaccine that needs to be given is clicked on (where the Name of the vaccine on the X-Axis and the Age at which the vaccine needs to be given intersects on the Y-Axis): A thick border will form around that rectangular bar.

At the same time, a new horizontal long bar occupying either the right half of the screen, or the left hand side of the screen will be created below the schedule which is shown on the top part of the screen. The details of the vaccine can then be entered into this bar. This will then be saved by clicking on the save button in the center towards the bottom. The space for each designated vaccine entry may be fixed in their allotted area on the screen and will only be slightly changeable if the patient gets more shot by accident than what was needed.

Figure 22J:
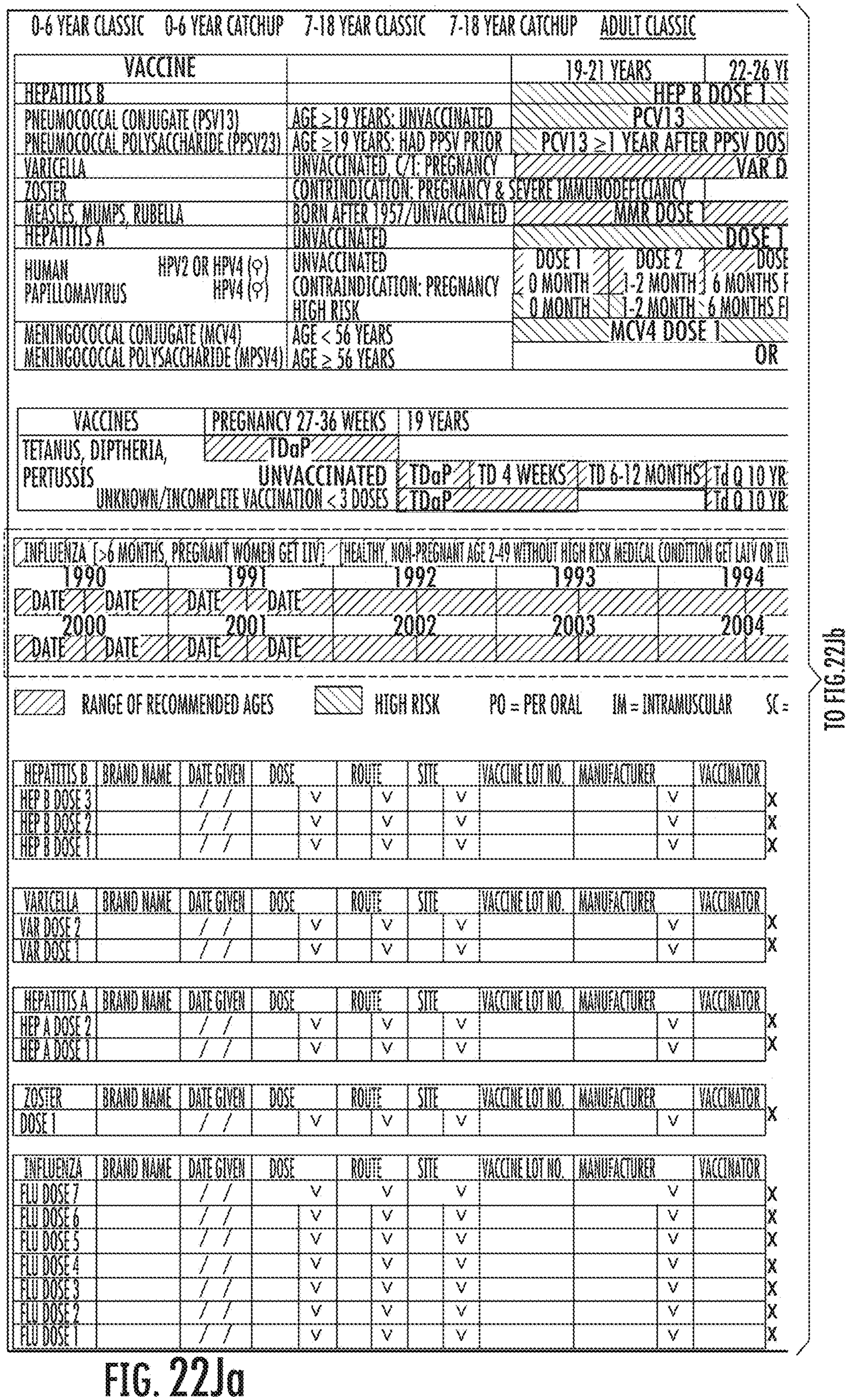
Figure 22J:
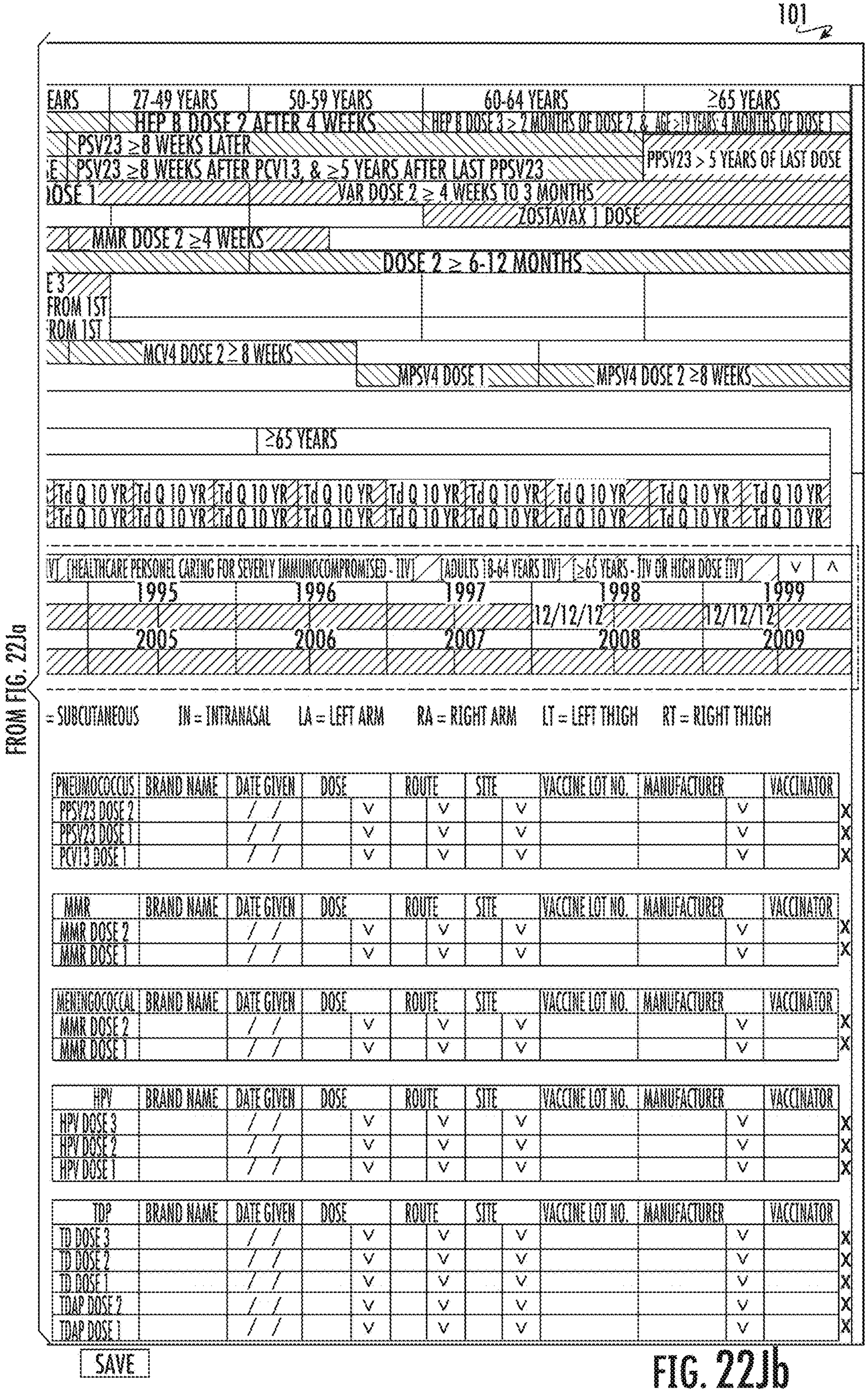

Immunization Adult Screen (FIGS. 22Ja-22Jb): The only exception is the influenza vaccine. This is represented by the dashed box, going partially across the screen. It has influenza written on the bar to the extreme left side. This vaccine can be given from birth yearly till the person dies which could be 125 years of age. To accommodate this vaccine a special bar has been created which will have 10 years in rectangular blocks, and each bar will have the year on it. Now, the rectangular bar below it will be divided into two halves. The left half of the rectangular bar will represent the first half of the year, and the right half will represent the second half of the year.

The influenza season starts from August of the previous year to March of the following year. Depending on which time of the year, the patient receives the vaccine will determine whether it will be recorded in the latter half of the previous year or the beginning half of the following year. So accordingly, the date of the vaccine will be entered into the rectangular block. As soon as the cursor is inserted into ne half of the block to add the date a bar will be created below to enter the details for that vaccination.

Because the flu could be up to 120 shots (i.e., theoretically from the time a person is born to the time he dies), it would be impossible to accommodate these many shots on the screen at the very top. Therefore, the influenza screen has been designed like the "wheel of fortune". When the whole 10 year row has been filled up, then the "green button" on the right upper hand corner can be clicked "down" to move the so called "wheel of fortune" to show another future 10 years to enter the date of future influenza. If someone wants to look at the past 10 years history or even earlier of the patient's influenza vaccination, then he can click on the UP arrow. With each click it will show the previous 10 years of his vaccination status. Thirteen rows of ten years each has been created, therefore theoretically covering anyone who lives up to an old ripe age of 130. As soon as the date of birth is inserted for the patient into the practice management system. It will automatically create the first row of ten years starting from the left starting from the year the patient is born going forwards.

For this reason, the influenza vaccine data entry bar is at the very bottom on the left hand of this screen shown in green. Any new vaccine entered in the block, for a particular year will create a bar which will push the previous bars for the vaccine down below it. In this way, the date of the last shot which the patient will always be on the top therefore avoiding the need to scroll down if it was the other way around. This is a measure designed to save time.

It should be appreciated that the features from the disclosed example embodiments of the EHR GUI 101 may be combined with other example embodiments. Further, the features of the disclosed example embodiments may be omitted in other embodiments.

Many modifications and other embodiments of the present disclosure will come to the mind of one skilled in the art having the benefit of the teachings presented in the foregoing descriptions and the associated drawings. Therefore, it is understood that the present disclosure is not to be limited to the specific embodiments disclosed, and that modifications and embodiments are intended to be included within the scope of the appended claims.

The invention claimed is:

1. An electronic health record (EHR) system providing an EHR graphical user interface (EHR GUI), the EHR system comprising:

a display;

a memory; and a processor cooperating with the display and the memory, the processor configured to store an EHR database for a plurality of patients, and render the EHR GUI on the display for accessing given patient data related to a given patient within the EHR database, the EHR GUI comprising a switchable interface area configured to switch between a plurality of EHR functions, each EHR function to provide access to a respective different type of information from the given patient data in the EHR database, a navigation tab menu adjacent to a first side of the switchable interface area and comprising a plurality of navigation tabs for accessing the plurality of EHR functions within the switchable interface area, a patient history tab menu adjacent to a second side of the switchable interface area, the second side being opposite the first side, the patient history tab menu comprising a plurality of patient history tabs for accessing different types of historical patient data from the given patient data in the EHR database, an alert footer menu entirely below the switchable interface area, the alert footer menu displaying a plurality of potential medical alerts for the given patient, the alert footer menu being persistently rendered for each of the plurality of EHR functions within the switchable interface area, the plurality of potential medical alerts for the given patient comprising an allergy alert and a life threatening condition alert, and a specialist footer menu adjacent to the alert footer menu and comprising a plurality of potential specialist notifications.

2. The EHR system of claim 1 wherein the plurality of patient history tabs comprises at least one of a patient prescription history tab, a patient surgical history tab, a patient medical history tab, and a patient problem list tab.

3. The EHR system of claim 2 wherein the patient prescription history tab comprises a medication name and an associated disease.

4. The EHR system of claim 1 wherein the plurality of potential specialist notifications comprises at least one of a practice specific specialty notification, and a doctor specific and location specific notification.

5. The EHR system of claim 1 wherein each potential specialist notification comprises a visual indicator for a quantity of notifications.

6. The EHR system of claim 1 wherein the switchable interface area has a multi-page side-by-side format; and wherein the alert footer menu comprises a plurality of page navigation buttons.

7. The EHR system of claim 1 wherein the plurality of navigation tabs comprises at least one of a laboratory results tab, a radiology tab, a referral tab, and a prescription tab.

8. The EHR system of claim 7 wherein the plurality of EHR functions comprises a consult function permitting selection of at least one of an assessment column, a specialty column, a referral doctor column, and a reason for consult column.

9. The EHR system of claim 8 wherein each of the assessment column, the specialty column, and the referral doctor column comprises a respective search menu.

10. A non-transitory computer-readable medium for an electronic health record (EHR) system comprising a display, the EHR system providing an EHR graphical user interface (EHR GUI), the non-transitory computer-readable medium having computer-executable instructions for causing the EHR system to perform steps comprising:

storing an EHR database for a plurality of patients; and rendering the EHR GUI on the display for accessing given patient data related to a given patient within the EHR database, the EHR GUI comprising a switchable interface area configured to switch between a plurality of EHR functions, each EHR function to provide access to a respective different type of information from the given patient data in the EHR database, a navigation tab menu adjacent to a first side of the switchable interface area and comprising a plurality of navigation tabs for accessing the plurality of EHR functions within the switchable interface area, a patient history tab menu adjacent to a second side of the switchable interface area, the second side being opposite the first side, the patient history tab menu comprising a plurality of patient history tabs for accessing different types of historical patient data from the given patient data in the EHR database, an alert footer menu entirely below the switchable interface area, the alert footer menu displaying a plurality of potential medical alerts for the given patient, the alert footer menu being persistently rendered for each of the plurality of EHR functions within the switchable interface area, the plurality of potential medical alerts for the given patient comprising an allergy alert and a life threatening condition alert, and a specialist footer menu adjacent to the alert footer menu and comprising a plurality of potential specialist notifications.

11. The non-transitory computer-readable medium of claim 10 wherein the plurality of patient history tabs comprises at least one of a patient prescription history tab, a patient surgical history tab, a patient medical history tab, and a patient problem list tab.

12. The non-transitory computer-readable medium of claim 11 wherein the patient prescription history tab comprises a medication name and an associated disease.

13. The non-transitory computer-readable medium of claim 10 wherein the plurality of potential specialist notifications comprises at least one of a practice specific specialty notification, and a doctor specific and location specific notification.

14. A method for operating an electronic health record (EHR) system comprising a display, the EHR system providing an EHR graphical user interface (EHR GUI), the method comprising:

storing an EHR database for a plurality of patients; and rendering the EHR GUI on the display for accessing given patient data related to a given patient within the EHR database, the EHR GUI comprising a switchable interface area configured to switch between a plurality of EHR functions, each EHR function to provide access to a respective different type of information from the given patient data in the EHR database, a navigation tab menu adjacent to a first side of the switchable interface area and comprising a plurality of navigation tabs for accessing the plurality of EHR functions within the switchable interface area, a patient history tab menu adjacent to a second side of the switchable interface area, the second side being opposite the first side, the patient history tab menu comprising a plurality of patient history tabs for accessing different types of historical patient data from the given patient data in the EHR database, an alert footer menu entirely below the switchable interface area, the alert footer menu displaying a plurality of potential medical alerts for the given patient, the alert footer menu being persistently rendered for each of the plurality of EHR functions within the switchable interface area, the plurality of potential medical alerts for the given patient comprising an allergy alert and a life threatening condition alert, and a specialist footer menu adjacent to the alert footer menu and comprising a plurality of potential specialist notifications.

15. The method of claim 14 wherein the plurality of patient history tabs comprises at least one of a patient prescription history tab, a patient surgical history tab, a patient medical history tab, and a patient problem list tab.

16. The method of claim 15 wherein the patient prescription history tab comprises a medication name and an associated disease.

17. The method of claim 14 wherein the plurality of potential specialist notifications comprises at least one of a practice specific specialty notification, and a doctor specific and location specific notification.

18. The non-transitory computer-readable medium of claim 10 wherein each potential specialist notification comprises a visual indicator for a quantity of notifications.

19. The non-transitory computer-readable medium of claim 10 wherein the switchable interface area has a multi-page side-by-side format; and wherein the alert footer menu comprises a plurality of page navigation buttons.

20. The non-transitory computer-readable medium of claim 10 wherein the plurality of navigation tabs comprises at least one of a laboratory results tab, a radiology tab, a referral tab, and a prescription tab.

* * * * *